US007649082B2

(12) United States Patent
Johnson et al.

(10) Patent No.: US 7,649,082 B2
(45) Date of Patent: Jan. 19, 2010

(54) PERSEPHIN SPECIFIC ANTIBODIES

(75) Inventors: Eugene M. Johnson, Pacific City, OR (US); Jeffrey D. Milbrandt, St. Louis, MO (US); Paul T. Kotzbauer, Aston, PA (US); Patricia A. Lampe, St. Louis, MO (US); Robert D. Klein, Palo Alto, CA (US); Frederic J. de Sauvage, Foster City, CA (US)

(73) Assignees: Washington University, St. Louis, MO (US); Genentech, Inc., San Francisco, CA (US)

( * ) Notice: Subject to any disclaimer, the term of this patent is extended or adjusted under 35 U.S.C. 154(b) by 561 days.

(21) Appl. No.: 11/037,782

(22) Filed: Jan. 18, 2005

(65) Prior Publication Data

US 2005/0234226 A1 Oct. 20, 2005

Related U.S. Application Data

(60) Continuation of application No. 09/474,980, filed on Dec. 29, 1999, now abandoned, which is a division of application No. 08/931,858, filed on Sep. 16, 1997, now Pat. No. 6,222,022, which is a continuation-in-part of application No. 08/881,172, filed on Jun. 23, 1997, now abandoned, which is a continuation-in-part of application No. 08/615,944, filed on Mar. 14, 1996, now abandoned, and a continuation-in-part of application No. PCT/US97/03461, filed on Mar. 14, 1997.

(51) Int. Cl.
*C07K 16/22* (2006.01)
(52) U.S. Cl. .................................. 530/388.24
(58) Field of Classification Search ............. None
See application file for complete search history.

(56) References Cited

U.S. PATENT DOCUMENTS

| 5,011,914 | A | 4/1991 | Collins et al. |
| 5,141,856 | A | 8/1992 | Collins et al. |
| 5,235,043 | A | 8/1993 | Collins et al. |
| 5,260,417 | A | 11/1993 | Grant et al. |
| 5,739,307 | A | 4/1998 | Johnson, Jr. et al. |
| 5,747,655 | A | 5/1998 | Johnson, Jr. et al. |
| 5,817,622 | A | 10/1998 | Johnson, Jr. et al. |
| 5,843,914 | A | 12/1998 | Johnson, Jr. et al. |
| 6,090,778 | A * | 7/2000 | Johnson et al. .......... 514/2 |
| 6,222,022 | B1 | 4/2001 | Johnson et al. |
| 6,232,449 | B1 | 5/2001 | Johnson et al. |
| 6,403,335 | B1 | 6/2002 | Johnson et al. |
| 6,645,937 | B1 | 11/2003 | Johnson et al. |
| 6,692,943 | B1 | 2/2004 | Johnson et al. |
| 6,716,600 | B1 | 4/2004 | Johnson et al. |
| 7,015,316 | B1 | 3/2006 | Johnson et al. |

FOREIGN PATENT DOCUMENTS

| WO | WO 93/06116 | 4/1993 |
| WO | WO 95/06662 | 3/1995 |
| WO | WO 95/17203 | 6/1995 |

OTHER PUBLICATIONS

Bowenkamp et al., Glial Cell Line-Derived Neurotrophic Factor Supports Survival of Injured Midbrain Dopaminergic Neurons, J. Comp. Neuro. 355:479-489 (1995).
Buj-Bello et al., GNDF is an Age-Specific Survival Factor for Sensory and Autonomic Neurons, Neuron 15:821-828 (1995).
Cheng et al., NGF and bFGF Protect Rat Hoppocampal and Human Cortical Neurons Against Hypoglycemic Damage by Stabilizing Calcium Homeostasis, Neuron 1:1031-1041 (1991).
Gibco-BRL Catalogue and Reference Guide, p. 296 (1992).
Henderson et al., GDNF: A Potent Survival Factor for Motoneurons Present in Peripheral Nerve and Muscle, Science 266:1062-1064 (1994).
Jackowski, Neural Injury Repair: Hope for the Future as Barriers to Effective CNS Regeneration Become Clearer, British J. of Neurosurgery 9:303-317 (1995).
Kearns et al., GDNF Protects Nigral Dopamine Neurons Against 6-Hydroxydopamine in vivo, Brain Research 672:104-111 (1995).
Kingsley, The TGF-β Superfamily: New Members, New Receptors, and New Genetic Tests of Function in Different Organisms, Genes and Dev. 8:133-146 (1994).
Klein, Role of neurotrophins in Mouse Neuronal Development, FASEB J 8:738-744 (1994).
Kotzbauer et al., Neurturin, a Relative of Glial-Cell-Line-Derived Neurotrophic Factor, Nature 384(6608):467-470 (1996).
Kotzbauer et al., Postnatal Development of Survival Responsiveness in Rat Sympathetic Neurons to Leukemia Inhibitory Factor and Ciliary Neurotrophic Factor, Neuron 12:763-773 (1994).
Levi-Montalcini et al., Selective Growth Stimulating Effects of Mouse Sarcoma on the Sensory and Sympathetic Nervous System of the Chick Embryo, J. Exp. Zool. 116:321-361 (1951).
Liebrock et al., Molecular Cloning and Expression of Brain-Derived Neurotrophic Factor, Nature 341:149-152 (1989).
Lin at al., Purification, Cloning and Expression of Ciliary Neurotrophic Factor (CNTF), Science 246:1023-1025 (1989).
Lin et al., GDNF: A Glial Cell Line-Derived Neurotrophic Factor for Midbrain Dopaminergic Neurons, Science 260:1130-1132 (1993).
Oppenheim et al., Developing Motor Neurons Rescued from Programmed and Axotomy-Induced Cell Death by GDNF, Nature 373:344-346 (1995).
Rudinger, In Peptide Hormones, ed. J.A. Parsons, University Park Press, Baltimore, pp. 1-7 (Jun. 1976).

(Continued)

*Primary Examiner*—Robert C Hayes
(74) *Attorney, Agent, or Firm*—Thompson Coburn LLP; Charles P. Romano

(57) ABSTRACT

A novel growth factor, persephin, which belongs to the GDNF/neurturin family of growth factors, is disclosed. The human, mouse and rat amino acid sequences have been identified. Human, mouse and rat persephin genomic DNA sequences have been cloned and sequenced and the respective cDNA sequences identified. In addition, methods for treating degenerative conditions using persephin, methods for detecting persephin gene alterations and methods for detecting and monitoring patient levels of persephin are provided. Methods for identifying additional members of the persephin-neurturin-GDNF family of growth factors are also provided.

2 Claims, 31 Drawing Sheets

OTHER PUBLICATIONS

Springer et al., CDNA Sequence and Differential mRNA Regulation of Two Forms of Glial Cell Line-Derived neurotrophic Factor in Schwann Cells and Rat Skeletal Muscle, Exp. Neurol. 131:47-52 (1995).

Stull et al., Antigene, Ribozyme and Aptamer Nucleic Acid Drugs: Progress and Prospects, Pharmaceutical Research 12(4):465-483 (1995).

Trupp et al., Peripheral Expression and Biological Activities of GDNF, a New Neurotrophic Factor for Avian and Mammalian Peripheral Neurons, J. Cell. Bio. 130:137-148 (1995).

Tuszynski et al., Neurotrophic Factors and Diseases of the Nervous System, Ann. Neurol. 35:S9-S12 (1994).

Watabe et al., Spontaneously Immortalized Adult Mouse Schwann Cells Secrete Autocrine and Paracrine Growth-Promoting Activities, J. Neurosci. Res. 41:279-290 (1995).

Yan et al., In Vivo Neurotrophic Effects of GDNF on Neonatal and Adult Facial Motor Neurons, Nature 373:341-344 (1995).

Milbrandt et al., Persephin, a Novel Neurotrophic Factor Related to GDNF and Neuturin, Neuron, Feb. 1998, pp. 245-253, vol. 20, Cell Press.

* cited by examiner

NGF

Anti-NGF

Anti-NGF + Neurturin

FIGURE 5

ATGCAGCGCTGGAAGGCGGCGGCCTTGGCCTCAGTGCTCTGCAGCTCCGTGCTGTCCATC 60
Met Gln Arg Trp Lys Ala Ala Ala Leu Ala Ser Val Leu Cys Ser Ser Val Leu Ser Ile

TGGATGTGTCGAGAGGGCCTGCTTCTCAGCCACCGCCTCGGACCTGCGCTGGTCCCCCTG 120
Trp Met Cys Arg Glu Gly Leu Leu Leu Ser His Arg Leu Gly Pro Ala Leu Val Pro Leu

CACCGCCTGCCTCGAACCCTGGACGCCCGGATTGCCCGCCTGGCCCAGTACCGTGCACTC 180
His Arg Leu Pro Arg Thr Leu Asp Ala Arg Ile Ala Arg Leu Ala Gln Tyr Arg Ala Leu

CTGCAGGGGGCCCCGGATGCGATGGAGCTGCGCGAGCTGACGCCCTGGGCTGGGCGGCCC 240
Leu Gln Gly Ala Pro Asp Ala Met Glu Leu Arg Glu Leu Thr Pro Trp Ala Gly Arg Pro

CCAGGTCCGCGCCGTCGGGCGGGGCCCCGGCGGCGGCGCGCGCGTGCGCGGTTGGGGGCG 300
Pro Gly Pro Arg Arg Arg Ala Gly Pro Arg Arg Arg Arg Ala Arg Ala Arg Leu Gly Ala

CGGCCTTGCGGGCTGCGCGAGCTGGAGGTGCGCGTGAGCGAGCTGGGCCTGGGCTACGCG 360
Arg Pro Cys Gly Leu Arg Glu Leu Glu Val Arg Val Ser Glu Leu Gly Leu Gly Tyr Ala

TCCGACGAGACGGTGCTGTTCCGCTACTGCGCAGGCGCCTGCGAGGCTGCCGCGCGCGTC 420
Ser Asp Glu Thr Val Leu Phe Arg Tyr Cys Ala Gly Ala Cys Glu Ala Ala Ala Arg Val

TACGACCTCGGGCTGCGACGACTGCGCCAGCGGCGGCGCCTGCGGCGGGAGCGGGTGCGC 480
Tyr Asp Leu Gly Leu Arg Arg Leu Arg Gln Arg Arg Arg Leu Arg Arg Glu Arg Val Arg

GCGCAGCCCTGCTGCCGCCCGACGGCCTACGAGGACGAGGTGTCCTTCCTGGACGCGCAC 540
Ala Gln Pro Cys Cys Arg Pro Thr Ala Tyr Glu Asp Glu Val Ser Phe Leu Asp Ala His

AGCCGCTACCACACGGTGCACGAGCTGTCGGCGCGCGAGTGCGCCTGCGTGTGA 594
Ser Arg Tyr His Thr Val His Glu Leu Ser Ala Arg Glu Cys Ala Cys Val

FIGURE 7

```
ATGAGGCGCTGGAAGGCAGCGGCCCTGGTGTCGCTCATCTGCAGCTCCCTGCTATCTGTC  60
Met Arg Arg Trp Lys Ala Ala Ala Leu Val Ser Leu Ile Cys Ser Ser Leu Leu Ser Val

TGGATGTGCCAGGAGGGTCTGCTCTTGGGCCACCGCCTGGGACCCGCGCTTGCCCCGCTA 120
Trp Met Cys Gln Glu Gly Leu Leu Leu Gly His Arg Leu Gly Pro Ala Leu Ala Pro Leu

CGACGCCCTCCACGCACCCTGGACGCCCGCATCGCCCGCCTGGCCCAGTATCGCGCTCTG 180
Arg Arg Pro Pro Arg Thr Leu Asp Ala Arg Ile Ala Arg Leu Ala Gln Tyr Arg Ala Leu

CTCCAGGGCGCCCCCGACGCGGTGGAGCTTCGAGAACTTTCTCCCTGGGCTGCCCGCATC 240
Leu Gln Gly Ala Pro Asp Ala Val Glu Leu Arg Glu Leu Ser Pro Trp Ala Ala Arg Ile

CCGGGACCGCGCCGTCGAGCGGGTCCCCGGCGTCGGCGGGCGCGGCCGGGGGCTCGGCCT 300
Pro Gly Pro Arg Arg Arg Ala Gly Pro Arg Arg Arg Ala Arg Pro Gly Ala Arg Pro

TGTGGGCTGCGCGAGCTCGAGGTGCGCGTGAGCGAGCTGGGCCTGGGCTACACGTCGGAT 360
Cys Gly Leu Arg Glu Leu Glu Val Arg Val Ser Glu Leu Gly Leu Gly Tyr Thr Ser Asp

GAGACCGTGCTGTTCCGCTACTGCGCAGGCGCGTGCGAGGCGGCCATCCGCATCTACGAC 420
Glu Thr Val Leu Phe Arg Tyr Cys Ala Gly Ala Cys Glu Ala Ala Ile Arg Ile Tyr Asp

CTGGGCCTTCGGCGCCTGCGCCAGCGGAGGCGCGTGCGCAGAGAGCGGGCGCGGGCGCAC 480
Leu Gly Leu Arg Arg Leu Arg Gln Arg Arg Arg Val Arg Arg Glu Arg Ala Arg Ala His

CCGTGTTGTCGCCCGACGGCCTATGAGGACGAGGTGTCCTTCCTGGACGTGCACAGCCGC 540
Pro Cys Cys Arg Pro Thr Ala Tyr Glu Asp Glu Val Ser Phe Leu Asp Val His Ser Arg

TACCACACGCTGCAAGAGCTGTCGGCGCGGGAGTGCGCGTGCGTGTGA 588
Tyr His Thr Leu Gln Glu Leu Ser Ala Arg Glu Cys Ala Cys Val
```

FIGURE 8

```
GGAGGGAGAGCGCGCGGTGGTTTCGTCCGTGTGCCCCGCGCCCGGCGC         -301
TCCTCGCGTGGCCCCGCGTCCTGAGCGCGCTCCAGCCTCCCACGCGCGCC       -251
ACCCCGGGGTTCACTGAGCCCGGCGAGCCCGGGGAAGACAGAGAAAGAGA       -201
GGCCAGGGGGGGAACCCCATGGCCCGGCCCGTGTCCCGCACCCTGTGCGG       -151
TGGCCTCCTCCGGCACGGGGTCCCCGGGTCGCCTCCGGTCCCCGCGATCC       -101
GGATGGCGCACGCAGTGGCTGGGGCCGGGCCGGGCTCGGGTGGTCGGAGG       -51
AGTCACCACTGACCGGGTCATCTGGAGCCCGTGGCAGGCCGAGGCCCAGG       -1
ATGAGGCGCTGGAAGGCAGCGGCCCTGGTGTCGCTCATCTGCAGCTCCCT        50
GCTATCTGTCTGGATGTGCCAGGAGGGTCTGCTCTTGGGCCACCGCCTGG       100
GACCCGCGCTTGCCCCGCTACGACGCCCTCCACGCACCCTGGACGCCCGC       150
ATCGCCCGCCTGGCCCAGTATCGCGCTCTGCTCCAGGGCGCCCCCGACGC       200
GGTGGAGCTTCGAGAACTTTCTCCCTGGGCTGCCCGCATCCCGGGACCGC       250
GCCGTCGAGCGGGTCCCCGGCGTCGGCGGGCGCGGCCGGGGGCTCGGCCT       300
TGTGGGCTGCGCGAGCTCGAGGTGCGCGTGAGCGAGCTGGGCCTGGGCTA       350
CACGTCGGATGAGACCGTGCTGTTCCGCTACTGCGCAGGCGCGTGCGAGG       400
CGGCCATCCGCATCTACGACCTGGGCCTTCGGCGCCTGCGCCAGCGGAGG       450
CGCGTGCGCAGAGAGCGGGCGCGGGCGCACCCGTGTTGTCGCCCGACGGC       500
CTATGAGGACGAGGTGTCCTTCCTGGACGTGCACAGCCGCTACCACACGC       550
TGCAAGAGCTGTCGGCGCGGGAGTGCGCGTGCGTGTGATGCTACCTCACG       600
CCCCCCGACCTGCGAAAGGGCCCTCCCTGCCGACCCTCGCTGAGAACTGA       650
CTTCACATAAAGTGTGGGAACTCCC                                675
```

FIGURE 9

| | |
|---|---|
| GAGGGACCTGGACGCCCCATCAGGGTAAGAATTCCTGGGGGCCTCCCGACTCCCCAATTC | 60 |
| Glu Gly Pro Gly Arg Pro Ile Arg Val Arg Ile Pro Gly Gly Leu Pro Thr Pro Gln Phe | 20 |
| CTTCTCTCAAAGCCCTCACTTTGCCTTACAATCCTACTCTACCTTGCACTAGGTAACAAC | 120 |
| Leu Leu Ser Lys Pro Ser Leu Cys Leu Thr Ile Leu Leu Tyr Leu Ala Leu Gly Asn Asn | 40 |
| CATGTCCGTCTTCCAAGAGCCTTGGCTGGTTCATGCCGACTGTGGAGCCTGACCCTACCA | 180 |
| His Val Arg Leu Pro Arg Ala Leu Ala Gly Ser Cys Arg Leu Trp Ser Leu Thr Leu Pro | 60 |
| GTGGCTGAGCTGGGCCTGGGCTATGCCTCGGAGGAGAAGGTCATCTTCCGATACTGTGCT | 240 |
| Val Ala Glu Leu Gly Leu Gly Tyr Ala Ser Glu Glu Lys Val Ile Phe Arg Tyr Cys Ala | 80 |
| GGCAGCTGTCCCCAAGAGGCCCGTACCCAGCACAGTCTGGTACTGGCCCGGCTTCGAGGG | 300 |
| Gly Ser Cys Pro Gln Glu Ala Arg Thr Gln His Ser Leu Val Leu Ala Arg Leu Arg Gly | 100 |
| CGGGGTCGAGCCCATGGCCGACCCTGCTGCCAGCCCACCAGCTATGCTGATGTGACCTTC | 360 |
| Arg Gly Arg Ala His Gly Arg Pro Cys Cys Gln Pro Thr Ser Tyr Ala Asp Val Thr Phe | 120 |
| CTTGATGATCAGCACCATTGGCAGCAGCTGCCTCAGCTCTCAGCTGCAGCTTGTGGCTGT | 420 |
| Leu Asp Asp Gln His His Trp Gln Gln Leu Pro Gln Leu Ser Ala Ala Ala Cys Gly Cys | 140 |
| GGTGGCTGAAGGAGGCCAGTCTGGTGTCTCAGAATCACAAGCATGAGACAGGCTGGGCTT | 480 |
| Gly Gly | 142 |
| TGAAAGGCTCAGGTGACATTACTAGAAATTTGCATAGGTAAAGATAAGAAGGGAAAGGAC | 540 |
| CAGG | 544 |

```
CCTCAGAGGAGAAGATTATCTTCCGATACTGTGCTGGCAGCTGTCCCCAAGAGGTCCGTACC    62
  Ser Glu Glu Lys Ile Ile Phe Arg Tyr Cys Ala Gly Ser Cys Pro Gln Glu Val Arg Thr    20

CAGCACAGTCTGGTGCTGGCCCGTCTTCGAGGGCAGGGTCGAGCTCATGGCAGACCTTGC    122
 Gln His Ser Leu Val Leu Ala Arg Leu Arg Gly Gln Gly Arg Ala His Gly Arg Pro Cys    40

TGCCAGCCCACCAGCTATGCTGATGTGACCTTCCTTGATGACCACCACCATTGGCAGCAG    182
 Cys Gln Pro Thr Ser Tyr Ala Asp Val Thr Phe Leu Asp Asp His His His Trp Gln Gln    60

CTGCCTCAGCTCTCAGCCGCAGCTTGTGGCTGTGGTGGCTGAAGGCGGCCAGCCTGGTCT    242
 Leu Pro Gln Leu Ser Ala Ala Ala Cys Gly Cys Gly Gly                               73

CTCAGAATCACAAGCAAGAGGCAGCCTTTGAAAGGCTCAGGTGACGTTATTAGAAACTTG    302

CATAGGAGAAGATTAAGAAGAGAAAGGGGACCTG                              336
```

FIGURE 13

```
TGCCGGCTGTGGAGCCTGACCCTACCAGTGGCTGAGCTTGGCCTGGGCTATGCCTCAGAG    60
Cys Arg Leu Trp Ser Leu Thr Leu Pro Val Ala Glu Leu Gly Leu Gly Tyr Ala Ser Glu    20

GAGAAGATTATCTTCCGATACTGTGCTGGCAGCTGTCCCCAAGAGGTCCGTACCCAGCAC    120
Glu Lys Ile Ile Phe Arg Tyr Cys Ala Gly Ser Cys Pro Gln Glu Val Arg Thr Gln His    40

AGTCTGGTGCTGGCCCGTCTTCGAGGGCAGGGTCGAGCTCATGGCAGACCTTGCTGCCAG    180
Ser Leu Val Leu Ala Arg Leu Arg Gly Gln Gly Arg Ala His Gly Arg Pro Cys Cys Gln    60

CCCACCAGCTATGCTGATGTGACCTTCCTTGATGACCACCACCATTGGCAGCAGCTGCCT    240
Pro Thr Ser Tyr Ala Asp Val Thr Phe Leu Asp Asp His His His Trp Gln Gln Leu Pro    80

CAGCTCTCAGCCGCAGCTTGTGGCTGTGGTGGCTGAAGGCGGCCAGCCTGGTCTCTCAGA    300
Gln Leu Ser Ala Ala Ala Cys Gly Cys Gly Gly    91

ATCACAAGCAAGAGGCAGCCTTTGAAAGGCTCAGGTGACGTTATTAGAAACTTGCATAGG    360

AGAAGATTAAGAAGAGAAAGGGGACCTGATT    391
```

FIGURE 14

```
              10                  20                  30                  40
   ┌─────────────────────────────────────────────────────────────────────────┐
 1 │C V L T A I H L N V T D L G L G Y E T K E E L I F R Y C S G S C D A A E T T - Y│ GDNF(human)
 1 │C V L T A I H L N V T D L G L G Y E T K E E L I F R Y C S G S C E A A E T M - Y│ GDNF(rat)
 1 │C V L T A I H L N V T D L G L G Y E T K E E L I F R Y C S G S C E S A E T M - Y│ GDNF(mouse)
 1 │C G L R E L E V R V S E L G L G Y A S D E T V L F R Y C A G A C E A A A R V - Y│ NTN(human)
 1 │C G L R E L E V R V S E L G L G Y T S D E T V L F R Y C A G A C E A A I R I - Y│ NTN(mouse)
 1 │C R L W S L T L P V A E L G L G Y A S E E K I I F R Y C A G S C P Q E V R T Q H│ PSP(rat)
 1 │C R L W S L T L P V A E L G L G Y A S E E K V I F R Y C A G S C P Q E A R T Q H│ PSP(mouse)
   └─────────────────────────────────────────────────────────────────────────┘

50                  60                  70                  80
   ┌─────────────────────────────────────────────────────────────────────────┐
40 │D K I L K N L S R N R R L V S D K V - G Q A C C R P I A F D D D L S F L D D N L│ GDNF(human)
40 │D K I L K N L S R S R R L T S D K V - G Q A C C R P V A F D D D L S F L D D S L│ GDNF(rat)
40 │D K I L K N L S R S R R L T S D K V - G Q A C C R P V A F D D D L S F L D D N L│ GDNF(mouse)
40 │D L G L R R L R Q R R R L R R E R V R A Q P C C R P T A Y E D E V S F L D A H S│ NTN(human)
40 │D L G L R R L R Q R R R V R R E R A R A H P C C R P T A Y E D E V S F L D V H S│ NTN(mouse)
41 │S L V L A R L R - - - - - G Q G R A H G R P C C Q P T S Y A D - V T F L D D H H│ PSP(rat)
41 │S L V L A R L R - - - - - G R G R A H G R P C C Q P T S Y A D - V T F L D D Q H│ PSP(mouse)
   └─────────────────────────────────────────────────────────────────────────┘

90
   ┌─────────────────────────┐
79 │V Y H I L R K H S A K R C G C│ .   GDNF(human)
79 │V Y H I L R K H S A K R C G C│ .   GDNF(rat)
79 │V Y H I L R K H S A K R C G C│ .   GDNF(mouse)
80 │R Y H T V H E L S A R E C A C│ .   NTN(human)
80 │R Y H T L Q E L S A R E C A C│ .   NTN(mouse)
75 │H W Q Q L P Q L S A A A C G C│ .   PSP(rat)
75 │H W Q Q L P Q L S A A A C G C│ .   PSP(mouse)
   └─────────────────────────┘
```

```
              10                  20                  30
  1 A L L T R C S A L P L L T T L P V A E L G L G Y A S E E K V I F    mPSP
  1 A L L T R C R L W L P L T T L P V A E L G L G Y A S E E K V I H    rPSP
  1 A L L S Q C R Q L P G P W L T L S V A E L G L G Y A S E E K V I F    hPSP 40                  50                  60
 31 R Y C A G S C P Q E A R T Q H S L V L A R L R G R G Q G R A H G    mPSP
 31 R Y C A G S C P Q E V R T Q H S L V L A R L R G Q G G R A H G    rPSP
 31 R L C A G P C P R G A R T Q L G L L A L G L A R R L R G R A H G    hPSP 70                  80                  90
 61 R P C C Q P P T S Y A D V T F L D D Q H W Q L P Q Q L S A A        mPSP
 61 R P C C Q P P T S Y A D V T F L D D H H W Q L P Q L S A A          rPSP
 61 G P C R P T R Y T D V A F L D D R H W Q R L P Q L S A A            hPSP

91 A C G G G                                                         rPSP
 91 A C G G G                                                         rPSP
 91 A C G G G                                                         hPSP
```

| SEQ ID NO: | GROWTH FACTOR | SEQUENCE |
|---|---|---|
| 150 | TGFB1 | CCVRQLYIDFRKDLGWK-WIHEPKGYHANFCLGPCPYIWSLDT------------QYSKVLALYNQHNPGASAA-PCCV--PQALEPLPIVYYVGRKPKV--EQLSNMIVRSCKCS |
| 151 | TGFB2 | CCLRPLYIDFKRDLGWK-WIHEPKGYNANFCAGACPYLWSSDT------------QHSRVLSLYNTINPEASAS-PCCV--SQDLEPLTILYYIGKTPKI--EQLSNMIVKSCKCS |
| 152 | TGFB3 | CCVRPLYIDFRQDLGWK-WVHEPKGYYANFCSGPCPYLRSADT------------THSTVLGLYNTLNPEASAS-PCCV--PQDLEPLTILYYVGRTPKV--EQLSNMVVSCKCS |
| 153 | INHBA | CCKKQFFVSFK-DIGWNDWIIAPSGYHANYCEGECPSHIAG-TSGSSLSFHSTVINHYRMRGHSPFANLKSCCV--PTKLRPMSMLYDDGQNII-KKDIQNMIVEECGCS |
| 154 | INHBB | CCRQQFFIDFR-LIGWNDWIIAPTGYYGNYCEGSCPAYLAG-VPGSASSFHTAVVNQYRMRGLNP-GTVNSCCI--PTKLSTMSMLYFDDEYNIV-KRDVPNMIVEECGCA |
| 155 | NODAL | CRRVKFQVDFN-LIGWGSWIIYPKQYNAYRCEGECPNPVGEEFHPT-----NHAYIQSLLKRYQPHR-VPSTCCA--PVKTKPLSMLYDNGR---VLLEHHKDMIVEECGCL |
| 156 | BMP2 | CKRHPLYVDFS-DVGWNDWIVAPPGYHAFYCHGECPFPLADHLNST-----NHAIVQTLVNSVNS-K-IPKACCV--PTELSAISMLYLDENEKVVLK--NYQDMVVEGCGCR |
| 157 | BMP4 | CRRHSLYVDFS-DVGWNDWIVAPPGYQAFYCHGDCPFPLADHLNST-----NHAIVQTLVNSVNS-S-IPKACCV--PTELSAISMLYLDEYDKVVLK--NYQEMVVEGCGCR |
| 158 | DPP | CRRHSLYVDFS-DVGWQDWIVAPLGYDAYYCHGKCPFPLADHFNST-----NHAVVQTLVNNMPGK-VPKACCV--PTQLDSVAMLYLNDQSTVVLK--NYQEMTVVGCGCR |
| 159 | BMP5 | CKRHELYVSFR-DLGWQDWIIAPEGYAAFYCDGECSFPLNAHMNAT-----NHAIVQTLVHLMFPDH-VPKPCCA--PTKLNAISVLYFDDSSNVILK--KYRNMVVRSCGCH |
| 160 | BMP6 | CKRHELYVSFQ-DLGWQDWIIAPKGYAANYCDGECSFPLNAHMNAT-----NHAIVQTLVHLMNPEY-VPKPCCA--PTKLNAISVLYFDDNSNVILK--KYRNMVVRACGCH |
| 161 | BMP7 | CKKHELYVSFR-DLGWQDWIIAPEGYAAYYCEGECAFPLNSYMNAT-----NHAIVQTLVHFINPET-VPKPCCA--PTQLNAISVLYFDDSSNVILK--KYRNMVVRACGCH |
| 162 | BMP8 | CRRHELYVSFQ-DLGWLDWVIAPQGYSAYYCEGSCAFPLDSCMNAT-----NHAILQSLVHLMKPNA-VPKACCA--PTKLSATSVLYYDSSNNVILR--KHRNMVVKACGCH |
| 163 | 60A | CQMQTLYIDFK-DLGWQDWIIAPEGYGAFYCSGECNFPLNAHMNAT-----NHAIVQTLVHLLEPKK-VPKPCCA--PTRLGALPVLYHLNDENVNLK--KYRNMVKSCGCH |
| 164 | BMP3 | CARRYLKVDFA-DIGWSEWIISPKSFDAYYCSGACFPMPKSLKPS-----NHATIQSIVRAVGVVPGIPEPCCV--PEKMSSLSILFFDNNNDNVLKV-YPNMTVESCACR |
| 165 | VG1 | CKKRHLYVEFK-DVGWQNWVIAPQGYMANYCYGECPYPLTEILNGS-----NHAILQTLVHSIEPED-IPLPCCV--PTKMSPISMLFYDNNSDNVVLR--HYENMAVDECGCR |
| 166 | GDF1 | CRARRLYVSFR-EVGAHRAWIAPRGFLANYCQGQCALPVALSGSGGPPALNHAVLRALMHAAAPGA-ADLPCCV--PARLSPISVLFFDNSDNVVLR--QYEDMVVDECGCR |
| 167 | GDF3 | CHRHQLFINFQ-DLGWHKWVIAPKGFMANYCHGECPFSMTTYLNSS-----NYAFMQALMHMADP-K-VPKAVCV--PTKLSPISMLYQDSDKNVILR--HYEDMVVDECGCG |
| 168 | DORSLN | CRRTSLHVNFK-EIGWDSWIIAPKDYEAFECKGGCFFPLTDNVTPT-----KHAIVQTLVHLQNPKK-ASKACCV--PTKLDAISILYKDDAGVPTLIYNYEGMKVAECGCR |
| 169 | INHα | CHRVALNISF-QELGWERWIVYPPSFIFHYCHGGCGLHIPPNLSLPVPGAPPTPAQPYSL------PGAQPCCAALPGTMRPLHVRTTSDGGYSFKYETVPNLLTQHCACI |
| 170 | MIS | CALRELSVDLRAERS-----VLIPETYQANNCQGACGWPQSDR----NPRYGNHVVLLLKMQARGATLARPPCCV--PTAYT-GKLLISLSEERISAHHVPNMVATECGCR |
| 171 | GDF9 | CELHDFSLSFS-QLKWDNWIVAPHSYNPSYCKGDCPSAVSHRYGSPV---HTMVQNMIYE-KLDPSVPSPSCV--PGKYSPLSVLTIEPDGSIAYK-EYEDMATSCTCR |
| 172 | GDNF | CVLTAIHLNVT-DLGLG--YETKEELIFRYCSGSCD-AAETTYDKILKNLSRN------RRLVSDKV-GQACCRPIAFD-DDLSFL------DDNLVYHILRKHSAKRCGCI |
| 173 | NTN | CGLRELEVRVS-ELGLG--YASDETVLFRYCAGACE-AAARVYDLGLRRLRQR------RLRERVRAQPCCRPTAYE-DEVSFL------DAHSRYHTVHELSARECACV |

FIGURE 16

```
ATGGCTGCAG GAAGACTTCG GATCCTGTGT CTGCTGCTCC TGTCCTTGCA CCCGAGCCTC
TACCGACGTC CTTCTGAAGC CTAGGACACA GACGACGAGG ACAGGAACGT GGGCTCGGAG

GGCTGGGTCC TTGATCTTCA AGAGGCTTCT GTGGCAGATA AGCTCTCATT TGGGAAGATG
CCGACCCAGG AACTAGAAGT TCTCCGAAGA CACCGTCTAT TCGAGAGTAA ACCCTTCTAC

GCAGAGACTA GAGGGACCTG GACGCCCCAT CAGGGTAAGA ATTCCTGGGG GCCTCCCGAC
CGTCTCTGAT CTCCCTGGAC CTGCGGGGTA GTCCCATTCT TAAGGACCCC CGGAGGGCTG

TCCCCAATTC CTTCTCTCAA AGCCCTCACT TTGCCTTACA ATCCTACTCT ACCTTGCACT
AGGGGTTAAG GAAGAGAGTT TCGGGAGTGA AACGGAATGT TAGGATGAGA TGGAACGTGA

AGTAACAAC CATGTCCGTC TTCCAAGAGC CTTGGCTGGT TCATGCCGAC TGTGGAGCCT
TCCATTGTTG GTACAGGCAG AAGGTTCTCG GAACCGACCA AGTACGGCTG ACACCTCGGA

GACCCTACCA GTGGCTGAGC TGGGCCTGGG CTATGCCTCG GAGGAGAAGG TCATCTTCCG
CTGGGATGGT CACCGACTCG ACCCGGACCC GATACGGAGC CTCCTCTTCC AGTAGAAGGC

ATACTGTGCT GGCAGCTGTC CCCAAGAGCC CCGTACCCAG CACAGTCTGG TACTGGCCCG
TATGACACGA CCGTCGACAG GGGTTCTCCG GGCATGGGTC GTGTCAGACC ATGACCGGGC

GCTTCGAGGG CGGGGTCGAG CCCATGGCCG CAGCGACGTG ACCCTGCTGC GCTATGCTGA
CGAAGCTCCC GCCCCAGCTC GGGTACCGGC GTCGCTGCAC TGGGACGACG CGATACGACT

TGTGACCTTC CTTGATGATC AGCACCATTG GCAGCAGCTG CCTCAGCTCT CAGCTGCAGC
ACACTGGAAG GAACTACTAG TCGTGGTAAC CGTCGTCGAC GGAGTCGAGA GTCGACGTCG

TTGTGGCTGT GGTGGCTGAA GGAGGCCAGT CTGGTGTCTC AGAATCACAA GCATGAGACA
AACACCGACA CCACCGACTT CCTCCGGTCA GACCACAGAG TCTTAGTGTT CGTACTCTGT

GGCTGGGCTT TGAAAGGCTC AGTGACATT ACTAGAAATT TGCATAGGTA AAGATAAGAA
CCGACCCGAA ACTTTCCGAG TCCACTGTAA TGATCTTTAA ACGTATCCAT TTCTATTCTT

GGGAAAGGAC CAGGGGTTTT TTGTTTCTTT CTTTGCTTGC TTGTTAGTTT TTTTTTTTT
CCCTTTCCTG GTCCCCAAAA AACAAAGAAA GAAACGAACG AACAATCAAA AAAAAAAAA

TTT
AAA
```

FIGURE 17A

```
ATGGCTGCAG GAAGACTTCG GATCCTGTGT CTGCTGCTCC TGTCCTTGCA CCCGAGCCTC
TACCGACGTC CTTCTGAAGC CTAGGACACA GACGACGAGG ACAGGAACGT GGGCTCGGAG
 M  A  A  G  R  L  R  I  L  C  L  L  L  S  L  H  P  S  L

GGCTGGGTCC TTGATCTTCA AGAGGCTTCT GTGGCAGATA AGCTCTCATT TGGAAGATG
CCGACCCAGG AACTAGAAGT TCTCCGAAGA CACCGTCTAT TCGAGAGTAA ACCCTTCTAC
 G  W  V  L  D  L  Q  E  A  S  V  A  D  K  L  S  F  G  K  M

GCAGAGACTA GAGGGACCTG GACGCCCCAT CAGGGTAACA ACCATGTCCG TCTTCCAAGA
CGTCTCTGAT CTCCCTGGAC CTGCGGGGTA GTCCCATTGT TGGTACAGGC AGAAGGTTCT
 A  E  T  R  G  T  W  T  P  H  Q  G  N  N  H  V  R  L  P  R

GCCTTGGCTG GTTCATGCCG ACTGTGGAGC CTGACCCTAC CAGTGGCTGA GCTGGGCCTG
CGGAACCGAC CAAGTACGGC TGACACCTCG GACTGGGATG GTCACCGACT CGACCCGGAC
 A  L  A  G  S  C  R  L  W  S  L  T  L  P  V  A  E  L  G  L

GGCTATGCCT CGGAGGAGAA GGTCATCTTC CGATACTGTG CTGGCAGCTG TCCCCAAGAG
CCGATACGGA GCCTCCTCTT CCAGTAGAAG GCTATGACAC GACCGTCGAC AGGGGTTCTC
 G  Y  A  S  E  E  K  V  I  F  R  Y  C  A  G  S  C  P  Q  E

GCCCGTACCC AGCACAGTCT GGTACTGGCC CGGCTTCGAG GGCGGGGTCG AGCCCATGGC
CGGGCATGGG TCGTGTCAGA CCATGACCGG GCCGAAGCTC CCGCCCCAGC TCGGGTACCG
 A  R  T  Q  H  S  L  V  L  A  R  L  R  G  R  G  R  A  H  G

CGACCCTGCT GCCAGCCCAC CAGCTATGCT GATGTGACCT TCCTTGATGA TCAGCACCAT
GCTGGGACGA CGGTCGGGTG GTCGATACGA CTACACTGGA AGGAACTACT AGTCGTGGTA
 R  P  C  C  Q  P  T  S  Y  A  D  V  T  F  L  D  D  Q  H  H

TGGCAGCAGC TGCCTCAGCT CTCAGCTGCA GCTTGTGGCT GTGGTGGCTG A
ACCGTCGTCG ACGGAGTCGA GAGTCGACGT CGAACACCGA CACCACCGAC T
 W  Q  Q  L  P  Q  L  S  A  A  A  C  G  C  G  G
```

Figure 17B

```
  1  ATGGCTGCAG  GAAGACTTCG  GATCTTGTTT  CTGCTGCTCC  TGTCCTTGCA  CCTGGCCTT
     TACCGACGTC  CTTCTGAAGC  CTAGAACAAA  GACGACGAGG  ACAGGAACGT  GGACCCGAA

51  GGCTGGGTCC  TTGATCTTCA  AGAGGCTCCT  GCGGCAGATG  AGCTCTCATC  TGGGAAAATG
     CCGACCCAGG  AACTAGAAGT  TCTCCGAGGA  CGCCGTCTAC  TCGAGAGTAG  ACCCTTTTAC

101  GCAGAGACTG  GAAGGACCTG  GAAGCCCCAT  CAGGGTAAGA  ATTCTTGGGG  GCCTCCTAAC
     CGTCTCTGAC  CTTCCTGGAC  CTTCGGGGTA  GTCCCATTCT  TAAGAACCCC  CGGAGGATTG

151  TCTACAGTTC  TTCCTCTCAA  AGCCCTCACT  TTGCCTCACA  ATCCTATTCT  ACCTTGCACT
     AGATGTCAAG  AAGGAGAGTT  TCGGGAGTGA  AACGGAGTGT  TAGGATAAGA  TGGAACGTGA

201  AGGTAACAAC  AATGTCCGCC  TTCCAAGAGC  CTTACCTGGT  TTGTGCCGGC  TGTGGAGCCT
     TCCATTGTTG  TTACAGGCGG  AAGGTTCTCG  GAATGGACCA  AACACGGCCG  ACACCTCGGA

251  GACCCTACCA  GTGGCTGAGC  TTGGCCTGGG  CTATGCCTCA  GAGGAGAAGA  TTATCTTCCG
     CTGGGATGGT  CACCGACTCG  AACCGGACCC  GATACGGAGT  CTCCTCTTCT  AATAGAAGGC

301  ATACTGTGCT  GGCAGCTGTC  CCCAAGAGGT  CACAGTCTGG  CCGTACCCAG  TGCTGGCCCG
     TATGACACGA  CCGTCGACAG  GGGTTCTCCA  GTGTCAGACC  GGCATGGGTC  ACGACCGGGC

351  TCTTCGAGGG  CAGGGTCGAG  CTCATGGCAG  ACCTTGCTGC  CAGCCCACCA  GCTATGCTGA
     AGAAGCTCCC  GTCCCAGCTC  GAGTACCGTC  TGGAACGACG  GTCGGGTGGT  CGATACGACT

401  TGTGACCTTC  CTGATGACC   ACCACCATTG  GCAGCAGCTG  CCTCAGCTCT  CAGCCGCAGC
     ACACTGGAAG  GAACTACTGG  TGGTGGTAAC  CGTCGTCGAC  GGAGTCGAGA  GTCGGGTCG

451  TTGTGGCTGT  GGTGGCTGA
     AACACCGACA  CCACCGACT
```

Figure 18A

```
  1   ATGGCTGCAG GAAGACTTCG GATCTTGTTT CTGCTGCTCC TGTCCTTGCA CCTGGGCCTT
      TACCGACGTC CTTCTGAAGC CTAGAACAAA GACGACGAGG ACAGGAACGT GGACCCGGAA
  1    M  A  A  G  R  L  R  I  L  F  L  L  L  L  S  L  H  L  G  L

61   GGCTGGGTCC TTGATCTTCA AGAGGCTCCT GCGGCAGATG AGCTCTCATC TGGAAAATG
      CCGACCCAGG AACTAGAAGT TCTCCGAGGA CGCCGTCTAC TCGAGAGTAG ACCCTTTAC
 21    G  W  V  L  D  L  Q  E  A  P  A  A  D  E  L  S  S  G  K  M

121   GCAGAGACTG GAAGGACCTG GAAGCCCCAT CAGGGTAACA ACAATGTCCG CCTTCCAAGA
      CGTCTCTGAC CTTCCTGGAC CTTCGGGGTA GTCCCATTGT TGTTACAGGC GGAAGGTTCT
 41    A  E  T  G  R  T  W  K  P  H  Q  G  N  N  N  V  R  L  P  R

181   GCCTTACCTG GTTTGTGCCG GCTGTGGAGC CTGACCCTAC CAGTGGCTGA GCTTGGCCTG
      CGGAATGGAC CAAACACGGC CGACACCTCG GACTGGGATG GTCACCGACT CGAACCGGAC
 61    A  L  P  G  L  C  R  L  W  S  L  T  L  P  V  A  E  L  G  L

241   GGCTATGCCT CAGAGAGAA GATTATCTTC CGATACTGTG CTGGCAGCTG TCCCCAAGAG
      CCGATACGGA GTCTCCCTCT CTAATAGAAG GCTATGACAC GACCGTCGAC AGGGGTTCTC
 81    G  Y  A  S  E  E  K  I  I  F  R  Y  C  A  G  S  C  P  Q  E

301   GTCCGTACCC AGCACAGTCT GGTGCTGGCC CGTCTTCGAG GGCAGGGTCG AGCTCATGGC
      CAGGCATGGG TCGTGTCAGA CCACGACCGG GCAGAAGCTC CCGTCCCAGC TCGAGTACCG
101    V  R  T  Q  H  S  L  V  L  A  R  L  R  G  Q  G  R  A  H  G

361   AGACCTTGCT GCCAGCCCAC CAGCTATGCT GATGTGACCT TCCTTGATGA CCACCACCAT
      TCTGGAACGA CGGTCGGGTG GTCGATACGA CTACACTGGA AGGAACTACT GGTGGTGGTA
121    R  P  C  C  Q  P  T  S  Y  A  D  V  T  F  L  D  D  H  H  H

421   TGGCAGCAGC TGCCCTCAGCT CTCAGCCGCA GCTTGTGGCT GTGGTGGCTG A
      ACCGTCGTCG ACGGAGTCGA GAGTCGGCGT CGAACACCGA CACCACCGAC T
141    W  Q  Q  L  P  Q  L  S  A  A  A  C  G  G  G
```

PSP/NTN (SEQ ID NO:137)

ALAGSCRLWSLTLPVAELGLGYASEEKVIFRYCAGSCPQEARTQHSLVLA     50
↓
RLRGRGRAHGRPCCRPTAYEDEVSFLDVHSRYHTLQELSARECACV     96

NTN/PSP (SEQ ID NO:142)

PGARPCGLRELEVRVSELGLGYTSDETVLFRYCAGACEAAIRIYDLGLRR     50
↓
LRQRRRVRRERARAHPCCQPTSYADVTFLDDQHHWQQLPQLSAAACGCGG     100

FIGURE 20B

 Water
 Kidney no RT
 Cerebellum
 Lung
 Brain
 Kidney
 Persephin
FIGURE 23

```
                                        ┌C
                                        └G
  1 ATGGCGGTAG GGAAGTTCCT GCTGGGCTCT|CTGCTGCTCC TGTCCCTGCA GCTGGGACAG
    TACCGGCATC CCTTCAAGGA CGACCCGAGA|GACGACGAGG ACAGGGACGT CGACCCTGTC
  1  M  A  V  G  K  F  L  L  G  S   L  L  L  L  S  L  Q  L  G  Q

61 GGCTGGGGCC CCGATGCCCG TGGGGTTCCC GTGGCCGATG GAGAGTTCTC GTCTGAACAG
    CCGACCCCGG GGCTACGGGC ACCCCAAGGG CACCGGCTAC CTCTCAAGAG CAGACTTGTC
 21  G  W  G  P  D  A  R  G  V  P  V  A  D  G  E  F  S  S  E  Q
           **

121 GTGGCAAAGG CTGGAGGGAC CTGGCTGGGC ACCCACCGCC CCCTTGCCCG CCTGCGCCGA
    CACCGTTTCC GACCTCCCTG GACCGACCCG TGGGTGGCGG GGGAACGGGC GGACGCGGCT
 41  V  A  K  A  G  G  T  W  L  G  T  H  R  P  L  A  R  L  R  R
              ↓
181 GCCCTGTCTG GTCCATGCCA GCTGTGGAGC CTGACCCTGT CCGTGGCAGA GCTAGGCCTG
    CGGGACAGAC CAGGTACGGT CGACACCTCG GACTGGGACA GGCACCGTCT CGATCCGGAC
 61  A  L  S  G  P  C  Q  L  W  S  L  T  L  S  V  A  E  L  G  L
     *

241 GGCTACGCCT CAGAGAGAA GGTCATCTTC CGCTACTGCG CCGGCAGCTG CCCCCGTGGT
    CCGATGCGGA GTCTCTCTT CCAGTAGAAG GCGATGACGC GGCCGTCGAC GGGGGCACCA
 81  G  Y  A  S  E  E  K  V  I  F  R  Y  C  A  G  S  C  P  R  G
                                                        ┌C
                                                        └G
301 GCCCGCACCC AGCATGGCCT GGCGCTGGCC CGGCTGCAGG GCCAGGGCCG AGCCCACGGT
    CGGGCGTGGG TCGTACCGGA CCGCGACCGG GCCGACGTCC CGGTCCCGGC TCGGGTGCCA
101  A  R  T  Q  H  G  L  A  L  A  R  L  Q  G  Q  G  R  A  H  G

361 GGGCCCTGCT GCCGGCCCAC TCGCTACACC GACGTGGCCT TCCTCGATGA CCGCCACCGC
    CCCGGGACGA CGGCCGGGTG AGCGATGTGG CTGCACCGGA AGGAGCTACT GGCGGTGGCG
121  G  P  C  C  R  P  T  R  Y  T  D  V  A  F  L  D  D  R  H  R

421 TGGCAGCGGC TGCCCCAGCT CTCGGCGGCT GCCTGCGGCT GTGGTGGCTG A
    ACCGTCGCCG ACGGGGTCGA GAGCCGCCGA CGGACGCCGA CACCACCGAC T
141  W  Q  R  L  P  Q  L  S  A  A  A  C  G  C  G  G
```

FIGURE 24

SEQUENCE LISTING

<160> NUMBER OF SEQ ID NOS: 242

<210> SEQ ID NO 1
<211> LENGTH: 102
<212> TYPE: PRT
<213> ORGANISM: Homo sapiens

```
<400> SEQUENCE: 1

Ala Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
             20                  25                  30

Arg Tyr Cys Ala Gly Ala Cys Glu Ala Ala Arg Val Tyr Asp Leu
         35                  40                  45

Gly Leu Arg Arg Leu Arg Gln Arg Arg Arg Leu Arg Arg Glu Arg Val
     50                  55                  60

Arg Ala Gln Pro Cys Cys Arg Pro Thr Ala Tyr Glu Asp Glu Val Ser
 65                  70                  75                  80

Phe Leu Asp Ala His Ser Arg Tyr His Thr Val His Glu Leu Ser Ala
                 85                  90                  95

Arg Glu Cys Ala Cys Val
            100

<210> SEQ ID NO 2
<211> LENGTH: 100
<212> TYPE: PRT
<213> ORGANISM: Mus musculus

<400> SEQUENCE: 2

Pro Gly Ala Arg Pro Cys Gly Leu Arg Glu Leu Glu Val Arg Val Ser
 1               5                  10                  15

Glu Leu Gly Leu Gly Tyr Thr Ser Asp Glu Thr Val Leu Phe Arg Tyr
             20                  25                  30

Cys Ala Gly Ala Cys Glu Ala Ala Ile Arg Ile Tyr Asp Leu Gly Leu
         35                  40                  45

Arg Arg Leu Arg Gln Arg Arg Val Arg Arg Glu Arg Ala Arg Ala
     50                  55                  60

His Pro Cys Cys Arg Pro Thr Ala Tyr Glu Asp Glu Val Ser Phe Leu
 65                  70                  75                  80

Asp Val His Ser Arg Tyr His Thr Leu Gln Glu Leu Ser Ala Arg Glu
                 85                  90                  95

Cys Ala Cys Val
            100

<210> SEQ ID NO 3
<211> LENGTH: 16
<212> TYPE: PRT
<213> ORGANISM: Mus musculus
<220> FEATURE:
<221> NAME/KEY: PRT
<222> LOCATION: (6)
<223> OTHER INFORMATION: Any Amino Acid

<400> SEQUENCE: 3

Ser Gly Ala Arg Pro Xaa Gly Leu Arg Glu Leu Glu Val Ser Val Ser
 1               5                  10                  15

<210> SEQ ID NO 4
<211> LENGTH: 10
<212> TYPE: PRT
<213> ORGANISM: Mus musculus
<220> FEATURE:
<221> NAME/KEY: PRT
<222> LOCATION: (1)
<223> OTHER INFORMATION: Any Amino Acid
```

```
<220> FEATURE:
<221> NAME/KEY: PRT
<222> LOCATION: (6)
<223> OTHER INFORMATION: Serine or Cysteine

<400> SEQUENCE: 4

Xaa Cys Ala Gly Ala Xaa Glu Ala Ala Val
 1               5                  10

<210> SEQ ID NO 5
<211> LENGTH: 23
<212> TYPE: PRT
<213> ORGANISM: Mus musculus
<220> FEATURE:
<221> NAME/KEY: PRT
<222> LOCATION: (1)..(2)
<223> OTHER INFORMATION: Any Amino Acid
<220> FEATURE:
<221> NAME/KEY: PRT
<222> LOCATION: (17)
<223> OTHER INFORMATION: Glutamine or Glutamic Acid

<400> SEQUENCE: 5

Xaa Xaa Val Glu Ala Lys Pro Cys Cys Gly Pro Thr Ala Tyr Glu Asp
 1               5                  10                  15

Xaa Val Ser Phe Leu Ser Val
            20

<210> SEQ ID NO 6
<211> LENGTH: 10
<212> TYPE: PRT
<213> ORGANISM: Mus musculus

<400> SEQUENCE: 6

Tyr His Thr Leu Gln Glu Leu Ser Ala Arg
 1               5                  10

<210> SEQ ID NO 7
<211> LENGTH: 197
<212> TYPE: PRT
<213> ORGANISM: Homo sapiens

<400> SEQUENCE: 7

Met Gln Arg Trp Lys Ala Ala Ala Leu Ala Ser Val Leu Cys Ser Ser
 1               5                  10                  15

Val Leu Ser Ile Trp Met Cys Arg Glu Gly Leu Leu Leu Ser His Arg
            20                  25                  30

Leu Gly Pro Ala Leu Val Pro Leu His Arg Leu Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Met Glu Leu Arg Glu Leu Thr Pro Trp Ala Gly Arg Pro
65                  70                  75                  80

Pro Gly Pro Arg Arg Arg Ala Gly Pro Arg Arg Arg Ala Arg Ala
                85                  90                  95

Arg Leu Gly Ala Arg Pro Cys Gly Leu Arg Glu Leu Glu Val Arg Val
            100                 105                 110

Ser Glu Leu Gly Leu Gly Tyr Ala Ser Asp Glu Thr Val Leu Phe Arg
        115                 120                 125

Tyr Cys Ala Gly Ala Cys Glu Ala Ala Ala Arg Val Tyr Asp Leu Gly
    130                 135                 140
```

Leu Arg Arg Leu Arg Gln Arg Arg Leu Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
                180                 185                 190

Glu Cys Ala Cys Val
        195

<210> SEQ ID NO 8
<211> LENGTH: 195
<212> TYPE: PRT
<213> ORGANISM: Mus musculus

<400> SEQUENCE: 8

Met Arg Arg Trp Lys Ala Ala Leu Val Ser Leu Ile Cys Ser Ser
1               5                   10                  15

Leu Leu Ser Val Trp Met Cys Gln Glu Gly Leu Leu Gly His Arg
                20                  25                  30

Leu Gly Pro Ala Leu Ala Pro Leu Arg Arg Pro Pro Arg Thr Leu Asp
                35                  40                  45

Ala Arg Ile Ala Arg Leu Ala Gln Tyr Arg Ala Leu Leu Gln Gly Ala
        50                  55                  60

Pro Asp Ala Val Glu Leu Arg Glu Leu Ser Pro Trp Ala Ala Arg Ile
65                  70                  75                  80

Pro Gly Pro Arg Arg Arg Ala Gly Pro Arg Arg Arg Ala Arg Pro
                85                  90                  95

Gly Ala Arg Pro Cys Gly Leu Arg Glu Leu Glu Val Arg Val Ser Glu
                100                 105                 110

Leu Gly Leu Gly Tyr Thr Ser Asp Glu Thr Val Leu Phe Arg Tyr Cys
                115                 120                 125

Ala Gly Ala Cys Glu Ala Ala Ile Arg Ile Tyr Asp Leu Gly Leu Arg
        130                 135                 140

Arg Leu Arg Gln Arg Arg Arg Val Arg Arg Glu Arg Ala Arg Ala His
145                 150                 155                 160

Pro Cys Cys Arg Pro Thr Ala Tyr Glu Asp Glu Val Ser Phe Leu Asp
                165                 170                 175

Val His Ser Arg Tyr His Thr Leu Gln Glu Leu Ser Ala Arg Glu Cys
                180                 185                 190

Ala Cys Val
        195

<210> SEQ ID NO 9
<211> LENGTH: 306
<212> TYPE: DNA
<213> ORGANISM: Homo sapiens

<400> SEQUENCE: 9
gcgcggttgg gggcgcggcc ttgcgggctg cgcgagctgg aggtgcgcgt gagcgagctg      60
ggcctgggct acgcgtccga cgagacggtg ctgttccgct actgcgcagg cgcctgcgag     120
gctgccgcgc gcgtctacga cctcgggctg cgacgactgc gccagcggcg cgcgcctgcgg    180 cgggagcggg tgcgcgcgca gccctgctgc cgcccgacgg cctacgagga cgaggtgtcc     240
ttcctggacg cgcacagccg ctaccacacg gtgcacgagc tgtcggcgcg cgagtgcgcc     300
tgcgtg                                                                306

<210> SEQ ID NO 10
<211> LENGTH: 300
<212> TYPE: DNA
<213> ORGANISM: Mus musculus

<400> SEQUENCE: 10

| | | | | | |
|---|---|---|---|---|---|
| ccgggggctc | ggccttgtgg | gctgcgcgag | ctcgaggtgc | gcgtgagcga | gctgggcctg | 60 |
| ggctacacgt | cggatgagac | cgtgctgttc | cgctactgcg | caggcgcgtg | cgaggcggcc | 120 |
| atccgcatct | acgacctggg | ccttcggcgc | ctgcgccagc | ggaggcgcgt | gcgcagagag | 180 |
| cgggcgcggg | cgcacccgtg | ttgtcgcccg | acggcctatg | aggacgaggt | gtccttcctg | 240 |
| gacgtgcaca | gccgctacca | cacgctgcaa | gagctgtcgg | cgcgggagtg | cgcgtgcgtg | 300 |

<210> SEQ ID NO 11
<211> LENGTH: 594
<212> TYPE: DNA
<213> ORGANISM: Homo sapiens

<400> SEQUENCE: 11

| | | | | | |
|---|---|---|---|---|---|
| atgcagcgct | ggaaggcggc | ggccttggcc | tcagtgctct | gcagctccgt | gctgtccatc | 60 |
| tggatgtgtc | gagagggcct | gcttctcagc | caccgcctcg | gacctgcgct | ggtcccctg | 120 |
| caccgcctgc | ctcgaaccct | ggacgcccgg | attgcccgcc | tggcccagta | ccgtgcactc | 180 |
| ctgcagggg | ccccggatgc | gatggagctg | cgcgagctga | cgccctgggc | tgggcggccc | 240 |
| ccaggtccgc | gccgtcgggc | ggggccccgg | cggcggcgcg | cgcgtgcgcg | gttgggggcg | 300 |
| cggccttgcg | ggctgcgcga | gctggaggtg | cgcgtgagcg | agctgggcct | gggctacgcg | 360 |
| tccgacgaga | cggtgctgtt | ccgctactgc | gcaggcgcct | gcgaggctgc | gcgcgcgtc | 420 |
| tacgacctcg | ggctgcgacg | actgcgccag | cggcggcgcc | tgcggcggga | gcgggtgcgc | 480 |
| gcgcagccct | gctgccgccc | gacggcctac | gaggacgagg | tgtccttcct | ggacgcgcac | 540 |
| agccgctacc | acacggtgca | cgagctgtcg | gcgcgcgagt | gcgcctgcgt | gtga | 594 |

<210> SEQ ID NO 12
<211> LENGTH: 588
<212> TYPE: DNA
<213> ORGANISM: Mus musculus

<400> SEQUENCE: 12

| | | | | | |
|---|---|---|---|---|---|
| atgaggcgct | ggaaggcagc | ggccctggtg | tcgctcatct | gcagctccct | gctatctgtc | 60 |
| tggatgtgcc | aggagggtct | gctcttgggc | caccgcctgg | acccgcgct | tgccccgcta | 120 |
| cgacgccctc | cacgcaccct | ggacgcccgc | atcgcccgcc | tggcccagta | tcgcgctctg | 180 |
| ctccagggcg | ccccgacgc | ggtggagctt | cgagaacttt | ctccctgggc | tgcccgcatc | 240 |
| ccgggaccgc | gccgtcgagc | gggtccccgg | cgtcggcggg | cgcggccggg | ggctcggcct | 300 |
| tgtgggctgc | gcgagctcga | ggtgcgcgtg | agcgagctgg | gcctgggcta | cacgtcggat | 360 |
| gagaccgtgc | tgttccgcta | ctgcgcaggc | gcgtgcgagg | cggccatccg | catctacgac | 420 |
| ctgggccttc | ggcgcctgcg | ccagcggagg | cgcgtgcgca | gagagcgggc | gcgggcgcac | 480 |
| ccgtgttgtc | gcccgacggc | ctatgaggac | gaggtgtcct | tcctggacgt | gcacagccgc | 540 |
| taccacacgc | tgcaagagct | gtcggcgcgg | gagtgcgcgt | gcgtgtga | | 588 |

<210> SEQ ID NO 13
<211> LENGTH: 348
<212> TYPE: DNA
<213> ORGANISM: Mus musculus

<400> SEQUENCE: 13

```
ggagggagag cgcgcggtgg tttcgtccgt gtgccccgcg cccggcgctc ctcgcgtggc    60
cccgcgtcct gagcgcgctc cagcctccca cgcgcgccac cccggggttc actgagcccg   120
gcgagcccgg ggaagacaga gaaagagagg ccagggggg aaccccatgg cccggccgt    180
gtcccgcacc ctgtgcggtg gcctcctccg gcacggggtc cccgggtcgc ctccggtccc   240
cgcgatccgg atggcgcacg cagtggctgg ggccgggccg ggctcgggtg gtcggaggag   300
tcaccactga ccgggtcatc tggagcccgt ggcaggccga ggcccagg                348
```

<210> SEQ ID NO 14
<211> LENGTH: 87
<212> TYPE: DNA
<213> ORGANISM: Mus musculus

<400> SEQUENCE: 14

```
tgctacctca cgccccccga cctgcgaaag ggccctccct gccgaccctc gctgagaact    60
gacttcacat aaagtgtggg aactccc                                       87
```

<210> SEQ ID NO 15
<211> LENGTH: 19
<212> TYPE: PRT
<213> ORGANISM: Homo sapiens

<400> SEQUENCE: 15

Met Gln Arg Trp Lys Ala Ala Ala Leu Ala Ser Val Leu Cys Ser Ser
 1               5                  10                  15

Val Leu Ser

<210> SEQ ID NO 16
<211> LENGTH: 19
<212> TYPE: PRT
<213> ORGANISM: Mus musculus

<400> SEQUENCE: 16

Met Arg Arg Trp Lys Ala Ala Ala Leu Val Ser Leu Ile Cys Ser Ser
 1               5                  10                  15

Leu Leu Ser

<210> SEQ ID NO 17
<211> LENGTH: 57
<212> TYPE: DNA
<213> ORGANISM: Homo sapiens

<400> SEQUENCE: 17

```
atgcagcgct ggaaggcggc ggccttggcc tcagtgctct gcagctccgt gctgtcc      57
```

<210> SEQ ID NO 18
<211> LENGTH: 57
<212> TYPE: DNA
<213> ORGANISM: Mus musculus

<400> SEQUENCE: 18

```
atgaggcgct ggaaggcagc ggccctggtg tcgctcatct gcagctccct gctatct      57
```

<210> SEQ ID NO 19
<211> LENGTH: 76
<212> TYPE: PRT
<213> ORGANISM: Homo sapiens

<400> SEQUENCE: 19

Ile Trp Met Cys Arg Glu Gly Leu Leu Leu Ser His Arg Leu Gly Pro
1               5                   10                  15

Ala Leu Val Pro Leu His Arg Leu Pro Arg Thr Leu Asp Ala Arg Ile
            20                  25                  30

Ala Arg Leu Ala Gln Tyr Arg Ala Leu Leu Gln Gly Ala Pro Asp Ala
        35                  40                  45

Met Glu Leu Arg Glu Leu Thr Pro Trp Ala Gly Arg Pro Pro Gly Pro
    50                  55                  60

Arg Arg Arg Ala Gly Pro Arg Arg Arg Ala Arg
65                  70                  75

<210> SEQ ID NO 20
<211> LENGTH: 228
<212> TYPE: DNA
<213> ORGANISM: Mus musculus

<400> SEQUENCE: 20
atctggatgt gtcgagaggg cctgcttctc agccaccgcc tcggacctgc gctggtcccc     60
ctgcaccgcc tgcctcgaac cctggacgcc cggattgccc gcctggccca gtaccgtgca    120
ctcctgcagg gggcccccgga tgcgatggag ctgcgcgagc tgacgccctg gctgggcgg    180 cccccaggtc cgcgccgtcg ggcggggccc cggcggcggc gcgcgcgt                 228

<210> SEQ ID NO 21
<211> LENGTH: 228
<212> TYPE: DNA
<213> ORGANISM: Mus musculus

<400> SEQUENCE: 21
gtctggatgt gccaggaggg tctgctcttg ggccaccgcc tgggaccgc gcttgccccg     60 ctacgacgcc ctccacgcac cctggacgcc cgcatcgccc gcctggccca gtatcgcgct    120
ctgctccagg gcgcccccga cgcggtggag cttcgagaac tttctccctg gctgcccgc    180 atcccgggac cgcgccgtcg agcgggtccc cggcgtcggc gggcgcgg                228

<210> SEQ ID NO 22
<211> LENGTH: 76
<212> TYPE: PRT
<213> ORGANISM: Mus musculus

<400> SEQUENCE: 22

Val Trp Met Cys Gln Glu Gly Leu Leu Leu Gly His Arg Leu Gly Pro
1               5                   10                  15

Ala Leu Ala Pro Leu Arg Arg Pro Pro Arg Thr Leu Asp Ala Arg Ile
            20                  25                  30

Ala Arg Leu Ala Gln Tyr Arg Ala Leu Leu Gln Gly Ala Pro Asp Ala
        35                  40                  45

Val Glu Leu Arg Glu Leu Ser Pro Trp Ala Ala Arg Ile Pro Gly Pro
    50                  55                  60

Arg Arg Arg Ala Gly Pro Arg Arg Arg Ala Arg
65                  70                  75

<210> SEQ ID NO 23
<211> LENGTH: 95
<212> TYPE: PRT
<213> ORGANISM: Mus musculus

<400> SEQUENCE: 23

Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Ser His Arg
            20                  25                  30

Leu Gly Pro Ala Leu Val Pro Leu His Arg Leu Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Met Glu Leu Arg Glu Leu Thr Pro Trp Ala Gly Arg Pro
65                  70                  75                  80

Pro Gly Pro Arg Arg Arg Ala Gly Pro Arg Arg Arg Ala Arg
                85                  90                  95

<210> SEQ ID NO 24
<211> LENGTH: 95
<212> TYPE: PRT
<213> ORGANISM: Mus musculus

<400> SEQUENCE: 24

Met Arg Arg Trp Lys Ala Ala Ala Leu Val Ser Leu Ile Cys Ser Ser
1               5                   10                  15

Leu Leu Ser Val Trp Met Cys Gln Glu Gly Leu Leu Gly His Arg
            20                  25                  30

Leu Gly Pro Ala Leu Ala Pro Leu Arg Arg Pro Pro Arg Thr Leu Asp
        35                  40                  45

Ala Arg Ile Ala Arg Leu Ala Gln Tyr Arg Ala Leu Leu Gln Gly Ala
    50                  55                  60

Pro Asp Ala Val Glu Leu Arg Glu Leu Ser Pro Trp Ala Ala Arg Ile
65                  70                  75                  80

Pro Gly Pro Arg Arg Ala Gly Pro Arg Arg Arg Ala Arg
                85                  90                  95

<210> SEQ ID NO 25
<211> LENGTH: 285
<212> TYPE: DNA
<213> ORGANISM: Mus musculus

<400> SEQUENCE: 25
atgcagcgct ggaaggcggc ggccttggcc tcagtgctct gcagctccgt gctgtccatc     60
tggatgtgtc gagagggcct gcttctcagc caccgcctcg gacctgcgct ggtccccctg    120
caccgcctgc ctcgaacccct ggacgcccgg attgcccgcc tggcccagta ccgtgcactc    180 ctgcagggg ccccggatgc gatggagctg cgcgagctga cgccctgggc tgggcggccc    240
ccaggtccgc gccgtcgggc ggggccccgg cggcggcgcg cgcgt                    285

<210> SEQ ID NO 26
<211> LENGTH: 285
<212> TYPE: DNA
<213> ORGANISM: Mus musculus

<400> SEQUENCE: 26
atgaggcgct ggaaggcagc ggccctggtg tcgctcatct gcagctccct gctatctgtc     60
tggatgtgcc aggagggtct gcttctgggc accgcctgg acccgcgct tgccccgcta    120 cgacgccctc cacgcaccct ggacgcccgc atcgcccgcc tggcccagta ccgcgctctg    180

```
ctccagggcg ccccgacgc ggtggagctt cgagaacttt ctccctgggc tgcccgcatc      240
ccgggaccgc gccgtcgagc gggtccccgg cgtcggcggg cgcgg                     285

<210> SEQ ID NO 27
<211> LENGTH: 169
<212> TYPE: DNA
<213> ORGANISM: Mus musculus

<400> SEQUENCE: 27
atgcagcgct ggaaggcggc ggccttggcc tcagtgctct gcagctccgt gctgtccatc      60
tggatgtgtc gagagggcct gcttctcagc caccgcctcg gacctgcgct ggtcccctg      120 caccgcctgc ctcgaaccct ggacgcccgg attgcccgcc tggcccagt                 169

<210> SEQ ID NO 28
<211> LENGTH: 425
<212> TYPE: DNA
<213> ORGANISM: Mus musculus

<400> SEQUENCE: 28
accgtgcact cctgcagggg gccccggatg cgatggagct gcgcgagctg acgccctggg      60
ctgggcggcc cccaggtccg cgccgtcggg cggggccccg gcggcggcgc gcgcgtgcgc     120 ggttggggc gcggccttgc gggctgcgcg agctggaggt gcgcgtgagc gagctgggcc     180
tgggctacgc gtccgacgag acggtgctgt ccgctactg cgcaggcgcc tgcgaggctg     240
ccgcgcgcgt ctacgacctc gggctgcgac gactgcgcca ggcggcgc ctgcggcggg      300 agcgggtgcg cgcgcagccc tgctgccgcc cgacggccta cgaggacgag gtgtccttcc     360
tggacgcgca cagccgctac cacacggtgc acgagctgtc ggcgcgcgag tgcgcctgcg     420
tgtga                                                                 425

<210> SEQ ID NO 29
<211> LENGTH: 169
<212> TYPE: DNA
<213> ORGANISM: Mus musculus

<400> SEQUENCE: 29
atgaggcgct ggaaggcagc ggccctggtg tcgctcatct gcagctccct gctatctgtc      60
tggatgtgcc aggagggtct gctcttgggc caccgcctgg acccgcgct tgccccgcta     120 cgacgccctc cacgcaccct ggacgcccgc atcgcccgcc tggcccagt                 169

<210> SEQ ID NO 30
<211> LENGTH: 419
<212> TYPE: DNA
<213> ORGANISM: Mus musculus

<400> SEQUENCE: 30
atcgcgctct gctccagggc gccccgacg cggtggagct tcgagaactt tctccctggg       60
ctgcccgcat cccgggaccg cgccgtcgag cgggtccccg gcgtcggcgg gcgcggccgg     120
gggctcggcc ttgtgggctg cgcgagctcg aggtgcgcgt gagcgagctg ggcctgggct     180
acacgtcgga tgagaccgtg ctgttccgct actgcgcagg cgcgtgcgag gcggccatcc     240
gcatctacga cctgggcctt cggcgcctgc gccagcggag gcgcgtgcgc agagagcggg     300
cgcgggcgca cccgtgttgt cgcccgacgg cctatgagga cgaggtgtcc ttcctggacg     360
tgcacagccg ctaccacacg ctgcaagagc tgtcggcgcg ggagtgcgcg tgcgtgtga     419
```

```
<210> SEQ ID NO 31
<211> LENGTH: 94
<212> TYPE: PRT
<213> ORGANISM: Homo sapiens

<400> SEQUENCE: 31

Cys Gly Leu Arg Glu Leu Glu Val Arg Val Ser Glu Leu Gly Leu Gly
 1               5                   10                  15

Tyr Ala Ser Asp Glu Thr Val Leu Phe Arg Tyr Cys Ala Gly Ala Cys
            20                  25                  30

Glu Ala Ala Ala Arg Val Tyr Asp Leu Gly Leu Arg Arg Leu Arg Gln
        35                  40                  45

Arg Arg Arg Leu Arg Arg Glu Arg Val Arg Ala Gln Pro Cys Cys Arg
    50                  55                  60

Pro Thr Ala Tyr Glu Asp Glu Val Ser Phe Leu Asp Ala His Ser Arg
65                  70                  75                  80

Tyr His Thr Val His Glu Leu Ser Ala Arg Glu Cys Ala Cys
                85                  90

<210> SEQ ID NO 32
<211> LENGTH: 94
<212> TYPE: PRT
<213> ORGANISM: Mus musculus

<400> SEQUENCE: 32

Cys Gly Leu Arg Glu Leu Glu Val Arg Val Ser Glu Leu Gly Leu Gly
 1               5                   10                  15

Tyr Thr Ser Asp Glu Thr Val Leu Phe Arg Tyr Cys Ala Gly Ala Cys
            20                  25                  30

Glu Ala Ala Ile Arg Ile Tyr Asp Leu Gly Leu Arg Arg Leu Arg Gln
        35                  40                  45

Arg Arg Arg Val Arg Arg Glu Arg Ala Arg Ala His Pro Cys Cys Arg
    50                  55                  60

Pro Thr Ala Tyr Glu Asp Glu Val Ser Phe Leu Asp Val His Ser Arg
65                  70                  75                  80

Tyr His Thr Leu Gln Glu Leu Ser Ala Arg Glu Cys Ala Cys
                85                  90

<210> SEQ ID NO 33
<211> LENGTH: 8
<212> TYPE: PRT
<213> ORGANISM: Mus musculus
<220> FEATURE:
<221> NAME/KEY: PRT
<222> LOCATION: (2)
<223> OTHER INFORMATION: Serine or Threonine
<220> FEATURE:
<221> NAME/KEY: PRT
<222> LOCATION: (3)
<223> OTHER INFORMATION: Glutamic Acid or Aspartic Acid

<400> SEQUENCE: 33

Val Xaa Xaa Leu Gly Leu Gly Tyr
 1               5

<210> SEQ ID NO 34
<211> LENGTH: 15
<212> TYPE: PRT
<213> ORGANISM: Mus musculus
<220> FEATURE:
<221> NAME/KEY: PRT
<222> LOCATION: (2)
<223> OTHER INFORMATION: Threonine or Glutamic Acid
```

-continued

```
<220> FEATURE:
<221> NAME/KEY: PRT
<222> LOCATION: (3)
<223> OTHER INFORMATION: Valine or Leucine
<220> FEATURE:
<221> NAME/KEY: PRT
<222> LOCATION: (4)
<223> OTHER INFORMATION: Leucine or Isoleucine
<220> FEATURE:
<221> NAME/KEY: PRT
<222> LOCATION: (9)
<223> OTHER INFORMATION: Alanine or Serine
<220> FEATURE:
<221> NAME/KEY: PRT
<222> LOCATION: (11)
<223> OTHER INFORMATION: Alanine or Serine
<220> FEATURE:
<221> NAME/KEY: PRT
<222> LOCATION: (13)
<223> OTHER INFORMATION: Glutamic Acid or Aspartic Acid
<220> FEATURE:
<221> NAME/KEY: PRT
<222> LOCATION: (14)
<223> OTHER INFORMATION: Alanine or Serine

<400> SEQUENCE: 34

Glu Xaa Xaa Xaa Phe Arg Tyr Cys Xaa Gly Xaa Cys Xaa Xaa Ala
 1               5                  10                  15

<210> SEQ ID NO 35
<211> LENGTH: 15
<212> TYPE: PRT
<213> ORGANISM: Mus musculus
<220> FEATURE:
<221> NAME/KEY: PRT
<222> LOCATION: (5)
<223> OTHER INFORMATION: Threonine or Valine or Isoleucine
<220> FEATURE:
<221> NAME/KEY: PRT
<222> LOCATION: (7)
<223> OTHER INFORMATION: Tyrosine or Phenylalanine
<220> FEATURE:
<221> NAME/KEY: PRT
<222> LOCATION: (8)
<223> OTHER INFORMATION: Glutamic Acid or Aspartic Acid
<220> FEATURE:
<221> NAME/KEY: PRT
<222> LOCATION: (10)
<223> OTHER INFORMATION: Glutamic Acid or Aspartic Acid
<220> FEATURE:
<221> NAME/KEY: PRT
<222> LOCATION: (11)
<223> OTHER INFORMATION: Valine or Leucine

<400> SEQUENCE: 35

Cys Cys Arg Pro Xaa Ala Xaa Xaa Asp Xaa Xaa Ser Phe Leu Asp
 1               5                  10                  15

<210> SEQ ID NO 36
<211> LENGTH: 11
<212> TYPE: PRT
<213> ORGANISM: Mus musculus
<220> FEATURE:
<221> NAME/KEY: PRT
<222> LOCATION: (5)
<223> OTHER INFORMATION: Alanine or Serine
<220> FEATURE:
<221> NAME/KEY: PRT
<222> LOCATION: (7)
<223> OTHER INFORMATION: Alanine or Serine
<220> FEATURE:
<221> NAME/KEY: PRT
<222> LOCATION: (9)
<223> OTHER INFORMATION: Glutamic Acid or Aspartic Acid
```

```
<220> FEATURE:
<221> NAME/KEY: PRT
<222> LOCATION: (10)
<223> OTHER INFORMATION: Serine or Alanine

<400> SEQUENCE: 36

Phe Arg Tyr Cys Xaa Gly Xaa Cys Xaa Xaa Ala
 1               5                  10

<210> SEQ ID NO 37
<211> LENGTH: 11
<212> TYPE: PRT
<213> ORGANISM: Mus musculus
<220> FEATURE:
<221> NAME/KEY: PRT
<222> LOCATION: (5)
<223> OTHER INFORMATION: Alanine or Serine
<220> FEATURE:
<221> NAME/KEY: PRT
<222> LOCATION: (7)
<223> OTHER INFORMATION: Alanine or Serine
<220> FEATURE:
<221> NAME/KEY: PRT
<222> LOCATION: (9)
<223> OTHER INFORMATION: Glutamic Acid or Aspartic Acid
<220> FEATURE:
<221> NAME/KEY: PRT
<222> LOCATION: (10)
<223> OTHER INFORMATION: Serine or Alanine

<400> SEQUENCE: 37

Phe Arg Tyr Cys Xaa Gly Xaa Cys Xaa Xaa Ala
 1               5                  10

<210> SEQ ID NO 38
<211> LENGTH: 10
<212> TYPE: PRT
<213> ORGANISM: Mus musculus
<220> FEATURE:
<221> NAME/KEY: PRT
<222> LOCATION: (5)
<223> OTHER INFORMATION: Isoleucine or Threonine or Valine
<220> FEATURE:
<221> NAME/KEY: PRT
<222> LOCATION: (7)
<223> OTHER INFORMATION: Tyrosine or Phenylalanine
<220> FEATURE:
<221> NAME/KEY: PRT
<222> LOCATION: (8)
<223> OTHER INFORMATION: Glutamic Acid or Aspartic Acid
<220> FEATURE:
<221> NAME/KEY: PRT
<222> LOCATION: (10)
<223> OTHER INFORMATION: Glutamic Acid or Aspartic Acid

<400> SEQUENCE: 38

Cys Cys Arg Pro Xaa Ala Xaa Xaa Asp Xaa
 1               5                  10

<210> SEQ ID NO 39
<211> LENGTH: 10
<212> TYPE: PRT
<213> ORGANISM: Mus musculus
<220> FEATURE:
<221> NAME/KEY: PRT
<222> LOCATION: (2)
<223> OTHER INFORMATION: Tyrosine or Phenylalanine
<220> FEATURE:
<221> NAME/KEY: PRT
<222> LOCATION: (3)
<223> OTHER INFORMATION: Glutamic Acid or Aspartic Acid
```

<220> FEATURE:
<221> NAME/KEY: PRT
<222> LOCATION: (5)
<223> OTHER INFORMATION: Glutamic Acid or Aspartic Acid
<220> FEATURE:
<221> NAME/KEY: PRT
<222> LOCATION: (6)
<223> OTHER INFORMATION: Valine or Leucine

<400> SEQUENCE: 39

Ala Xaa Xaa Asp Xaa Xaa Ser Phe Leu Asp
 1               5                  10

<210> SEQ ID NO 40
<211> LENGTH: 8
<212> TYPE: PRT
<213> ORGANISM: Mus musculus
<220> FEATURE:
<221> NAME/KEY: PRT
<222> LOCATION: (2)
<223> OTHER INFORMATION: Glutamic acid or Threonine
<220> FEATURE:
<221> NAME/KEY: PRT
<222> LOCATION: (3)
<223> OTHER INFORMATION: Leucine or Valine
<220> FEATURE:
<221> NAME/KEY: PRT
<222> LOCATION: (4)
<223> OTHER INFORMATION: Isoleucine or Leucine

<400> SEQUENCE: 40

Glu Xaa Xaa Xaa Phe Arg Tyr Cys
 1               5

<210> SEQ ID NO 41
<211> LENGTH: 13
<212> TYPE: PRT
<213> ORGANISM: Mus musculus
<220> FEATURE:
<221> NAME/KEY: PRT
<222> LOCATION: (2)
<223> OTHER INFORMATION: Glutamic Acid or Threonine
<220> FEATURE:
<221> NAME/KEY: PRT
<222> LOCATION: (3)
<223> OTHER INFORMATION: Leucine or Valine
<220> FEATURE:
<221> NAME/KEY: PRT
<222> LOCATION: (4)
<223> OTHER INFORMATION: Isoleucine or Leucine
<220> FEATURE:
<221> NAME/KEY: PRT
<222> LOCATION: (9)
<223> OTHER INFORMATION: Serine or Alanine
<220> FEATURE:
<221> NAME/KEY: PRT
<222> LOCATION: (11)
<223> OTHER INFORMATION: Serine or Alanine
<220> FEATURE:
<221> NAME/KEY: PRT
<222> LOCATION: (13)
<223> OTHER INFORMATION: Glutamic Acid or Aspartic Acid

<400> SEQUENCE: 41

Glu Xaa Xaa Xaa Phe Arg Tyr Cys Xaa Gly Xaa Cys Xaa
 1               5                  10

<210> SEQ ID NO 42
<211> LENGTH: 23
<212> TYPE: DNA
<213> ORGANISM: Mus musculus

```
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: w = a or t
<220> FEATURE:
<221> NAME/KEY: misc_feature
<222> LOCATION: (5)
<223> OTHER INFORMATION: s = g or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: y = t or c
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (16)
<223> OTHER INFORMATION: y = t or c
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (21)
<223> OTHER INFORMATION: n = a, t, c or g

<400> SEQUENCE: 42
gtnwsngany tnggnytngg nta                                              23

<210> SEQ ID NO 43
<211> LENGTH: 32
<212> TYPE: DNA
<213> ORGANISM: Homo sapiens
<220> FEATURE:
<221> NAME/KEY: misc_feature
<222> LOCATION: (3)
<223> OTHER INFORMATION: y = t or c
<220> FEATURE:
<221> NAME/KEY: misc_feature
<222> LOCATION: (4)
<223> OTHER INFORMATION: m = a or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: y = t or c
<220> FEATURE:
<221> NAME/KEY: misc_feature
<222> LOCATION: (12)
<223> OTHER INFORMATION: y = t or c
<220> FEATURE:
<221> NAME/KEY: misc_feature
<222> LOCATION: (13)
<223> OTHER INFORMATION: d = g, a, or t
```

```
<220> FEATURE:
<221> NAME/KEY: misc_feature
<222> LOCATION: (14)
<223> OTHER INFORMATION: s = g or c
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (19)
<223> OTHER INFORMATION: d = g, a, or t
<220> FEATURE:
<221> NAME/KEY: misc_feature
<222> LOCATION: (20)
<223> OTHER INFORMATION: s = g or c
<220> FEATURE:
<221> NAME/KEY: misc_feature
<222> LOCATION: (21)
<223> OTHER INFORMATION: n = a, t, c or g
<220> FEATURE:
<221> NAME/KEY: misc_feature
<222> LOCATION: (24)
<223> OTHER INFORMATION: y = t or c
<220> FEATURE:
<221> NAME/KEY: misc_feature
<222> LOCATION: (27)
<223> OTHER INFORMATION: n = a, t, c or g
<220> FEATURE:
<221> NAME/KEY: misc_feature
<222> LOCATION: (28)
<223> OTHER INFORMATION: k = g or t
<220> FEATURE:
<221> NAME/KEY: misc_feature
<222> LOCATION: (30)
<223> OTHER INFORMATION: n = a, t, c or g

<400> SEQUENCE: 43
ttymgntayt gydsnggnds ntgygankcn gc                                    32

<210> SEQ ID NO 44
<211> LENGTH: 32
<212> TYPE: DNA
<213> ORGANISM: Homo sapiens
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (5)
<223> OTHER INFORMATION: m = a or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: r = g or a
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (13)
<223> OTHER INFORMATION: s = g or c
<220> FEATURE:
<221> NAME/KEY: misc_feature
<222> LOCATION: (14)
<223> OTHER INFORMATION: h = a, c or t
```

```
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (19)
<223> OTHER INFORMATION: s = g or c
<220> FEATURE:
<221> NAME/KEY: misc_feature
<222> LOCATION: (20)
<223> OTHER INFORMATION: h = a, c or t
<220> FEATURE:
<221> NAME/KEY: misc_feature
<222> LOCATION: (21)
<223> OTHER INFORMATION: r = g or a
<220> FEATURE:
<221> NAME/KEY: misc_feature
<222> LOCATION: (24)
<223> OTHER INFORMATION: r = g or a
<220> FEATURE:
<221> NAME/KEY: misc_feature
<222> LOCATION: (27)
<223> OTHER INFORMATION: n = a, t, c or g
<220> FEATURE:
<221> NAME/KEY: misc_feature
<222> LOCATION: (29)
<223> OTHER INFORMATION: k = g or t
<220> FEATURE:
<221> NAME/KEY: misc_feature
<222> LOCATION: (30)
<223> OTHER INFORMATION: r = g or a

<400> SEQUENCE: 44
gcngmntcrc anshnccnsh rcartanckr aa                                32

<210> SEQ ID NO 45
<211> LENGTH: 29
<212> TYPE: DNA
<213> ORGANISM: Homo sapiens
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (21)
<223> OTHER INFORMATION: n = a, t, c or g

<400> SEQUENCE: 45
tcrtcntcrw angcnryngg nckrcarca                                    29

<210> SEQ ID NO 46
<211> LENGTH: 29
<212> TYPE: DNA
<213> ORGANISM: Mus musculus
```

```
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (5)
<223> OTHER INFORMATION: r = a or g
<220> FEATURE:
<221> NAME/KEY: misc_feature
<222> LOCATION: (6)
<223> OTHER INFORMATION: r = a or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: s = c or g
<220> FEATURE:
<221> NAME/KEY: misc_feature
<222> LOCATION: (11)
<223> OTHER INFORMATION: w = a or t
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (14)
<223> OTHER INFORMATION: v = a, c or g
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: r = a or g
<220> FEATURE:
<221> NAME/KEY: misc_feature
<222> LOCATION: (21)
<223> OTHER INFORMATION: n = a, t, c or g
<220> FEATURE:
<221> NAME/KEY: misc_feature
<222> LOCATION: (24)
<223> OTHER INFORMATION: r = a or g
<220> FEATURE:
<221> NAME/KEY: misc_feature
<222> LOCATION: (25)
<223> OTHER INFORMATION: w = a or t
<220> FEATURE:
<221> NAME/KEY: misc_feature
<222> LOCATION: (27)
<223> OTHER INFORMATION: n = a, t, c or g

<400> SEQUENCE: 46
tcnarraans wnavntcrtc ntcrwangc                                29

<210> SEQ ID NO 47
<211> LENGTH: 23
<212> TYPE: DNA
<213> ORGANISM: Mus musculus
<220> FEATURE:
<221> NAME/KEY: misc_feature
<222> LOCATION: (3)
<223> OTHER INFORMATION: r = a or g
<220> FEATURE:
<221> NAME/KEY: misc_feature
<222> LOCATION: (4)
<223> OTHER INFORMATION: r = a or g
<220> FEATURE:
<221> NAME/KEY: misc_feature
<222> LOCATION: (5)
<223> OTHER INFORMATION: m = a or c
```

```
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (7)
<223> OTHER INFORMATION: b = t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: h = a, t, or c
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (15)
<223> OTHER INFORMATION: y = t or c
<220> FEATURE:
<221> NAME/KEY: misc_feature
<222> LOCATION: (16)
<223> OTHER INFORMATION: m = a or c
<220> FEATURE:
<221> NAME/KEY: misc_feature
<222> LOCATION: (21)
<223> OTHER INFORMATION: y = t or c

<400> SEQUENCE: 47
garrmnbtnh tnttymgnta ytg                                              23

<210> SEQ ID NO 48
<211> LENGTH: 38
<212> TYPE: DNA
<213> ORGANISM: Mus musculus
<220> FEATURE:
<221> NAME/KEY: misc_feature
<222> LOCATION: (3)
<223> OTHER INFORMATION: r = a or g
<220> FEATURE:
<221> NAME/KEY: misc_feature
<222> LOCATION: (4)
<223> OTHER INFORMATION: r = a or g
<220> FEATURE:
<221> NAME/KEY: misc_feature
<222> LOCATION: (5)
<223> OTHER INFORMATION: m = a or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (7)
<223> OTHER INFORMATION: b = t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: h = a, t, or c
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (15)
<223> OTHER INFORMATION: y = t or c
```

```
<220> FEATURE:
<221> NAME/KEY: misc_feature
<222> LOCATION: (16)
<223> OTHER INFORMATION: m = a or c
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (21)
<223> OTHER INFORMATION: y = t or c
<220> FEATURE:
<221> NAME/KEY: misc_feature
<222> LOCATION: (24)
<223> OTHER INFORMATION: y = t or c
<220> FEATURE:
<221> NAME/KEY: misc_feature
<222> LOCATION: (25)
<223> OTHER INFORMATION: d = a, t, or g
<220> FEATURE:
<221> NAME/KEY: misc_feature
<222> LOCATION: (26)
<223> OTHER INFORMATION: s = c or g
<220> FEATURE:
<221> NAME/KEY: misc_feature
<222> LOCATION: (27)
<223> OTHER INFORMATION: n = a, t, c or g
<220> FEATURE:
<221> NAME/KEY: misc_feature
<222> LOCATION: (30)
<223> OTHER INFORMATION: n = a, t, c or g
<220> FEATURE:
<221> NAME/KEY: misc_feature
<222> LOCATION: (31)
<223> OTHER INFORMATION: d = a, t, or g
<220> FEATURE:
<221> NAME/KEY: misc_feature
<222> LOCATION: (32)
<223> OTHER INFORMATION: s = c or g
<220> FEATURE:
<221> NAME/KEY: misc_feature
<222> LOCATION: (33)
<223> OTHER INFORMATION: n = a, t, c or g
<220> FEATURE:
<221> NAME/KEY: misc_feature
<222> LOCATION: (36)
<223> OTHER INFORMATION: h = a, t or c

<400> SEQUENCE: 48
garrmnbtnh tnttymgnta ytgydsnggn dsntghga                            38

<210> SEQ ID NO 49
<211> LENGTH: 93
<212> TYPE: PRT
<213> ORGANISM: Mus musculus

<400> SEQUENCE: 49

Cys Val Leu Thr Ala Ile His Leu Asn Val Thr Asp Leu Gly Leu Gly
 1               5                  10                  15

Tyr Glu Thr Lys Glu Glu Leu Ile Phe Arg Tyr Cys Ser Gly Ser Cys
                20                  25                  30

Asp Ala Ala Glu Thr Thr Tyr Asp Lys Ile Leu Lys Asn Leu Ser Arg
            35                  40                  45

Asn Arg Arg Leu Val Ser Asp Lys Val Gly Gln Ala Cys Cys Arg Pro
        50                  55                  60

Ile Ala Phe Asp Asp Asp Leu Ser Phe Leu Asp Asn Leu Val Tyr
 65                  70                  75                  80

His Ile Leu Arg Lys His Ser Ala Lys Arg Cys Gly Cys
                85                  90
```

```
<210> SEQ ID NO 50
<211> LENGTH: 17
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (12)
<223> OTHER INFORMATION: y = t or c
<220> FEATURE:
<221> NAME/KEY: misc_feature
<222> LOCATION: (15)
<223> OTHER INFORMATION: r = a or g

<400> SEQUENCE: 50
ccnacngcnt aygarga                                               17

<210> SEQ ID NO 51
<211> LENGTH:
<212> TYPE:
<213> ORGANISM:

<400> SEQUENCE: 51

000

<210> SEQ ID NO 52
<211> LENGTH: 20
<212> TYPE: DNA
<213> ORGANISM: Mus musculus
<220> FEATURE:
<221> NAME/KEY: misc_feature
<222> LOCATION: (2)
<223> OTHER INFORMATION: r = a or g
<220> FEATURE:
<221> NAME/KEY: misc_feature
<222> LOCATION: (3)
<223> OTHER INFORMATION: y = t or c
<220> FEATURE:
<221> NAME/KEY: misc_feature
<222> LOCATION: (6)
<223> OTHER INFORMATION: y = t or c
<220> FEATURE:
<221> NAME/KEY: misc_feature
<222> LOCATION: (12)
<223> OTHER INFORMATION: y = t or c
<220> FEATURE:
<221> NAME/KEY: misc_feature
<222> LOCATION: (15)
<223> OTHER INFORMATION: r = a or g

<400> SEQUENCE: 52
arytcytgna rngtrtgrta                                            20

<210> SEQ ID NO 53
<211> LENGTH: 28
<212> TYPE: DNA
<213> ORGANISM: Rattus norvegicus

<400> SEQUENCE: 53
gacgaggtgt ccttcctgga cgtacaca                                   28
```

```
<210> SEQ ID NO 54
<211> LENGTH: 34
<212> TYPE: DNA
<213> ORGANISM: Mus musculus

<400> SEQUENCE: 54
tagcggctgt gtacgtccag gaaggacacc tcgt                                    34

<210> SEQ ID NO 55
<211> LENGTH: 26
<212> TYPE: DNA
<213> ORGANISM: Mus musculus

<400> SEQUENCE: 55
cagcgacgac gcgtgcgcaa agagcg                                             26

<210> SEQ ID NO 56
<211> LENGTH: 47
<212> TYPE: DNA
<213> ORGANISM: Mus musculus
<220> FEATURE:
<221> NAME/KEY: misc_feature
<222> LOCATION: (3)
<223> OTHER INFORMATION: y = t or c
<220> FEATURE:
<221> NAME/KEY: misc_feature
<222> LOCATION: (6)
<223> OTHER INFORMATION: r = a or g
<220> FEATURE:
<221> NAME/KEY: misc_feature
<222> LOCATION: (42)
<223> OTHER INFORMATION: y = t or c
<220> FEATURE:
<221> NAME/KEY: misc_feature
<222> LOCATION: (45)
<223> OTHER INFORMATION: y = t or c

<400> SEQUENCE: 56
taygargacg aggtgtcctt cctggacgta cacagccgct aycayac                      47

<210> SEQ ID NO 57
<211> LENGTH: 26
<212> TYPE: DNA
<213> ORGANISM: Mus musculus

<400> SEQUENCE: 57
gcggccatcc gcatctacga cctggg                                             26

<210> SEQ ID NO 58
<211> LENGTH: 27
<212> TYPE: DNA
<213> ORGANISM: Mus musculus
<220> FEATURE:
<221> NAME/KEY: misc_feature
<222> LOCATION: (2)
<223> OTHER INFORMATION: r = a or g
<220> FEATURE:
<221> NAME/KEY: misc_feature
<222> LOCATION: (17)
<223> OTHER INFORMATION: r = a or g
<220> FEATURE:
<221> NAME/KEY: misc_feature
<222> LOCATION: (20)
<223> OTHER INFORMATION: r = a or g

<400> SEQUENCE: 58
crtaggccgt cgggcgrcar cacgggt                                            27
```

```
<210> SEQ ID NO 59
<211> LENGTH: 27
<212> TYPE: DNA
<213> ORGANISM: Mus musculus

<400> SEQUENCE: 59
gcgccgaagg cccaggtcgt agatgcg                                              27

<210> SEQ ID NO 60
<211> LENGTH: 29
<212> TYPE: DNA
<213> ORGANISM: Homo sapiens
<220> FEATURE:
<221> NAME/KEY: misc_feature
<222> LOCATION: (24)
<223> OTHER INFORMATION: r = a or g

<400> SEQUENCE: 60
cgctactgcg caggcgcgtg cgargcggc                                            29

<210> SEQ ID NO 61
<211> LENGTH: 27
<212> TYPE: DNA
<213> ORGANISM: Homo sapiens
<220> FEATURE:
<221> NAME/KEY: misc_feature
<222> LOCATION: (22)
<223> OTHER INFORMATION: r = a or g

<400> SEQUENCE: 61
cgccgacagc tcttgcagcg trtggta                                              27

<210> SEQ ID NO 62
<211> LENGTH: 30
<212> TYPE: DNA
<213> ORGANISM: Homo sapiens

<400> SEQUENCE: 62
gagctgggcc tgggctacgc gtccgacgag                                           30

<210> SEQ ID NO 63
<211> LENGTH: 39
<212> TYPE: DNA
<213> ORGANISM: Mus musculus

<400> SEQUENCE: 63
gcgacgcgta ccatgaggcg ctggaaggca gcggccctg                                 39

<210> SEQ ID NO 64
<211> LENGTH: 30
<212> TYPE: DNA
<213> ORGANISM: Mus musculus

<400> SEQUENCE: 64
gacggatccg catcacacgc acgcgcactc                                           30

<210> SEQ ID NO 65
<211> LENGTH: 29
<212> TYPE: DNA
<213> ORGANISM: Mus musculus

<400> SEQUENCE: 65
gaccatatgc cggggctcg gccttgtgg                                             29
```

```
<210> SEQ ID NO 66
<211> LENGTH: 30
<212> TYPE: DNA
<213> ORGANISM: Mus musculus

<400> SEQUENCE: 66
gacggatccg catcacacgc acgcgcactc                                30

<210> SEQ ID NO 67
<211> LENGTH: 26
<212> TYPE: DNA
<213> ORGANISM: Mus musculus

<400> SEQUENCE: 67
cagcgacgac gcgtgcgcaa agagcg                                    26

<210> SEQ ID NO 68
<211> LENGTH: 34
<212> TYPE: DNA
<213> ORGANISM: Mus musculus

<400> SEQUENCE: 68
tagcggctgt gtacgtccag gaaggacacc tcgt                           34

<210> SEQ ID NO 69
<211> LENGTH: 21
<212> TYPE: DNA
<213> ORGANISM: Mus musculus
<220> FEATURE:
<221> NAME/KEY: misc_feature
<222> LOCATION: (15)
<223> OTHER INFORMATION: y = c or t

<400> SEQUENCE: 69
aaaaatcggg ggtgygtctt a                                         21

<210> SEQ ID NO 70
<211> LENGTH: 21
<212> TYPE: DNA
<213> ORGANISM: Mus musculus
<220> FEATURE:
<221> NAME/KEY: misc_feature
<222> LOCATION: (15)
<223> OTHER INFORMATION: y = c or t

<400> SEQUENCE: 70
catgcctggc ctacyttgtc a                                         21

<210> SEQ ID NO 71
<211> LENGTH: 24
<212> TYPE: DNA
<213> ORGANISM: Homo sapiens
<220> FEATURE:
<221> NAME/KEY: misc_feature
<222> LOCATION: (12)
<223> OTHER INFORMATION: m = a or c

<400> SEQUENCE: 71
ctggcgtccc amcaagggtc ttcg                                      24

<210> SEQ ID NO 72
<211> LENGTH: 23
<212> TYPE: DNA
<213> ORGANISM: Homo sapiens
```

```
<400> SEQUENCE: 72
gccagtggtg ccgtcgaggc ggg                                          23

<210> SEQ ID NO 73
<211> LENGTH: 24
<212> TYPE: DNA
<213> ORGANISM: Mus musculus

<400> SEQUENCE: 73
ggcccaggat gaggcgctgg aagg                                         24

<210> SEQ ID NO 74
<211> LENGTH: 27
<212> TYPE: DNA
<213> ORGANISM: Homo sapiens
<220> FEATURE:
<221> NAME/KEY: misc_feature
<222> LOCATION: (17)
<223> OTHER INFORMATION: w = a or t
<220> FEATURE:
<221> NAME/KEY: misc_feature
<222> LOCATION: (22)
<223> OTHER INFORMATION: w = a or t

<400> SEQUENCE: 74
ccactccact gcctgawatt cwacccc                                      27

<210> SEQ ID NO 75
<211> LENGTH: 24
<212> TYPE: DNA
<213> ORGANISM: Homo sapiens

<400> SEQUENCE: 75
ccatgtgatt atcgaccatt cggc                                         24

<210> SEQ ID NO 76
<211> LENGTH: 134
<212> TYPE: PRT
<213> ORGANISM: Homo sapiens

<400> SEQUENCE: 76
```

Ser Pro Asp Lys Gln Met Ala Val Leu Pro Arg Arg Glu Arg Asn Arg
 1               5                  10                  15

Gln Ala Ala Ala Asn Pro Glu Asn Ser Arg Gly Lys Gly Arg Arg
             20                  25                  30

Gly Gln Arg Gly Lys Asn Arg Gly Cys Val Leu Thr Ala Ile His Leu
         35                  40                  45

Asn Val Thr Asp Leu Gly Leu Gly Tyr Glu Thr Lys Glu Glu Leu Ile
     50                  55                  60

Phe Arg Tyr Cys Ser Gly Ser Cys Asp Ala Ala Glu Thr Thr Tyr Asp
 65                  70                  75                  80

Lys Ile Leu Lys Asn Leu Ser Arg Asn Arg Arg Leu Val Ser Asp Lys
                 85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
    130

```
<210> SEQ ID NO 77
<211> LENGTH: 134
<212> TYPE: PRT
<213> ORGANISM: Mus musculus

<400> SEQUENCE: 77

Ser Pro Asp Lys Gln Ala Ala Ala Leu Pro Arg Arg Glu Arg Asn Arg
 1               5                   10                  15

Gln Ala Ala Ala Ser Pro Glu Asn Ser Arg Gly Lys Gly Arg Arg
             20                  25                  30

Gly Gln Arg Gly Lys Asn Arg Gly Cys Val Leu Thr Ala Ile His Leu
         35                  40                  45

Asn Val Thr Asp Leu Gly Leu Gly Tyr Glu Thr Lys Glu Glu Leu Ile
     50                  55                  60

Phe Arg Tyr Cys Ser Gly Ser Cys Glu Ser Ala Glu Thr Met Tyr Asp
 65                  70                  75                  80

Lys Ile Leu Lys Asn Leu Ser Arg Ser Arg Arg Leu Thr Ser Asp Lys
                 85                  90                  95

Val Gly Gln Ala Cys Cys Arg Pro Val Ala Phe Asp Asp Leu Ser
             100                 105                 110

Phe Leu Asp Asp Asn Leu Val Tyr His Ile Leu Arg Lys His Ser Ala
             115                 120                 125

Lys Arg Cys Gly Cys Ile
             130

<210> SEQ ID NO 78
<211> LENGTH: 134
<212> TYPE: PRT
<213> ORGANISM: Mus musculus

<400> SEQUENCE: 78

Ser Pro Asp Lys Gln Ala Ala Ala Leu Pro Arg Arg Glu Arg Asn Arg
 1               5                   10                  15

Gln Ala Ala Ala Ser Pro Glu Asn Ser Arg Gly Lys Gly Arg Arg
             20                  25                  30

Gly Gln Arg Gly Lys Asn Arg Gly Cys Val Leu Thr Ala Ile His Leu
         35                  40                  45

Asn Val Thr Asp Leu Gly Leu Gly Tyr Glu Thr Lys Glu Glu Leu Ile
     50                  55                  60

Phe Arg Tyr Cys Ser Gly Ser Cys Glu Ala Ala Glu Thr Met Tyr Asp
 65                  70                  75                  80

Lys Ile Leu Lys Asn Leu Ser Arg Ser Arg Arg Leu Thr Ser Asp Lys
                 85                  90                  95

Val Gly Gln Ala Cys Cys Arg Pro Val Ala Phe Asp Asp Leu Ser
             100                 105                 110

Phe Leu Asp Asp Ser Leu Val Tyr His Ile Leu Arg Lys His Ser Ala
             115                 120                 125

Lys Arg Cys Gly Cys Ile
             130

<210> SEQ ID NO 79
<211> LENGTH: 89
<212> TYPE: PRT
<213> ORGANISM: Mus musculus
```

```
<400> SEQUENCE: 79

Cys Arg Leu Trp Ser Leu Thr Leu Pro Val Ala Glu Leu Gly Leu Gly
1               5                   10                  15

Tyr Ala Ser Glu Glu Lys Val Ile Phe Arg Tyr Cys Ala Gly Ser Cys
            20                  25                  30

Pro Gln Glu Ala Arg Thr Gln His Ser Leu Val Leu Ala Arg Leu Arg
        35                  40                  45

Gly Arg Gly Arg Ala His Gly Arg Pro Cys Cys Gln Pro Thr Ser Tyr
    50                  55                  60

Ala Asp Val Thr Phe Leu Asp Asp Gln His His Trp Gln Gln Leu Pro
65                  70                  75                  80

Gln Leu Ser Ala Ala Ala Cys Gly Cys
                85

<210> SEQ ID NO 80
<211> LENGTH: 96
<212> TYPE: PRT
<213> ORGANISM: Mus musculus

<400> SEQUENCE: 80

Ala Leu Ala Gly Ser Cys Arg Leu Trp Ser Leu Thr Leu Pro Val Ala
1               5                   10                  15

Glu Leu Gly Leu Gly Tyr Ala Ser Glu Glu Lys Val Ile Phe Arg Tyr
            20                  25                  30

Cys Ala Gly Ser Cys Pro Gln Glu Ala Arg Thr Gln His Ser Leu Val
        35                  40                  45

Leu Ala Arg Leu Arg Gly Arg Gly Arg Ala His Gly Arg Pro Cys Cys
    50                  55                  60

Gln Pro Thr Ser Tyr Ala Asp Val Thr Phe Leu Asp Asp Gln His His
65                  70                  75                  80

Trp Gln Gln Leu Pro Gln Leu Ser Ala Ala Ala Cys Gly Cys Gly Gly
                85                  90                  95

<210> SEQ ID NO 81
<211> LENGTH: 134
<212> TYPE: PRT
<213> ORGANISM: Mus musculus

<400> SEQUENCE: 81

Val Arg Ile Pro Gly Gly Leu Pro Thr Pro Gln Phe Leu Leu Ser Lys
1               5                   10                  15

Pro Ser Leu Cys Leu Thr Ile Leu Leu Tyr Leu Ala Leu Gly Asn Asn
            20                  25                  30

His Val Arg Leu Pro Arg Ala Leu Ala Gly Ser Cys Arg Leu Trp Ser
        35                  40                  45

Leu Thr Leu Pro Val Ala Glu Leu Gly Leu Gly Tyr Ala Ser Glu Glu
    50                  55                  60

Lys Val Ile Phe Arg Tyr Cys Ala Gly Ser Cys Pro Gln Glu Ala Arg
65                  70                  75                  80

Thr Gln His Ser Leu Val Leu Ala Arg Leu Arg Gly Arg Gly Arg Ala
                85                  90                  95

His Gly Arg Pro Cys Cys Gln Pro Thr Ser Tyr Ala Asp Val Thr Phe
            100                 105                 110
```

```
Leu Asp Asp Gln His His Trp Gln Gln Leu Pro Gln Leu Ser Ala Ala
        115                 120                 125

Ala Cys Gly Cys Gly Gly
    130

<210> SEQ ID NO 82
<211> LENGTH: 89
<212> TYPE: PRT
<213> ORGANISM: Rattus norvegicus

<400> SEQUENCE: 82

Cys Arg Leu Trp Ser Leu Thr Leu Pro Val Ala Glu Leu Gly Leu Gly
  1               5                  10                  15

Tyr Ala Ser Glu Glu Lys Ile Ile Phe Arg Tyr Cys Ala Gly Ser Cys
                20                  25                  30

Pro Gln Glu Val Arg Thr Gln His Ser Leu Val Leu Ala Arg Leu Arg
            35                  40                  45

Gly Gln Gly Arg Ala His Gly Arg Pro Cys Cys Gln Pro Thr Ser Tyr
        50                  55                  60

Ala Asp Val Thr Phe Leu Asp Asp His His Trp Gln Gln Leu Pro
 65                  70                  75                  80

Gln Leu Ser Ala Ala Ala Cys Gly Cys
                85

<210> SEQ ID NO 83
<211> LENGTH: 91
<212> TYPE: PRT
<213> ORGANISM: Rattus norvegicus

<400> SEQUENCE: 83

Cys Arg Leu Trp Ser Leu Thr Leu Pro Val Ala Glu Leu Gly Leu Gly
  1               5                  10                  15

Tyr Ala Ser Glu Glu Lys Ile Ile Phe Arg Tyr Cys Ala Gly Ser Cys
                20                  25                  30

Pro Gln Glu Val Arg Thr Gln His Ser Leu Val Leu Ala Arg Leu Arg
            35                  40                  45

Gly Gln Gly Arg Ala His Gly Arg Pro Cys Cys Gln Pro Thr Ser Tyr
        50                  55                  60

Ala Asp Val Thr Phe Leu Asp Asp His His Trp Gln Gln Leu Pro
 65                  70                  75                  80

Gln Leu Ser Ala Ala Ala Cys Gly Cys Gly Gly
                85                  90

<210> SEQ ID NO 84
<211> LENGTH: 267
<212> TYPE: DNA
<213> ORGANISM: Mus musculus

<400> SEQUENCE: 84
tgccgactgt ggagcctgac cctaccagtg gctgagctgg gcctgggcta tgcctcggag    60
gagaaggtca tcttccgata ctgtgctggc agctgtcccc aagaggcccg tacccagcac   120
agtctggtac tggcccggct tcgagggcgg ggtcgagccc atggccgacc ctgctgccag   180
cccaccagct atgctgatgt gaccttcctt gatgatcagc accattggca gcagctgcct   240
cagctctcag ctgcagcttg tggctgt                                       267
```

<210> SEQ ID NO 85
<211> LENGTH: 267
<212> TYPE: DNA
<213> ORGANISM: Mus musculus

<400> SEQUENCE: 85
tgccggctgt ggagcctgac cctaccagtg gctgagcttg gcctgggcta tgcctcagag      60
gagaagatta tcttccgata ctgtgctggc agctgtcccc aagaggtccg tacccagcac     120
agtctggtgc tggcccgtct tcgagggcag ggtcgagctc atggcagacc ttgctgccag     180
cccaccagct atgctgatgt gaccttcctt gatgaccacc accattggca gcagctgcct     240
cagctctcag ccgcagcttg tggctgt                                          267

<210> SEQ ID NO 86
<211> LENGTH: 273
<212> TYPE: DNA
<213> ORGANISM: Rattus norvegicus

<400> SEQUENCE: 86
tgccggctgt ggagcctgac cctaccagtg gctgagcttg gcctgggcta tgcctcagag      60
gagaagatta tcttccgata ctgtgctggc agctgtcccc aagaggtccg tacccagcac     120
agtctggtgc tggcccgtct tcgagggcag ggtcgagctc atggcagacc ttgctgccag     180
cccaccagct atgctgatgt gaccttcctt gatgaccacc accattggca gcagctgcct     240
cagctctcag ccgcagcttg tggctgtggt ggc                                   273

<210> SEQ ID NO 87
<211> LENGTH: 94
<212> TYPE: PRT
<213> ORGANISM: Mus musculus

<400> SEQUENCE: 87

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
                 20                  25                  30

Glu Ser Ala Glu Thr Met Tyr Asp Lys Ile Leu Lys Asn Leu Ser Arg
             35                  40                  45

Ser Arg Arg Leu Thr Ser Asp Lys Val Gly Gln Ala Cys Cys Arg Pro
         50                  55                  60

Val Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys Ile
                 85                  90

<210> SEQ ID NO 88
<211> LENGTH: 95
<212> TYPE: PRT
<213> ORGANISM: Mus musculus

<400> SEQUENCE: 88

Cys Gly Leu Arg Glu Leu Glu Val Arg Val Ser Glu Leu Gly Leu Gly
  1               5                  10                  15

Tyr Thr Ser Asp Glu Thr Val Leu Phe Arg Tyr Cys Ala Gly Ala Cys
                 20                  25                  30

Glu Ala Ala Ile Arg Ile Tyr Asp Leu Gly Leu Arg Arg Leu Arg Gln
             35                  40                  45

```
Arg Arg Arg Val Arg Arg Glu Arg Ala Arg Ala His Pro Cys Cys Arg
    50                  55                  60

Pro Thr Ala Tyr Glu Asp Glu Val Ser Phe Leu Asp Val His Ser Arg
65                  70                  75                  80

Tyr His Thr Leu Gln Glu Leu Ser Ala Arg Glu Cys Ala Cys Val
                85                  90                  95
```

<210> SEQ ID NO 89
<211> LENGTH: 91
<212> TYPE: PRT
<213> ORGANISM: Mus musculus

<400> SEQUENCE: 89

```
Cys Arg Leu Trp Ser Leu Thr Leu Pro Val Ala Glu Leu Gly Leu Gly
1               5                   10                  15

Tyr Ala Ser Glu Glu Lys Val Ile Phe Arg Tyr Cys Ala Gly Ser Cys
                20                  25                  30

Pro Gln Glu Ala Arg Thr Gln His Ser Leu Val Leu Ala Arg Leu Arg
            35                  40                  45

Gly Arg Gly Arg Ala His Gly Arg Pro Cys Cys Gln Pro Thr Ser Tyr
    50                  55                  60

Ala Asp Val Thr Phe Leu Asp Asp Gln His His Trp Gln Gln Leu Pro
65                  70                  75                  80

Gln Leu Ser Ala Ala Ala Cys Gly Cys Gly Gly
                85                  90
```

<210> SEQ ID NO 90
<211> LENGTH: 22
<212> TYPE: DNA
<213> ORGANISM: Rattus norvegicus

<400> SEQUENCE: 90
tgcctcagag gagaagatta tc                                      22

<210> SEQ ID NO 91
<211> LENGTH: 7
<212> TYPE: PRT
<213> ORGANISM: Rattus norvegicus

<400> SEQUENCE: 91

```
Ala Ser Glu Glu Lys Ile Ile
1               5
```

<210> SEQ ID NO 92
<211> LENGTH: 16
<212> TYPE: PRT
<213> ORGANISM: Rattus norvegicus

<400> SEQUENCE: 92

```
Leu Gly Leu Gly Tyr Glu Thr Lys Glu Glu Leu Ile Phe Arg Tyr Cys
1               5                   10                  15
```

<210> SEQ ID NO 93
<211> LENGTH: 16
<212> TYPE: PRT
<213> ORGANISM: Rattus norvegicus

<400> SEQUENCE: 93

Leu Gly Leu Gly Tyr Thr Ser Asp Glu Thr Val Leu Phe Arg Tyr Cys
1               5                   10                  15

<210> SEQ ID NO 94
<211> LENGTH: 16
<212> TYPE: PRT
<213> ORGANISM: Rattus norvegicus

<400> SEQUENCE: 94

Leu Gly Leu Gly Tyr Ala Ser Glu Glu Lys Ile Ile Phe Arg Tyr Cys
1               5                   10                  15

<210> SEQ ID NO 95
<211> LENGTH: 23
<212> TYPE: DNA
<213> ORGANISM: Rattus norvegicus

<400> SEQUENCE: 95
agtcggggtt ggggtatgcc tca                                          23

<210> SEQ ID NO 96
<211> LENGTH: 26
<212> TYPE: DNA
<213> ORGANISM: Rattus norvegicus

<400> SEQUENCE: 96
tatgcctcag aggagaagat tatctt                                       26

<210> SEQ ID NO 97
<211> LENGTH: 336
<212> TYPE: DNA
<213> ORGANISM: Rattus norvegicus

<400> SEQUENCE: 97
cctcagagga gaagattatc ttccgatact gtgctggcag ctgtcccaa gaggtccgta    60 cccagcacag tctggtgctg ccccgtcttc gagggcaggg tcgagctcat ggcagacctt   120
gctgccagcc caccagctat gctgatgtga ccttccttga tgaccaccac cattggcagc   180
agctgcctca gctctcagcc gcagcttgtg gctgtggtgg ctgaaggcgg ccagcctggt   240
ctctcagaat cacaagcaag aggcagcctt tgaaaggctc aggtgacgtt attagaaact   300
tgcataggag aagattaaga agagaaaggg gacctg                            336

<210> SEQ ID NO 98
<211> LENGTH: 17
<212> TYPE: PRT
<213> ORGANISM: Rattus norvegicus

<400> SEQUENCE: 98

Ala Cys Cys Arg Pro Val Ala Phe Asp Asp Leu Ser Phe Leu Asp
1               5                   10                  15

Asp

<210> SEQ ID NO 99
<211> LENGTH: 17
<212> TYPE: PRT
<213> ORGANISM: Rattus norvegicus

```
<400> SEQUENCE: 99

Pro Cys Cys Arg Pro Thr Ala Tyr Glu Asp Glu Val Ser Phe Lys Asp
 1               5                  10                  15
Val

<210> SEQ ID NO 100
<211> LENGTH: 16
<212> TYPE: PRT
<213> ORGANISM: Rattus norvegicus

<400> SEQUENCE: 100

Pro Cys Cys Gln Pro Thr Ser Tyr Ala Asp Val Thr Phe Leu Asp Asp
 1               5                  10                  15

<210> SEQ ID NO 101
<211> LENGTH: 26
<212> TYPE: DNA
<213> ORGANISM: Mus musculus

<400> SEQUENCE: 101
tcatcaagga aggtcacatc agcata                                        26

<210> SEQ ID NO 102
<211> LENGTH: 32
<212> TYPE: DNA
<213> ORGANISM: Mus musculus
<220> FEATURE:
<221> NAME/KEY: misc_feature
<222> LOCATION: (23)
<223> OTHER INFORMATION: s = c or g

<400> SEQUENCE: 102
ccaccacagc cacaagctgc ggstgagagc tg                                 32

<210> SEQ ID NO 103
<211> LENGTH: 5
<212> TYPE: PRT
<213> ORGANISM: Mus musculus

<400> SEQUENCE: 103

Ala Leu Ala Gly Ser
 1               5

<210> SEQ ID NO 104
<211> LENGTH:
<212> TYPE:
<213> ORGANISM:

<400> SEQUENCE: 104

000

<210> SEQ ID NO 105
<211> LENGTH: 544
<212> TYPE: DNA
<213> ORGANISM: Homo sapiens

<400> SEQUENCE: 105
gagggacctg gacgccccat cagggtaaga attcctgggg gcctcccgac tccccaattc     60
cttctctcaa agccctcact ttgccttaca atcctactct accttgcact aggtaacaac    120
catgtccgtc ttccaagagc cttggctggt tcatgccgac tgtggagcct gaccctacca    180
gtggctgagc tgggcctggg ctatgcctcg gaggagaagg tcatcttccg atactgtgct    240
```

```
ggcagctgtc cccaagaggc ccgtacccag cacagtctgg tactggcccg gcttcgaggg      300
cggggtcgag cccatggccg accctgctgc cagcccacca gctatgctga tgtgaccttc      360
cttgatgatc agcaccattg gcagcagctg cctcagctct cagctgcagc ttgtggctgt      420
ggtggctgaa ggaggccagt ctggtgtctc agaatcacaa gcatgagaca ggctgggctt      480
tgaaaggctc aggtgacatt actagaaatt tgcataggta aagataagaa gggaaaggac      540
cagg                                                                  544
```

\<210\> SEQ ID NO 106
\<211\> LENGTH: 73
\<212\> TYPE: PRT
\<213\> ORGANISM: Rattus norvegicus

\<400\> SEQUENCE: 106

Ser Glu Glu Lys Ile Ile Phe Arg Tyr Cys Ala Gly Ser Cys Pro Gln
 1               5                  10                  15

Glu Val Arg Thr Gln His Ser Leu Val Leu Ala Arg Leu Arg Gly Gln
            20                  25                  30

Gly Arg Ala His Gly Arg Pro Cys Cys Gln Pro Thr Ser Tyr Ala Asp
        35                  40                  45

Val Thr Phe Leu Asp Asp His His His Trp Gln Gln Leu Pro Gln Leu
    50                  55                  60

Ser Ala Ala Ala Cys Gly Cys Gly Gly
65                  70

\<210\> SEQ ID NO 107
\<211\> LENGTH: 391
\<212\> TYPE: DNA
\<213\> ORGANISM: Homo sapiens

\<400\> SEQUENCE: 107

```
tgccggctgt ggagcctgac cctaccagtg gctgagcttg gcctgggcta tgcctcagag      60
gagaagatta tcttccgata ctgtgctggc agctgtcccc aagaggtccg tacccagcac     120
agtctggtgc tggcccgtct tcgagggcag ggtcgagctc atggcagacc ttgctgccag     180
cccaccagct atgctgatgt gaccttcctt gatgaccacc accattggca gcagctgcct     240
cagctctcag ccgcagcttg tggctgtggt ggctgaaggc ggccagcctg gtctctcaga     300
atcacaagca agaggcagcc tttgaaaggc tcaggtgacg ttattagaaa cttgcatagg     360
agaagattaa gaagagaaag gggacctgat t                                    391
```

\<210\> SEQ ID NO 108
\<211\> LENGTH: 8
\<212\> TYPE: PRT
\<213\> ORGANISM: Mus musculus
\<220\> FEATURE:
\<221\> NAME/KEY: SITE
\<222\> LOCATION: (2)
\<223\> OTHER INFORMATION: Serine, Threonine, or Alanine
\<220\> FEATURE:
\<221\> NAME/KEY: SITE
\<222\> LOCATION: (3)
\<223\> OTHER INFORMATION: Glutamic Acid or Aspartic Acid

\<400\> SEQUENCE: 108

Val Xaa Xaa Leu Gly Leu Gly Tyr
 1               5

```
<210> SEQ ID NO 109
<211> LENGTH: 8
<212> TYPE: PRT
<213> ORGANISM: Homo sapiens
<220> FEATURE:
<221> NAME/KEY: SITE
<222> LOCATION: (5)
<223> OTHER INFORMATION: Alanine or Serine
<220> FEATURE:
<221> NAME/KEY: SITE
<222> LOCATION: (7)
<223> OTHER INFORMATION: Alanine or Serine

<400> SEQUENCE: 109

Phe Arg Tyr Cys Xaa Gly Xaa Cys
 1               5

<210> SEQ ID NO 110
<211> LENGTH: 8
<212> TYPE: PRT
<213> ORGANISM: Mus musculus
<220> FEATURE:
<221> NAME/KEY: SITE
<222> LOCATION: (2)
<223> OTHER INFORMATION: Aspartic Acid, Glutamic Acid or No Amino Acid
<220> FEATURE:
<221> NAME/KEY: SITE
<222> LOCATION: (3)
<223> OTHER INFORMATION: Valine or Leucine
<220> FEATURE:
<221> NAME/KEY: SITE
<222> LOCATION: (4)
<223> OTHER INFORMATION: Serine or Threonine
<220> FEATURE:
<221> NAME/KEY: SITE
<222> LOCATION: (8)
<223> OTHER INFORMATION: Valine or Aspartic Acid

<400> SEQUENCE: 110

Asp Xaa Xaa Xaa Phe Leu Asp Xaa
 1               5

<210> SEQ ID NO 111
<211> LENGTH: 142
<212> TYPE: PRT
<213> ORGANISM: Mus musculus

<400> SEQUENCE: 111

Glu Gly Pro Gly Arg Pro Ile Arg Val Arg Ile Pro Gly Gly Leu Pro
 1               5                  10                  15

Thr Pro Gln Phe Leu Leu Ser Lys Pro Ser Leu Cys Leu Thr Ile Leu
                20                  25                  30

Leu Tyr Leu Ala Leu Gly Asn Asn His Val Arg Leu Pro Arg Ala Leu
            35                  40                  45

Ala Gly Ser Cys Arg Leu Trp Ser Leu Thr Leu Pro Val Ala Glu Leu
        50                  55                  60

Gly Leu Gly Tyr Ala Ser Glu Glu Lys Val Ile Phe Arg Tyr Cys Ala
 65                  70                  75                  80

Gly Ser Cys Pro Gln Glu Ala Arg Thr Gln His Ser Leu Val Leu Ala
                85                  90                  95

Arg Leu Arg Gly Arg Gly Arg Ala His Gly Arg Pro Cys Cys Gln Pro
            100                 105                 110

Thr Ser Tyr Ala Asp Val Thr Phe Leu Asp Asp Gln His His Trp Gln
        115                 120                 125

Gln Leu Pro Gln Leu Ser Ala Ala Ala Cys Gly Cys Gly Gly
    130                 135                 140
```

```
<210> SEQ ID NO 112
<211> LENGTH: 5
<212> TYPE: PRT
<213> ORGANISM: Rattus norvegicus

<400> SEQUENCE: 112

Ala Leu Pro Gly Leu
 1               5

<210> SEQ ID NO 113
<211> LENGTH: 12
<212> TYPE: PRT
<213> ORGANISM: Mus musculus
<220> FEATURE:
<221> NAME/KEY: SITE
<222> LOCATION: (2)
<223> OTHER INFORMATION: Threonine, Glutamic Acid or Lysine
<220> FEATURE:
<221> NAME/KEY: SITE
<222> LOCATION: (3)
<223> OTHER INFORMATION: Valine, Leucine or Isoleucine
<220> FEATURE:
<221> NAME/KEY: SITE
<222> LOCATION: (4)
<223> OTHER INFORMATION: Leucine or Isoleucine
<220> FEATURE:
<221> NAME/KEY: SITE
<222> LOCATION: (9)
<223> OTHER INFORMATION: Alanine or Serine
<220> FEATURE:
<221> NAME/KEY: SITE
<222> LOCATION: (11)
<223> OTHER INFORMATION: Alanine or Serine

<400> SEQUENCE: 113

Glu Xaa Xaa Xaa Phe Arg Tyr Cys Xaa Gly Xaa Cys
 1               5                  10

<210> SEQ ID NO 114
<211> LENGTH: 16
<212> TYPE: PRT
<213> ORGANISM: Mus musculus
<220> FEATURE:
<221> NAME/KEY: SITE
<222> LOCATION: (3)
<223> OTHER INFORMATION: Arginine or Glutamine
<220> FEATURE:
<221> NAME/KEY: SITE
<222> LOCATION: (5)
<223> OTHER INFORMATION: Threonine, Valine or Isoleucine
<220> FEATURE:
<221> NAME/KEY: SITE
<222> LOCATION: (6)
<223> OTHER INFORMATION: Alanine or Serine
<220> FEATURE:
<221> NAME/KEY: SITE
<222> LOCATION: (7)
<223> OTHER INFORMATION: Tyrosine or Phenylalanine
<220> FEATURE:
<221> NAME/KEY: SITE
<222> LOCATION: (8)
<223> OTHER INFORMATION: Glutamic Acid, Aspartic Acid or Alanine
<220> FEATURE:
<221> NAME/KEY: SITE
<222> LOCATION: (10)
<223> OTHER INFORMATION: Glutamic Acid, Aspartic Acid or No Amino Acid
<220> FEATURE:
<221> NAME/KEY: SITE
<222> LOCATION: (11)
<223> OTHER INFORMATION: Valine or Leucine
<220> FEATURE:
<221> NAME/KEY: SITE
<222> LOCATION: (12)
<223> OTHER INFORMATION: Serine or Threonine
```

```
<220> FEATURE:
<221> NAME/KEY: SITE
<222> LOCATION: (16)
<223> OTHER INFORMATION: Aspartic Acid or Valine

<400> SEQUENCE: 114

Cys Cys Xaa Pro Xaa Xaa Xaa Asp Xaa Xaa Xaa Phe Leu Asp Xaa
  1               5                   10                  15

<210> SEQ ID NO 115
<211> LENGTH: 23
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: d = a, t or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (10)
<223> OTHER INFORMATION: y = t or c
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (16)
<223> OTHER INFORMATION: y = t or c
<220> FEATURE:
<221> NAME/KEY: misc_feature
<222> LOCATION: (21)
<223> OTHER INFORMATION: n = a, t, c or g

<400> SEQUENCE: 115
gtndgngany tgggnytggg nta                                      23

<210> SEQ ID NO 116
<211> LENGTH: 19
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: b = t, c or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (7)
<223> OTHER INFORMATION: w = a or t
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (12)
<223> OTHER INFORMATION: y = t or c
```

```
<220> FEATURE:
<221> NAME/KEY: misc_feature
<222> LOCATION: (13)
<223> OTHER INFORMATION: y = t or c
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g

<400> SEQUENCE: 116
ganbtnwcnt tyytngang                                              19

<210> SEQ ID NO 117
<211> LENGTH: 20
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: b = t, c or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (7)
<223> OTHER INFORMATION: w = a or t
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (12)
<223> OTHER INFORMATION: y = t or c
<220> FEATURE:
<221> NAME/KEY: misc_feature
<222> LOCATION: (13)
<223> OTHER INFORMATION: y = t or c
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (20)
<223> OTHER INFORMATION: w = a or t

<400> SEQUENCE: 117
ganbtnwcnt tyytngangw                                             20

<210> SEQ ID NO 118
<211> LENGTH: 23
<212> TYPE: DNA
<213> ORGANISM: Mus musculus
<220> FEATURE:
<221> NAME/KEY: misc_feature
<222> LOCATION: (3)
<223> OTHER INFORMATION: y = t or c
```

```
<220> FEATURE:
<221> NAME/KEY: misc_feature
<222> LOCATION: (4)
<223> OTHER INFORMATION: m = a or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: y = t or c
<220> FEATURE:
<221> NAME/KEY: misc_feature
<222> LOCATION: (12)
<223> OTHER INFORMATION: y = t or c
<220> FEATURE:
<221> NAME/KEY: misc_feature
<222> LOCATION: (13)
<223> OTHER INFORMATION: d = a, t or g
<220> FEATURE:
<221> NAME/KEY: misc_feature
<222> LOCATION: (14)
<223> OTHER INFORMATION: s = c or g
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (19)
<223> OTHER INFORMATION: d = a, t or g
<220> FEATURE:
<221> NAME/KEY: misc_feature
<222> LOCATION: (20)
<223> OTHER INFORMATION: s = c or g
<220> FEATURE:
<221> NAME/KEY: misc_feature
<222> LOCATION: (21)
<223> OTHER INFORMATION: n = a, t, c or g

<400> SEQUENCE: 118
ttymgntayt gydsnggnds ntg                                             23

<210> SEQ ID NO 119
<211> LENGTH: 20
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: d = a, t or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: y = t or c
<220> FEATURE:
<221> NAME/KEY: misc_feature
<222> LOCATION: (15)
<223> OTHER INFORMATION: n = a, t, c or g
```

```
<220> FEATURE:
<221> NAME/KEY: misc_feature
<222> LOCATION: (16)
<223> OTHER INFORMATION: y = t or c
<220> FEATURE:
<221> NAME/KEY: misc_feature
<222> LOCATION: (18)
<223> OTHER INFORMATION: n = a, t, c or g

<400> SEQUENCE: 119
gtndgngany tgggnytngg                                                   20

<210> SEQ ID NO 120
<211> LENGTH: 23
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: d = a, t or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: y = t or c
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (16)
<223> OTHER INFORMATION: y = t or c
<220> FEATURE:
<221> NAME/KEY: misc_feature
<222> LOCATION: (21)
<223> OTHER INFORMATION: n = a, t, c or g

<400> SEQUENCE: 120
gtndgngany tgggnytggg ntt                                               23

<210> SEQ ID NO 121
<211> LENGTH: 20
<212> TYPE: DNA
<213> ORGANISM: Mus musculus
<220> FEATURE:
<221> NAME/KEY: misc_feature
<222> LOCATION: (1)
<223> OTHER INFORMATION: w = a or t
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (8)
<223> OTHER INFORMATION: r = a or g
```

```
<220> FEATURE:
<221> NAME/KEY: misc_feature
<222> LOCATION: (9)
<223> OTHER INFORMATION: r = a or g
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (14)
<223> OTHER INFORMATION: w = a or t
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (17)
<223> OTHER INFORMATION: v = a, c or g
<220> FEATURE:
<221> NAME/KEY: misc_feature
<222> LOCATION: (18)
<223> OTHER INFORMATION: n = a, t, c or g

<400> SEQUENCE: 121
wcntcnarra angwnavntc                                              20

<210> SEQ ID NO 122
<211> LENGTH: 19
<212> TYPE: DNA
<213> ORGANISM: Mus musculus
<220> FEATURE:
<221> NAME/KEY: misc_feature
<222> LOCATION: (1)
<223> OTHER INFORMATION: w = a or t
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (8)
<223> OTHER INFORMATION: r = a or g
<220> FEATURE:
<221> NAME/KEY: misc_feature
<222> LOCATION: (9)
<223> OTHER INFORMATION: r = a or g
<220> FEATURE:
<221> NAME/KEY: misc_feature
<222> LOCATION: (12)
<223> OTHER INFORMATION: n = a, t, c or g
<220> FEATURE:
<221> NAME/KEY: misc_feature
<222> LOCATION: (14)
<223> OTHER INFORMATION: w = a or t
<220> FEATURE:
<221> NAME/KEY: misc_feature
<222> LOCATION: (15)
<223> OTHER INFORMATION: n = a, t, c or g
<220> FEATURE:
<221> NAME/KEY: misc_feature
<222> LOCATION: (17)
<223> OTHER INFORMATION: v = a, c or g
<220> FEATURE:
<221> NAME/KEY: misc_feature
<222> LOCATION: (18)
<223> OTHER INFORMATION: n = a, t, c or g

<400> SEQUENCE: 122
wcntcnarra angwnavnt                                               19
```

```
<210> SEQ ID NO 123
<211> LENGTH: 23
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: s = c or g
<220> FEATURE:
<221> NAME/KEY: misc_feature
<222> LOCATION: (5)
<223> OTHER INFORMATION: h = a, t or c
<220> FEATURE:
<221> NAME/KEY: misc_feature
<222> LOCATION: (6)
<223> OTHER INFORMATION: n = a, t, c or g
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: s = c or g
<220> FEATURE:
<221> NAME/KEY: misc_feature
<222> LOCATION: (11)
<223> OTHER INFORMATION: h = a, t or c
<220> FEATURE:
<221> NAME/KEY: misc_feature
<222> LOCATION: (12)
<223> OTHER INFORMATION: r = a or g
<220> FEATURE:
<221> NAME/KEY: misc_feature
<222> LOCATION: (15)
<223> OTHER INFORMATION: r = a or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (20)
<223> OTHER INFORMATION: k = t or g
<220> FEATURE:
<221> NAME/KEY: misc_feature
<222> LOCATION: (21)
<223> OTHER INFORMATION: r = a or g

<400> SEQUENCE: 123
canshnccns hrcartanck raa                                           23

<210> SEQ ID NO 124
<211> LENGTH: 25
<212> TYPE: DNA
<213> ORGANISM: Mus musculus
<220> FEATURE:
<221> NAME/KEY: misc_feature
<222> LOCATION: (3)
<223> OTHER INFORMATION: n = a, t, c or g
<220> FEATURE:
<221> NAME/KEY: misc_feature
<222> LOCATION: (4)
<223> OTHER INFORMATION: s = c or g
<220> FEATURE:
<221> NAME/KEY: misc_feature
<222> LOCATION: (5)
<223> OTHER INFORMATION: h = a, t or c
<220> FEATURE:
<221> NAME/KEY: misc_feature
<222> LOCATION: (6)
<223> OTHER INFORMATION: n = a, t, c or g
```

```
<220> FEATURE:
<221> NAME/KEY: misc_feature
<222> LOCATION: (9)
<223> OTHER INFORMATION: n = a, t, c or g
<220> FEATURE:
<221> NAME/KEY: misc_feature
<222> LOCATION: (10)
<223> OTHER INFORMATION: s = c or g
<220> FEATURE:
<221> NAME/KEY: misc_feature
<222> LOCATION: (11)
<223> OTHER INFORMATION: h = a, t or c
<220> FEATURE:
<221> NAME/KEY: misc_feature
<222> LOCATION: (12)
<223> OTHER INFORMATION: r = a or g
<220> FEATURE:
<221> NAME/KEY: misc_feature
<222> LOCATION: (15)
<223> OTHER INFORMATION: r = a or g
<220> FEATURE:
<221> NAME/KEY: misc_feature
<222> LOCATION: (18)
<223> OTHER INFORMATION: n = a, t, c or g
<220> FEATURE:
<221> NAME/KEY: misc_feature
<222> LOCATION: (20)
<223> OTHER INFORMATION: k = t or g
<220> FEATURE:
<221> NAME/KEY: misc_feature
<222> LOCATION: (21)
<223> OTHER INFORMATION: r = a or g
<220> FEATURE:
<221> NAME/KEY: misc_feature
<222> LOCATION: (24)
<223> OTHER INFORMATION: n = a, t, c or g

<400> SEQUENCE: 124
canshnccns hrcartanck raana                                              25

<210> SEQ ID NO 125
<211> LENGTH: 8
<212> TYPE: PRT
<213> ORGANISM: Mus musculus
<220> FEATURE:
<221> NAME/KEY: SITE
<222> LOCATION: (2)
<223> OTHER INFORMATION: Threonine, Serine or Alanine
<220> FEATURE:
<221> NAME/KEY: SITE
<222> LOCATION: (3)
<223> OTHER INFORMATION: Glutamic Acid or Aspartic Acid

<400> SEQUENCE: 125

Val Xaa Xaa Leu Gly Leu Gly Tyr
 1               5

<210> SEQ ID NO 126
<211> LENGTH: 7
<212> TYPE: PRT
<213> ORGANISM: Mus musculus
<220> FEATURE:
<221> NAME/KEY: SITE
<222> LOCATION: (1)
<223> OTHER INFORMATION: Aspartic Acid or Glutamic Acid
<220> FEATURE:
<221> NAME/KEY: SITE
<222> LOCATION: (2)
<223> OTHER INFORMATION: Valine or Leucine
<220> FEATURE:
<221> NAME/KEY: SITE
<222> LOCATION: (3)
<223> OTHER INFORMATION: Threonine or Serine
```

```
<220> FEATURE:
<221> NAME/KEY: SITE
<222> LOCATION: (6)
<223> OTHER INFORMATION: Aspartic Acid or Glutamic Acid
<220> FEATURE:
<221> NAME/KEY: SITE
<222> LOCATION: (7)
<223> OTHER INFORMATION: Aspartic Acid or Valine

<400> SEQUENCE: 126

Xaa Xaa Xaa Phe Leu Xaa Xaa
 1               5

<210> SEQ ID NO 127
<211> LENGTH: 8
<212> TYPE: PRT
<213> ORGANISM: Mus musculus
<220> FEATURE:
<221> NAME/KEY: SITE
<222> LOCATION: (5)
<223> OTHER INFORMATION: Serine or Alanine
<220> FEATURE:
<221> NAME/KEY: SITE
<222> LOCATION: (7)
<223> OTHER INFORMATION: Serine or Alanine

<400> SEQUENCE: 127

Phe Arg Tyr Cys Xaa Gly Xaa Cys
 1               5

<210> SEQ ID NO 128
<211> LENGTH: 7
<212> TYPE: PRT
<213> ORGANISM: Mus musculus
<220> FEATURE:
<221> NAME/KEY: SITE
<222> LOCATION: (2)
<223> OTHER INFORMATION: Threonine, Serine or Alanine
<220> FEATURE:
<221> NAME/KEY: SITE
<222> LOCATION: (3)
<223> OTHER INFORMATION: Aspartic Acid or Glutamic Acid

<400> SEQUENCE: 128

Val Xaa Xaa Leu Gly Leu Gly
 1               5

<210> SEQ ID NO 129
<211> LENGTH: 8
<212> TYPE: PRT
<213> ORGANISM: Mus musculus
<220> FEATURE:
<221> NAME/KEY: SITE
<222> LOCATION: (2)
<223> OTHER INFORMATION: Threonine, Serine or Alanine
<220> FEATURE:
<221> NAME/KEY: SITE
<222> LOCATION: (3)
<223> OTHER INFORMATION: Glutamic Acid or Aspartic Acid

<400> SEQUENCE: 129

Val Xaa Xaa Leu Gly Leu Gly Phe
 1               5

<210> SEQ ID NO 130
<211> LENGTH: 9
<212> TYPE: PRT
<213> ORGANISM: Mus musculus
```

-continued

```
<220> FEATURE:
<221> NAME/KEY: SITE
<222> LOCATION: (1)
<223> OTHER INFORMATION: Isoleucine or Leucine
<220> FEATURE:
<221> NAME/KEY: SITE
<222> LOCATION: (6)
<223> OTHER INFORMATION: Serine or Alanine
<220> FEATURE:
<221> NAME/KEY: SITE
<222> LOCATION: (8)
<223> OTHER INFORMATION: Serine or Alanine

<400> SEQUENCE: 130

Xaa Phe Arg Tyr Cys Xaa Gly Xaa Cys
  1               5

<210> SEQ ID NO 131
<211> LENGTH: 559
<212> TYPE: DNA
<213> ORGANISM: Mus musculus

<400> SEQUENCE: 131
atggctgcag gaagacttcg gatcctgtgt ctgctgctcc tgtccttgca cccgagcctc     60
ggctgggtcc ttgatcttca agaggcttct gtggcagata agctctcatt tgggaagatg    120
gcagagacta gagggacctg gacgccccat cagggtaaga attcctgggg gcctcccgac    180
tccccaattc cttctctcaa agccctcact ttgccttaca atcctactct accttgcact    240
aggtaacaac catgtccgtc ttccaagagc cttggctggt tcatgccgac tgtggagcct    300
gaccctacca gtggctgagc tgggcctggg atatgcctcg gaggagaagg tcatcttccg    360
atactgtgct ggcagctgtc cccaagaggc ccgtacccag cacagtctgg tactggcccg    420
gcttcgaggg cggggtcgag cccatggccg accctgctgc agcccacca gctatgctga    480 tgtgaccttc cttgatgatc agcaccattg gcagctgctg cctcagctct cagctgcagc    540
ttgtggctgt ggtggctga                                                559

<210> SEQ ID NO 132
<211> LENGTH: 133
<212> TYPE: PRT
<213> ORGANISM: Homo sapiens

<400> SEQUENCE: 132:

Pro Asp Ala Arg Gly Val Pro Val Ala Asp Gly Glu Phe Ser Ser Glu
  1               5                  10                  15

Gln Val Ala Lys Ala Gly Gly Thr Trp Leu Gly Thr His Arg Pro Leu
             20                  25                  30

Ala Arg Leu Arg Arg Ala Leu Ser Gly Pro Cys Gln Leu Trp Ser Leu
         35                  40                  45

Thr Leu Ser Val Ala Glu Leu Gly Leu Gly Tyr Ala Ser Glu Glu Lys
     50                  55                  60

Val Ile Phe Arg Tyr Cys Ala Gly Ser Cys Pro Arg Gly Ala Arg Thr
 65                  70                  75                  80

Gln His Gly Leu Ala Leu Ala Arg Leu Gln Gly Gln Gly Arg Ala His
                 85                  90                  95

Gly Gly Pro Cys Cys Arg Pro Thr Arg Tyr Thr Asp Val Ala Phe Leu
            100                 105                 110
```

Asp Asp Arg His Arg Trp Gln Arg Leu Pro Gln Leu Ser Ala Ala Ala
        115                 120                 125

Cys Gly Cys Gly Gly
        130

<210> SEQ ID NO 133
<211> LENGTH:
<212> TYPE:
<213> ORGANISM:

<400> SEQUENCE: 133

000

<210> SEQ ID NO 134
<211> LENGTH: 93
<212> TYPE: PRT
<213> ORGANISM: Rattus norvegicus

<400> SEQUENCE: 134

Cys Val Leu Thr Ala Ile His Leu Asn Val Thr Asp Leu Gly Leu Gly
 1               5                  10                  15

Tyr Glu Thr Lys Glu Leu Ile Phe Arg Tyr Cys Ser Gly Ser Cys
            20                  25                  30

Glu Ala Ala Glu Thr Met Tyr Asp Lys Ile Leu Lys Asn Leu Ser Arg
        35                  40                  45

Ser Arg Arg Leu Thr Ser Asp Lys Val Gly Gln Ala Cys Cys Arg Pro
    50                  55                  60

Val Ala Phe Asp Asp Asp Leu Ser Phe Leu Asp Asp Ser Leu Val Tyr
65                  70                  75                  80

His Ile Leu Arg Lys His Ser Ala Lys Arg Cys Gly Cys
                85                  90

<210> SEQ ID NO 135
<211> LENGTH: 23
<212> TYPE: PRT
<213> ORGANISM: Mus musculus

<400> SEQUENCE: 135

Met Ala Ala Gly Arg Leu Arg Ile Leu Cys Leu Leu Leu Ser Leu
 1               5                  10                  15

His Pro Ser Leu Gly Trp Val
            20

<210> SEQ ID NO 136
<211> LENGTH: 23
<212> TYPE: PRT
<213> ORGANISM: Rattus norvegicus

<400> SEQUENCE: 136

Met Ala Ala Gly Arg Leu Arg Ile Leu Phe Leu Leu Leu Ser Leu
 1               5                  10                  15

His Leu Gly Leu Gly Trp Val
            20

<210> SEQ ID NO 137
<211> LENGTH: 23
<212> TYPE: DNA
<213> ORGANISM: Rattus norvegicus

<400> SEQUENCE: 137
aatccccagg acaggcaggg aat                                          23

```
<210> SEQ ID NO 138
<211> LENGTH: 35
<212> TYPE: DNA
<213> ORGANISM: Rattus norvegicus

<400> SEQUENCE: 138
cggtacccag atcttcagcc accacagcca caagc                              35

<210> SEQ ID NO 139
<211> LENGTH: 76
<212> TYPE: DNA
<213> ORGANISM: Mus musculus

<400> SEQUENCE: 139
ggactatcat atgcccacc accaccacca ccaccaccac gacgacgacg acaaggcctt    60
ggctggttca tgccga                                                   76

<210> SEQ ID NO 140
<211> LENGTH: 32
<212> TYPE: DNA
<213> ORGANISM: Mus musculus

<400> SEQUENCE: 140
tgctgtcacc atggctgcag gaagacttcg ga                                 32

<210> SEQ ID NO 141
<211> LENGTH: 96
<212> TYPE: PRT
<213> ORGANISM: Mus musculus

<400> SEQUENCE: 141

Ala Leu Ala Gly Ser Cys Arg Leu Trp Ser Leu Thr Leu Pro Val Ala
  1               5                  10                  15

Glu Leu Gly Leu Gly Tyr Ala Ser Glu Glu Lys Val Ile Phe Arg Tyr
             20                  25                  30

Cys Ala Gly Ser Cys Pro Gln Glu Ala Arg Thr Gln His Ser Leu Val
         35                  40                  45

Leu Ala Arg Leu Arg Gly Arg Gly Arg Ala His Gly Arg Pro Cys Cys
     50                  55                  60

Arg Pro Thr Ala Tyr Glu Asp Glu Val Ser Phe Leu Asp Val His Ser
 65                  70                  75                  80

Arg Tyr His Thr Leu Gln Glu Leu Ser Ala Arg Glu Cys Ala Cys Val
                 85                  90                  95

<210> SEQ ID NO 142
<211> LENGTH: 23
<212> TYPE: DNA
<213> ORGANISM: Artificial sequence
<220> FEATURE:
<221> NAME/KEY:
<222> LOCATION:
<223> OTHER INFORMATION: Plasmid vector sequence

<400> SEQUENCE: 142
taatacgact cactataggg gaa                                           23

<210> SEQ ID NO 143
<211> LENGTH: 49
<212> TYPE: DNA
<213> ORGANISM: Mus musculus
```

-continued

<400> SEQUENCE: 143
tcgtcttcgt aagcagtcgg acggcagcag ggtcggccat gggctcgac                49

<210> SEQ ID NO 144
<211> LENGTH: 29
<212> TYPE: DNA
<213> ORGANISM: Homo sapiens

<400> SEQUENCE: 144
tgctgccgtc cgactgctta cgaagacga                                      29

<210> SEQ ID NO 145
<211> LENGTH: 25
<212> TYPE: DNA
<213> ORGANISM: Artificial sequence
<220> FEATURE:
<221> NAME/KEY:
<222> LOCATION:
<223> OTHER INFORMATION: Plasmid vector sequence

<400> SEQUENCE: 145
gttatgctag ttattgctca gcggt                                          25

<210> SEQ ID NO 146
<211> LENGTH: 100
<212> TYPE: PRT
<213> ORGANISM: Mus musculus

<400> SEQUENCE: 146

Pro Gly Ala Arg Pro Cys Gly Leu Arg Glu Leu Glu Val Arg Val Ser
 1               5                  10                  15

Glu Leu Gly Leu Gly Tyr Thr Ser Asp Glu Thr Val Leu Phe Arg Tyr
             20                  25                  30

Cys Ala Gly Ala Cys Glu Ala Ala Ile Arg Ile Tyr Asp Leu Gly Leu
         35                  40                  45

Arg Arg Leu Arg Gln Arg Arg Val Arg Arg Glu Arg Ala Arg Ala
     50                  55                  60

His Pro Cys Cys Gln Pro Thr Ser Tyr Ala Asp Val Thr Phe Leu Asp
 65                  70                  75                  80

Asp Gln His His Trp Gln Gln Leu Pro Gln Leu Ser Ala Ala Ala Cys
                 85                  90                  95

Gly Cys Gly Gly
        100

<210> SEQ ID NO 147
<211> LENGTH: 50
<212> TYPE: DNA
<213> ORGANISM: Mus musculus

<400> SEQUENCE: 147
cacatcagca tagctggtgg gctggcagca cgggtgagca cgagcacgtt                50

<210> SEQ ID NO 148
<211> LENGTH: 25
<212> TYPE: DNA
<213> ORGANISM: Mus musculus

<400> SEQUENCE: 148
tgctgccagc ccaccagcta tgctg                                          25

```
<210> SEQ ID NO 149
<211> LENGTH: 23
<212> TYPE: DNA
<213> ORGANISM: Mus musculus

<400> SEQUENCE: 149
cctcggagga gaaggtcatc ttc                                            23

<210> SEQ ID NO 150
<211> LENGTH: 98
<212> TYPE: PRT
<213> ORGANISM: Homo sapiens

<400> SEQUENCE: 150
```

Cys Cys Val Arg Gln Leu Tyr Ile Asp Phe Arg Lys Asp Leu Gly Trp
 1               5                  10                  15

Lys Trp Ile His Glu Pro Lys Gly Tyr His Ala Asn Phe Cys Leu Gly
            20                  25                  30

Pro Cys Pro Tyr Ile Trp Ser Leu Asp Thr Gln Tyr Ser Lys Val Leu
        35                  40                  45

Ala Leu Tyr Asn Gln His Asn Pro Gly Ala Ser Ala Ala Pro Cys Cys
    50                  55                  60

Val Pro Gln Ala Leu Glu Pro Leu Pro Ile Val Tyr Tyr Val Gly Arg
65                  70                  75                  80

Lys Pro Lys Val Glu Gln Leu Ser Asn Met Ile Val Arg Ser Cys Lys
                85                  90                  95

Cys Ser

```
<210> SEQ ID NO 151
<211> LENGTH: 98
<212> TYPE: PRT
<213> ORGANISM: Homo sapiens

<400> SEQUENCE: 151
```

Cys Cys Leu Arg Pro Leu Tyr Ile Asp Phe Lys Arg Asp Leu Gly Trp
 1               5                  10                  15

Lys Trp Ile His Glu Pro Lys Gly Tyr Asn Ala Asn Phe Cys Ala Gly
            20                  25                  30

Ala Cys Pro Tyr Leu Trp Ser Ser Asp Thr Gln His Ser Arg Val Leu
        35                  40                  45

Ser Leu Tyr Asn Thr Ile Asn Pro Glu Ala Ser Ala Ser Pro Cys Cys
    50                  55                  60

Val Ser Gln Asp Leu Glu Pro Leu Thr Ile Leu Tyr Tyr Ile Gly Lys
65                  70                  75                  80

Thr Pro Lys Ile Glu Gln Leu Ser Asn Met Ile Val Lys Ser Cys Lys
                85                  90                  95

Cys Ser

```
<210> SEQ ID NO 152
<211> LENGTH: 98
<212> TYPE: PRT
<213> ORGANISM: Homo sapiens

<400> SEQUENCE: 152
```

Cys Cys Val Arg Pro Leu Tyr Ile Asp Phe Arg Gln Asp Leu Gly Trp
 1               5                  10                  15

Lys Trp Val His Glu Pro Lys Gly Tyr Tyr Ala Asn Phe Cys Ser Gly
            20                  25                  30

```
Pro Cys Pro Tyr Leu Arg Ser Ala Asp Thr Thr His Ser Thr Val Leu
        35                  40                  45

Gly Leu Tyr Asn Thr Leu Asn Pro Glu Ala Ser Ala Ser Pro Cys Cys
    50                  55                  60

Val Pro Gln Asp Leu Glu Pro Leu Thr Ile Leu Tyr Tyr Val Gly Arg
65                  70                  75                  80

Thr Pro Lys Val Glu Gln Leu Ser Asn Met Val Val Lys Ser Cys Lys
                85                  90                  95

Cys Ser

<210> SEQ ID NO 153
<211> LENGTH: 106
<212> TYPE: PRT
<213> ORGANISM: Homo sapiens

<400> SEQUENCE: 153

Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
    50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
            100                 105

<210> SEQ ID NO 154
<211> LENGTH: 105
<212> TYPE: PRT
<213> ORGANISM: Homo sapiens

<400> SEQUENCE: 154

Cys Cys Arg Gln Gln Phe Phe Ile Asp Phe Arg Leu Ile Gly Trp Asn
1               5                   10                  15

Asp Trp Ile Ile Ala Pro Thr Gly Tyr Tyr Gly Asn Tyr Cys Glu Gly
            20                  25                  30

Ser Cys Pro Ala Tyr Leu Ala Gly Val Pro Gly Ser Ala Ser Ser Phe
        35                  40                  45

His Thr Ala Val Val Asn Gln Tyr Arg Met Arg Gly Leu Asn Pro Gly
    50                  55                  60

Thr Val Asn Ser Cys Cys Ile Pro Thr Lys Leu Ser Thr Met Ser Met
65                  70                  75                  80

Leu Tyr Phe Asp Asp Glu Tyr Asn Ile Val Lys Arg Asp Val Pro Asn
                85                  90                  95

Met Ile Val Glu Glu Cys Gly Cys Ala
            100                 105

<210> SEQ ID NO 155
<211> LENGTH: 101
<212> TYPE: PRT
<213> ORGANISM: Mus musculus
```

```
<400> SEQUENCE: 155

Cys Arg Arg Val Lys Phe Gln Val Asp Phe Asn Leu Ile Gly Trp Gly
 1               5                  10                  15

Ser Trp Ile Ile Tyr Pro Lys Gln Tyr Asn Ala Tyr Arg Cys Glu Gly
                20                  25                  30

Glu Cys Pro Asn Pro Val Gly Glu Glu Phe His Pro Thr Asn His Ala
            35                  40                  45

Tyr Ile Gln Ser Leu Leu Lys Arg Tyr Gln Pro His Arg Val Pro Ser
        50                  55                  60

Thr Cys Cys Ala Pro Val Lys Thr Lys Pro Leu Ser Met Leu Tyr Val
65                  70                  75                  80

Asp Asn Gly Arg Val Leu Leu Glu His His Lys Asp Met Ile Val Glu
                85                  90                  95

Glu Cys Gly Cys Leu
            100

<210> SEQ ID NO 156
<211> LENGTH: 101
<212> TYPE: PRT
<213> ORGANISM: Homo sapiens

<400> SEQUENCE: 156

Cys Lys Arg His Pro Leu Tyr Val Asp Phe Ser Asp Val Gly Trp Asn
 1               5                  10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

<210> SEQ ID NO 157
<211> LENGTH: 101
<212> TYPE: PRT
<213> ORGANISM: Homo sapiens

<400> SEQUENCE: 157

Cys Arg Arg His Ser Leu Tyr Val Asp Phe Ser Asp Val Gly Trp Asn
 1               5                  10                  15

Asp Trp Ile Val Ala Pro Pro Gly Tyr Gln Ala Phe Tyr Cys His Gly
                20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ile Pro Lys Ala
        50                  55                  60

Cys Cys Val Pro Thr Glu Leu Ser Ala Ile Ser Met Leu Tyr Leu Asp
65                  70                  75                  80
```

```
Glu Tyr Asp Lys Val Val Leu Lys Asn Tyr Gln Glu Met Val Val Glu
             85                  90                  95

Gly Cys Gly Cys Arg
            100

<210> SEQ ID NO 158
<211> LENGTH: 102
<212> TYPE: PRT
<213> ORGANISM: Drosophila melanogaster

<400> SEQUENCE: 158

Cys Arg Arg His Ser Leu Tyr Val Asp Phe Ser Asp Val Gly Trp Asp
  1               5                  10                  15

Asp Trp Ile Val Ala Pro Leu Gly Tyr Asp Ala Tyr Tyr Cys His Gly
             20                  25                  30

Lys Cys Pro Phe Pro Leu Ala Asp His Phe Asn Ser Thr Asn His Ala
         35                  40                  45

Val Val Gln Thr Leu Val Asn Asn Met Asn Pro Gly Lys Val Pro Lys
     50                  55                  60

Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
             85                  90                  95

Val Gly Cys Gly Cys Arg
            100

<210> SEQ ID NO 159
<211> LENGTH: 102
<212> TYPE: PRT
<213> ORGANISM: Homo sapiens

<400> SEQUENCE: 159

Cys Lys Lys His Glu Leu Tyr Val Ser Phe Arg Asp Leu Gly Trp Gln
  1               5                  10                  15

Asp Trp Ile Ile Ala Pro Glu Gly Tyr Ala Ala Phe Tyr Cys Asp Gly
             20                  25                  30

Glu Cys Ser Phe Pro Leu Asn Ala His Met Asn Ala Thr Asn His Ala
         35                  40                  45

Ile Val Gln Thr Leu Val His Leu Met Phe Pro Asp His Val Pro Lys
     50                  55                  60

Pro Cys Cys Ala Pro Thr Lys Leu Asn Ala Ile Ser Val Leu Tyr Phe
 65                  70                  75                  80

Asp Asp Ser Ser Asn Val Ile Leu Lys Lys Tyr Arg Asn Met Val Val
             85                  90                  95

Arg Ser Cys Gly Cys His
            100

<210> SEQ ID NO 160
<211> LENGTH: 102
<212> TYPE: PRT
<213> ORGANISM: Homo sapiens

<400> SEQUENCE: 160

Cys Arg Lys His Glu Leu Tyr Val Ser Phe Gln Asp Leu Gly Trp Gln
  1               5                  10                  15

Asp Trp Ile Ile Ala Pro Lys Gly Tyr Ala Ala Asn Tyr Cys Asp Gly
             20                  25                  30
```

```
Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
 50                  55                  60

Pro Cys Cys Ala Pro Thr Lys Leu Asn Ala Ile Ser Val Leu Tyr Phe
 65                  70                  75                  80

Asp Asp Asn Ser Asn Val Ile Leu Lys Lys Tyr Arg Asn Met Val Val
                85                  90                  95

Arg Ala Cys Gly Cys His
            100

<210> SEQ ID NO 161
<211> LENGTH: 102
<212> TYPE: PRT
<213> ORGANISM: Homo sapiens

<400> SEQUENCE: 161

Cys Lys Lys His Glu Leu Tyr Val Ser Phe Arg Asp Leu Gly Trp Gln
 1               5                  10                  15

Asp Trp Ile Ile Ala Pro Glu Gly Tyr Ala Ala Tyr Tyr Cys Glu Gly
                20                  25                  30

Glu Cys Ala Phe Pro Leu Asn Ser Tyr Met Asn Ala Thr Asn His Ala
        35                  40                  45

Ile Val Gln Thr Leu Val His Phe Ile Asn Pro Glu Thr Val Pro Lys
 50                  55                  60

Pro Cys Cys Ala Pro Thr Gln Leu Asn Ala Ile Ser Val Leu Tyr Phe
 65                  70                  75                  80

Asp Asp Ser Ser Asn Val Ile Leu Lys Lys Tyr Arg Asn Met Val Val
                85                  90                  95

Arg Ala Cys Gly Cys His
            100

<210> SEQ ID NO 162
<211> LENGTH: 102
<212> TYPE: PRT
<213> ORGANISM: Homo sapiens

<400> SEQUENCE: 162

Cys Arg Arg His Glu Leu Tyr Val Ser Phe Gln Asp Leu Gly Trp Leu
 1               5                  10                  15

Asp Trp Val Ile Ala Pro Gln Gly Tyr Ser Ala Tyr Tyr Cys Glu Gly
                20                  25                  30

Glu Cys Ser Phe Pro Leu Asp Ser Cys Met Asn Ala Thr Asn His Ala
        35                  40                  45

Ile Leu Gln Ser Leu Val His Leu Met Lys Pro Asn Ala Val Pro Lys
 50                  55                  60

Ala Cys Cys Ala Pro Thr Lys Leu Ser Ala Thr Ser Val Leu Tyr Tyr
 65                  70                  75                  80

Asp Ser Ser Asn Asn Val Ile Leu Arg Lys His Arg Asn Met Val Val
                85                  90                  95

Lys Ala Cys Gly Cys His
            100

<210> SEQ ID NO 163
<211> LENGTH: 102
<212> TYPE: PRT
<213> ORGANISM: Drosophila
```

```
<400> SEQUENCE: 163

Cys Gln Met Gln Thr Leu Tyr Ile Asp Phe Lys Asp Leu Gly Trp His
  1               5                  10                  15

Asp Trp Ile Ile Ala Pro Glu Gly Tyr Gly Ala Phe Tyr Cys Ser Gly
                 20                  25                  30

Glu Cys Asn Phe Pro Leu Asn Ala His Met Asn Ala Thr Asn His Ala
             35                  40                  45

Ile Val Gln Thr Leu Val His Leu Leu Glu Pro Lys Lys Val Pro Lys
         50                  55                  60

Pro Cys Cys Ala Pro Thr Arg Leu Gly Ala Leu Pro Val Leu Tyr His
 65                  70                  75                  80

Leu Asn Asp Glu Asn Val Asn Leu Lys Lys Tyr Arg Asn Met Ile Val
                 85                  90                  95

Lys Ser Cys Gly Cys His
            100

<210> SEQ ID NO 164
<211> LENGTH: 103
<212> TYPE: PRT
<213> ORGANISM: Homo sapiens

<400> SEQUENCE: 164

Cys Ala Arg Arg Tyr Leu Lys Val Asp Phe Ala Asp Ile Gly Trp Ser
  1               5                  10                  15

Glu Trp Ile Ile Ser Pro Lys Ser Phe Asp Ala Tyr Tyr Cys Ser Gly
                 20                  25                  30

Ala Cys Gln Phe Pro Met Pro Lys Ser Leu Lys Pro Ser Asn His Ala
             35                  40                  45

Thr Ile Gln Ser Ile Val Arg Ala Val Gly Val Val Pro Gly Ile Pro
         50                  55                  60

Glu Pro Cys Cys Val Pro Glu Lys Met Ser Ser Leu Ser Ile Leu Phe
 65                  70                  75                  80

Phe Asp Glu Asn Lys Asn Val Val Leu Lys Val Tyr Pro Asn Met Thr
                 85                  90                  95

Val Glu Ser Cys Ala Cys Arg
            100

<210> SEQ ID NO 165
<211> LENGTH: 102
<212> TYPE: PRT
<213> ORGANISM: Xenopus laevis

<400> SEQUENCE: 165

Cys Lys Lys Arg His Leu Tyr Val Glu Phe Lys Asp Val Gly Trp Gln
  1               5                  10                  15

Asn Trp Val Ile Ala Pro Gln Gly Tyr Met Ala Asn Tyr Cys Tyr Gly
                 20                  25                  30

Glu Cys Pro Tyr Pro Leu Thr Glu Ile Leu Asn Gly Ser Asn His Ala
             35                  40                  45

Ile Leu Gln Thr Leu Val His Ser Ile Glu Pro Glu Asp Ile Pro Leu
         50                  55                  60

Pro Cys Cys Val Pro Thr Lys Met Ser Pro Ile Ser Met Leu Phe Tyr
 65                  70                  75                  80
```

-continued

```
Asp Asn Asn Asp Asn Val Val Leu Arg His Tyr Glu Asn Met Ala Val
                 85                  90                  95

Asp Glu Cys Gly Cys Arg
            100
```

<210> SEQ ID NO 166
<211> LENGTH: 106
<212> TYPE: PRT
<213> ORGANISM: Homo sapiens

<400> SEQUENCE: 166

```
Cys Arg Ala Arg Arg Leu Tyr Val Ser Phe Arg Glu Val Gly Trp His
 1               5                  10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
        50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105
```

<210> SEQ ID NO 167
<211> LENGTH: 101
<212> TYPE: PRT
<213> ORGANISM: Mus musculus

<400> SEQUENCE: 167

```
Cys His Arg His Gln Leu Phe Ile Asn Phe Gln Asp Leu Gly Trp His
 1               5                  10                  15

Lys Trp Val Ile Ala Pro Lys Gly Phe Met Ala Asn Tyr Cys His Gly
                20                  25                  30

Glu Cys Pro Phe Ser Met Thr Thr Tyr Leu Asn Ser Ser Asn Tyr Ala
            35                  40                  45

Phe Met Gln Ala Leu Met His Met Ala Asp Pro Lys Val Pro Lys Ala
        50                  55                  60

Val Cys Val Pro Thr Lys Leu Ser Pro Ile Ser Met Leu Tyr Gln Asp
65                  70                  75                  80

Ser Asp Lys Asn Val Ile Leu Arg His Tyr Glu Asp Met Val Val Asp
                85                  90                  95

Glu Cys Gly Cys Gly
            100
```

<210> SEQ ID NO 168
<211> LENGTH: 103
<212> TYPE: PRT
<213> ORGANISM: Gallus gallus

<400> SEQUENCE: 168

```
Cys Arg Arg Thr Ser Leu His Val Asn Phe Lys Glu Ile Gly Trp Asp
 1               5                  10                  15

Ser Trp Ile Ile Ala Pro Lys Asp Tyr Glu Ala Phe Glu Cys Lys Gly
                20                  25                  30
```

```
Gly Cys Phe Phe Pro Leu Thr Asp Asn Val Thr Pro Thr Lys His Ala
            35                  40                  45

Ile Val Gln Thr Leu Val His Leu Gln Asn Pro Lys Lys Ala Ser Lys
 50                  55                  60

Ala Cys Cys Val Pro Thr Lys Leu Asp Ala Ile Ser Ile Leu Tyr Lys
 65                  70                  75                  80

Asp Asp Ala Gly Val Pro Thr Leu Ile Tyr Asn Tyr Glu Gly Met Lys
                    85                  90                  95

Val Ala Glu Cys Gly Cys Arg
                100

<210> SEQ ID NO 169
<211> LENGTH: 105
<212> TYPE: PRT
<213> ORGANISM: Homo sapiens

<400> SEQUENCE: 169

Cys His Arg Val Ala Leu Asn Ile Ser Phe Gln Glu Leu Gly Trp Glu
  1               5                  10                  15

Arg Trp Ile Val Tyr Pro Pro Ser Phe Ile Phe His Tyr Cys His Gly
                 20                  25                  30

Gly Cys Gly Leu His Ile Pro Pro Asn Leu Ser Leu Pro Val Pro Gly
            35                  40                  45

Ala Pro Pro Thr Pro Ala Gln Pro Tyr Ser Leu Leu Pro Gly Ala Gln
 50                  55                  60

Pro Cys Cys Ala Ala Leu Pro Gly Thr Met Arg Pro Leu His Val Arg
 65                  70                  75                  80

Thr Thr Ser Asp Gly Gly Tyr Ser Phe Lys Tyr Glu Thr Val Pro Asn
                    85                  90                  95

Leu Leu Thr Gln His Cys Ala Cys Ile
                100                 105

<210> SEQ ID NO 170
<211> LENGTH: 99
<212> TYPE: PRT
<213> ORGANISM: Homo sapiens

<400> SEQUENCE: 170

Cys Ala Leu Arg Glu Leu Ser Val Asp Leu Arg Ala Glu Arg Ser Val
  1               5                  10                  15

Leu Ile Pro Glu Thr Tyr Gln Ala Asn Asn Cys Gln Gly Ala Cys Gly
                 20                  25                  30

Trp Pro Gln Ser Asp Arg Asn Pro Arg Tyr Gly Asn His Val Val Leu
            35                  40                  45

Leu Leu Lys Met Gln Ala Arg Gly Ala Thr Leu Ala Arg Pro Pro Cys
 50                  55                  60

Cys Val Pro Thr Ala Tyr Thr Gly Lys Leu Leu Ile Ser Leu Ser Glu
 65                  70                  75                  80

Glu Arg Ile Ser Ala His His Val Pro Asn Met Val Ala Thr Glu Cys
                    85                  90                  95

Gly Cys Arg

<210> SEQ ID NO 171
<211> LENGTH: 102
<212> TYPE: PRT
<213> ORGANISM: Homo sapiens
```

```
<400> SEQUENCE: 171

Cys Gln Leu His Asp Phe Ser Leu Ser Phe Ser Gln Leu Lys Trp Asp
  1               5                  10                  15

Asn Trp Ile Val Ala Pro His Ser Tyr Asn Pro Ser Tyr Cys Lys Gly
                 20                  25                  30

Asp Cys Pro Ser Ala Val Ser His Arg Tyr Gly Ser Pro Val His Thr
             35                  40                  45

Met Val Gln Asn Met Ile Tyr Glu Lys Leu Asp Pro Ser Val Pro Ser
 50                  55                  60

Pro Ser Cys Val Pro Gly Lys Tyr Ser Pro Leu Ser Val Leu Thr Ile
 65                  70                  75                  80

Glu Pro Asp Gly Ser Ile Ala Tyr Lys Glu Tyr Glu Asp Met Met Ala
                 85                  90                  95

Thr Ser Cys Thr Cys Arg
                100

<210> SEQ ID NO 172
<211> LENGTH: 94
<212> TYPE: PRT
<213> ORGANISM: Homo sapiens

<400> SEQUENCE: 172

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
                 20                  25                  30

Asp Ala Ala Glu Thr Thr Tyr Asp Lys Ile Leu Lys Asn Leu Ser Arg
             35                  40                  45

Asn Arg Arg Leu Val Ser Asp Lys Val Gly Gln Ala Cys Cys Arg Pro
 50                  55                  60

Ile Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys Ile
                 85                  90

<210> SEQ ID NO 173
<211> LENGTH: 95
<212> TYPE: PRT
<213> ORGANISM: Homo sapiens

<400> SEQUENCE: 173

Cys Gly Leu Arg Glu Leu Glu Val Arg Val Ser Glu Leu Gly Leu Gly
  1               5                  10                  15

Tyr Ala Ser Asp Glu Thr Val Leu Phe Arg Tyr Cys Ala Gly Ala Cys
                 20                  25                  30

Glu Ala Ala Ala Arg Val Tyr Asp Leu Gly Leu Arg Arg Leu Arg Gln
             35                  40                  45

Arg Arg Arg Leu Arg Arg Glu Arg Val Arg Ala Gln Pro Cys Cys Arg
 50                  55                  60

Pro Thr Ala Tyr Glu Asp Glu Val Ser Phe Leu Asp Ala His Ser Arg
 65                  70                  75                  80

Tyr His Thr Val His Glu Leu Ser Ala Arg Glu Cys Ala Cys Val
                 85                  90                  95
```

```
<210> SEQ ID NO 174
<211> LENGTH: 37
<212> TYPE: PRT
<213> ORGANISM: Mus musculus

<400> SEQUENCE: 174

Leu Asp Leu Gln Glu Ala Ser Val Ala Asp Lys Leu Ser Phe Gly Lys
 1               5                  10                  15

Met Ala Glu Thr Arg Gly Thr Trp Thr Pro His Gln Gly Asn Asn His
            20                  25                  30

Val Arg Leu Pro Arg
        35

<210> SEQ ID NO 175
<211> LENGTH: 37
<212> TYPE: PRT
<213> ORGANISM: Rattus norvegicus

<400> SEQUENCE: 175

Leu Asp Leu Gln Glu Ala Pro Ala Ala Asp Glu Leu Ser Ser Gly Lys
 1               5                  10                  15

Met Ala Glu Thr Gly Arg Thr Trp Lys Pro His Gln Gly Asn Asn Asn
            20                  25                  30

Val Arg Leu Pro Arg
        35

<210> SEQ ID NO 176
<211> LENGTH: 93
<212> TYPE: PRT
<213> ORGANISM: Mus musculus

<400> SEQUENCE: 176

Cys Val Leu Thr Ala Ile His Leu Asn Val Thr Asp Leu Gly Leu Gly
 1               5                  10                  15

Tyr Glu Thr Lys Glu Glu Leu Ile Phe Arg Tyr Cys Ser Gly Ser Cys
            20                  25                  30

Glu Ser Ala Glu Thr Met Tyr Asp Lys Ile Leu Lys Asn Leu Ser Arg
        35                  40                  45

Ser Arg Arg Leu Thr Ser Asp Lys Val Gly Gln Ala Cys Cys Arg Pro
    50                  55                  60

Val Ala Phe Asp Asp Asp Leu Ser Phe Leu Asp Asp Asn Leu Val Tyr
65                  70                  75                  80

His Ile Leu Arg Lys His Ser Ala Lys Arg Cys Gly Cys
                85                  90

<210> SEQ ID NO 177
<211> LENGTH: 723
<212> TYPE: DNA
<213> ORGANISM: Mus musculus

<400> SEQUENCE: 177
atggctgcag gaagacttcg gatcctgtgt ctgctgctcc tgtccttgca cccgagcctc      60
ggctgggtcc ttgatcttca agaggcttct gtggcagata agctctcatt tgggaagatg    120
gcagagactc gagggacctg gacgccccat cagggtaaga attcctgggg gcctcccgac    180
tccccaattc cttctctcaa agccctcatc ttgccttaca atcctactct accttgcact    240
aggtaacaac catgtccgtc ttccaagacg cttggctggt tcatgccgac tgtgagcct    300 gaccctacca gtggctgagc tgggcctggg ctatgcctcg gaggagaagg tcatcttccg    360
```

```
atactgtgct ggcagctgtc cccaagaggc ccgtacccag cacagtctgg tactggcccg      420
gcttcgaggg cggggtcgag cccatggccg accctgctgc cagcccacca gctatgctga      480
tgtgaccttc cttgatgatc agcaccattg gcagcagctg cctcagctct cagctgcagc      540
ttgtggctgt ggtggctgaa ggaggccagt ctggtgtctc agaatcacaa gcatgagaca      600
ggctgggctt tgaaaggctc aggtgacatt actagaaatt tgcataggta aagataagaa      660
gggaaaggac caggggtttt ttgtttcttt ctttgcttgc ttgttagttt ttttttttt      720 ttt                                                                    723
```

<210> SEQ ID NO 178
<211> LENGTH: 723
<212> TYPE: DNA
<213> ORGANISM: Mus musculus

<400> SEQUENCE: 178

```
aaaaaaaaaa aaaaaactaa caagcaagca aagaaagaaa caaaaaaccc ctggtccttt       60
cccttcttat ctttacctat gcaaatttct agtaatgtca cctgagcctt tcaaagccca      120
gcctgtctca tgcttgtgat tctgagacac cagactggcc tccttcagcc accacagcca      180
caagctgcag ctgagagctg aggcagctgc tgccaatggt gctgatcatc aaggaaggtc      240
acatcagcat agctggtggg ctggcagcag ggtcggccat gggctcgacc cgcccctcga      300
agccgggcca gtaccagact gtgctgggta cgggcctctt ggggacagct gccagcacag      360
tatcggaaga tgaccttctc ctccgaggca tagcccaggc ccagctcagc cactggtagg      420
gtcaggctcc acagtcggca tgaaccagcc aaggctcttg aagacggac atggttgtta      480 cctagtgcaa ggtagagtag gattgtaagg caaagtgagg gctttgagag aaggaattgg      540
ggagtcggga ggcccccagg aattcttacc ctgatggggc gtccaggtcc ctctagtctc      600
tgccatcttc ccaaatgaga gcttatctgc cacagaagcc tcttgaagat caaggaccca      660
gccgaggctc gggtgcaagg acaggagcag cagacacagg atccgaagtc ttcctgcagc      720
cat                                                                    723
```

<210> SEQ ID NO 179
<211> LENGTH: 471
<212> TYPE: DNA
<213> ORGANISM: Mus musculus

<400> SEQUENCE: 179

```
atggctgcag gaagacttcg gatcctgtgt ctgctgctcc tgtccttgca cccgagcctc       60
ggctgggtcc ttgatcttca agaggcttct gtggcagata gctctcatt tgggaagatg      120 gcagagacta gagggacctg gacgccccat cagggtaaca accatgtccg tcttccaaga      180
gccttggctg ttcatgccg actgtggagc ctgaccctac cagtggctga gctgggcctg      240
ggctatgcct cggaggagaa ggtcatcttc cgatactgtg ctggcagctg tccccaagag      300
gcccgtaccc agcacagtct ggtactggcc cggcttcgag ggcggggtcg agcccatggc      360
cgaccctgct gccagcccac cagctatgct gatgtgacct tccttgatga tcagcaccat      420
tggcagcagc tgcctcagct ctcagctgca gcttgtggct gtggtggctg a             471
```

<210> SEQ ID NO 180
<211> LENGTH: 471
<212> TYPE: DNA
<213> ORGANISM: Mus musculus -continued

```
<400> SEQUENCE: 180
tcagccacca cagccacaag ctgcagctga gagctgaggc agctgctgcc aatggtgctg      60
atcatcaagg aaggtcacat cagcatagct ggtgggctgg cagcagggtc ggccatgggc     120
tcgaccccgc cctcgaagcc gggccagtac cagactgtgc tgggtacggg cctcttgggg     180
acagctgcca gcacagtatc ggaagatgac cttctcctcc gaggcatagc ccaggcccag     240
ctcagccact ggtagggtca ggctccacag tcggcatgaa ccagccaagg ctcttggaag     300
acggacatgg ttgttaccct gatggggcgt ccaggtccct ctagtctctg ccatcttccc     360
aaatgagagc ttatctgcca cagaagcctc ttgaagatca aggacccagc cgaggctcgg     420
gtgcaaggac aggagcagca gacacaggat ccgaagtctt cctgcagcca t             471

<210> SEQ ID NO 181
<211> LENGTH: 180
<212> TYPE: DNA
<213> ORGANISM: Mus musculus

<400> SEQUENCE: 181
atggctgcag gaagacttcg gatcctgtgt ctgctgctcc tgtccttgca cccgagcctc      60
ggctgggtcc ttgatcttca agaggcttct gtggcagata agctctcatt tgggaagatg     120
gcagagacta gagggacctg gacgccccat cagggtaaca accatgtccg tcttccaaga     180

<210> SEQ ID NO 182
<211> LENGTH: 180
<212> TYPE: DNA
<213> ORGANISM: Mus musculus

<400> SEQUENCE: 182
tcttggaaga cggacatggt tgttaccctg atggggcgtc caggtccctc tagtctctgc      60
catcttccca aatgagagct tatctgccac agaagcctct tgaagatcaa ggacccagcc     120
gaggctcggg tgcaaggaca ggagcagcag acacaggatc cgaagtcttc ctgcagccat     180

<210> SEQ ID NO 183
<211> LENGTH: 291
<212> TYPE: DNA
<213> ORGANISM: Mus musculus

<400> SEQUENCE: 183
gccttggctg gttcatgccg actgtggagc ctgaccctac cagtggctga gctgggcctg      60
ggctatgcct cggaggagaa ggtcatcttc cgatactgtg ctggcagctg tccccaagag     120
gcccgtaccc agcacagtct ggtactggcc cggcttcgag ggcggggtcg agcccatggc     180
cgaccctgct gccagcccac cagctatgct gatgtgacct tccttgatga tcagcaccat     240
tggcagcagc tgcctcagct ctcagctgca gcttgtggct gtggtggctg a              291

<210> SEQ ID NO 184
<211> LENGTH: 291
<212> TYPE: DNA
<213> ORGANISM: Mus musculus

<400> SEQUENCE: 184
tcagccacca cagccacaag ctgcagctga gagctgaggc agctgctgcc aatggtgctg      60
atcatcaagg aaggtcacat cagcatagct ggtgggctgg cagcagggtc ggccatgggc     120
tcgaccccgc cctcgaagcc gggccagtac cagactgtgc tgggtacggg cctcttgggg     180
```

```
acagctgcca gcacagtatc ggaagatgac cttctcctcc gaggcatagc ccaggcccag    240
ctcagccact ggtagggtca ggctccacag tcggcatgaa ccagccaagg c             291
```

<210> SEQ ID NO 185
<211> LENGTH: 156
<212> TYPE: PRT
<213> ORGANISM: Mus musculus

<400> SEQUENCE: 185

```
Met Ala Ala Gly Arg Leu Arg Ile Leu Cys Leu Leu Leu Ser Leu
 1               5                  10                  15

His Pro Ser Leu Gly Trp Val Leu Asp Leu Gln Glu Ala Ser Val Ala
                 20                  25                  30

Asp Lys Leu Ser Phe Gly Lys Met Ala Glu Thr Arg Gly Thr Trp Thr
             35                  40                  45

Pro His Gln Gly Asn Asn His Val Arg Leu Pro Arg Ala Leu Ala Gly
         50                  55                  60

Ser Cys Arg Leu Trp Ser Leu Thr Leu Pro Val Ala Glu Leu Gly Leu
 65                  70                  75                  80

Gly Tyr Ala Ser Glu Glu Lys Val Ile Phe Arg Tyr Cys Ala Gly Ser
                 85                  90                  95

Cys Pro Gln Glu Ala Arg Thr Gln His Ser Leu Val Leu Ala Arg Leu
            100                 105                 110

Arg Gly Arg Gly Arg Ala His Gly Arg Pro Cys Cys Gln Pro Thr Ser
        115                 120                 125

Tyr Ala Asp Val Thr Phe Leu Asp Asp Gln His His Trp Gln Gln Leu
    130                 135                 140

Pro Gln Leu Ser Ala Ala Ala Cys Gly Cys Gly Gly
145                 150                 155
```

<210> SEQ ID NO 186
<211> LENGTH: 60
<212> TYPE: PRT
<213> ORGANISM: Mus musculus

<400> SEQUENCE: 186

```
Met Ala Ala Gly Arg Leu Arg Ile Leu Cys Leu Leu Leu Ser Leu
 1               5                  10                  15

His Pro Ser Leu Gly Trp Val Leu Asp Leu Gln Glu Ala Ser Val Ala
                 20                  25                  30

Asp Lys Leu Ser Phe Gly Lys Met Ala Glu Thr Arg Gly Thr Trp Thr
             35                  40                  45

Pro His Gln Gly Asn Asn His Val Arg Leu Pro Arg
         50                  55                  60
```

<210> SEQ ID NO 187
<211> LENGTH: 96
<212> TYPE: PRT
<213> ORGANISM: Mus musculus

<400> SEQUENCE: 187

```
Ala Leu Ala Gly Ser Cys Arg Leu Trp Ser Leu Thr Leu Pro Val Ala
 1               5                  10                  15

Glu Leu Gly Leu Gly Tyr Ala Ser Glu Glu Lys Val Ile Phe Arg Tyr
                 20                  25                  30

Cys Ala Gly Ser Cys Pro Gln Glu Ala Arg Thr Gln His Ser Leu Val
             35                  40                  45
```

```
Leu Ala Arg Leu Arg Gly Arg Gly Arg Ala His Gly Arg Pro Cys Cys
 50                  55                  60

Gln Pro Thr Ser Tyr Ala Asp Val Thr Phe Leu Asp Asp Gln His His
 65                  70                  75                  80

Trp Gln Gln Leu Pro Gln Leu Ser Ala Ala Ala Cys Gly Cys Gly Gly
                 85                  90                  95

<210> SEQ ID NO 188
<211> LENGTH: 559
<212> TYPE: DNA
<213> ORGANISM: Rattus norvegicus

<400> SEQUENCE: 188
atggctgcag aagacttcg gatcttgttt ctgctgctcc tgtccttgca cctgggcctt        60
ggctgggtcc ttgatcttca agaggctcct gcggcagatg agctctcatc tgggaaaatg       120
gcagagactg aaggacctg gaagccccat cagggtaaga attcttgggg gcctcctaac        180
tctacagttc ttcctctcaa agccctcact ttgcctcaca atcctattct accttgcact       240
aggtaacaac aatgtccgcc ttccaagagc cttacctggt tgtgccggc tgtggagcct       300 gaccctacca gtggctgagc ttggcctggg ctatgcctca gaggagaaga ttatcttccg       360
atactgtgct ggcagctgtc cccaagaggt ccgtacccag cacagtctgg tgctggcccg       420
tcttcgaggg cagggtcgag ctcatggcag accttgctgc cagcccacca gctatgctga       480
tgtgaccttc cttgatgacc accaccattg gcagcagctg cctcagctct cagccgcagc       540
ttgtggctgt ggtggctga                                                  559

<210> SEQ ID NO 189
<211> LENGTH: 559
<212> TYPE: DNA
<213> ORGANISM: Rattus norvegicus

<400> SEQUENCE: 189
tcagccacca cagccacaag ctgcggctga gagctgaggc agctgctgcc aatggtggtg        60
gtcatcaagg aaggtcacat cagcatagct ggtgggctgg cagcaaggtc tgccatgagc       120
tcgaccctgc cctcgaagac gggccagcac cagactgtgc tgggtacgga cctcttgggg       180
acagctgcca gcacagtatc ggaagataat cttctcctct gaggcatagc ccaggccaag       240
ctcagccact ggtagggtca ggctccacag ccggcacaaa ccaggtaagg ctcttggaag       300
gcggacattg ttgttaccta gtgcaaggta aataggatt gtgaggcaaa gtgagggctt       360
tgagaggaag aactgtagag ttaggaggcc cccaagaatt cttaccctga tggggcttcc       420
aggtccttcc agtctctgcc attttcccag atgagagctc atctgccgca ggagcctctt       480
gaagatcaag gacccagcca aggccagggt gcaaggacag gagcagcaga aacaagatcc       540
gaagtcttcc tgcagccat                                                  559

<210> SEQ ID NO 190
<211> LENGTH: 471
<212> TYPE: DNA
<213> ORGANISM: Rattus norvegicus

<400> SEQUENCE: 190
atggctgcag aagacttcg gatcttgttt ctgctgctcc tgtccttgca cctgggcctt        60
ggctgggtcc ttgatcttca agaggctcct gcggcagatg agctctcatc tgggaaaatg       120
gcagagactg aaggacctg gaagccccat cagggtaaca acaatgtccg ccttccaaga       180
```

```
gccttacctg gtttgtgccg gctgtggagc ctgaccctac cagtggctga gcttggcctg    240
ggctatgcct cagaggagaa gattatcttc cgatactgtg ctggcagctg tccccaagag    300
gtccgtaccc agcacagtct ggtgctggcc cgtcttcgag ggcagggtcg agctcatggc    360
agaccttgct gccagcccac cagctatgct gatgtgacct tccttgatga ccaccaccat    420
tggcagcagc tgcctcagct ctcagccgca gcttgtggct gtggtggctg a             471
```

<210> SEQ ID NO 191
<211> LENGTH: 471
<212> TYPE: DNA
<213> ORGANISM: Rattus norvegicus

<400> SEQUENCE: 191

```
tcagccacca cagccacaag ctgcggctga gagctgaggc agctgctgcc aatggtggtg    60
gtcatcaagg aaggtcacat cagcatagct ggtgggctgg cagcaaggtc tgccatgagc    120
tcgaccctgc cctcgaagac gggccagcac cagactgtgc tgggtacgga cctcttgggg    180
acagctgcca gcacagtatc ggaagataat cttctcctct gaggcatagc ccaggccaag    240
ctcagccact ggtagggtca ggctccacag ccggcacaaa ccaggtaagg ctcttggaag    300
gcggacattg ttgttaccct gatggggctt ccaggtcctt ccagtctctg ccattttccc    360
agatgagagc tcatctgccg caggagcctc ttgaagatca aggacccagc caaggcccag    420
gtgcaaggac aggagcagca gaaacaagat ccgaagtctt cctgcagcca t             471
```

<210> SEQ ID NO 192
<211> LENGTH: 180
<212> TYPE: DNA
<213> ORGANISM: Rattus norvegicus

<400> SEQUENCE: 192

```
atggctgcag gaagacttcg gatcttgttt ctgctgctcc tgtccttgca cctgggcctt    60
ggctgggtcc ttgatcttca agaggctcct gcggcagatg agctctcatc tgggaaaatg    120
gcagagactg gaaggacctg gaagccccat cagggtaaca acaatgtccg ccttccaaga    180
```

<210> SEQ ID NO 193
<211> LENGTH: 180
<212> TYPE: DNA
<213> ORGANISM: Rattus norvegicus

<400> SEQUENCE: 193

```
tcttggaagg cggacattgt tgttaccctg atggggcttc caggtccttc cagtctctgc    60
cattttccca gatgagagct catctgccgc aggagcctct tgaagatcaa ggacccagcc    120
aaggcccagg tgcaaggaca ggagcagcag aaacaagatc cgaagtcttc ctgcagccat    180
```

<210> SEQ ID NO 194
<211> LENGTH: 291
<212> TYPE: DNA
<213> ORGANISM: Rattus norvegicus

<400> SEQUENCE: 194

```
gccttacctg gtttgtgccg gctgtggagc ctgaccctac cagtggctga gcttggcctg    60
ggctatgcct cagaggagaa gattatcttc cgatactgtg ctggcagctg tccccaagag    120
gtccgtaccc agcacagtct ggtgctggcc cgtcttcgag ggcagggtcg agctcatggc    180
agaccttgct gccagcccac cagctatgct gatgtgacct tccttgatga ccaccaccat    240
tggcagcagc tgcctcagct ctcagccgca gcttgtggct gtggtggctg a             291
```

<210> SEQ ID NO 195
<211> LENGTH: 291
<212> TYPE: DNA
<213> ORGANISM: Rattus norvegicus

<400> SEQUENCE: 195

```
tcagccacca cagccacaag ctgcggctga gagctgaggc agctgctgcc aatggtggtg      60
gtcatcaagg aaggtcacat cagcatagct ggtgggctgg cagcaaggtc tgccatgagc     120
tcgaccctgc cctcgaagac gggccagcac cagactgtgc tgggtacgga cctcttgggg     180
acagctgcca gcacagtatc ggaagataat cttctcctct gaggcatagc ccaggccaag     240
ctcagccact ggtagggtca ggctccacag ccggcacaaa ccaggtaagg c              291
```

<210> SEQ ID NO 196
<211> LENGTH: 156
<212> TYPE: PRT
<213> ORGANISM: Rattus norvegicus

<400> SEQUENCE: 196

```
Met Ala Ala Gly Arg Leu Arg Ile Leu Phe Leu Leu Leu Leu Ser Leu
 1               5                  10                  15

His Leu Gly Leu Gly Trp Val Leu Asp Leu Gln Glu Ala Pro Ala Ala
            20                  25                  30

Asp Glu Leu Ser Ser Gly Lys Met Ala Glu Thr Gly Arg Thr Trp Lys
        35                  40                  45

Pro His Gln Gly Asn Asn Asn Val Arg Leu Pro Arg Ala Leu Pro Gly
    50                  55                  60

Leu Cys Arg Leu Trp Ser Leu Thr Leu Pro Val Ala Glu Leu Gly Leu
65                  70                  75                  80

Gly Tyr Ala Ser Glu Glu Lys Ile Ile Phe Arg Tyr Cys Ala Gly Ser
                85                  90                  95

Cys Pro Gln Glu Val Arg Thr Gln His Ser Leu Val Leu Ala Arg Leu
            100                 105                 110

Arg Gly Gln Gly Arg Ala His Gly Arg Pro Cys Cys Gln Pro Thr Ser
        115                 120                 125

Tyr Ala Asp Val Thr Phe Leu Asp Asp His His Trp Gln Gln Leu
    130                 135                 140

Pro Gln Leu Ser Ala Ala Ala Cys Gly Cys Gly Gly
145                 150                 155
```

<210> SEQ ID NO 197
<211> LENGTH: 60
<212> TYPE: PRT
<213> ORGANISM: Rattus norvegicus

<400> SEQUENCE: 197

```
Met Ala Ala Gly Arg Leu Arg Ile Leu Phe Leu Leu Leu Leu Ser Leu
 1               5                  10                  15

His Leu Gly Leu Gly Trp Val Leu Asp Leu Gln Glu Ala Pro Ala Ala
            20                  25                  30

Asp Glu Leu Ser Ser Gly Lys Met Ala Glu Thr Gly Arg Thr Trp Lys
        35                  40                  45

Pro His Gln Gly Asn Asn Asn Val Arg Leu Pro Arg
    50                  55                  60
```

```
<210> SEQ ID NO 198
<211> LENGTH: 96
<212> TYPE: PRT
<213> ORGANISM: Rattus norvegicus

<400> SEQUENCE: 198

Ala Leu Pro Gly Leu Cys Arg Leu Trp Ser Leu Thr Leu Pro Val Ala
 1               5                  10                  15

Glu Leu Gly Leu Gly Tyr Ala Ser Glu Glu Lys Ile Ile Phe Arg Tyr
                20                  25                  30

Cys Ala Gly Ser Cys Pro Gln Glu Val Arg Thr Gln His Ser Leu Val
            35                  40                  45

Leu Ala Arg Leu Arg Gly Gln Gly Arg Ala His Gly Arg Pro Cys Cys
        50                  55                  60

Gln Pro Thr Ser Tyr Ala Asp Val Thr Phe Leu Asp Asp His His His
65                  70                  75                  80

Trp Gln Gln Leu Pro Gln Leu Ser Ala Ala Cys Gly Cys Gly Gly
                85                  90                  95

<210> SEQ ID NO 199
<211> LENGTH: 291
<212> TYPE: DNA
<213> ORGANISM: Homo sapiens

<400> SEQUENCE: 199
gccctgtctg gtccatgcca gctgtggagc ctgaccctgt ccgtggcaga gctaggcctg      60
ggctacgcct cagaggagaa ggtcatcttc cgctactgcg ccggcagctg ccccgtggt     120 gcccgcaccc agcatggcct ggcgctggcc cggctgcagg gccagggccg agcccacggt    180
gggccctgct gccggcccac tcgctacacc gacgtggcct cctcgatga ccgccaccgc     240 tggcagcggc tgccccagct ctcggcggct gcctgcggct  gtggtggctg a             291

<210> SEQ ID NO 200
<211> LENGTH: 291
<212> TYPE: DNA
<213> ORGANISM: Homo sapiens

<400> SEQUENCE: 200
tcagccacca cagccgcagg cagccgccga gagctggggc agccgctgcc agcggtggcg     60
gtcatcgagg aaggccacgt cggtgtagcg agtgggccgg cagcagggcc caccgtgggc    120
tcggccctgg ccctgcagcc gggccagcgc caggccatgc tgggtgcggg caccacgggg    180
gcagctgccg gcgcagtagc ggaagatgac cttctcctct gaggcgtagc ccaggcctag    240
ctctgccacg gacagggtca ggctccacag ctggcatgga ccagacaggg c             291

<210> SEQ ID NO 201
<211> LENGTH: 291
<212> TYPE: DNA
<213> ORGANISM: Homo sapiens

<400> SEQUENCE: 201
gccctgtctg gtccatgcca gctgtggagc ctgaccctgt ccgtggcaga gctaggcctg      60
ggctacgcct cagaggagaa ggtcatcttc cgctactgcg ccggcagctg ccccgtggt     120 gcccgcaccc agcatggcct ggcgctggcc cggctgcagg gccagggccg agcccacggc    180
gggccctgct gccggcccac tcgctacacc gacgtggcct cctcgatga ccgccaccgc     240 tggcagcggc tgccccagct ctcggcggct gcctgcggct gtggtggctg a              291
```

<210> SEQ ID NO 202
<211> LENGTH: 291
<212> TYPE: DNA
<213> ORGANISM: Homo sapiens

<400> SEQUENCE: 202

| | | | | | |
|---|---|---|---|---|---|
| tcagccacca | cagccgcagg | cagccgccga | gagctggggc | agccgctgcc | agcggtggcg | 60 |
| gtcatcgagg | aaggccacgt | cggtgtagcg | agtgggccgg | cagcagggcc | cgccgtgggc | 120 |
| tcggccctgg | ccctgcagcc | gggccagcgc | caggccatgc | tgggtgcggg | caccacgggg | 180 |
| gcagctgccg | gcgcagtagc | ggaagatgac | cttctcctct | gaggcgtagc | ccaggcctag | 240 |
| ctctgccacg | gacagggtca | ggctccacag | ctggcatgga | ccagacaggg | c | 291 |

<210> SEQ ID NO 203
<211> LENGTH: 471
<212> TYPE: DNA
<213> ORGANISM: Homo sapiens

<400> SEQUENCE: 203

| | | | | | |
|---|---|---|---|---|---|
| atggccgtag | ggaagttcct | gctgggctct | ctgctgctcc | tgtccctgca | gctgggacag | 60 |
| ggctggggcc | ccgatgcccg | tggggttccc | gtggccgatg | gagagttctc | gtctgaacag | 120 |
| gtggcaaagg | ctggagggac | ctggctgggc | acccaccgcc | cccttgcccg | cctgcgccga | 180 |
| gccctgtctg | gtccatgcca | gctgtggagc | ctgaccctgt | ccgtggcaga | gctaggcctg | 240 |
| ggctacgcct | cagaggagaa | ggtcatcttc | cgctactgcg | ccggcagctg | ccccgtggt | 300 |
| gcccgcaccc | agcatggcct | ggcgctggcc | cggctgcagg | gccagggccg | agcccacggt | 360 |
| gggccctgct | ccggcccac | tcgctacacc | gacgtggcct | tcctcgatga | ccgccaccgc | 420 |
| tggcagcggc | tgcccagct | ctcggcggct | gcctgcggct | gtggtggctg | a | 471 |

<210> SEQ ID NO 204
<211> LENGTH: 471
<212> TYPE: DNA
<213> ORGANISM: Homo sapiens

<400> SEQUENCE: 204

| | | | | | |
|---|---|---|---|---|---|
| tcagccacca | cagccgcagg | cagccgccga | gagctggggc | agccgctgcc | agcggtggcg | 60 |
| gtcatcgagg | aaggccacgt | cggtgtagcg | agtgggccgg | cagcagggcc | caccgtgggc | 120 |
| tcggccctgg | ccctgcagcc | gggccagcgc | caggccatgc | tgggtgcggg | caccacgggg | 180 |
| gcagctgccg | gcgcagtagc | ggaagatgac | cttctcctct | gaggcgtagc | ccaggcctag | 240 |
| ctctgccacg | gacagggtca | ggctccacag | ctggcatgga | ccagacaggg | ctcggcgcag | 300 |
| gcgggcaagg | gggcggtggg | tgcccagcca | ggtccctcca | gcctttgcca | cctgttcaga | 360 |
| cgagaactct | ccatcggcca | cgggaacccc | acgggcatcg | ggccccagc | cctgtcccag | 420 |
| ctgcagggac | aggagcagca | gagagcccag | caggaacttc | cctacggcca | t | 471 |

<210> SEQ ID NO 205
<211> LENGTH: 471
<212> TYPE: DNA
<213> ORGANISM: Homo sapiens

<400> SEQUENCE: 205

| | | | | | |
|---|---|---|---|---|---|
| atggccgtag | ggaagttcct | gctgggctcc | ctgctgctcc | tgtccctgca | gctgggacag | 60 |
| ggctggggcc | ccgatgcccg | tggggttccc | gtggccgatg | gagagttctc | gtctgaacag | 120 |
| gtggcaaagg | ctggagggac | ctggctgggc | acccaccgcc | cccttgcccg | cctgcgccga | 180 |

```
gccctgtctg gtccatgcca gctgtggagc ctgaccctgt ccgtggcaga gctaggcctg    240
ggctacgcct cagaggagaa ggtcatcttc cgctactgcg ccggcagctg ccccgtggt     300 gcccgcaccc agcatggcct ggcgctggcc cggctgcagg gccagggccg agcccacggc    360
gggccctgct gccggcccac tcgctacacc gacgtggcct tcctcgatga ccgccaccgc    420
tggcagcggc tgccccagct ctcggcggct gcctgcggct gtggtggctg a             471
```

<210> SEQ ID NO 206
<211> LENGTH: 471
<212> TYPE: DNA
<213> ORGANISM: Homo sapiens

<400> SEQUENCE: 206

```
tcagccacca cagccgcagg cagccgccga gagctggggc agccgctgcc agcggtggcg    60
gtcatcgagg aaggccacgt cggtgtagcg agtgggccgg cagcagggcc cgccgtgggc    120
tcggccctgg ccctgcagcc gggccagcgc caggccatgc tgggtgcggg caccacgggg   180
gcagctgccg cgcagtagc ggaagatgac cttctcctct gaggcgtagc ccaggcctag    240
ctctgccacg gacagggtca ggctccacag ctggcatgga ccagacaggg ctcggcgcag   300
gcgggcaagg gggcggtggg tgcccagcca ggtccctcca gcctttgcca cctgttcaga   360
cgagaactct ccatcggcca cgggaacccc acgggcatcg ggccccagc cctgtcccag    420 ctgcagggac aggagcagca gggagcccag caggaacttc cctacggcca t             471
```

<210> SEQ ID NO 207
<211> LENGTH: 69
<212> TYPE: DNA
<213> ORGANISM: Homo sapiens

<400> SEQUENCE: 207

```
atggccgtag ggaagttcct gctgggctct ctgctgctcc tgtccctgca gctgggacag   60
ggctggggc                                                            69
```

<210> SEQ ID NO 208
<211> LENGTH: 69
<212> TYPE: DNA
<213> ORGANISM: Homo sapiens

<400> SEQUENCE: 208

```
gccccagccc tgtcccagct gcagggacag gagcagcaga gagcccagca ggaacttccc   60
tacggccat                                                            69
```

<210> SEQ ID NO 209
<211> LENGTH: 69
<212> TYPE: DNA
<213> ORGANISM: Homo sapiens

<400> SEQUENCE: 209

```
atggccgtag ggaagttcct gctgggctcc ctgctgctcc tgtccctgca gctgggacag   60
ggctggggc                                                            69
```

<210> SEQ ID NO 210
<211> LENGTH: 69
<212> TYPE: DNA
<213> ORGANISM: Homo sapiens

<400> SEQUENCE: 210

```
gccccagccc tgtcccagct gcagggacag gagcagcagg gagcccagca ggaacttccc      60
tacggccat                                                              69
```

<210> SEQ ID NO 211
<211> LENGTH: 111
<212> TYPE: DNA
<213> ORGANISM: Homo sapiens

<400> SEQUENCE: 211

```
cccgatgccc gtggggttcc cgtggccgat ggagagttct cgtctgaaca ggtggcaaag      60
gctggaggga cctggctggg cacccaccgc cccttgccc gcctgcgccg a               111
```

<210> SEQ ID NO 212
<211> LENGTH: 111
<212> TYPE: DNA
<213> ORGANISM: Homo sapiens

<400> SEQUENCE: 212

```
tcggcgcagg cgggcaaggg ggcggtgggt gcccagccag gtccctccag cctttgccac      60
ctgttcagac gagaactctc catcggccac gggaacccca cgggcatcgg g              111
```

<210> SEQ ID NO 213
<211> LENGTH: 180
<212> TYPE: DNA
<213> ORGANISM: Homo sapiens

<400> SEQUENCE: 213

```
atggccgtag ggaagttcct gctgggctct ctgctgctcc tgtccctgca gctgggacag      60
ggctggggcc ccgatgcccg tggggttccc gtggccgatg gagagttctc gtctgaacag     120
gtggcaaagg ctggagggac ctggctgggc acccaccgcc cccttgcccg cctgcgccga     180
```

<210> SEQ ID NO 214
<211> LENGTH: 180
<212> TYPE: DNA
<213> ORGANISM: Homo sapiens

<400> SEQUENCE: 214

```
tcggcgcagg cgggcaaggg ggcggtgggt gcccagccag gtccctccag cctttgccac      60
ctgttcagac gagaactctc catcggccac gggaacccca cgggcatcgg ggccccagcc     120
ctgtcccagc tgcagggaca ggagcagcag agagcccagc aggaacttcc ctacggccat     180
```

<210> SEQ ID NO 215
<211> LENGTH: 180
<212> TYPE: DNA
<213> ORGANISM: Homo sapiens

<400> SEQUENCE: 215

```
atggccgtag ggaagttcct gctgggctcc ctgctgctcc tgtccctgca gctgggacag      60
ggctggggcc ccgatgcccg tggggttccc gtggccgatg gagagttctc gtctgaacag     120
gtggcaaagg ctggagggac ctggctgggc acccaccgcc cccttgcccg cctgcgccga     180
```

<210> SEQ ID NO 216
<211> LENGTH: 180
<212> TYPE: DNA
<213> ORGANISM: Homo sapiens

<400> SEQUENCE: 216

```
tcggcgcagg cgggcaaggg ggcggtgggt gcccagccag gtccctccag cctttgccac      60
ctgttcagac gagaactctc catcggccac gggaacccca cgggcatcgg ggccccagcc     120
ctgtcccagc tgcagggaca ggagcagcag ggagcccagc aggaacttcc ctacggccat     180
```

<210> SEQ ID NO 217
<211> LENGTH: 156
<212> TYPE: PRT
<213> ORGANISM: Homo sapiens

<400> SEQUENCE: 217

```
Met Ala Val Gly Lys Phe Leu Leu Gly Ser Leu Leu Leu Ser Leu
  1               5                  10                  15

Gln Leu Gly Gln Gly Trp Gly Pro Asp Ala Arg Gly Val Pro Val Ala
             20                  25                  30

Asp Gly Glu Phe Ser Ser Glu Gln Val Ala Lys Ala Gly Gly Thr Trp
         35                  40                  45

Leu Gly Thr His Arg Pro Leu Ala Arg Leu Arg Arg Ala Leu Ser Gly
     50                  55                  60

Pro Cys Gln Leu Trp Ser Leu Thr Leu Ser Val Ala Glu Leu Gly Leu
 65                  70                  75                  80

Gly Tyr Ala Ser Glu Glu Lys Val Ile Phe Arg Tyr Cys Ala Gly Ser
                 85                  90                  95

Cys Pro Arg Gly Ala Arg Thr Gln His Gly Leu Ala Leu Ala Arg Leu
            100                 105                 110

Gln Gly Gln Gly Arg Ala His Gly Gly Pro Cys Cys Arg Pro Thr Arg
        115                 120                 125

Tyr Thr Asp Val Ala Phe Leu Asp Asp Arg His Arg Trp Gln Arg Leu
    130                 135                 140

Pro Gln Leu Ser Ala Ala Ala Cys Gly Cys Gly Gly
145                 150                 155
```

<210> SEQ ID NO 218
<211> LENGTH: 60
<212> TYPE: PRT
<213> ORGANISM: Homo sapiens

<400> SEQUENCE: 218

```
Met Ala Val Gly Lys Phe Leu Leu Gly Ser Leu Leu Leu Ser Leu
  1               5                  10                  15

Gln Leu Gly Gln Gly Trp Gly Pro Asp Ala Arg Gly Val Pro Val Ala
             20                  25                  30

Asp Gly Glu Phe Ser Ser Glu Gln Val Ala Lys Ala Gly Gly Thr Trp
         35                  40                  45

Leu Gly Thr His Arg Pro Leu Ala Arg Leu Arg Arg
     50                  55                  60
```

<210> SEQ ID NO 219
<211> LENGTH: 23
<212> TYPE: PRT
<213> ORGANISM: Homo sapiens

<400> SEQUENCE: 219

```
Met Ala Val Gly Lys Phe Leu Leu Gly Ser Leu Leu Leu Ser Leu
  1               5                  10                  15

Gln Leu Gly Gln Gly Trp Gly
             20
```

```
<210> SEQ ID NO 220
<211> LENGTH: 37
<212> TYPE: PRT
<213> ORGANISM: Homo sapiens

<400> SEQUENCE: 220

Pro Asp Ala Arg Gly Val Pro Val Ala Asp Gly Glu Phe Ser Ser Glu
1               5                   10                  15

Gln Val Ala Lys Ala Gly Gly Thr Trp Leu Gly Thr His Arg Pro Leu
            20                  25                  30

Ala Arg Leu Arg Arg
        35

<210> SEQ ID NO 221
<211> LENGTH: 96
<212> TYPE: PRT
<213> ORGANISM: Homo sapiens

<400> SEQUENCE: 221

Ala Leu Ser Gly Pro Cys Gln Leu Trp Ser Leu Thr Leu Ser Val Ala
1               5                   10                  15

Glu Leu Gly Leu Gly Tyr Ala Ser Glu Glu Lys Val Ile Phe Arg Tyr
            20                  25                  30

Cys Ala Gly Ser Cys Pro Arg Gly Ala Arg Thr Gln His Gly Leu Ala
        35                  40                  45

Leu Ala Arg Leu Gln Gly Gln Gly Arg Ala His Gly Gly Pro Cys Cys
    50                  55                  60

Arg Pro Thr Arg Tyr Thr Asp Val Ala Phe Leu Asp Asp Arg His Arg
65                  70                  75                  80

Trp Gln Arg Leu Pro Gln Leu Ser Ala Ala Ala Cys Gly Cys Gly Gly
                85                  90                  95

<210> SEQ ID NO 222
<211> LENGTH: 267
<212> TYPE: DNA
<213> ORGANISM: Homo sapiens

<400> SEQUENCE: 222
tgccagctgt ggagcctgac cctgtccgtg gcagagctag gcctgggcta cgcctcagag     60
gagaaggtca tcttccgcta ctgcgccggc agctgccccc gtggtgcccg cacccagcat    120
ggcctggcgc tggcccggct gcagggccag ggccgagccc acggtgggcc ctgctgccgg    180
cccactcgct acaccgacgt ggccttcctc gatgaccgcc accgctggca gcggctgccc    240
cagctctcgg cggctgcctg cggctgt                                         267

<210> SEQ ID NO 223
<211> LENGTH: 89
<212> TYPE: PRT
<213> ORGANISM: Homo sapiens

<400> SEQUENCE: 223

Cys Gln Leu Trp Ser Leu Thr Leu Ser Val Ala Glu Leu Gly Leu Gly
1               5                   10                  15

Tyr Ala Ser Glu Glu Lys Val Ile Phe Arg Tyr Cys Ala Gly Ser Cys
            20                  25                  30

Pro Arg Gly Ala Arg Thr Gln His Gly Leu Ala Leu Ala Arg Leu Gln
        35                  40                  45

Gly Gln Gly Arg Ala His Gly Gly Pro Cys Cys Arg Pro Thr Arg Tyr
    50                  55                  60
```

```
Thr Asp Val Ala Phe Leu Asp Asp Arg His Arg Trp Gln Arg Leu Pro
 65                  70                  75                  80

Gln Leu Ser Ala Ala Ala Cys Gly Cys
                 85
```

<210> SEQ ID NO 224
<211> LENGTH: 5
<212> TYPE: PRT
<213> ORGANISM: Homo sapiens

<400> SEQUENCE: 224

```
Ala Leu Ser Gly Pro
 1               5
```

<210> SEQ ID NO 225
<211> LENGTH: 24
<212> TYPE: DNA
<213> ORGANISM: Homo sapiens
<220> FEATURE:
<221> NAME/KEY: misc_feature
<222> LOCATION: (3)
<223> OTHER INFORMATION: s = c or g
<220> FEATURE:
<221> NAME/KEY: misc_feature
<222> LOCATION: (5)
<223> OTHER INFORMATION: s = c or g
<220> FEATURE:
<221> NAME/KEY: misc_feature
<222> LOCATION: (6)
<223> OTHER INFORMATION: y = t or c
<220> FEATURE:
<221> NAME/KEY: misc_feature
<222> LOCATION: (9)
<223> OTHER INFORMATION: s = c or g
<220> FEATURE:
<221> NAME/KEY: misc_feature
<222> LOCATION: (10)
<223> OTHER INFORMATION: y = t or c
<220> FEATURE:
<221> NAME/KEY: misc_feature
<222> LOCATION: (15)
<223> OTHER INFORMATION: y = t or c
<220> FEATURE:
<221> NAME/KEY: misc_feature
<222> LOCATION: (24)
<223> OTHER INFORMATION: y = t or c

<400> SEQUENCE: 225
gtsasygasy tgggyctggg ctay                                       24

<210> SEQ ID NO 226
<211> LENGTH: 24
<212> TYPE: DNA
<213> ORGANISM: Homo sapiens
<220> FEATURE:
<221> NAME/KEY: misc_feature
<222> LOCATION: (3)
<223> OTHER INFORMATION: y = t or c
<220> FEATURE:
<221> NAME/KEY: misc_feature
<222> LOCATION: (4)
<223> OTHER INFORMATION: m = a or c
<220> FEATURE:
<221> NAME/KEY: misc_feature
<222> LOCATION: (6)
<223> OTHER INFORMATION: s = c or g
<220> FEATURE:
<221> NAME/KEY: misc_feature
<222> LOCATION: (13)
<223> OTHER INFORMATION: r = a or g

```
<220> FEATURE:
<221> NAME/KEY: misc_feature
<222> LOCATION: (14)
<223> OTHER INFORMATION: s = c or g
<220> FEATURE:
<221> NAME/KEY: misc_feature
<222> LOCATION: (15)
<223> OTHER INFORMATION: m = a or c
<220> FEATURE:
<221> NAME/KEY: misc_feature
<222> LOCATION: (19)
<223> OTHER INFORMATION: k = t or g
<220> FEATURE:
<221> NAME/KEY: misc_feature
<222> LOCATION: (21)
<223> OTHER INFORMATION: y = t or c

<400> SEQUENCE: 226
ttymgstact gcrsmggckc ytgc                                              24

<210> SEQ ID NO 227
<211> LENGTH: 24
<212> TYPE: DNA
<213> ORGANISM: Homo sapiens
<220> FEATURE:
<221> NAME/KEY: misc_feature
<222> LOCATION: (1)
<223> OTHER INFORMATION: r = a or g
<220> FEATURE:
<221> NAME/KEY: misc_feature
<222> LOCATION: (2)
<223> OTHER INFORMATION: w = a or t
<220> FEATURE:
<221> NAME/KEY: misc_feature
<222> LOCATION: (7)
<223> OTHER INFORMATION: s = c or g
<220> FEATURE:
<221> NAME/KEY: misc_feature
<222> LOCATION: (8)
<223> OTHER INFORMATION: r = a or g
<220> FEATURE:
<221> NAME/KEY: misc_feature
<222> LOCATION: (10)
<223> OTHER INFORMATION: s = c or g
<220> FEATURE:
<221> NAME/KEY: misc_feature
<222> LOCATION: (13)
<223> OTHER INFORMATION: k = t or g
<220> FEATURE:
<221> NAME/KEY: misc_feature
<222> LOCATION: (15)
<223> OTHER INFORMATION: k = t or g
<220> FEATURE:
<221> NAME/KEY: misc_feature
<222> LOCATION: (19)
<223> OTHER INFORMATION: r = a or g
<220> FEATURE:
<221> NAME/KEY: misc_feature
<222> LOCATION: (22)
<223> OTHER INFORMATION: k = t or g
<220> FEATURE:
<221> NAME/KEY: misc_feature
<222> LOCATION: (24)
<223> OTHER INFORMATION: s = c or g

<400> SEQUENCE: 227
rwaggcsrts ggkckgcarc akgs                                              24

<210> SEQ ID NO 228
<211> LENGTH: 21
<212> TYPE: DNA
<213> ORGANISM: Homo sapiens
```

```
<220> FEATURE:
<221> NAME/KEY: misc_feature
<222> LOCATION: (1)
<223> OTHER INFORMATION: m = a or c
<220> FEATURE:
<221> NAME/KEY: misc_feature
<222> LOCATION: (2)
<223> OTHER INFORMATION: k = g or t
<220> FEATURE:
<221> NAME/KEY: misc_feature
<222> LOCATION: (4)
<223> OTHER INFORMATION: r = a or g
<220> FEATURE:
<221> NAME/KEY: misc_feature
<222> LOCATION: (7)
<223> OTHER INFORMATION: y = t or c
<220> FEATURE:
<221> NAME/KEY: misc_feature
<222> LOCATION: (9)
<223> OTHER INFORMATION: r = a or g
<220> FEATURE:
<221> NAME/KEY: misc_feature
<222> LOCATION: (10)
<223> OTHER INFORMATION: r = a or g
<220> FEATURE:
<221> NAME/KEY: misc_feature
<222> LOCATION: (13)
<223> OTHER INFORMATION: s = c or g
<220> FEATURE:
<221> NAME/KEY: misc_feature
<222> LOCATION: (18)
<223> OTHER INFORMATION: s = c or g
<220> FEATURE:
<221> NAME/KEY: misc_feature
<222> LOCATION: (19)
<223> OTHER INFORMATION: s = c or g

<400> SEQUENCE: 228
mkcrtcyarr aasgacasst c                                          21

<210> SEQ ID NO 229
<211> LENGTH: 168
<212> TYPE: DNA
<213> ORGANISM: Homo sapiens

<400> SEQUENCE: 229
cggcttgtga ccgagctggg cctgggctac gcctcagagg agaaggtcat cttccgctac    60
tgcgccggca gctgccccg tggtgcccgc acccagcatg gcctggcgct ggcccggctg    120
cagggccagg gccgagccca cggcgggccc tgctgccgcc ccatggcc               168

<210> SEQ ID NO 230
<211> LENGTH: 20
<212> TYPE: DNA
<213> ORGANISM: Homo sapiens

<400> SEQUENCE: 230
gaggagaagg tcatcttccg                                            20

<210> SEQ ID NO 231
<211> LENGTH: 20
<212> TYPE: DNA
<213> ORGANISM: Homo sapiens

<400> SEQUENCE: 231
gccgtgggct cggccctggc                                            20
```

```
<210> SEQ ID NO 232
<211> LENGTH: 24
<212> TYPE: DNA
<213> ORGANISM: Homo sapiens

<400> SEQUENCE: 232
agaggagaag gtcatcttcc gcta                                          24

<210> SEQ ID NO 233
<211> LENGTH: 20
<212> TYPE: DNA
<213> ORGANISM: Homo sapiens

<400> SEQUENCE: 233
ctcggccctg gccctgcagc                                               20

<210> SEQ ID NO 234
<211> LENGTH: 20
<212> TYPE: DNA
<213> ORGANISM: Homo sapiens

<400> SEQUENCE: 234
tgcagccggg ccagcgccag                                               20

<210> SEQ ID NO 235
<211> LENGTH: 31
<212> TYPE: DNA
<213> ORGANISM: Homo sapiens

<400> SEQUENCE: 235
cgcggatcca tgcctggatt cgagggtgca g                                  31

<210> SEQ ID NO 236
<211> LENGTH: 31
<212> TYPE: DNA
<213> ORGANISM: Homo sapiens

<400> SEQUENCE: 236
cgcggatcca tggccgtagg gaagttcctg c                                  31

<210> SEQ ID NO 237
<211> LENGTH: 60
<212> TYPE: DNA
<213> ORGANISM: Homo sapiens

<400> SEQUENCE: 237
ctcccaagct tttacttgtc atcgtcgtcc ttgtagtcgc caccacagcc gcaggcagcc   60

<210> SEQ ID NO 238
<211> LENGTH: 59
<212> TYPE: DNA
<213> ORGANISM: Homo sapiens

<400> SEQUENCE: 238
ctcccaagct tttacttgtc atcgtcgtcc ttgtagtctc gaggaaggcc acgtcggtg    59

<210> SEQ ID NO 239
<211> LENGTH: 25
<212> TYPE: DNA
<213> ORGANISM: Homo sapiens

<400> SEQUENCE: 239
tcagccacca cagccgcagg cagcc                                         25
```

```
<210> SEQ ID NO 240
<211> LENGTH: 73
<212> TYPE: PRT
<213> ORGANISM: Homo sapiens

<400> SEQUENCE: 240

Ser Glu Glu Lys Ile Ile Phe Arg Tyr Cys Ala Gly Ser Cys Pro Gln
                  5                  10                  15

Glu Val Arg Thr Gln His Ser Leu Val Leu Ala Arg Leu Arg Gly Gln
             20                  25                  30

Gly Arg Ala His Gly Arg Pro Cys Cys Gln Pro Thr Ser Tyr Ala Asp
         35                  40                  45

Val Thr Phe Leu Asp Asp His His Trp Gln Gln Leu Pro Gln Leu
     50                  55                  60

Ser Ala Ala Ala Cys Gly Cys Gly Gly
 65                  70

<210> SEQ ID NO 241
<211> LENGTH: 93
<212> TYPE: PRT
<213> ORGANISM: Rattus norvegicus

<400> SEQUENCE: 241

Cys Val Leu Thr Ala Ile His Leu Asn Val Thr Asp Leu Gly Leu Gly
                  5                  10                  15

Tyr Glu Thr Lys Glu Glu Leu Ile Phe Arg Tyr Cys Ser Gly Ser Cys
             20                  25                  30

Glu Ala Ala Glu Thr Met Tyr Asp Lys Ile Leu Lys Asn Leu Ser Arg
         35                  40                  45

Ser Arg Arg Leu Thr Ser Asp Lys Val Gly Gln Ala Cys Cys Arg Pro
     50                  55                  60

Val Ala Phe Asp Asp Asp Leu Ser Phe Leu Asp Asp Ser Leu Val Tyr
 65                  70                  75                  80

His Ile Leu Arg Lys His Ser Ala Lys Arg Cys Gly Cys
                 85                  90

<210> SEQ ID NO 242
<211> LENGTH: 93
<212> TYPE: PRT
<213> ORGANISM: Mus musculus

<400> SEQUENCE: 242

Cys Val Leu Thr Ala Ile His Leu Asn Val Thr Asp Leu Gly Leu Gly
                  5                  10                  15

Tyr Glu Thr Lys Glu Glu Leu Ile Phe Arg Tyr Cys Ser Gly Ser Cys
             20                  25                  30

Glu Ser Ala Glu Thr Met Tyr Asp Lys Ile Leu Lys Asn Leu Ser Arg
         35                  40                  45

Ser Arg Arg Leu Thr Ser Asp Lys Val Gly Gln Ala Cys Cys Arg Pro
     50                  55                  60

Val Ala Phe Asp Asp Asp Leu Ser Phe Leu Asp Asp Asn Leu Val Tyr
 65                  70                  75                  80

His Ile Leu Arg Lys His Ser Ala Lys Arg Cys Gly Cys
                 85                  90
```

PERSEPHIN SPECIFIC ANTIBODIES

RELATED APPLICATIONS

This application is a continuation of U.S. patent application Ser. No. 09/474,980 filed Dec. 29, 1999, which is a divisional of prior U.S. patent application Ser. No. 08/931,858 filed Sep. 16, 1997, now U.S. Pat. No. 6,222,022, which is a continuation-in-part of U.S. patent application Ser. No. 08/881,172 filed Jun. 23, 1997, which is a continuation-in part of U.S. patent application Ser. No. 08/615,944 filed Mar. 14, 1996, and is also a continuation-in-part of International application no. PCT/US97/03461 filed Mar. 14, 1997.

REFERENCE TO GOVERNMENT GRANT

This invention was made with government support under Grant Numbers NS24679 and CA53524. The government has certain rights in this invention.

BACKGROUND OF THE INVENTION (1) Field of the Invention

This invention relates generally to trophic or growth factors and, more particularly, to novel growth factors of the neurturin-GDNF family of growth factors.

(2) Description of the Related Art

The development and maintenance of tissues in complex organisms requires precise control over the processes of cell proliferation, differentiation, survival and function. A major mechanism whereby these processes are controlled is through the actions of polypeptides known as "growth factors". These structurally diverse molecules act through specific cell surface receptors to produce these actions.

Growth factors, termed "neurotrophic factors" promote the differentiation, growth and survival of neurons and reside in the nervous system or in innervated tissues. Nerve growth factor (NGF) was the first neurotrophic factor to be identified and characterized (Levi-Montalcini et al., *J. Exp. Zool.* 116:321, 1951 which is incorporated by reference). NGF exists as a non-covalently bound homodimer that promotes the survival and growth of sympathetic, neural crest-derived sensory, and basal forebrain cholinergic neurons. In sympathetic neurons this substance produces neurite outgrowth in vitro and increased axonal and dendritic growth in vivo. (See Levi-Montalcini and Booker, *Proc Nat'l Acad Sci* 46:384-391, 1960; Johnson et al. *Science* 210: 916-918, 1980; Crowley et al., *Cell* 76:1001-12, 1994 which are incorporated by reference). NGF has effects on cognition and neuronal plasticity, and can promote the survival of neurons that have suffered damage due to a variety of mechanical, chemical, viral, and immunological insults (Snider and Johnson, *Ann Neurol* 26:489-506, 1989; Hefti, *J Neurobiol* 25:1418-35, 1994 which are incorporated by reference). NGF also is known to extensively interact with the endocrine system and in immune and inflammatory processes. (Reviewed in Scully and Otten, *Cell Biol Int* 19:459-469, 1995; Otten and Gadient, *Int. J. Devl Neurosci* 13:147-151, 1995 which are incorporated by reference). For example, NGF promotes the survival of mast cells. (Horigome et al,. *J Biol Chem* 269:2695-2707, 1994 which is incorporated by reference).

In recent years it has become apparent that growth factors fall into classes, i.e. families or superfamilies based upon the similarities in their amino acid sequences. These families include, for example, the fibroblast growth factor family, the neurotrophin family and the transforming growth factor-beta (TGF-β) family. As an example of family member sequence similarities, TGF-β family members have 7 canonical framework cysteine residues which identify members of this superfamily.

NGF is the prototype of such a family of growth factors. Brain-derived neurotrophic factor (BDNF), the second member of this family to be discovered, was shown to be related to NGF by virtue of the conservation of all six cysteines that form the three internal disulfides of the NGF monomer (Barde, *Prog Growth Factor Res* 2:237-248, 1990 and Liebrock et al. *Nature* 341:149-152, 1989 which are incorporated by reference). By utilizing the information provided by BDNF of the highly conserved portions of two factors, additional members (NT-3, NT-4/5) of this neurotrophin family were rapidly found by several groups (Klein, *FASEB J* 8:738-44, 1994 which is incorporated by reference).

Neurotrophic factors structurally unrelated to NGF have been recently identified. These include factors originally isolated based upon a "neurotrophic action" such as ciliary neurotrophic factor (CNTF) (Lin et al., *Science* 246:1023-5, 1989 which is incorporated by reference) along with others originally isolated as a result of non-neuronal activities (e.g. fibroblast growth factors (Cheng and Mattson *Neuron* 1:1031-41, 1991 which is incorporated by reference), IGF-I (Kanje et al, *Brain Res* 486:396-398, 1989 which is incorporated by reference) leukemia inhibitory factor (Kotzbauer et al, *Neuron* 12:763-773, 1994 which is incorporated by reference).

Glial-derived neurotrophic factor (GDNF), is one such neurotrophic factor structurally unrelated to NGF. GDNF was, thus, a unique factor, which, up until now, was not known to be a member of any subfamily of factors. The discovery, purification and cloning of GDNF resulted from a search for factors crucial to the survival of midbrain dopaminergic neurons, which degenerate in Parkinson's disease. GDNF was purified from rat B49 glial cell conditioned media (Lin et al., *Science* 260:1130-2, 1993 which is incorporated by reference). Sequence analysis revealed it to be a distant member of the TGF-β superfamily of growth factors, having approximately 20% identity based primarily on the characteristic alignment of the 7 canonical framework cysteine residues (Lin et al., *Science* 260:1130-2, 1993 which is incorporated by reference). Thus, GDNF could possibly have represented a new subfamily within the TGF-β superfamily.

Recombinant GDNF produced in bacteria specifically promotes the survival and morphological differentiation of dopaminergic neurons (Lin et al., *Science* 260:1130-2, 1993); Tomac et al., *Nature* 373:335-9, 1995; Beck et al., *Nature* 373:339-41, 1995 and Ebendal et al., *J Neurosci Res* 40:276-84, 1995 which are incorporated by reference) and motor neurons (Henderson et al., *Science* 266:1062-4, 1994; Yan et al., *Nature* 373:341-4, 1995; and Oppenheim et al., *Nature* 373:344-6, 1995 which are incorporated by reference). Overall, GDNF was a more potent factor for promoting the survival of motor neurons than the other factors, and it was the only factor that prevented neuronal atrophy in response to these lesions, thereby positioning it as a promising therapeutic agent for motor neuron diseases.

It is now generally believed that neurotrophic factors regulate many aspects of neuronal function, including survival and development in fetal life, and structural integrity and plasticity in adulthood. Since both acute nervous system injuries as well as chronic neurodegenerative diseases are characterized by structural damage and, possibly, by disease-induced apoptosis, it is likely that neurotrophic factors play some role in these afflictions. Indeed, a considerable body of evidence suggests that neurotrophic factors may be valuable therapeutic agents for treatment of these neurodegenerative conditions, which are perhaps the most socially and economically destructive diseases now afflicting our society. Nevertheless, because different neurotrophic factors can potentially act preferentially through different receptors and on different neuronal or non-neuronal cell types, there remains a continuing need for the identification of new members of neurotrophic factor families for use in the diagnosis and treatment of a variety of acute and chronic diseases of the nervous system.

SUMMARY OF THE INVENTION

Briefly, therefore, the present invention is directed to the identification and isolation of substantially purified factors that promote the survival and growth of neurons as well as non-neuronal cells. Accordingly, the inventors herein have succeeded in discovering novel protein growth factors belonging to a family of growth factors for which GDNF was the first known member. The first such newly discovered family member was neurturin and this is the subject of copending application Ser. No. 08/519,777. Based upon the sequence of GDNF and neurturin the inventors herein have discovered another member of the GDNF-Neurturin family of growth factors referenced herein as persephin (PSP). This growth factor is believed to show at least 75% sequence identity among homologous sequences from different mammalian species although sequence homology may be as low as 65% in non-mammalian species such as avian species. Indeed, the mouse, rat and human mature persephin sequences show from about 80% to about 94% sequence identity. Mature persephin proteins identified herein comprise mouse sequences as set forth in SEQ ID NOS:79 and 187 (FIG. 17B amino acids 66 through 154 and 61 through 156, respectively), rat sequences as set forth in SEQ ID NOS: 82 and 196 (FIG. 18B amino acids 6 through 94 and 1 through 96, respectively), and human sequences as set forth in SEQ ID NOS:221 and 223 (FIG. 24; amino acids 61-156 and 66-154, respectively).

Persephin has been identified and obtained by a method based upon the conserved regions of the GDNF-Neurturin family discovered by the inventors herein. Accordingly, a new method has been devised that utilizes degenerate primers constructed from the sequences of these conserved regions for use in the polymerase chain reaction procedure. By utilizing this method the mouse, rat and human orthologs of the new family member, persephin, have been identified and obtained.

The present invention thus provides both amino acid sequences and nucleotide sequences that encode mouse, rat and human persephin including amino acid sequences of SEQ ID NOS:79, 82, 187, 196, 221 and 223 and nucleotide sequences of SEQ ID NOS: 183, 193 and 199 and 201 as well as the complements of such nucleotide sequences (SEQ ID NOS:184, 194, 200 and 202). In addition, the present invention includes pre-, pro- and prepro- regions as well as pre-pro persephin amino acid and nucleotide sequences.

Expression vectors and stably transformed cells comprising persephin polynucleotides are also within the scope of this invention. The transformed cells can be used in a method for producing persephin.

In another embodiment, the present invention provides a method for preventing or treating cellular degeneration comprising administering to a patient in need thereof a therapeutically effective amount of persephin. A patient may also be treated by implanting transformed cells which express persephin or a DNA sequence which encodes persephin into a patient, or cells cultured and expanded by growth in persephin.

The present invention also provides compositions and methods for detecting persephin. One method is based upon persephin antibodies and other methods are based upon detecting mRNA or CDNA or genomic DNA encoding persephin using recombinant DNA techniques.

In still further embodiments, the present invention includes pan-growth factors comprising a segment of a persephin sequence and a segment of at least one growth factor other than persephin. Also included are polynucleotides encoding the pan-growth factors, vectors containing such polynucleotides and host cells comprising the polynucleotides.

Among the several advantages found to be achieved by the present invention, therefore, may be noted the provision of a new growth factor, persephin, for use in preventing the atrophy, degeneration or death of certain cells, in particular neurons; the provision of human persephin; the provision of other members of the neurturin-persephin-GDNF family of growth factors by making available new methods capable of obtaining other family members; the provision of methods for obtaining persephin by recombinant techniques; the provision of methods for preventing or treating diseases producing cellular degeneration and, particularly neuronal degeneration; the provision of methods that can detect and monitor persephin levels in a patient; and the provision of methods that can detect alterations in the persephin gene.

BRIEF DESCRIPTION OF THE DRAWINGS

FIG. 5 illustrates the homology of the amino acid sequences for the mature growth factors, human neurturin (hNTN), mouse neurturin (mNTN), rat GDNF (rGDNF), mouse GDNF (mGDNF) and human GDNF (hGDNF) with identical amino acid residues enclosed in boxes;

FIG. 7 illustrates the cDNA and encoded amino acid sequence of human pre-pro neurturin (SEQ ID NO:11) showing the pre- region from nucleic acid 1 through 57 (SEQ ID NO:17), the pro- region from nucleic acid 58 through 285 (SEQ ID NO:20), human neurturin from nucleic acid 286 through 591 (SEQ.ID NO:9) and the splice site between nucleic acids 169 and 170 which defines the coding sequence portion of two exons from nucleic acids 1 through 169 (SEQ ID NO:27) and 170 through 594 (SEQ ID NO:28);

FIG. 8 illustrates the cDNA and encoded amino acid sequence of mouse pre-pro neurturin (SEQ ID NO:12) showing the pre- region from nucleic acid 1 through 57 (SEQ ID NO:18), the pro- region from nucleic acid 58 through 285

Figure 10:
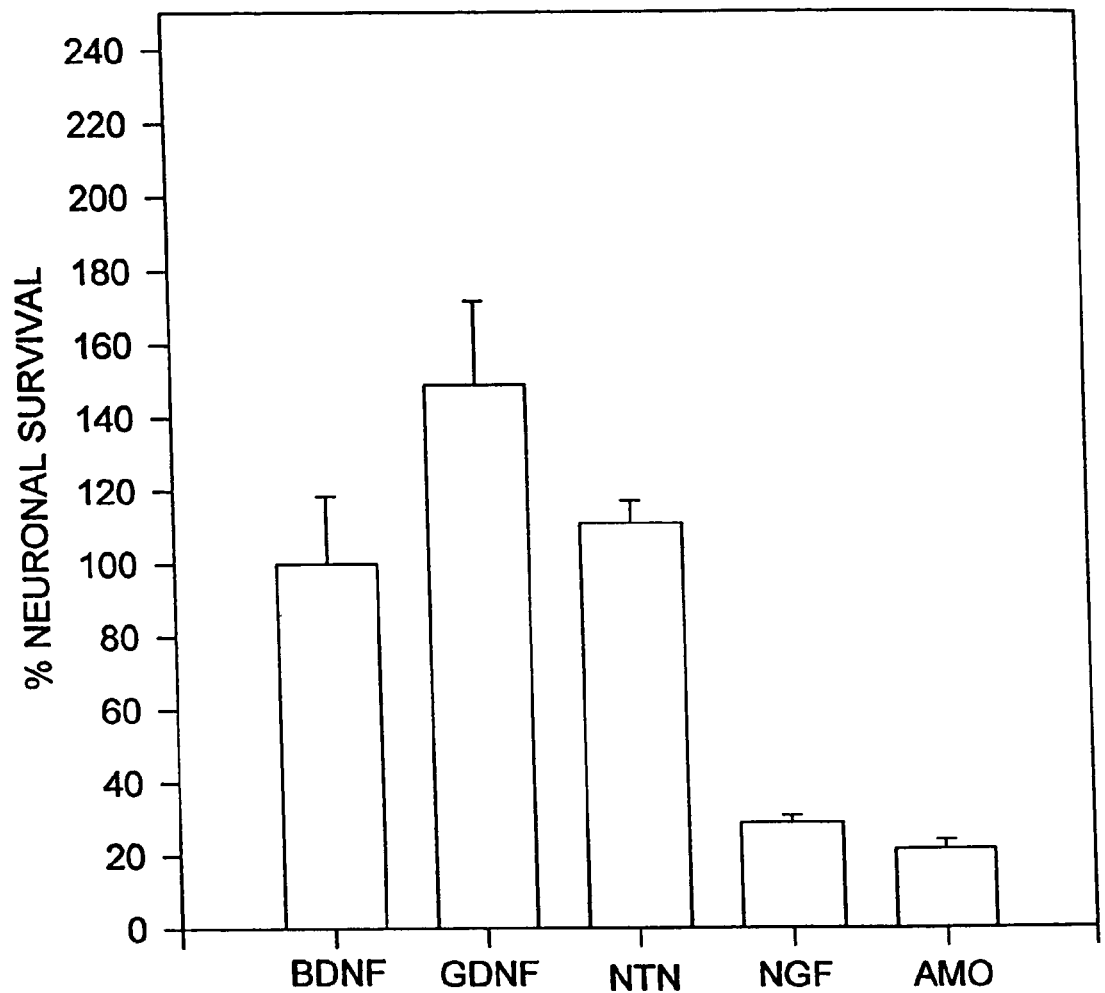
Figure 19:
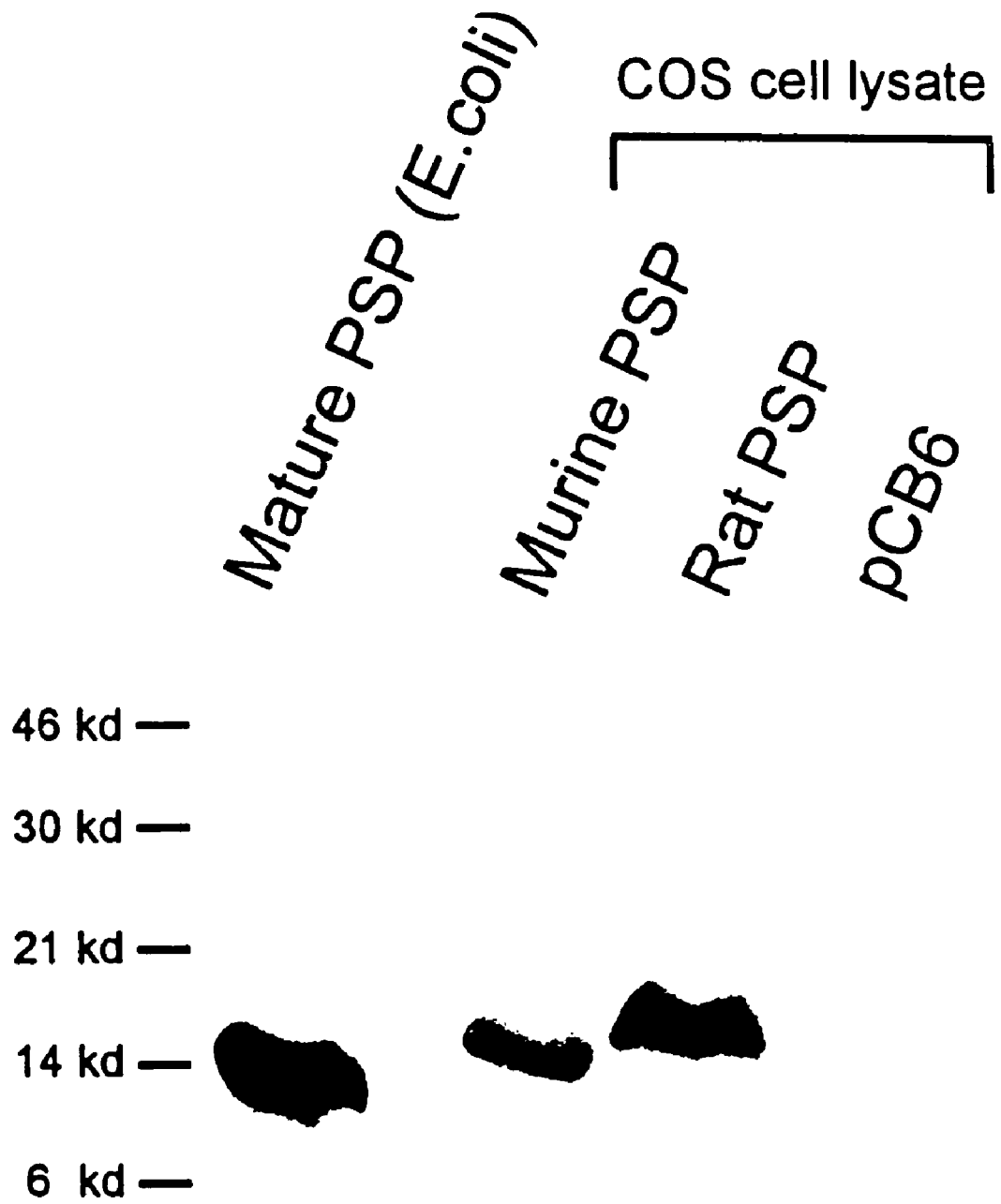
Figure 22:
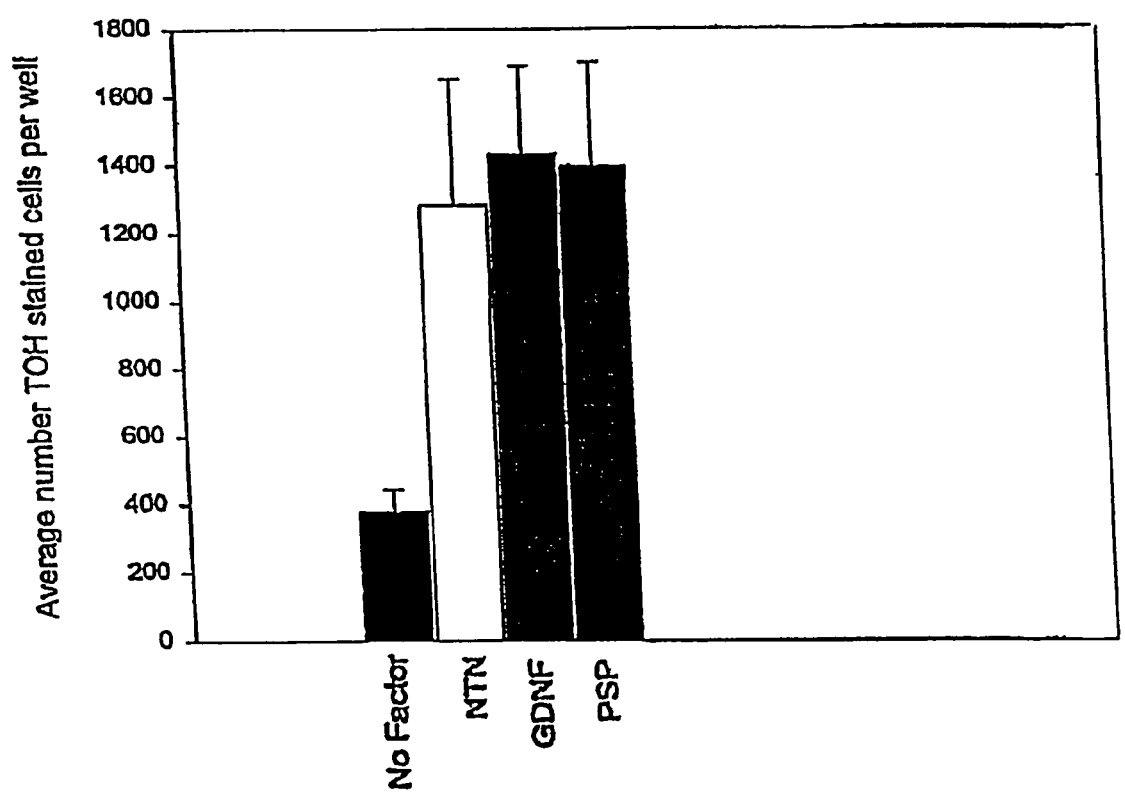

(SEQ ID NO:21), mouse neurturin from nucleic acid 286 through 585 (SEQ ID NO:10) and the splice site between nucleic acids 169 and 170 which defines the coding sequence portion of two exons from nucleic acids 1 through 169 (SEQ ID NO:29) and 170 through 588 (SEQ ID NO:30);

FIG. 9 illustrates the mouse cDNA sequence containing a 5' non-coding region (SEQ ID NO:13) and a 3' non-coding region (SEQ ID NO:14) each of which are contiguous to the coding region of pre-pro neurturin;

FIG. 10 illustrates the percent neuronal survival in E18 rat nodose ganglia neurons treated 24 hours post-plating for NTN, GDNF, BDNF, NGF and AMO;

FIG. 11 illustrates the nucleotide and amino acid sequence of murine persephin (SEQ ID NOS:79, 80 and 81; amino acid residues 52 through 140, 47 through 142, and 9 through 142, respectively);

Figure 12:
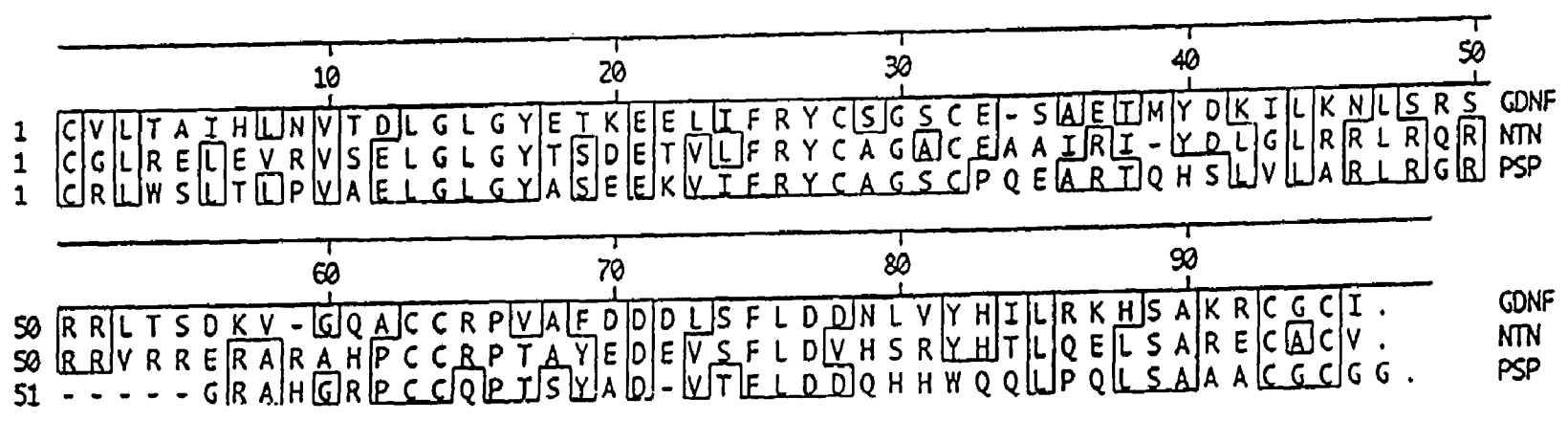

FIG. 12 illustrates the family member sequence identity in the region between the first and seventh canonical framework cysteine residues aligned beginning with the first canonical framework cysteine for murine GDNF (SEQ ID NO:87), murine neurturin (NTN) (SEQ ID NO:88) and murine persephin (PSP) (SEQ ID NO:89);

FIG. 13 illustrates the partial sequence of rat persephin cDNA (SEQ ID NO:97) obtained by the technique of rapid amplification of cDNA ends;

FIG. 14 illustrates the partial sequence beginning with the first canonical framework cysteine for rat persephin (SEQ ID NO:83) and the corresponding polynucleotide sequence (SEQ ID NO:86);

FIG. 15 shows (A) the family member aligned partial amino acid sequences from the first through the seventh canonical framework cysteine residues illustrating family member sequence homology of the mature growth factors, human GDNF (SEQ ID NO:240), rat GDNF (SEQ ID NO:241), mouse GDNF (SEQ ID NO:242), human neurturin (NTN (human); SEQ ID NO:31), mouse neurturin (NTN (mouse); SEQ ID NO:32), rat persephin (PSP (rat); SEQ ID NO:79), and mouse persephin (PSP(mouse); SEQ ID NO:82) in which boxes enclose the 28 conserved amino acid residues present in all and (B) the aligned sequences of mature mouse persephin (mPSP; SEQ ID NO:187), mature rat persephin (mPSP; SEQ ID NO:198) and mature human persephin (hPSP; SEQ ID NO:221);

FIG. 16 illustrates the sequences of TGF-β superfamily members aligned using the Clustal method, from the first canonical framework cysteine to the end of the sequence for transforming growth factor-β1 (TGFβ1), transforming growth factor-β2 (TGFβ2), transforming growth factor-β3 (TGFβ3), inhibin β A (INHβA), inhibin β B (INHβB), the nodal gene (NODAL), bone morphogenetic proteins 2 and 4 (BMP2 and BMP4), the *Drosophila* decapentaplegic gene (dpp), bone morphogenetic proteins 5-8 (BMP5, BMP6, BMP7 and BMP8), the *Drosophila* 60A gene family (60A), bone morphogenetic protein 3 (BMP3), the Vgl gene, growth differentiation factors 1 and 3 (GDF1 and GDF3), dorsalin (drsln), inhibin α (INHα), the MIS gene (MIS), growth factor 9 (GDF-9), glial-derived neurotropic growth factor (GDNF) and neurturin (NTN);

FIG. 17 illustrates (A) full length murine persephin gene (SEQ ID NO:177) with arrows indicating an 88 nt intron from positions 155-242 and (B) the nucleotide sequence of murine pre-pro persephin (SEQ ID NO:179) with encoded amino acid sequence (SEQ ID NO:185);

FIG. 18 illustrates (A) full length rat persephin gene (SEQ ID NO:188) with arrows indicating an 88 nt intron from positions 155-242 and (B) the nucleotide sequence of rat pre-pro persephin (SEQ ID NO:190) with encoded amino acid sequence (SEQ ID NO:196);

FIG. 19 illustrates a western blot analysis using anti-persephin antibodies to detect persephin protein in cell lysates from COS monkey cells transfected with the murine persephin gene (lane 2) or the rat persephin gene (lane 3) compared to cells transfected with the non-recombinant vector alone (pCB6, lane 4) and the mature protein produced by *E. Coli* (lane 1);

FIG. 20 illustrates the murine chimeric molecules (A) PSP/NTN containing the persephin fragment (residues 1-63) and the neurturin fragment (residues 68-100) and (B) NTN/PSP containing the neurturin fragment (residues 1-67) and the persephin fragment (residues 64-96) with the arrow indicating the crossover point in each;

FIG. 21 illustrates the survival promoting effect of persephin in murine embryonic day-14 mesencephalic cells cultured for three days (a) in the absence of persephin where almost all of the cells are dead and (b) in the presence of persephin (100 ng/ml) where substantial neuronal cell survival is evident;

FIG. 22 illustrates the survival promoting effect of persephin (PSP) in murine embryonic day-14 mesencephalic cells compared to effects of neurturin (NTN) and GDNF, measured by the number of cells stained with tyrosine hydroxylase (TOH);

FIG. 23 illustrates RT/PCT survey for persephin expression in adult mouse tissues showing persephin expression by Kidney cells; and FIG. 24 illustrates the CDNA sequence of human pre-pro persephin (SEQ ID NO:203) with two silent mutations indicated at positions 30 and 360 and the encoded amino acid sequence (SEQ ID NO:217) with the first amino acid of the pro- region indicated by the double asterisks (**) at amino acid position 24 and the first amino acid of mature human persephin indicated by the single asterisk (*) at amino acid position 61.

DESCRIPTION OF THE PREFERRED EMBODIMENTS

The present invention is based upon the identification, isolation and sequencing of a DNA molecule that encodes a new growth factor, persephin. Persephin promotes cell survival and, in particular, the survival of neuronal cells. Prior to this invention, persephin was unknown and had not been identified as a discrete biological substance nor had it been isolated in pure form.

The growth factor, neurturin (NTN) was identified and isolated as set forth in copending application Ser. No. 08/519,777 filed Aug. 28, 1995, which is incorporated in its entirety by reference. From the sequence of neurturin and the sequence of the closely related growth factor, glial-derived neurotrophic factor (GDNF), the inventors herein have devised and pursued strategies to find additional related factors. Neurturin is approximately 40% identical to GDNF, but less than 20% identical to any other member of the TGF-β superfamily. Together these two proteins define a new subfamily within the TGF-β superfamily. Several sequence regions within neurturin and GDNF were identified that are highly conserved, such that they are likely to be present in any additional members of this subfamily. This sequence information can, therefore, be used to isolate previously unknown members of this subfamily by designing degenerate oligonucleotides to be used as either primers in PCR reactions or as probes in hybridization studies.

Using the new degenerate primer PCR strategy described in Example II of copending application Ser. No. 08/519,777, the inventors herein have succeeded in identifying a third factor, persephin, that is approximately 40-50% identical to both GDNF and neurturin. Primers corresponding to the amino acid sequence from conserved regions of neurturin and GDNF (SEQ ID NO:42 and SEQ ID NO:44) were used to amplify a 77 nt fragment from rat genomic DNA. The resulting products were subcloned into the Bluescript KS plasmid and sequenced. The sequence of one of the amplified products predicted amino acid sequence data internal to the PCR primers that was different from that of GDNF or neurturin but had more than 20% identity with GDNF and neurturin, whereas the sequences of other amplified products we obtained corresponded to GDNF or neurturin, as would be expected. The 22 nucleotide sequence (SEQ ID NO:90) was then aligned with the rat sequences of GDNF and neurturin and found to be unique. This novel sequence, thus, suggested that we had identified a new family member referenced herein as persephin.

To obtain additional persephin sequence information, primers containing the unique 22 nucleotide sequence of the amplified fragment were used in the rapid amplification of cDNA ends (RACE) technique (Frohman, M. A. Methods in Enzymology 218:340-356, 1993) using cDNA obtained from neonatal rat brain. An approximately 350 nt fragment was obtained from this PCR reaction which constituted a partial rat persephin cDNA sequence of approximately 350 nucleotides (SEQ ID NO:106). The predicted amino acid sequence of this cDNA was compared to that of GDNF and neurturin, and found to have approximately 40% identity with each of these proteins. Importantly, the characteristic spacing of the canonical framework cysteine residues in members of the TGF-β superfamily was present. Furthermore, in addition to the region of similarity encoded by the degenerate primers used to isolate persephin, another region of high homology shared between GDNF and neurturin, but absent in other members of the TGF-β superfamily, was also present in persephin

```
GDNF  ACCRPVAFDDDLSFLDD  (aa 60-76)  (SEQ ID NO:98)

NTN   PCCRPTAYEDEVSFKDV  (aa 61-77)  (SEQ ID NO:99)

PSP   PCCQPTSYAD-VTFLDD  (aa 57-72)  (SEQ ID NO:100)
```

(Amino Acid Numbering Uses the First Cys Residue as Amino Acid 1).

With the confirmation that persephin was indeed a new member of the GDNF/NTN subfamily, we isolated murine genomic clones of persephin to obtain additional sequence information. Primers corresponding to rat cDNA sequence were used in a PCR reaction to amplify a 155 nucleotide (nt) fragment from mouse genomic DNA which was homologous to the rat persephin cDNA sequence. These primers were then used to obtain murine persephin genomic clones from a mouse 129/Sv library in a P1 bacteriophage vector (library screening service of Genome Systems, Inc., St. Louis, Mo.).

Restriction fragments (3.4 kb Nco I and a 3.3 kb Bam H1) from this P1 clone containing the persephin gene were identified by hybridization with a 210 nt fragment of persephin obtained by PCR using mouse genomic DNA and persephin-specific primers. The Nco I and Bam H1 fragments were sequenced and found to encode a stretch of amino acids corresponding to that present in the rat persephin RACE product, as well as being homologous to the mature regions of both neurturin and GDNF (FIG. 11).

Human persephin was obtained in a manner similar to that of mouse persephin. Degenerate PCR primers were used to amplify human genomic DNA and one clone was determined to have a sequence homologous to mouse persephin. Primers based upon the identified sequence were then used to screen cDNA libraries. Positive clones were identified by hybridization with a DNA probe derived from the identified sequence and these clones were then sequenced.

When the amino acid sequences of mature murine GDNF, NTN and PSP are aligned using the first canonical framework cysteine as the starting point, which is done because alterations in the cleavage sites between family members creates variability in the segments upstream of the first cysteine, persephin (91 amino acids) is somewhat smaller than either neurturin (95 amino acids) or GDNF (94 amino acids). The overall identity within this region is about 50% with neurturin and about 40% with GDNF (FIG. 12).

Further nucleotide sequencing of the murine persephin NcoI fragment revealed the nucleotide sequence of the entire murine persephin gene as shown in FIG. 17. In addition, the entire rat persephin gene has been determined by sequencing a PCR amplified fragment of rat genomic DNA as shown in FIG. 18. In both the murine and rat persephin gene, an open reading frame extends from the sequence coding for an initiator methionine up to a stop codon at positions 244-246. However, somewhere in this sequence an apparent anomaly was found to occur such that the sequence encoding the RXXR cleavage site (positions 257-268) and the sequence corresponding to the mature persephin protein (positions 269-556) are not co-linear with this open reading frame. Instead, a second reading frame encodes the cleavage site and the mature persephin. Irrespective of this apparent anomaly, mammalian cells were found to express persephin from either the murine or rat full length genomic sequence (see Example 14 below).

To pursue the genesis of this anomaly, we prepared mammalian expression vectors for both murine and rat persephin. To construct the murine plasmid, a P1 clone containing the murine persephin gene was used as a template in a PCR assay. Primers were designed such that the resulting fragment would contain the persephin gene extending from the initiator Methionine to the stop codon. The PCR reaction utilized a forward primer M3175 [5'-TGCTGTCACCATGGCTG-CAGGAAGACTTCGGA]$^{140}$ and reverse primer M3156 [5'-CGGTACCCAGATCTTCAGCCACCACAGCCACA-AGC]$^{138}$. To construct the analogous rat plasmid, rat genomic DNA was used as a template in a PCR assay. The PCR reaction utilized a forward primer M3175 [5'-TGCTGTCAC-CATGGCTGCAGGAAGACTTCGGA] and reverse primer M3156 [5'-CGGTACCCAGATCTTCAGCCACCACAGC-CACAAGC]. The amplified products were cloned into BSKS and sequenced to verify that the correct clone had been obtained. The rat and murine persephin fragments were excised using Sma I and Hind III and cloned into a Asp718 (blunted) and Hind III sites of the mammalian expression vector pCB6.

COS monkey cells were transfected with either the rat or murine persephin expression vectors or the non-recombinant vector (pCB6) itself. Forty eight hr later the cells were lysed, the samples were loaded onto a 15% SDS-polyacrylamide gel, and the proteins were separated by electrophoresis. The proteins were then transferred to nitrocellulose by electroblotting. This nitrocellulose membrane was incubated with anti-persephin antibodies (which we raised to mature persephin produced in bacteria from a pET plasmid) to detect the presence of persephin in the lysates. Lysates from cells transfected with either the rat or murine persephin expression vectors, but not the lysate from cells transfected with pCB6, contain high amounts of persephin. The size of the persephin detected was 10-15 kD, consistent with the size predicted for the processed (i.e. mature form of persephin). Conditioned media harvested from these cells also contained mature persephin. These results demonstrate that both the murine and rat persephin genes are capable of directing the synthesis of a properly processed persephin molecule.

To pursue the mechanism by which this occurred, we isolated RNA from cells transfected with either rat or murine persephin expression vector. RT/PCR analysis was performed using primers corresponding to the initiator Met and the stop codon. We detected two fragments: one corresponding to the predicted size of the persephin gene and the other somewhat smaller, suggesting that RNA splicing had occurred. We confirmed this with a number of other primer pairs. Both the large and small persephin fragments were cloned and sequenced. As expected, the larger fragment corresponded to the persephin gene. The small fragment corresponded to a spliced version of persephin. A small 88 nt intron within the pro-domain (situated 154 nt downstream of the start codon) had been spliced out. After this splicing event, the "frameshift" was no longer present (i.e. the initiator Met and the mature region are in-frame) in either rat or mouse persephin.

The N-terminus of persephin was predicted by reference to the N-terminal regions of neurturin or GDNF. Using neurturin sequence homology and cleavage signals, a characteristic RXXR cleavage motif is present beginning 9 residues upstream of the first canonical framework cysteine of persephin which would suggest that mature murine persephin would contain 5 amino acids (ALAGS) (SEQ ID NO:103) upstream of this cysteine (as does neurturin). The corresponding 5 amino acids in rat persephin are ALPGL (SEQ ID NO:112) and those in human persephin are ALSGP (SEQ ID NO:224). Using these parameters, mature persephin would consist of 96 amino acids and have a predicted molecular mass of 10.4 kD.

By "mature" growth factor reference is made to the secreted form of the growth factor in which any pre- or pro-regions have been cleaved and which may exist as a monomer or, by analogy to other members of the TGF-β superfamily, in the form of a homodimer linked by disulfide bonds.

The discovery of the new growth factor, persephin, as described above is a result of the prior discovery by the inventors herein of neurturin. Thus, the experiments leading to the discovery of neurturin are relevant to the current discovery of persephin as well as to the biological activity of persephin. The isolation, identification and characterization of neurturin is described in detail in Examples 1-5 below.

Reference to persephin herein is intended to be construed to include growth factors of any origin which are substantially homologous to and which are biologically equivalent to the persephin characterized and described herein. Such substantially homologous growth factors may be native to any tissue or species and, similarly, biological activity can be characterized in any of a number of biological assay systems. Reference to pre-pro persephin is intended to be construed to include pre-pro growth factors containing a pre- or leader or signal sequence region, a pro- sequence region and persephin as defined herein.

The terms "biologically equivalent" are intended to mean that the compositions of the present invention are capable of demonstrating some or all of the same growth promoting properties in a similar fashion, although not necessarily to the same degree as the recombinantly produced human, mouse or rat persephin as identified herein.

By "substantially homologous" it is meant that the degree of sequence identity of persephin orthologs including human, mouse and rat persephin as well as persephin from any other species, is greater than that between paralogs such as persephin and neurturin or persephin and GDNF, and greater than that reported previously for members of the TGF-β superfamily (For discussion of homology of TGF-β superfamily members see Kingsley, *Genes and Dev* 8:133-46, 1994 which is incorporated by reference).

Sequence identity or percent identity is intended to mean the percentage of same residues between two sequences. The reference sequence is human persephin when determining percent identity with mouse or rat persephin and with the non-persephin growth factors, human neurturin or human GDNF. The reference sequence is mouse persephin when determining percent identity with mouse GDNF and mouse neurturin and rat persephin when determining percent identity with rat GDNF and rat neurturin. Referencing is to human neurturin when determining percent identity with non-human neurturin and to human GDNF. In all of the above comparisons, the two sequences being compared are aligned using the Clustal method (Higgins et al, *Cabios* 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NBRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Using this criterion, preferred conservative amino acid changes are: R-K; E-D, Y-F, L-M; V-I, Q-H. Conservation is referenced to human persephin when determining percent conservation with persephin from other species or with non-persephin growth factors; referenced to human neurturin when determining percent conservation with non-human neurturin or with non-persephin, non-neurturin growth factors.

Table 1 shows the calculations of identity (I) and conservation (C) for comparisons of mature persephin, mature neurturin and mature GDNF from various species. Comparisons were made between mature human persephin (hPSP) and mature mouse and rat persephin (mPSP and rPSP, respectively) and between mature human persephin and mature human GDNF or neurturin (hGDNF and hNTN respectively). Neurturin comparisons were between mature human and mature mouse neurturin (hNTN and mNTN, respectively)

and between each of these and mature human, rat and mouse GDNF (hGDNF, rGDNF and mGDNF, respectively) as shown in the table.

TABLE 1

| COMPARISON | % IDENTITY | % CONSERVATION |
|---|---|---|
| hPSP v. mPSP | 81 | 81 |
| hPSP v. rPSP | 80 | 81 |
| mPSP v. rPSP | 94 | 96 |
| hPSP v. hNTN | 49 | 50 |
| hPSP v. hGDNF | 40 | 43 |
| hNTN v. mNTN | 90 | 93 |
| hNTN v. rGDNF | 44 | 53 |
| hNTN v. mGDNF | 43 | 52 |
| hNTN v. hGDNF | 43 | 53 |
| mNTN v. rGDNF | 42 | 52 |
| mNTN v. mGDNF | 41 | 51 |
| mNTN v. hGDNF | 41 | 52 |

The degree of homology between the human persephin and mouse or rat persephin is about 80% whereas the degree of homology between mouse and rat persephin is about 94%. The neurturin comparisons as shown in Table 1 indicate mature mouse and human neurturin proteins have about 90% sequence identity. Furthermore, all persephin and neurturin homologs of non-human mammalian species are believed to similarly have at least about 75% sequence identity with human persephin, human neurturin, or human GDNF. For non-mammalian species such as avian species, it is believed that the degree of homology with persephin is at least about 65% identity with human persephin, or neurturin human neurturin or human GDNF. By way of comparison, the variations between family members of the neurturin-persephin-GDNF family of growth factors can be seen by the comparison of persephin and GDNF or neurturin and GDNF. Human persephin has about 40% sequence identity and about 43% sequence conservation with human GDNF; and about 49% sequence identity and about 50% sequence conservation with human neurturin. Similarly, human neurturin has about 40% sequence identity and about 50% sequence conservation with human GDNF. It is believed that the different family members also have a similar sequence identity of about 40% of that of neurturin, about 40% of that of persephin or about 40% of that of GDNF and within a range of about 30% to about 75% identity with neurturin, within a range of about 30% to about 75% identity with persephin or within a range of about 30% to about 75% sequence identity with GDNF.

Thus, a given member of the GDNF-neurturin-persephin family would be expected to have lesser sequence identity with any other family member of the same species than is present in orthologs of that family member in other species just as human GDNF and human neurturin are more closely related to mouse GDNF and mouse neurturin, respectively, than to each other or to GDNF and any given family member would be expected to have greater sequence identity with another family member than to any other known member of the TGF-β superfamily (Kingsley, supra).

Homologs of pre-pro persephin in non-human mammalian species can be identified by virtue of the persephin portion of the amino acid sequence having at least about 75% sequence identity with human persephin and homologs of pre-pro persephin in non-mammalian species can be identified by virtue of the persephin portion of the amino acid sequence having at least about 65% identity with human persephin.

Persephin as used herein, can also include hybrid and modified forms of persephin, respectively, including fusion proteins and persephin fragments and hybrid and modified forms in which certain amino acids have been deleted or replaced and modifications such as where one or more amino acids have been changed to a modified amino acid or unusual amino acid and modifications such as glycosolations so long as the hybrid or modified form retains the biological activity of persephin. By retaining the biological activity, it is meant that neuronal survival is promoted, although not necessarily at the same level of potency as that of the human, mouse or rat persephin identified herein.

Also included within the meaning of substantially homologous is any persephin which may be isolated by virtue of cross-reactivity with antibodies to the persephin or whose encoding nucleotide sequences including genomic DNA, mRNA or cDNA may be isolated through hybridization with the complementary sequence of genomic or subgenomic nucleotide sequences or cDNA of the persephin or fragments thereof. It will also be appreciated by one skilled in the art that degenerate DNA sequences can encode human persephin and these are also intended to be included within the present invention as are allelic variants of persephin.

Conservatively substituted persephin proteins are also within the scope of the present invention. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H. In addition, Q-R-H and A-V are believed to be preferred substitutions for persephin inasmuch as they occur among the human, mouse and rat paralogs of persephin (see FIG. 15B).

In the case of pre-pro neurturin, alternatively spliced protein products, resulting from an intron located in the coding sequence of the pro region, may exist. The intron is believed to exist in the genomic sequence at a position corresponding to that between nucleic acids 169 and 170 of the cDNA which, in turn, corresponds to a position within amino acid 57 in both the mouse and human pre-pro neurturin sequences (see FIGS. 7 and 8). Thus, alternative splicing at this position might produce a sequence that differs from that identified herein for human and mouse pre-pro neurturin (SEQ ID NO:11 and SEQ ID NO:12, respectively) at the identified amino acid site by addition and/or deletion of one or more amino acids. Any and all alternatively spliced pre-pro neurturin proteins are intended to be included within the terms pre-pro neurturin and, similarly, any and all alternatively spliced pre-pro persephin proteins are also intended to be included within the terms pre-pro persephin as used herein.

Although it is not intended that the inventors herein be bound by any theory, it is thought that the human, mouse and rat persephin proteins identified herein as well as homologs from other tissues and species may exist as dimers in their biologically active form in a manner consistent with what is known for other factors of the TGF-β superfamily.

In addition to homodimers, the monomeric units of the dimers of persephin can be used to construct stable growth factor heterodimers or heteromultimers comprising at least one monomer unit derived from persephin. This can be done by dissociating a homodimer of persephin into its component monomeric units and reassociating in the presence of a monomeric unit of a second or subsequent homodimeric growth factor. This second or subsequent homodimeric growth factor can be selected from a variety of growth factors including neurturin, GDNF, a member of the NGF family such as NGF, BDNF, NT-3 and NT-4/5, a member of the TGF-β superfamily, a vascular endothelial growth factor, a member of the CNTF/LIF family and the like.

Growth factors are thought to act at specific receptors. For example, the receptors for TGF-β and activins have been identified and make up a family of Ser/Thr kinase transmembrane proteins (Kingsley, *Genes and Dev* 8:133-146, 1994; Bexk et al *Nature* 373:339-341, 1995 which are incorporated by reference). In the NGF family, NGF binds to the TrkA receptor in peripheral sensory and sympathetic neurons and in basal forebrain neurons; BDNF and NT-4/5 bind to trkB receptors; and NT-3 binds primarily to trkC receptors that possess a distinct distribution within the CNS (Tuszynski et al., *Ann Neurol* 35:S9-S12, 1994). Members of the persephin-neurturin-GDNF family also appear to act through specific receptors having distinct distributions as has been shown for other growth factor families. Recently, it was shown that GDNF acts through a multicomponent receptor complex in which a transmembrane signal transducing component, the Ret tyrosine kinase protein (Ret PTK), is activated upon the binding of GDNF with another protein, called GDNF Receptor α (GDNFR-α) which has no transmembrane domain and is attached to the cell surface via a glycosyl-phosphatidylinositol (GPI) linkage (Durbec et al., *Nature* 381:789-793, 1996; Jing et al., *Cell* 85:1113-1124, 1996; Treanor et al., *Nature* 382:80-83, 1996; Trupp et al., *Nature* 381:785-789, 1996, which are incorporated herein by reference). Furthermore, it has been shown that the signaling of neurturin and GDNF through the Ret tyrosine kinase receptor is mediated by a family of co-receptors, including the co-receptor protein GDNFR-α, also referred to as TrnR1, and the co-receptor protein, TrnR2, either of which can form a functional receptor complex with Ret for both neurturin and GDNF (Baloh et al., *Neuron* 18:793-802, 1997 which is incorporated by reference). By forming heterodimers or heteromultimers of persephin and one or more other growth factors, the resultant growth factor would be expected to be able to bind to at least two distinct receptor types preferentially having a different tissue distribution. The resultant heterodimers or heteromultimers would be expected to show a different and, possibly, an enlarged spectrum of cells upon which it could act or to provide greater potency. It is also possible that the heterodimer or heteromultimer might provide synergistic effects not seen with homodimers or homomultimers. For example, the combination of factors from different classes has been shown to promote long-term survival of oligodendrocytes whereas single factors or combinations of factors within the same class promoted short-term survival (Barres et al., *Development* 118:283-295, 1993).

Heterodimers can be formed by a number of methods. For example, homodimers can be mixed and subjected to conditions in which dissociation/unfolding occurs, such as in the presence of a dissociation/unfolding agent, followed by subjection to conditions which allow monomer reassociation and formation of heterodimers. Dissociation/unfolding agents include any agent known to promote the dissociation of proteins. Such agents include, but are not limited to, guanidine hydrochloride, urea, potassium thiocyanate, pH lowering agents such as buffered HCl solutions, and polar, water miscible organic solvents such as acetonitrile or alcohols such as propanol or isopropanol. In addition, for homodimers linked covalently by disulfide bonds as is the case with TGF-β family members, reducing agents such as dithiothreitol and β-mercaptoethanol can be used for dissociation/unfolding and for reassociation/refolding.

Heterodimers can also be made by transfecting a cell with two or more factors such that the transformed cell produces heterodimers as has been done with the neurotrophins. (Heymach and Schooter, *J Biol Chem* 270:12297-12304, 1995).

Another method of forming heterodimers is by combining persephin homodimers and a homodimer from a second growth factor and incubating the mixture at 37° C.

When heterodimers are produced from homodimers, the heterodimers may then be separated from homodimers using methods available to those skilled in the art such as, for example, by elution from preparative, non-denaturing polyacrylamide gels. Alternatively, heterodimers may be purified using high pressure cation exchange chromatography such as with a Mono S cation exchange column or by sequential immunoaffinity columns.

It is well known in the art that many proteins are synthesized within a cell with a signal sequence at the N-terminus of the mature protein sequence and the protein carrying such a leader sequence is referred to as a preprotein. The pre- portion of the protein is cleaved during cellular processing of the protein. In addition to a pre- leader sequence, many proteins contain a distinct pro sequence that describes a region on a protein that is a stable precursor of the mature protein. Proteins synthesized with both pre- and pro- regions are referred to as preproproteins. In view of the processing events known to occur with other TGF-β family members as well as the sequences determined herein, the inventors believe that the form of the persephin protein as synthesized within a cell is the pre-pro persephin. Human pre-pro persephin is believed to contain an N-terminal 23 amino acid signal sequence (human pre- signal sequence, SEQ ID NO:219, FIG. 24, amino acids 1 through 23 encoded by SEQ ID NOS:208 and 209, FIG. 24, nucleic acids 1 through 69). It is known that the full length of a leader sequence is not necessarily required for the sequence to act as a signal sequence and, therefore, within the definition of pre- region of persephin is included fragments thereof, usually N-terminal fragments, that retain the property of being able to act as a signal sequence, that is to facilitate co-translational insertion into the membranes of one or more cellular organelles such as endoplasmic reticulum, mitochondria, golgi, plasma membrane and the like.

The persephin signal sequence is followed by a pro-domain which contains an RXXR proteolytic processing site immediately before the N-terminal amino acid sequence for the mature persephin. (human pro- region sequence, SEQ ID NO:220, FIG. 24, amino acids 24 through 60 encoded by the nucleic acid sequence SEQ ID NO:211, FIG. 24 nucleic acids 70 through 180).

The persephin pre- and pro- regions together comprise a pre-pro sequence identified as the human pre-pro region sequence (SEQ ID NO:219, FIG. 24, amino acids 1 through 60 encoded by SEQ ID NOS:213 and 215, nucleic acids 1 through 285). The pre- region sequences and pro- region sequences as well as the pre-pro region sequences can be identified and obtained for non-human mammalian species and for non-mammalian species by virtue of the sequences being contained within the pre-pro persephin as defined herein.

Using the above landmarks, the human persephin cDNA has a 471 bp open reading frame encoding a 156 amino acid long protein (predicted Mr 16.6 kDA). Cleavage of the 23 amino acid long predicted signal peptide will lead to a 133 amino acid pro-persephin molecule (Mr 14.2 kDa), Proteolytic cleavage of the pro-persephin at a RXXR consensus sequence should yield a 96 amino acid mature protein with a molecular weight of 10.3 kDa. The mature, secreted persephin molecule is likely to form a disulfide linked homodimer by analogy to other members of the TGF-β family.

The nucleotide sequences of persephin pre- and/or pro-regions or similar regions that are believed to be associated with persephin DNA can be used to construct chimeric genes with the coding sequences of other growth factors or proteins. (Booth et al., Gene 146:303-8, 1994; Ibanez, Gene 146:303-8, 1994; Storici et al., FEBS Letters 337:303-7, 1994; Sha et al J Cell Biol 114:827-839, 1991 which are incorporated by reference). Such chimeric proteins can exhibit altered production or expression of the active protein species.

A preferred persephin according to the present invention is prepared by recombinant DNA technology although it is believed that persephin can be isolated in purified form from cell-conditioned medium as was done for neurturin.

By "pure form" or "purified form" or "substantially purified form" it is meant that a persephin composition is substantially free of other proteins which are not persephin. Preferably, a substantially purified persephin composition comprises at least about 50 percent persephin on a molar basis compared to total proteins or other macromolecular species present. More preferably, a substantially purified persephin composition will comprise at least about 80 to about 90 mole percent of the total protein or other macromolecular species present and still more preferably, at least about 95 mole percent or greater.

Recombinant persephin may be made by expressing the DNA sequences encoding persephin in a suitable transformed host cell. Using methods well known in the art, the DNA encoding persephin may be linked to an expression vector, transformed into a host cell and conditions established that are suitable for expression of persephin by the transformed cell.

Any suitable expression vector may be employed to produce recombinant human persephin such as, for example, the mammalian expression vector pCB6 (Brewer, Meth Cell Biol 43:233-245, 1994) or the E. coli pET expression vectors, specifically, pET-30a (Studier et al., Methods Enzymol 185:60-89, 1990 which is incorporated by reference) both of which were used herein. Other suitable expression vectors for expression in mammalian and bacterial cells are known in the art as are expression vectors for use in yeast or insect cells. Baculovirus expression systems can also be employed.

Persephin may be expressed in the monomeric units or such monomeric form may be produced by preparation under reducing conditions. In such instances refolding and renaturation can be accomplished using one of the agents noted above that is known to promote dissociation/association of proteins. For example, the monomeric form can be incubated with dithiothreitol followed by incubation with oxidized glutathione disodium salt followed by incubation with a buffer containing a refolding agent such as urea.

Persephin may exist as a dimer or other multimer and may be glycosylated or chemically modified in other ways. Mature human persephin contains no N-linked glycosylation sites (see FIG. 15B and SEQ ID NO:221). Potential O-linked glycosylation sites occur in mature human persephin at positions 3, 10, 12, 14, 24, 36, 43, 67, 70 and 88 in SEQ ID NO:221 (FIG. 15B).

As noted above, the human nucleic acid sequence suggests that persephin is initially translated as a pre-pro polypeptide and that proteolytic processing of the signal sequence and the "pro" portion of this molecule results in the mature sequence, referenced herein as "mature persephin" exists in human and in non-human species in homologous form. Therefore, persephin includes any and all "mature persephin" sequences from human and non-human species and any and all pre-pro persephin polypeptides that may be translated from the persephin gene.

By analogy to the neurturin protein, it is possible that isoforms of persephin may exist. For example, different possible cleavage sites (such as RXXR sites) may be present in the pre-pro neurturin sequence so that more than one possible isoform of pre-pro neurturin may exist. Thus, the mature neurturin protein may have a variable number of amino acids preceding the first canonical cysteine. Such alternate cleavage sites could be utilized differently among different organisms and among different tissues of the same organism. The N-terminal amino acids preceding the first of the seven conserved cysteines in the mature forms of members of the TGF-β family vary greatly in both length and sequence. Furthermore, insertion of a ten amino acid sequence two residues upstream of the first conserved cysteine does not affect the known biological activities of one family member, dorsalin (Basler et al., Cell 73:687-702, 1993). By analogy, it is also possible that persephin proteins containing sequences of different lengths preceding the first canonical cysteine may exist or could be made and that these would retain their biological activity.

The inventors herein believe that at a minimum the sequence of a persephin-neurturin-GDNF growth factor that will show biological activity will contain the sequence from the first through the seventh canonical cysteine. This sequence of human persephin is from cysteine 66 through cysteine 154 as shown in FIG. 24 (SEQ ID NO:223). The comparable sequence for murine persephin as shown in FIG. 12 is from cysteine 1 through cysteine 87 (SEQ ID NO:79) and that for rat persephin as shown in FIG. 14, from cysteine 1 through cysteine 87 (identified as SEQ ID NO:82). Thus, within the scope of persephin proteins of the present invention are amino acid sequences containing SEQ ID NO:223, SEQ ID NO:79 or SEQ ID NO:82 and nucleic acid molecules containing sequences encoding these amino acid sequences.

The present invention also encompasses nucleic acid molecules comprising sequences that encode mouse, rat and human persephin (FIGS. 11, 14 and 23). Also included within the scope of this invention are sequences that are substantially the same as the nucleic acid sequences encoding persephin. Such substantially the same sequences may, for example, be substituted with codons more readily expressed in a given host cell such as E. coli according to well known and standard procedures. Such modified nucleic acid sequences are included within the scope of this invention.

Specific nucleic acid sequences can be modified by those skilled in the art and, thus, all nucleic acid sequences which encode for the amino acid sequences of pre-pro persephin or the pre- region or the pro- region of persephin can likewise be so modified. The present invention also includes nucleic acid sequence having one or more substitutions, deletions or additions wherein the nucleic acid sequence will hybridize with a persephin nucleic acid sequences—or complement thereof where appropriate.

Specific hybridization is defined herein as the formation of hybrids between a polynucleotide (e.g. a persephin polynucleotide which may include one or more substitutions, deletions, and/or additions) and a specific reference polynucleotide (e.g. polynucleotides encoding mature persephin and having the sequences of SEQ ID NO:183, 184, 194, 195, 199, 200, 201 or 202) wherein the polynucleotide preferentially hybridizes to the specific reference polynucleotide. For example, a polynucleotide encoding a mature persephin will specifically hybridize to a reference persephin polynucleotide (e.g. SEQ ID NO:183, 184, 194, 195, 199, 200, 201 or 202) and not to a reference neurturin polynucleotide (e.g. SEQ ID NO:9 or 10 or sequences complementary thereto). Specific hybridization is preferably done under high stringency conditions which is well understood by those skilled in the art to be determined by a number of factors during hybridization and during the washing procedure, including temperature, ionic strength, length of time and concentration of formamide (see for example, Sambrook et al., 1989, supra).

The present invention also includes nucleic acid sequences which encode for polypeptides that have survival or growth promoting activity and that are recognized by antibodies that bind to persephin.

The present invention also encompasses vectors comprising an expression regulatory element operably linked to any of the nucleic acid sequences included within the scope of the invention. This invention also includes host cells—of any variety—that have been transformed with such vectors.

Methods are also provided herein for producing persephin. Preparation can be by isolation from conditioned medium from a variety of cell types so long as the cell type produces persephin. A second and preferred method involves utilization of recombinant methods by isolating a nucleic acid sequence encoding persephin, cloning the sequence along with appropriate regulatory sequences into suitable vectors and cell types, and expressing the sequence to produce persephin.

A mammalian gene family comprised of four neurotrophic factors has been identified including nerve growth factor (NGF), brain derived neurotrophic factor (BDGF), neurotrophin-3 (NT-3), and neurotrophin-4/5 (NT-4/5). These factors share approximately 60 percent nucleic acid sequence homology (Tuszynski and Gage, *Ann Neurol* 35:S9-S12, 1994 which is incorporated by reference). The persephin protein and the neurturin protein display no significant homology to the NGF family of neurotrophic factors. Either persephin or neurturin shares less than about 20% homology with the TGF-β superfamily of growth factors. However, both persephin and neurturin show approximately 40% sequence identity with GDNF and approximately 50% sequence identity with each other. In particular, the positions of the seven cysteine residues present in persephin, neurturin and GDNF are nearly exactly conserved. The inventors herein believe that other unidentified genes may exist that encode proteins that have substantial amino acid sequence homology to persephin, neurturin and GDNF and which function as growth factors selective for the same or different tissues and the same or different biological activities and may act at the same or different receptors. A different spectrum of activity with respect to tissues affected and/or response elicited could result from preferential activation of different receptors by different family members as is known to occur with members of the NGF family of neurotrophic factors (Tuszynski and Gage, 1994, supra).

As a consequence of members of a particular gene family showing substantial conservation of amino acid sequence among the protein products of the family members, there is considerable conservation of sequences at the DNA level. This forms the basis for a new approach for identifying other members of the gene family to which GDNF, neurturin and persephin belong. The method used for such identification is cross-hybridization using nucleic acid probes derived from one family member to form a stable hybrid duplex molecule with nucleic acid sequence from different members of the gene family or to amplify nucleic acid sequences from different family members. (see for example, Kaisho et al. *FEBS Letters* 266:187-191, 1990 which is incorporated by reference). The sequence from the different family member may not be identical to the probe, but will, nevertheless be sufficiently related to the probe sequence to hybridize with the probe. Alternatively, PCR using primers from one family member can be used to identify additional family members.

The above approaches have not heretofore been successful in identifying other gene family members because only one family member, GDNF was known. With the identification of neurturin in copending application Ser. No. 08/519,777, however, unique new probes and primers were made that contain sequences from the conserved regions of this gene family. The same conserved regions are also found in the third family member, persephin. In particular, three conserved regions have been identified herein which can be used as a basis for constructing new probes and primers. The new probes and primers made available from the work with neurturin and persephin make possible this powerful new approach which can now successfully identify other gene family members. Using this new approach, one may screen for genes related to GDNF, neurturin and persephin in sequence homology by preparing DNA or RNA probes based upon the conserved regions in the GDNF and neurturin molecules. Therefore, one embodiment of the present invention comprises probes and primers that are unique to or derived from a nucleotide sequence encoding such conserved regions and a method for identifying further members of the neurturin-persephin-GDNF gene family.

Conserved-region amino acid sequences have been identified herein to include Val-$Xaa_1$-$Xaa_2$-Leu-Gly-Leu-Gly-Tyr where $Xaa_1$ is Ser, Thr or Ala and $Xaa_2$ is Glu or Asp (SEQ ID NO:108); Glu-$Xaa_1$-$Xaa_2$-$Xaa_3$-Phe-Arg-Tyr-Cys-$Xaa_4$-Gly-$Xaa_5$-Cys in which $Xaa_1$ is Thr, Glu or lys, $Xaa_2$ is Val, Leu or Ile, $Xaa_3$ is Leu or Ile, $Xaa_4$ is Ala or Ser, and Xaa5 is Ala or Ser, (SEQ ID NO:113); and Cys-Cys-$Xaa_1$-Pro-$Xaa_2$-$Xaa_3$-$Xaa_4$-$Xaa_5$-Asp-$Xaa_6$-$Xaa_7$-$Xaa_8$-Phe-Leu-Asp-$Xaa_9$in which $Xaa_1$ is Arg or Gln, $Xaa_2$ is Thr or Val or Ile, $Xaa_3$ is Ala or Ser, $Xaa_4$ is Tyr or Phe, $Xaa_5$ is Glu, Asp or Ala, $Xaa_6$ is Glu, Asp or no amino acid, $Xaa_7$ is val or leu, $Xaa_8$ is Ser or Thr, and $Xaa_9$ is Asp or Val (SEQ ID NO:114). Nucleotide sequences containing a coding sequence for the above conserved sequences or fragments of the above conserved sequences can be used as probes. Exemplary probe and primer sequences encoding amino acid sequences and SEQ ID NOS:125-129; primers whose reverse complementary sequences encode amino acid sequences SEQ ID NO:126, SEQ ID NO:127, SEQ ID NO:130; and, in particular, nucleotide sequences, SEQ ID NOS:115-124. Additional primers based upon GDNF and neurturin include nucleic acid sequences encoding amino acid sequences, SEQ ID NO:33, SEQ ID NO:36, SEQ ID NO:40 and SEQ ID NO:41; primers whose reverse complementary sequences encode SEQ ID NO:37, SEQ ID NO:38 and SEQ ID NO 39; and, in particular, nucleic acid sequences, SEQ ID NOS:42-48.

Hybridization using the new probes from conserved regions of the nucleic acid sequences would be performed under reduced stringency conditions. Factors involved in determining stringency conditions are well known in the art (for example, see Sambrook et al., *Molecular Cloning*, 2nd Ed., 1989 which is incorporated by reference). Sources of nucleic acid for screening would include genomic DNA libraries from mammalian species or cDNA libraries constructed using RNA obtained from mammalian cells cloned into any suitable vector.

PCR primers would be utilized under PCR conditions of reduced annealing temperature which would allow amplification of sequences from gene family members other than GDNF, neurturin and persephin. Sources of nucleic acid for screening would include genomic DNA libraries from mammalian species cloned into any suitable vector, cDNA transcribed from RNA obtained from mammalian cells, and genomic DNA from mammalian species.

DNA sequences identified on the basis of hybridization or PCR assays would be sequenced and compared to GDNF, neurturin and persephin. The DNA sequences encoding the entire sequence of the novel factor would then be obtained in the same manner as described herein. Genomic DNA or libraries of genomic clones can also be used as templates because the intron/exon structures of GDNF and neurturin are conserved and coding sequences of the mature proteins are not interrupted by introns.

Using this approach as described above, the primers designed from the conserved regions of neurturin and GDNF have been used to identify and obtain the sequence of the new family member described herein, persephin. Degenerate primers designed from persephin, neurturin and GDNF can be further used to identify and obtain additional family members.

It is believed that all GDNF-neurturin-persephin family members will have a high degree of sequence identity with one or more of the three identified family-member consensus regions in the portion of the sequence between the first and seventh canonical framework cysteines (see FIG. 12). In particular, a new family member is anticipated to have at least a 62.5% identity with the consensus region octapeptide, Val-$Xaa_1$-$Xaa_2$-Leu-Gly-Leu-Gly-Tyr where $Xaa_1$ is Ser, Thr or Ala and $Xaa_2$ is Glu or Asp (SEQ ID NO:108) or at least a 62.5 percent sequence identity with the consensus region octapeptide, Phe-Arg-Tyr-Cys-$Xaa_1$-Gly-$Xaa_2$-Cys where $Xaa_1$ and $Xaa_2$ are alanine or serine (SEQ ID NO:109) or at least a 50 percent sequence identity with the consensus region octapeptide, Asp-$Xaa_1$-$Xaa_2$-$Xaa_3$-Phe-Leu-Asp-$Xaa_4$ where $Xaa_1$ is aspartic acid or glutamic acid or no amino acid, $Xaa_2$ is valine or leucine, $Xaa_3$ is serine or threonine; and $Xaa_4$ is valine or aspartic acid (SEQ ID NO:110). The inventors herein believed that any new family member will have 28 amino acids in the aligned sequence between the first and seventh canonical framework cysteine residues as set forth in FIG. 15 with residues numbered from the N-terminal end of the family member aligned sequence being (1) Cys, (3) Leu, (10) Val, (13) Leu, (14) Gly, (15) Leu, (16) Gly, (17) Tyr, (21) Glu, (25) Phe, (26) Arg, (27) Tyr, (28) Cys, (30) Gly, (32) Cys, (44) Leu, (47) Leu, (58) Cys, (59) Cys (61) Pro, (66) Asp, (69) Phe, (70) Leu, (71) Asp, (83) Ser, (84) Ala, (87) Cys, and (89) Cys, however, it is possible that there may be as many as three mismatches.

On the basis of the structural similarities of persephin to the sequences of neurturin and GDNF, persephin would be expected to promote the survival and growth of neuronal as well as non-neuronal cells. For example, neurturin has been shown to promote the survival of superior cervical ganglion cells as well as nodose sensory ganglion neurons (see Examples 1-3). Furthermore, GDNF has been shown to act on dopaminergic, sympathetic, motor and several sensory neurons (Henderson et al. supra, 1994; Miles et al, *J Cell Biol* 130:137-148, 1995; Yan et al, *Nature* 373:341-344, 1995; Lin et al, *Science* 260:1130-1132, 1993; Trupp et al, *J Cell Biol* 130:137-148, 1995; Martin et al *Brain Res* 683:172-178, 1995; Bowenkamp st al *J Comp Neurol* 355:479-489, 1995 which are incorporated by reference). Moreover, all other growth factors isolated to date have been shown to act on many different cell types (for example see Scully and Otten, *Cell Biol Int* 19:459-469, 1005; Hefti, *Neurotrophic Factor Therapy* 25:1418-1435, 1994 which are incorporated by reference). Thus, it is likely that persephin will show activity on a variety of different neuronal cells, both peripheral and central, as well as on non-neuronal cells. With respect to peripheral neuronal cells, the profile of cells for which persephin will show a survival promoting activity appears to be different from that of neurturin or GDNF. In contrast to the survival-promoting activity produced by neurturin and GDNF in sympathetic and sensory neurons, persephin showed no activity in these tissues at concentrations tested. Nevertheless, persephin showed survival-promoting activity in mesencephalic cells obtained from rat embryo brains. Furthermore, persephin activity on any particular target cell type can be determined by routine experimentation using standard reference models. Moreover, the inventors herein have identified brain and heart tissues as tissues expressing persephin, which further supports the conclusion that persephin can act to promote survival and growth in a variety of neuronal and non-neuronal cells.

As an example of the actions of neurotrophic factors on non-neuronal tissues, the prototypical neurotrophic factor, NGF, also acts upon mast cells to increase their number when injected into newborn rats (Aloe, *J Neuroimmunol* 18:1-12, 1988). In addition, mast cells express the trk receptor and respond to NGF such that NGF is a mast cell secretogogue and survival promoting factor (Horigome et al., *J Biol Chem* 269:2695-2707, 1994 which is incorporated by reference). Moreover, members of the TGF-β superfamily act on many cell types of different function and embryologic origin.

The inventors herein have identified brain and heart as tissues in which persephin is expressed and it is further believed that persephin is expressed in a number of other neuronal and non-neuronal tissues. The related family member, neurturin, is expressed in a number of non-neuronal tissues including blood, bone marrow, neonatal liver and mast cells. This suggests a role for neurturin in hematopoiesis, inflammation, allergy, and cardiomyopathy. Similarly, persephin may also have a similar profile of activity.

Neurotrophic factors of the NGF family are thought to act through factor-specific high affinity receptors (Tuszynski and Gage, 1994, supra). Only particular portions of the protein acting at a receptor site are required for binding to the receptor. Such particular portions or discrete fragments can serve as an agonist where the substance activates a persephin receptor to elicit the promoting action on cell survival and growth and antagonists to persephin where they bind to, but do not activate, the receptor or promote survival and growth. Such portions or fragments that are agonists and those that are antagonists are also within the scope of the present invention.

Synthetic, pan-growth factors can also be constructed by combining the active domains of persephin with the active domains of one or more other non-persephin growth factors. (For example, see Ilag et al., *Proc Nat'l Acad Sci* 92:607-611, 1995 which is incorporated by reference). These pan-growth factors would be expected to have the combined activities or other advantageous properties of persephin and the one or more other growth factors. As such, these pan-growth factors are believed to be potent and multispecific growth factors that are useful in the treatment of a wide spectrum of degenerative diseases and conditions including conditions that can be treated by any or all of the parent factors from which the active domains were obtained. Such pan-growth factors might also provide synergistic effects beyond the activities of the parent factors (Barres et al., supra).

Pan-growth factors within the scope of the present invention can include chimeric or hybrid polypeptides that are constructed from portions of fragments of at least two growth factors. Growth factors of the TGF-β superfamily are structurally related having highly conserved sequence landmarks whereby family members are identified. In particular, seven canonical framework cysteine residues are nearly invariant in members of the superfamily (Kingsley, *Genes & Dev* 8:133-146, 1994 which is incorporated by reference)(see FIG. 17). Chimeric polypeptide molecules can, therefore, be constructed from a sequence that is substantially identical to a portion of the persephin molecule, up to one or more crossover points, and one or more sequences each of which is substantially identical with a portion of another TGF-β superfamily member extending on the other side of the corresponding one or more crossover points. For example, a portion of the amino terminal end of the persephin polypeptide can be combined with a portion of the carboxy terminal end of a neurturin polypeptide or alternatively a portion of the amino terminal end of a neurturin polypeptide can be combined with a portion of the carboxy terminal end of a persephin polypeptide. Such portions of persephin or neurturin polypeptides are preferably from about 5 to about 95, more preferably from about 10 to about 90, still more preferably from about 20 to about 80 and most preferably from about 30 to about 70 contiguous amino acids and such portions of another, non-persephin or, as the case may be, non-neurturin TGF-β superfamily member are preferably from about 5 to about 95, more preferably from about 10 to about 90, still more preferably from about 20 to about 80 and most preferably from about 30 to about 70 contiguous amino acids. For example, a particular crossover point might be between the third and fourth canonical framework cysteine residues. One such exemplary construct would contain at the 5' end a sequence comprised of a persephin sequence from residue 1 through the third canonical framework cysteine residue 37 and up to a cross-over point somewhere between residue 37 and residue 63 but not including the fourth canonical framework cysteine residue 64 (for reference, see mature persephin, SEQ ID NO:80). The 3' end of the hybrid construct would constitute a sequence derived from another TGF-β superfamily member such as, for example, neurturin which is another TGF-β superfamily member that is closely related to persephin. Using neurturin as the other TGF-β family member, the hybrid construct beyond the crossover point would be comprised of a sequence beginning at the desired crossover point in the neurturin sequence between the third canonical framework cysteine residue 37 and the fourth canonical framework cysteine residue 67 of neurturin and continuing through residue 100 at the 3' end of neurturin (for alignment, see FIG. 12). A second exemplary hybrid construct would be comprised of residue 1 through a crossover point between residues 37 and 67 of neurturin contiguously linked with residues from the crossover point between residues 37 and 64 through residue 96 of persephin. The above constructs with persephin and neurturin are intended as examples only with the particular TGF-β family member being selected from family members including but not limited to transforming growth factor-β1 (TGFβB1), transforming growth factor-β2 (TGFβ2), transforming growth factor-β3 (TGFβ3), inhibin β A (INHβA), inhibin β B (INHβB), the nodal gene (NODAL), bone morphogenetic proteins 2 and 4 (BMP2 and BMP4), the *Drosophila* decapentaplegic gene (dpp), bone morphogenetic proteins 5-8 (BMP5, BMP6, BMP7 and BMP8), the *Drosophila* 60A gene family (60A), bone morphogenetic protein 3 (BMP3), the Vg1 gene, growth differentiation factors 1 and 3 (GDF1 and GDF3), dorsalin (drsln), inhibin α (INHα), the MIS gene (MIS), growth factor 9 (GDF-9), glial-derived neurotropic growth factor (GDNF), neurturin (NTN) and persephin (see FIG. 16). In addition, the crossover point can be any residue between the first and seventh canonical framework cysteines molecules of neurturin and the particular other family member. Furthermore, additional crossover points can be used to incorporate any desired number of persephin portions or fragments with portions or fragments of any one or more other family members.

In constructing a particular chimeric molecule, the portions of persephin and portions of the other, non-persephin growth factor are amplified using PCR, mixed and used as template for a PCR reaction using the forward primer from one and the reverse primer from the other of the two component portions of the chimeric molecule. Thus, for example a forward and reverse primers are selected to amplify the portion of persephin from the beginning to the selected crossover point between the third and fourth canonical cysteine residues using a persephin plasmid as template. A forward primer with a 5' portion overlapping with the persephin sequence and a reverse primer are then used to amplify the portion of the other, non-persephin growth factor member of the TGF-β superfamily from the corresponding crossover point through the 3' end using a plasmid template containing the coding sequence for the non-persephin TGF-β family member. The products of the two PCR reactions are gel purified and mixed together and a PCR reaction performed. Using an aliquot of this reaction as template a PCR reaction is performed using the persephin forward primer and the reverse primer for the non-persephin growth factor. The product is then cloned into an expression vector for production of the chimeric molecule.

Chimeric growth factors would be expected to be effective in promoting the growth and development of cells and for use in preventing the atrophy, degeneration or death of cells, particular in neurons. The chimeric polypeptides may also act as receptor antagonists of one or both of the full length growth factors from which the chimeric polypeptide was constructed or as an antagonist of any other growth factor that acts at the same receptor or receptors.

The present invention also includes therapeutic or pharmaceutical compositions comprising persephin in an effective amount for treating patients with cellular degeneration or dysfunction and a method comprising administering a therapeutically effective amount of persephin. These compositions and methods are useful for treating a number of degenerative diseases. Where the cellular degeneration involves neuronal degeneration, the diseases include, but are not limited to peripheral neuropathy, amyotrophic lateral sclerosis, Alzheimer's disease, Parkinson's disease, Huntington's disease, ischemic stroke, acute brain injury, acute spinal chord injury, nervous system tumors, multiple sclerosis, peripheral nerve trauma or injury, exposure to neurotoxins, metabolic diseases such as diabetes or renal dysfunctions and damage caused by infectious agents. In particular, the ability of persephin to promote survival in mesencephalic cells suggests an applicability of this growth factor in treating neuronal degenerative diseases of the CNS such as Parkinson's disease.

Where the cellular degeneration involves bone marrow cell degeneration, the diseases include, but are not limited to disorders of insufficient blood cells such as, for example, leukopenias including eosinopenia and/or basopenia, lymphopenia, monocytopenia, neutropenia, anemias, thrombocytopenia as well as an insufficiency of stem cells for any of the above. The cellular degeneration can also involve myocardial muscle cells in diseases such as cardiomyopathy and congestive heart failure. The above cells and tissues can also be treated for depressed function.

The compositions and methods herein can also be useful to prevent degeneration and/or promote survival in other non-neuronal tissues as well. One skilled in the art can readily determine using a variety of assays known in the art for identifying whether persephin would be useful in promoting survival or functioning in a particular cell type.

In certain circumstances, it may be desirable to modulate or decrease the amount of persephin expressed. Thus, in another aspect of the present invention, persephin anti-sense oligonucleotides can be made and a method utilized for diminishing the level of expression of persephin, respectively, by a cell comprising administering one or more persephin anti-sense oligonucleotides. By persephin anti-sense oligonucleotides reference is made to oligonucleotides that have a nucleotide sequence that interacts through base pairing with a specific complementary nucleic acid sequence involved in the expression of persephin such that the expression of persephin is reduced. Preferably, the specific nucleic acid sequence involved in the expression of persephin is a genomic DNA molecule or mRNA molecule that contains sequences of the persephin gene. This genomic DNA molecule can comprise flanking regions of the persephin gene, untranslated regions of persephin mRNA, the pre- or pro- portions of the persephin gene or the coding sequence for mature persephin protein. The term complementary to a nucleotide sequence in the context of persephin antisense oligonucleotides and methods therefor means sufficiently complementary to such a sequence as to allow hybridization to that sequence in a cell, i.e., under physiological conditions. The persephin antisense oligonucleotides preferably comprise a sequence containing from about 8 to about 100 nucleotides and more preferably the persephin antisense oligonucleotides comprise from about 15 to about 30 nucleotides. The persephin antisense oligonucleotides can also contain a variety of modifications that confer resistance to nucleolytic degradation such as, for example, modified internucleoside linkages (Uhlmann and Peyman, *Chemical Reviews* 90:543-548, 1990; Schneider and Banner, *Tetrahedron Lett* 31:335, 1990 which are incorporated by reference), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that persephin be administered to cells in the central nervous system, administration can be with one or more agents capable of promoting penetration of persephin across the blood-brain barrier.

Persephin can also be linked or conjugated with gents that provide desirable pharmaceutical or harmacodynamic properties. For example, persephin can e coupled to any substance known in the art to promote penetration or transport across the blood-brain barrier such as an antibody to the transferrin receptor, and administered by intravenous injection. (See for example, Friden et al., *Science* 259:373-377, 1993 which is incorporated by reference). Furthermore, persephin can be stably linked to a polymer such as polyethylene glycol to obtain desirable properties of solubility, stability, half-life and other pharmaceutically advantageous properties. (See for example Davis et al. *Enzyme Eng* 4:169-73, 1978; Burnham, *Am J Hosp Pharm* 51:210-218, 1994 which are incorporated by reference).

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Persephin can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing persephin are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity of persephin. The activity of neurturin in target cells data is disclosed herein and in copending application Ser. No. 08/519,777 and the concentration of persephin required for activity at the cellular level is believed to be similar to that of neurturin. The activity of persephin on mesencephalic cells is reported in Example 17 below. Persephin activity on a particular target cell type can be determined by routine experimentation. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, persephin may be therapeutically administered by implanting into patients vectors or cells capable of producing a biologically-active form of persephin or a precursor of persephin, i.e. a molecule that can be readily converted to a biological-active form of persephin by the body. In one approach cells that secrete persephin may be encapsulated into semipermeable membranes for implantation into a patient. The cells can be cells that normally express persephin or a precursor of persephin or the cells can be transformed to express persephin or a precursor thereof. It is preferred that the cell be of human origin and that the persephin be human persephin when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk & Lymph* 16:1-11, 1994 which is incorporated by reference). In another embodiment of the present invention, persephin can be used to promote the ex vivo expansion of a cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12:466-476, 1994 which is incorporated by reference). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12(Suppl 1):249-255, 1994 which is incorporated by reference). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review see Rummel and Van Zant, *J Hematotherapy* 3:213-218, 1994 which is incorporated by reference). Since persephin and the related growth factor, neurturin, may be expressed in the developing animal in particular tissues where proliferation and differentiation of progenitor cells occur, it is believed that persephin can function to regulate the proliferation of hematopoietic stem cells and the differentiation of mature hematopoietic cells. Thus, the addition of persephin to culture systems used for ex vivo expansion of cells could stimulate the rate at which certain populations of cells multiply or differentiate, and improve the effectiveness of these expansion systems in generating cells needed for transplant.

It is also believed that persephin can be used for the ex vivo expansion of precursor cells in the nervous system. Transplant or engraftment of cells is currently being explored as a therapy for diseases in which certain populations of neurons are lost due to degeneration such as, for example, in parkinson's disease (Bjorklund, *Curr Opin Neurobiol* 2:683-689, 1992 which is incorporated by reference). Neuronal precursor cells can be obtained from animal or human donors or from human fetal tissue and then expanded in culture using persephin. These cells can then be engrafted into patients where they would function to replace some of the cells lost due to degeneration. Because neurotrophins have been shown to be capable of stimulating the survival and proliferation of neuronal precursors cells such as, for example, NT-3 stimulation of sympathetic neuroblast cells (Birren et al., *Develop* 119:597-610, 1993 which is incorporated by reference), persephin could also function in similar ways during the development of the nervous system and could be useful in the ex vivo expansion of neuronal cells.

In a number of circumstances it would be desirable to determine the levels of persephin in a patient. The identification of persephin along with the present report that persephin is expressed by certain tissues provides the basis for the conclusion that the presence of persephin serves a normal physiologic function related to cell growth and survival. Indeed, other neurotrophic factors are known to play a role in the function of neuronal and non-neuronal tissues. (For review see Scully and Otten, *Cell Biol Int* 19:459-469, 1995; Otten and Gadient, *Int J Devl Neurosciences* 13:147-151, 1995 which are incorporated by reference). Endogenously produced persephin may also play a role in certain disease conditions, particularly where there is cellular degeneration such as in neurodegenerative conditions or diseases. Other neurotrophic factors are known to change during disease conditions. For example, in multiple sclerosis, levels of NGF protein in the cerebrospinal fluid are increased during acute phases of the disease (Bracci-Laudiero et al., *Neuroscience Lett* 147:9-12, 1992 which is incorporated by reference) and in systemic lupus erythematosus there is a correlation between inflammatory episodes and NGF levels in sera (Bracci-Laudiero et al. *NeuroReport* 4:563-565, 1993 which is incorporated by reference).

Given that persephin is expressed in certain tissues, it is thus likely that the level of persephin may be altered in a variety of conditions and that quantification of persephin levels would provide clinically useful information. Furthermore, in the treatment of degenerative conditions, compositions containing persephin can be administered and it would likely be desirable to achieve certain target levels of persephin in sera, in cerebrospinal fluid or in any desired tissue compartment. It would, therefore, be advantageous to be able to monitor the levels of persephin in a patient. Accordingly, the present invention also provides methods for detecting the presence of persephin in a sample from a patient.

The term "detection" as used herein in the context of detecting the presence of persephin in a patient is intended to include the determining of the amount of persephin or the ability to express an amount of persephin in a patient, the distinguishing of persephin from other growth factors, the estimation of prognosis in terms of probable outcome of a degenerative disease and prospect for recovery, the monitoring of the persephin levels over a period of time as a measure of status of the condition, and the monitoring of persephin levels for determining a preferred therapeutic regimen for the patient.

To detect the presence of persephin in a patient, a sample is obtained from the patient. The sample can be a tissue biopsy sample or a sample of blood, plasma, serum, CSF or the like. Persephin is expressed in kidney and brain tissues as shown in example 18 and it is believed that persephin is expressed in other tissues not tested as well. Samples for detecting persephin can be taken from any tissue expressing persephin. When assessing peripheral levels of persephin, it is preferred that the sample be a sample of blood, plasma or serum or alternatively from a tissue biopsy sample. When assessing the levels of persephin in the central nervous system a preferred sample is a sample obtained from cerebrospinal fluid.

In some instances it is desirable to determine whether the persephin gene is intact in the patient or in a tissue or cell line within the patient. By an intact persephin gene it is meant that there are no alterations in the gene such as point mutations, deletions, insertions, chromosomal breakage, chromosomal rearrangements and the like wherein such alteration might alter production of persephin or alter its biological activity, stability or the like to lead to disease processes or susceptibility to cellular degenerative conditions. Conversely, by a non-intact persephin gene it is meant that such alterations are present. Thus, in one embodiment of the present invention a method is provided for detecting and characterizing any alterations in the persephin gene. The method comprises providing an oligonucleotide that contains the persephin CDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the persephin gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact persephin gene or a persephin gene abnormality.

Hybridization to the persephin gene would involve denaturing the chromosomal DNA to obtain a single-stranded DNA; contacting the single-stranded DNA with a gene probe associated with the persephin gene sequence; and identifying the hybridized DNA-probe to detect chromosomal DNA containing at least a portion of the human persephin gene.

The term "probe" as used herein refers to a structure comprised of a polynucleotide which forms a hybrid structure with a target sequence, due to complementarity of probe sequence with a sequence in the target region. The probes need not reflect the exact sequence of the target sequence, but must be sufficiently complementary to selectively hybridize with the strand being amplified. By selective hybridization or specific hybridization it is meant that a polynucleotide preferentially hybridizes to a target polynucleotide. Oligomers suitable for use as probes may contain a minimum of about 8-12 contiguous nucleotides which are complementary to the targeted sequence and preferably a minimum of about 15 nucleotides although polynucleotide probes up to about 20 nucleotides and up to about 100 nucleotides or even greater are within the scope of this invention.

The persephin gene probes of the present invention can be DNA or RNA oligonucleotides and can be made by any method known in the art such as, for example, excision, transcription or chemical synthesis. Probes may be labelled with any detectable label known in the art such as, for example, radioactive or fluorescent labels or enzymatic marker. Labeling of the probe can be accomplished by any method known in the art such as by PCR, random priming, end labelling, nick translation or the like. One skilled in the art will also recognize that other methods not employing a labelled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25-45° C., more preferably at 32-40° C. and more preferably at 37-38° C. The time required for hybridization is from about 0.25 to about 96 hours, more preferably from about one to about 72 hours, and most preferably from about 4 to about 24 hours.

Persephin gene abnormalities can also be detected by using the PCR method and primers that flank or lie within the persephin gene. The PCR method is well known in the art. Briefly, this method is performed using two oligonucleotide primers which are capable of hybridizing to the nucleic acid sequences flanking a target sequence that lies within a persephin gene and amplifying the target sequence. The terms "oligonucleotide primer" as used herein refers to a short strand of DNA or RNA typically ranging in length from about 8 to about 30 bases. The upstream and downstream primers are preferably a minimum of from about 15 nucleotides to about 20 nucleotides and up to about 30 nucleotides or even greater in length. The primers can hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize or specifically hybridize with the strand being amplified. By selective hybridization or specific hybridization it is meant that a polynucleotide preferentially hybridizes to a target polynucleotide.

After PCR amplification, the DNA sequence comprising persephin or pre-pro persephin or a fragment thereof is then directly sequenced and analyzed by comparison of the sequence with the sequences disclosed herein to identify alterations which might change activity or expression levels or the like.

In another embodiment a method for detecting persephin is provided based upon an analysis of tissue expressing the persephin gene. Certain tissues such as those identified below in example 18 have been found to express the persephin gene. The method comprises hybridizing a polynucleotide probe to mRNA from a sample of tissues that normally express the persephin gene or from a CDNA produced from the mRNA of the sample. The sample is obtained from a patient suspected of having an abnormality in the persephin gene or from a particular patient tissue or cell type suspected of having an abnormality in the persephin gene. The reference persephin polynucleotide probe can comprise SEQ ID NO:179, SEQ ID NO:180, SEQ ID NO:190, SEQ ID NO:191, SEQ ID NOS: 203-206 or derivatives thereof or fragments thereof so long as such derivatives or fragments specifically hybridize to persephin mRNA or from a CDNA produced from a persephin mRNA.

To detect the presence of mRNA encoding persephin protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a nucleic acid serving as a probe to form hybrid duplexes. The use of a labeled probes as discussed above allows detection of the resulting duplex.

When using the cDNA encoding persephin protein or a derivative of the cDNA as a probe, high stringency conditions can be used in order to prevent false positives, that is the hybridization and apparent detection of persephin nucleotide sequences when in fact an intact and functioning persephin gene is not present. When using sequences derived from the persephin cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook, et al., 1989, supra).

Figure 6:
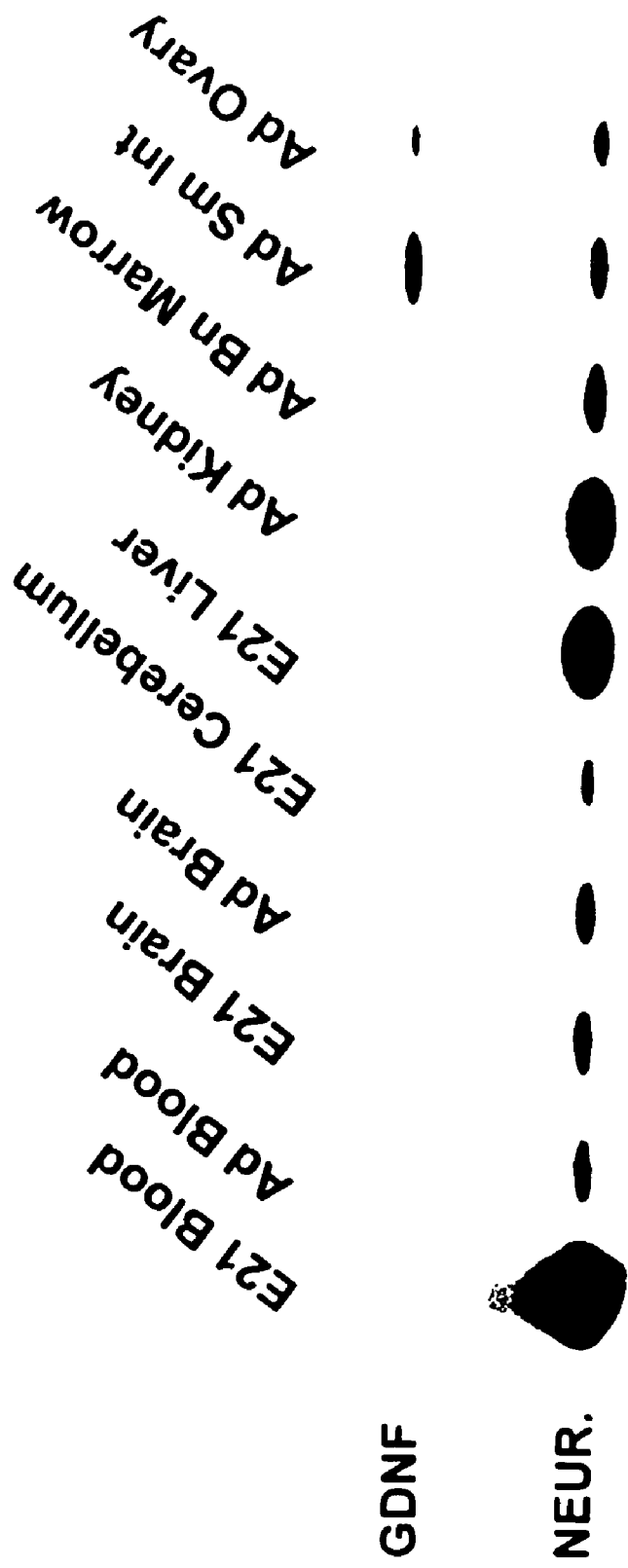
FIG. 6 illustrates the tissue distribution of neurturin mRNA and the mRNA for GDNF using RT/PCR analysis on RNA samples obtained from embryonic day 21 (E21) and adult rats.

In order to increase the sensitivity of the detection in a sample of mRNA encoding the persephin protein, the technique of reverse transcription/polymerization chain reaction (RT/PCR) can be used to amplify cDNA transcribed from MRNA encoding the persephin protein. The method of RT/PCR is well known in the art (see example 9 and FIG. 6 below).

The RT/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and persephin specific primers. (Belyavsky et al, *Nucl Acid Res* 17:2919-2932, 1989; Krug and Berger, *Methods in Enzymology*, Academic Press, N.Y., Vol.152, pp. 316-325, 1987 which are incorporated by reference).

The polymerase chain reaction method is performed as described above using two oligonucleotide primers that are substantially complementary to the two flanking regions of the DNA segment to be amplified.

Following amplification, the PCR product is then electrophoresed and detected by ethidium bromide staining or by phosphoimaging.

The present invention further provides for methods to detect the presence of the persephin protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology*, Sites and Terr, eds., Appleton & Lange, Norwalk, Conn. pp 217-262, 1991 which is incorporated by reference). Preferred are binder-ligand immunoassay methods including reacting antibodies with an epitope or epitopes of the persephin protein or derivative thereof and competitively displacing the labeled persephin protein or derivative thereof.

As used herein, a derivative of persephin protein is intended to include a polypeptide in which certain amino acids have been deleted or replaced with other amino acids or changed to modified or unusual amino acids wherein the persephin derivative is biologically equivalent to persephin and/or wherein the polypeptide derivative cross-reacts with antibodies raised against the persephin protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to the persephin protein or to an epitope thereof can be made for use in immunoassays by any of a number of methods known in the art. By epitope reference is made to an antigenic determinant of a polypeptide. The term epitope can also include persephin-specific B cell epitopes or T helper cell epitopes. An epitope could comprise 3 amino acids in a spacial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse (See Example 10).

Oligopeptides can be selected as candidates for the production of an antibody to the persephin protein based upon the oligopeptides lying in hydrophilic regions, which are thus likely to be exposed in the mature protein.

Antibodies to persephin can also be raised against oligopeptides that include one or more of the conserved regions identified herein such that the antibody can cross-react with other family members. Such antibodies can be used to identify and isolate the other family members.

Methods for preparation of the persephin protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J Am Chem Soc* 85:2149, 1963 which is incorporated by reference) or the FMOC strategy on a Rapid Automated Multiple Peptide Synthesis system (DuPont Company, Wilmington, Del. ) (Caprino and Han, *J Org Chem* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified persephin protein usually by ELISA or by bioassay based upon the ability to block the action of persephin. When using avian species, e.g. chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler *Nature* 256:495-497, 1975; Gulfre and Milstein, *Methods in Enzymology: Immunochemical Techniques* 73:1-46, Langone and Banatis eds., *Academic Press*, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an over expression of the protein. Thus, another aspect of the present invention provides for a method for preventing or treating diseases involving over expression of the persephin protein by treatment of a patient with specific antibodies to the persephin protein.

Specific antibodies, either polyclonal or monoclonal, to the persephin protein can be produced by any suitable method known in the art as discussed above. For example, murine or human monoclonal antibodies can be produced by hybridoma technology or, alternatively, the persephin protein, or an immunologically active fragment thereof, or an anti-idiotypic antibody, or fragment thereof can be administered to an animal to elicit the production of antibodies capable of recognizing and binding to the persephin protein. Such antibodies can be from any class of antibodies including, but not limited to IgG, IgA, IgM, IgD, and IgE or in the case of avian species, IgY and from any subclass of antibodies.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the isolation and purification of neurturin from CHO cell conditioned medium.

Preparation of CHO Cell Conditioned Medium:

A derivative of DG44 Chinese hamster ovary cells, DG44CHO-pHSP-NGFI-B (CHO) cells, was used (Day et al, *J Biol Chem* 265:15253-15260, 1990 which is incorporated by reference). The inventors herein have also obtained neurturin in partially purified form from other derivatives of DG44 Chinese hamster ovary cells. The CHO cells were maintained in 20 ml medium containing minimum essential medium (MEM) alpha (Gibco-BRL No. 12561, Gaithersburg, Md.) containing 10% fetal calf serum (Hyclone Laboratories, Logan, Utah), 2 mM 1-glutamine, 100 U/ml penicillin, 100 µg/ml streptomycin and 25nM methotrexate using 150 cm² flasks (Corning Inc., Corning N.Y.). For passage and expansion, medium from a confluent flask was aspirated; the cells were washed with 10 ml phosphate buffered saline (PBS) containing in g/l, 0.144 $KH_2PO_4$, 0.795 $Na_2HPO_4$ and 9.00 NaCl; and the flask was then incubated for 2-3 minutes with 2 ml 0.25% trypsin in PBS. Cells were then knocked off the flask surface, 8 ml of medium were added and cells were triturated several times with a pipette. The cells were split 1:5 or 1:10, incubated at 37° C. under an atmosphere of 5% $CO_2$ in air and grown to confluence for 3-4 days.

The cell culture was then expanded into 850 cm² roller bottles (Becton Dickinson, Bedford, Mass.). A confluent 150 cm² flask was trypsinized and seeded into one roller bottle containing 240 ml of the above modified MEM medium without methotrexate. The pH was maintained either by blanketing the medium with 5% $CO_2$ in air or by preparing the medium with 25 mM HEPES pH 7.4 (Sigma, St. Louis, Mo.). The roller bottles were rotated at 0.8-1.0 revolutions per minute. Cells reached confluence in 4 days.

For collecting conditioned medium, serum-free CHO cell (SF-CHO) medium was used. SF-CHO was prepared using 1:1 DME/F12 base medium, which was prepared by mixing 1:1 (v/v) DMEM (Gibco-BRL product No. 11965, Gibco-BRL, Gaithersburg, Md.) with Ham's F12 (Gibco-BRL product No. 11765). The final SF-CHO medium contained 15 mM HEPES pH 7.4 (Sigma, St. Louis, Mo.), 0.5 mg/ml bovine serum albumin (BSA, Sigma, St. Louis Mo.), 25 µg/ml heparin, (Sigma, St. Louis, Mo.), 1X insulin-transferrin-selenite supplement (bovine insulin, 5 µg/ml; human transferrin, 5 µg/ml; sodium selenite, 5 ng/ml; Sigma, St. Louis, Mo.), 2 mM 1-glutamine, 100 U/ml penicillin, and 100 µg/ml streptomycin. The medium from the confluent roller bottles was removed and the cells washed once with 30 ml SF-CHO medium to remove serum proteins. Cells were then incubated at 37° C. for 16-24 hrs in 80 ml SF-CHO medium to further remove serum proteins. The 80 ml medium was removed and discarded. A volume of 120 ml of SF-CHO medium was added to the flask and the cells incubated at 37° C. Every 48 hrs thereafter, 120 ml was collected and replaced with the same volume of SF-CHO medium.

Collected media was pooled and centrifuged at 4° C. in polypropylene conical tubes to remove cellular debris and the supernatant stored at −70° C. Media was collected 5 times over 10 days to yield a total of approximately 600 ml conditioned medium per roller bottle.

Fractions collected from the columns at each stage of purification were assayed for biological activity using the neuronal survival assay and for protein content by the dye binding assay of Bradford (*Anal Biochem* 72:248 et seq., 1976 which is incorporated by reference). The total mg of protein in the starting volume, typically 50 liters, of conditioned medium was determined.

Superior Cervical Ganglion Survival Assay:

The neurotrophic activity of CHO conditioned medium starting material and at various stages of purification was assessed using the superior cervical ganglion survival assay system previously reported (Martin, et al *J of Cell Biology* 106:829-844; Deckwerth and Johnson, *J Cell Bio* 123:1207-1222, 1993 which are incorporated by reference). Primary cultures of sympathetic neurons from superior cervical ganglion (SCG) were prepared by dissecting tissue from Day 20-21 rat embryo (E20-E21). The SCG's were placed in Leibovitz's L15 with 1-glutamine medium (Cat #11415-023 Gibco-BRL, Gaithersburg, Md.), digested for 30 minutes with 1 mg/ml collagenase (Cat #4188 Worthington Biochemical, Freehold, N.J.) in Leibovitz's. L15 medium at 37° C., followed by a 30 minute digestion in trypsin-lyophilized & irradiated (Type TRLVMF Cat #4454 Worthington Biochemical, Freehold, N.J.) which was resuspended in modified Hanks' Balanced Salt Solution (Cat #H-8389 Sigma Chemical Co., St. Louis, Mo.). The digestion was stopped using AM50 which contains Minimum Essential Medium with Earle's salts and without 1-glutamine (Cat #11090-016 Gibco-BRL), 10% fetal calf serum (Cat #1115 Hyclone Laboratories, Logan, Utah), 2mM 1-glutamine (Cat #G5763 Sigma Chemical Co., St. Louis, Mo.), 20 µM FuDr (F-0503 Sigma Chemical Co., St. Louis, Mo.), 20 µM Uridine (Cat #3003 Sigma Chemical Co., St. Louis, Mo.), 100 U/ml penicillin, 100 µg/ml Streptomycin, and 50 ng/ml 2.5 S NGF. The cells were dissociated into a suspension of single cells using a silanized and flame-polished Pasteur pipet. After filtration of the suspension through a nitex filter (size 3-20/14, Tetko Inc., Elmsford, N.Y.), the cells were placed in AM50 medium as above and preplated on a 100 mm Falcon or Primaria culture dish (Becton Dickinson Labware, Lincoln Park, N.J.) to reduce the number of non-neuronal cells. After 2 hours, the medium containing the unattached neuronal cells was removed from these dishes and triturated again through a silanized and flame-polished Pasteur pipet. The single cell suspension was plated on 24-well tissue culture plates (Costar, Wilmington, Mass.) that have been previously coated with a double layer of collagen, one layer of collagen that had been ammoniated and a second layer of collagen that had been air dried. They were allowed to attach for 30 minutes to 2 hours. A specific number of viable cells, usually about 1200 to about 3000 total cells per well, or a specific percentage of the ganglion, usually 25% of the cells obtained per ganglion were plated into each well. When cell counts were to be performed they were placed in the 24-well dishes as stated above or alternatively, on 2-well chamber slides (Nunc, Naperville, Ill.). Cultures were then incubated for 5-6 days at 37° in AM50 medium in a 5% $CO_2$/95% air atmosphere. The death of the cultured neurons was induced by exchanging the medium with medium without NGF and with 0.05% goat anti-NGF (final titer in the wells is 1:10). This NGF-deprivation results in death of the neurons over a period of 24-72 hours. Aliquots of partially purified or purified factor, or appropriate controls, were added to the cultures at the time of NGF removal to determine the ability to prevent the neuronal death.

Figure 3A:
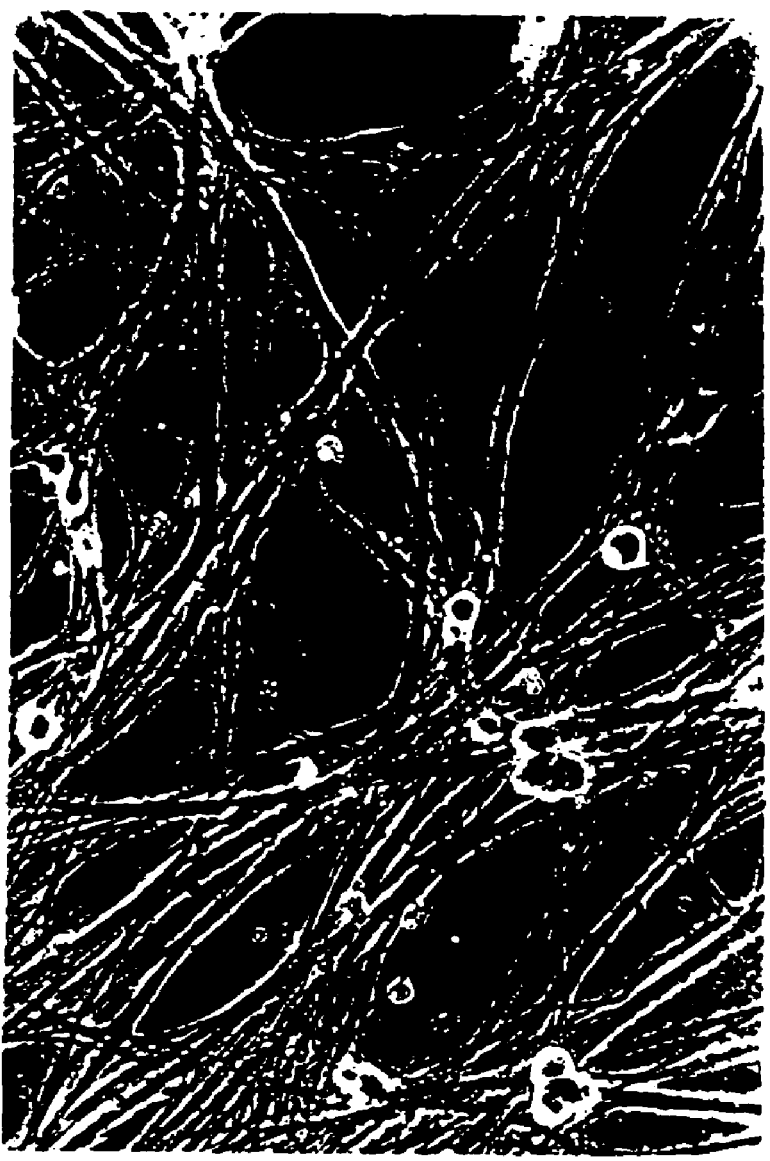
FIG. 3 illustrates the ability of neurturin to maintain survival of superior cervical ganglionic cells in culture showing (a) positive control cells maintained with nerve growth factor (NGF) (b) negative control cells treated with anti-NGF antibodies showing diminished survival and (c) cells treated with anti-NGF and neurturin (approximately 3 ng/ml) showing survival of neurons.

Evaluation of the ability of column fraction, gel eluates, or purified factor to prevent neuronal death was by visual inspection of cultures under phase contrast microscopy. Viable neurons remained phase bright with intact neurites, whereas dead neurons were shrunken, phase dark, had irregular membranes and neurites were fragmented (FIG. 3). Where precise quantitation of neuronal survival was required, the cultures were fixed in 4% paraformaldehyde or 10% Formalin in PBS, and stained with crystal violet solution, (Huntoon Formula Harleco E. M. Diagnostics Systems, Gibbstown, N.J.). When using 24 well dishes, 1 µl crystal violet solution was added to each well containing 10% formalin and the cells were counted using a phase contrast microscope. If the 2-well chamber slides were used, the cultures were fixed, stained with crystal violet, destained with water, dehydrated in increasing ethanol concentrations to toluene, and mounted in a toluene-based mounting solution. Neurons were scored as viable if they had a clear nucleolus and nuclei and were clearly stained with crystal violet.

Figure 3B:
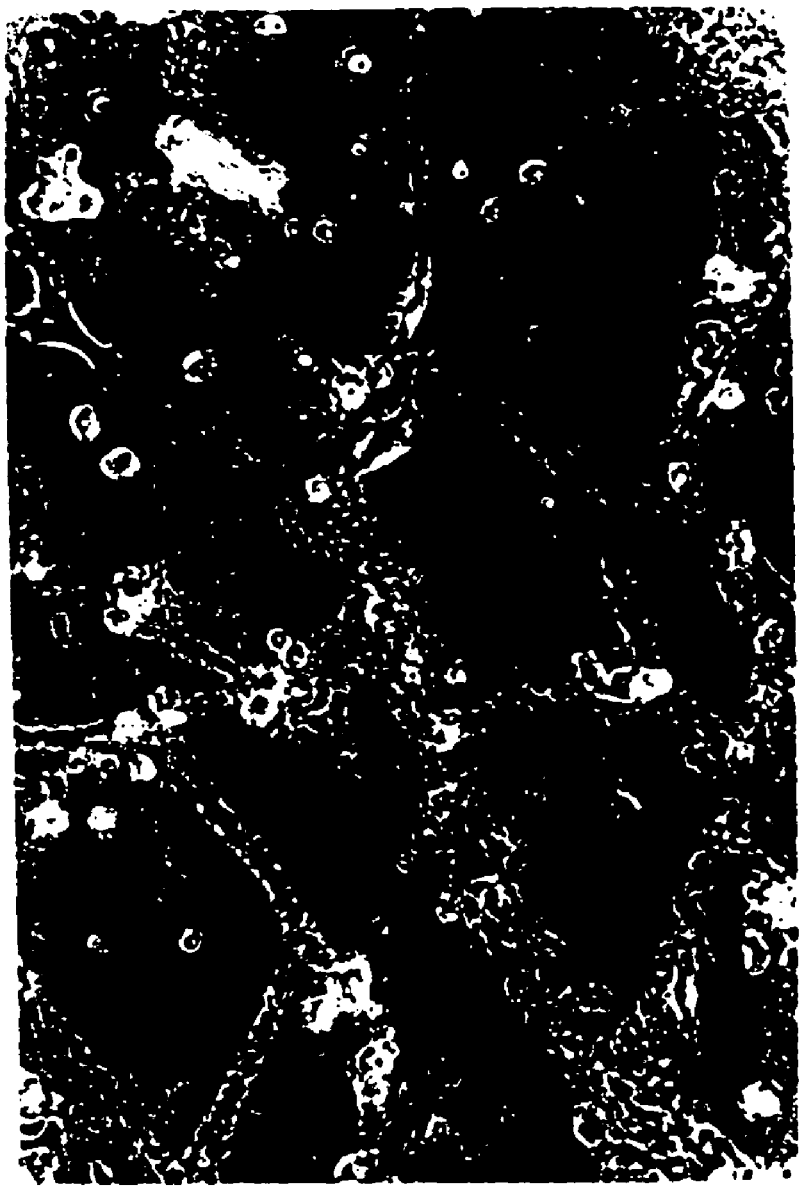
Figure 3C:
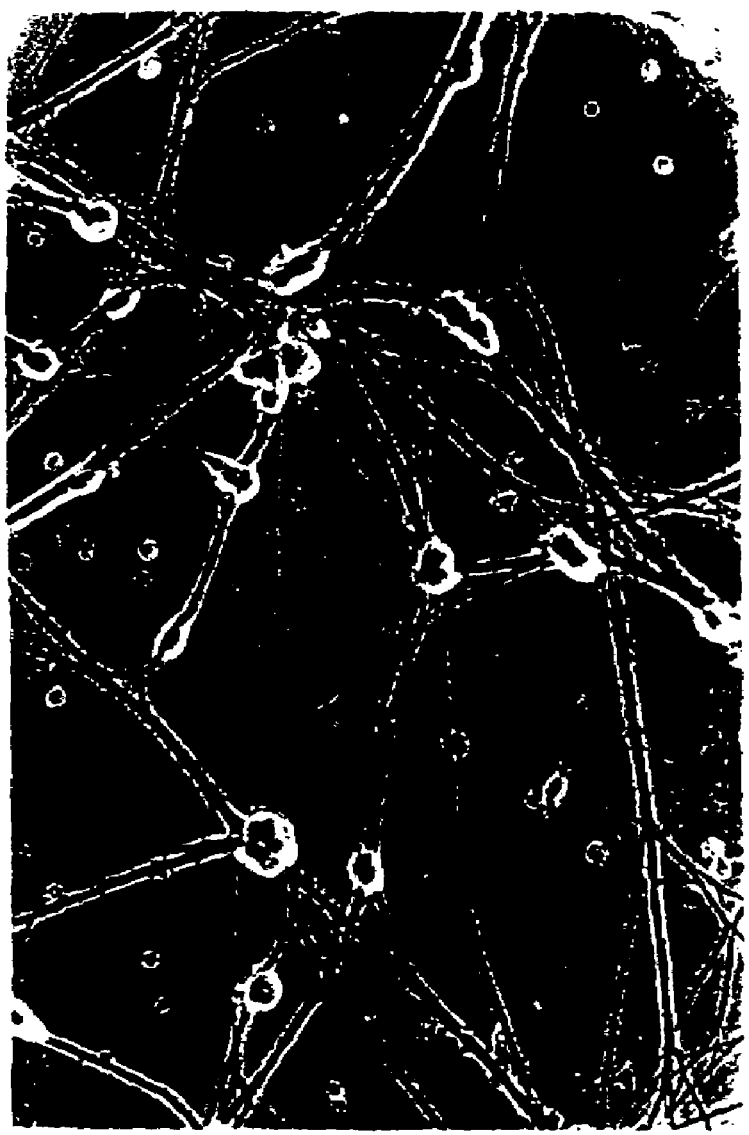

The neuronal death at 72 hours in shown in FIG. 3B. Also shown are (A) the positive control cells maintained with nerve growth factor and (C) the cells treated with anti-NGF and neurturin (approximately 3 ng/ml) showing survival of neurons.

Activity was quantitated by calculation of a "survival unit". The total survival units in a sample were defined as the minimal volume of an aliquot of the sample which produced maximal survival divided into the total volume of that sample. Specific activity was calculated as the survival units divided by the mg total protein.

Figure 4:
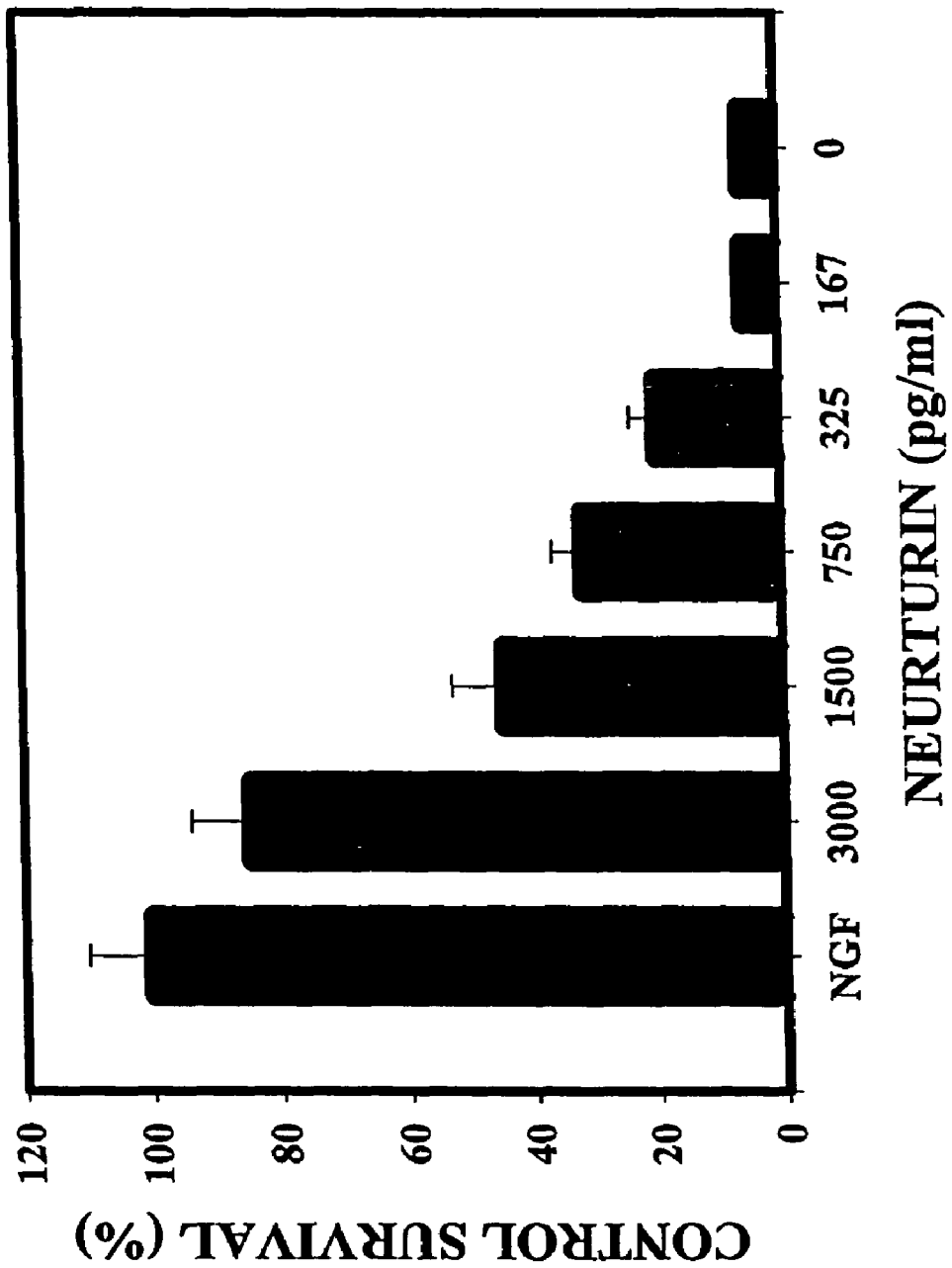
FIG. 4 illustrates the concentration-response effect of neurturin in the superior cervical ganglion survival assay.

Survival units were determined in an assay using approximately 1200 viable neurons in a 0.5 ml culture assay and a culture period of 48 hours following addition of the fraction. Survival was assessed visually after the 48 hours. Intrinsic activity as shown in FIG. 4 was determined in an assay using approximately 2700 neurons and a culture period of 72 hours. Survival was assessed by fixing the neurons and counting the number of surviving neurons. Because the stability, as assessed by half-life of activity, for neurturin decreases as the number of neurons increases, the intrinsic activity measurement would be expected to be lower than that predicted by Specific Activity determinations. The intrinsic activity measurement would also be expected to be lower than that predicted by specific activity because the survival was measured after 72 hours instead of 48 hours.

To ensure the reproducibility of these activity unit assays, it was necessary to plate the primary neuronal cultures at reproducible cell densities, as the stability of the activity decreases significantly with increasing neuronal density. The range of cell densities was from about 1200 to about 2700 cells per well. The presence of soluble heparin in the assay medium had no effect on the short-term (~3 days) stability of the survival activity.

Purification of Neurturin:

Pooled conditioned medium was filtered through 0.2 µl pore bottle-top filters (cellulose acetate membrane, Corning Inc., Corning, N.Y.). Typically 50 liters of conditioned medium was used and processed in 25 liter batches. Each 25 liter batch was introduced at a rate of 20 ml/min onto a 5×5 cm column containing 100 ml heparin-agarose (Sigma, St. Louis, Mo.) equilibrated with 25 mM HEPES, pH 7.4 buffer with 150 mM NaCl. The column was then washed with approximately 1000 ml 25 mM HEPES, pH 7.4 buffer containing 0.5 M NaCl at 20 ml/min and the activity was then eluted with 25 mM HEPES, pH 7.4 buffer containing 1.0 M NaCl. After switching to the 1.0M NaCL elution buffer, the first 50 ml of buffer was discarded and, thereafter, one 300 ml fraction was collected.

Pooled material eluted from the Heparin-agarose column was then diluted 1:1 (v/v) with 25 mM HEPES, pH 7.4 buffer containing 0.04% TWEEN 20 to a NaCl concentration of 0.5 M and introduced into a 1.5 cm×9 cm column containing 16 ml SP SEPHAROSE® High Performance ion exchange resin (Pharmacia, Piscataway, N.J.) equilibrated in 25 mM HEPES 7.4 containing 0.5 M NaCl and 0.02% TWEEN 20. The column was then washed with 160 ml 25 mM HEPES, pH 7.4 buffer containing 0.5 M NaCl and 0.02% TWEEN 20 and the activity was eluted with 25 mM HEPES, pH 7.4 buffer containing 1.0 M NaCl and 0.02% TWEEN 20 at a flow rate of 2 ml/min. One 50 ml fraction was collected after the first 7 ml of eluate from the column.

Material eluted from the SP SEPHAROSE® column was fractionated using fast protein liquid chromatography (FPLC) on a Chelating Superose HR 10/2 column charged with $Cu^{++}$ (Pharmacia, Piscataway, N.J.). The column had been prepared by washing with 10 ml water, charging with 3 ml of 2.5 mg/ml $CuSO_4.5H_2O$, washing with 10 ml water, and equilibrating with 10 ml of 25 mM HEPES pH 7.4 buffer containing 1.0 M NaCl and 0.02% TWEEN 20. The eluate was introduced into the column in 25 mM HEPES, pH 7.4 buffer containing 1.0 M NaCl at a rate of 1.0 ml/min. The bound proteins were eluted with a linear gradient of increasing glycine concentration (0-300 mM) in 25 mM HEPES, pH 7.4 buffer containing 1.0 M NaCl at a rate of 1.0 ml/min. The gradient was produced by a Pharmacia FPLC system using an LCC-500 controller and P-500 pumps to establish a 0-300 mM glycine gradient in 40 ml at 1.0 ml/min, thus increasing the gradient by 7.5 mM glucine per min. One ml fractions were collected and assayed for SCG survival promotion. Peak activity was observed in fractions 17-20, i.e. 17-20 min or ml from the start of the gradient.

Absorbance measurements at 280 nM by an in-line UV monitor indicated that most proteins eluted prior to the survival activity in fractions 17-20. Thus, significant purification was achieved at this step. A 25 kD band co-purified with the survival activity.

The combined eluted fractions from the $Cu^{++}$ superose column were diluted to 0.45 M NaCl using 25 mM HEPES pH 7.4 buffer containing 0.02% TWEEN 20 and introduced into a Mono S HR 5/5 cation exchange column (Pharmacia, Piscataway, N.J.) for further FPLC purification. The column had been equilibrated with 25 mM HEPES pH 7.4 buffer containing 0.45 M NaCl containing 0.02% TWEEN 20. Bound proteins were eluted with a linear gradient of increasing NaCl concentration (0.45-1.0 M). The gradient was produced as described above from 0.45 M -1.0 M NaCl in 35 mls at 1.0 ml/min, thus increasing concentration at 0.0157 M per ml or min. Thirteen 1.0 ml fractions (fractions 1-13) were collected followed by 44 0.5 ml fractions (fractions 14-53). Peak activity in SCG assay was in fractions 26-29. Each fraction was assayed in the SCG survival assay over a range of volumes of from 0.1 to 1.0 pl per 0.5 ml culture medium.

Figure 1:
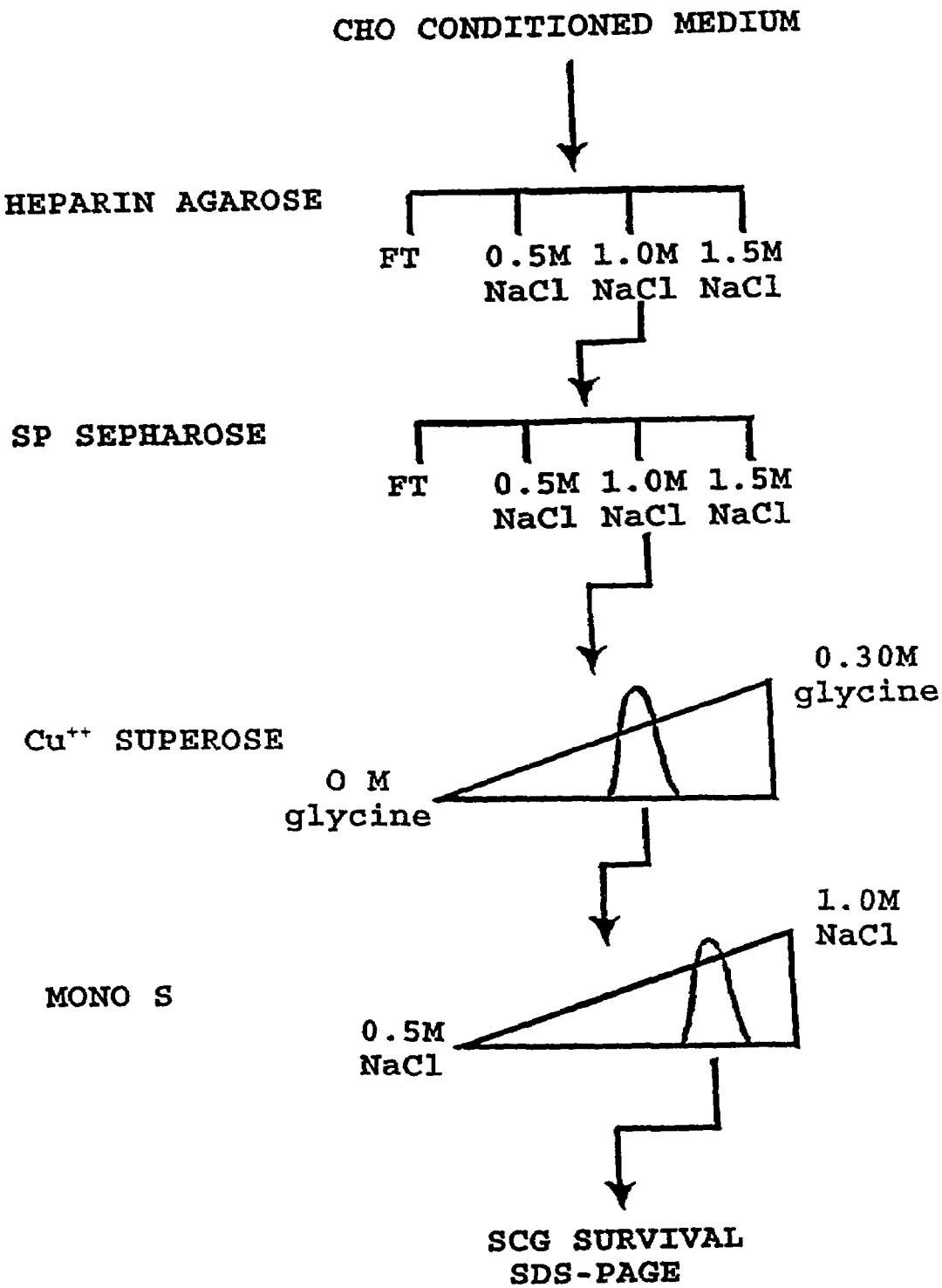
FIG. 1 illustrates the purification scheme for preparing neurturin from CHO cells.
Figure 2B:
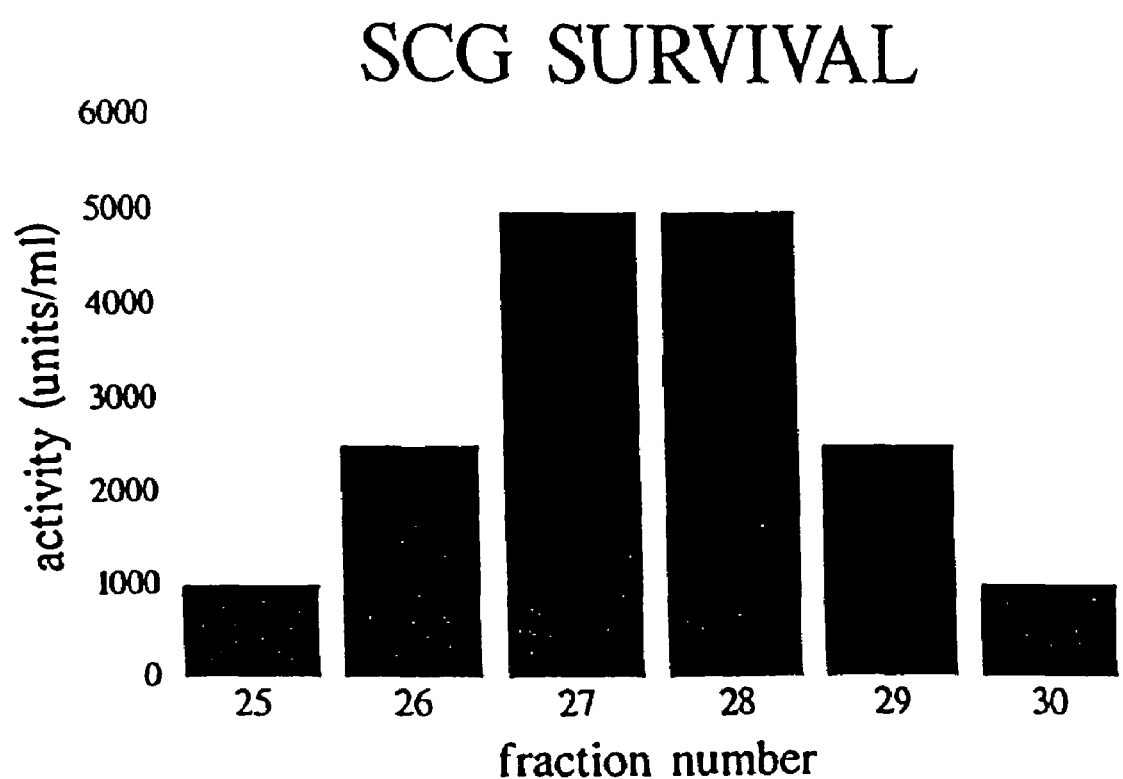
FIG. 2 illustrates the characterization of fractions eluted from Mono S column in purifying neurturin showing (a) electrophoresis of each fraction on a SDS-polyacrylamide gel and visualization of the proteins by silver stain and (b) the neurotrophic activity present in each fraction in the superior cervical ganglion survival assay.

One percent (5 µl) of each fraction was loaded onto a non-reducing, 14% SDS polyacrylamide gel and electrophoresed for 750 V-hr at 25° C. Proteins were visualized by silver stain. The results are shown in FIG. 2. Markers shown in lane M on the gel represent 20 ng of Bovine serum albumin, carbonic anhydrase, B-lactoglobulin, and lysozyme in the order of descending molecular weight.

A 25 kD band appeared in fractions 25-30, a 28 kD protein elutes earlier in the gradient and an 18 kD elutes later in the gradient. FIG. 2 illustrates the survival activity in each of the fractions. The survival activity is noted to correspond with the presence and apparent intensity of the 25 kD protein in fractions 25-30.

To demonstrate that the 25 kD band was responsible for survival promoting activity, the 25 kD protein was eluted from the polyacrylamide gel after electrophoresis and assayed for survival activity in the SCG assay. After electrophoresis of 150 µl of the SP SEPHAROSE® 1.0 M NaCl fraction in one lane of a non-reducing 14% SDS-polyacrylamide gel as above, the lane was cut into 12 slices and each slice was crushed and eluted by diffusion with rocking in buffer containing 25 mM HEPES, pH 7.4, 0.5 M NaCl, 0.02% Tween-20 for 18 hr at 25° C. BSA was added to the eluate to a final concentration of 200 µg/ml and the eluate was filtered through a 0.45 micron filter to remove acrylamide gel fragments. The filtrate was then added to a SP SEPHAROSE® column to concentrate and purify the sample. Before eluting the sample, the column was washed once in 400 µl 25 mM HEPES, pH 7.4 buffer containing 0.5 M NaCl, 0.02% Tween-20 and 200 µg BSA per ml and once in 400 µl 25 mM HEPES, pH 7.4 buffer containing 0.02% Tween-20 and 200 µg BSA per ml. The column was then washed again in 400 µl of 25 mM HEPES, pH 7.4 buffer containing 0.5 M NaCl, 0.02% TWEEN 20 and 200 µg BSA per ml. The sample was eluted with 25 mM HEPES, pH 7.4 buffer containing 1.0 M NaCl, 0.02% Tween-20 and 200 µg BSA per ml. Samples were then analyzed for survival activity. Only the slice corresponding to the 25 kD band showed evidence of survival activity. The 25 kD protein purified from CHO cell conditioned media is believed to be a homodimer.

The yield from the purification above was typically 1-1.5 µg from 50 liters of CHO cell conditioned medium. Overall recovery is estimated to be 10-30%, resulting in a purification of approximately 390,000 fold.

The progressive purification using the above steps as shown in table 2.

TABLE 2

| | Protein[a] (mg) | Activity[b] (units) | Specific Activity[d] (units/mg) | Yield (%) | Purification (fold) |
|---|---|---|---|---|---|
| Conditioned Medium | 5000 | 48000[c] | 9.6 | — | — |
| Heparin Agarose | 45 | 48000 | 1068 | 100 | 111 |
| SP Sepharose | 5.3 | 48000 | 9058 | 100 | 943 |
| Cu++ Superose | 0.31 | 30000 | 96700 | 62 | 10070 |
| Mono S | 0.004 | 15000 | 3750000 | 31 | 390000 |

[a]mg protein was determined using the dye binding method of Bradford (Anal Biochem 72: 248, 1976).
[b]The total activity units or survival units in a sample were defined as the minimal volume of an aliquot of the sample which produced maximal survival divided into the total volume of that sample.
[c]Activity for Conditioned Medium was derived from the assumption that 100% of the activity was recovered in the heparin agarose fraction because the activity of conditioned medium was too low to be directly assayed.
[d]Specific Activity was the Activity units divided by the mg total protein.

EXAMPLE 2

This example illustrates the characterization of neurturin and several members of the TGF-β family of growth factors in the SCG assay and the lack of cross reactivity of anti-GDNF antibodies with neurturin.

The SCG assay of the purified protein indicated that the factor is maximally active at a concentration of approximately 3 ng/ml or approximately 100 pM and the $EC_{50}$ was approximately 1.5 ng/ml or approximately 50 pM in the expected range for a diffusible peptide growth factor (FIG. 4).

Several members of the TGF-β family influence neuropeptide gene expression in sympathetic neurons, while others promote survival of different neuronal populations. Neurturin, which is a distant member of this family of proteins, is capable of promoting virtually complete survival of sympathetic neurons for 3 days. In addition, further culturing of the SCG cells revealed that neurturin could continue to maintain these neurons for at least 10 days after withdrawal of NGF.

We tested several other members of the TGF-β family for their ability to promote survival in the SCG assay including TGF-β, activin, BMP-2, BMP-4, BMP-6 and GDNF. Of these factors, only GDNF had survival promoting activity, however, the activity of GDNF was much less potent than neurturin in this activity showing an $EC_{50}$ of 2-4 nM in the 3-day survival assay. The GDNF tested in this assay was rhGDNF produced in E. Coli obtained from Prepro Tech, Inc., Rocky Hill, N.J. The duration of action of GDNF was also less than that of neurturin inasmuch as the ability of GDNF (50 ng/ml) to maintain survival longer than 3 days was substantially diminished. These experiments suggest the possibility that GDNF is a weak agonist for the neurturin receptor. Furthermore, the inability of activin and BMP-2 to promote survival, in contrast to their strong induction of transmitter-related gene expression in these neurons (Fann and Paterson, *Int J Dev Neurosci* 13:317-330, 1995; Fann and Patterson, *J Neurochem* 61:1349-1355, 1993) suggests that they signal through alternate receptors or signal transduction pathways.

To determine the cross-reactivity of anti-GDNF antibodies with partially purified neurturin, SCG neurons, that had been dissected and plated as described in Example 1 were treated on Day 6 with 1 ng/ml, 3 ng/ml, 10 ng/ml, or 30 ng/ml GDNF (Prepro Tech, Inc, Rocky Hill, N.J.) in the presence of anti-NGF alone, or in the presence of anti-NGF and anti-GDNF (goat IgG antibody to E. coli-derived rhGDNF, R & D Systems, Minneapolis, Minn). A partially purified 1.0 M SP Sepharose fraction of neurturin was used in the assay at the approximate concentrations of 375 pg/ml, 750 pg/ml, 1.5 ng/ml and 3 ng/ml. This fraction was tested in the presence of anti-NGF alone, and in the presence of anti-NGF and anti-GDNF. The anti-GDNF antibody blocked the survival promoting activity of GDNF at a concentration up to 30 ng/ml, but did not block the survival promoting activity of neurturin.

EXAMPLE 3

This example illustrates the effect of neurturin on sensory neurons in a nodose ganglion survival assay.

CHO cell conditioned media that had been partially purified on the SP Sepharose column was assayed for neurotrophic activity on sensory neurons using nodose ganglia. The survival assay is a modification of that previously reported above for superior cervical ganglia. Primary dissociated cultures of nodose ganglia were prepared by dissecting tissue from E18 Sprague Dawley rat (pups. The nodose ganglia were placed in Leibovitz's L15 with 2 mM 1-glutamine (Cat#11415-023, GIBCO-BRL. Gaithersburg, Md.) as the tissues was dissected, digested for 30 min with 1 mg/ml collagenase (Cat#4188, Worthington Biochemical, Freehold, N.J.) in Leibovitz's L15 medium at 37° C., followed by 30 min digestion in trypsin (lyophilized and irradiated, type TRLVMF, Cat #4454 Worthington Biochemical, Freehold, N.J.), and resuspension to a final concentration of 0.25% in modified Hank's Balanced Salt Solution (Cat#H8389, Sigma Chemical Co., St. Louis, Mo.). The digestion was stopped using AMO-BDNF100, a medium containing Minimum Essential Medium with Earle's salts and without 1-glutamine (#11090-016 GIBCO-BRL), 10% fetal Calf Serum (Cat#1115, Hyclone Laboratories, Logan, Utah), 2 mM 1-glutamine (Cat#G5763 Sigma Chemical Co., St. Louis, Mo.), 20 µM FuDr (F-0503, Sigma Chemical Co.), 20 µM Uridine (Cat #3003, Sigma Chemical Co., St. Louis, Mo.) 100 U/ml penicillin, 100 µg/ml Streptomycin, and 100 ng Brain Derived Neurotropic Factor (BDNF, Amgen, Thousand Oaks, Calif.). The cells were dissociated into a suspension of single cells using a silanized and flame-polished Pasteur pipet in the AMO-BDNF100 medium, and preplated on a 100 mm Falcon or Primaria culture dish (Becton Dickinson Labware, Lincoln Park, N.J.) to remove non-neuronal cells. After 2 hours, the medium containing the unattached neuronal cells was removed from these dishes and triturated again through a silanized and flame-polished Pasteur pipet. The single cell suspension was plated on 24-well tissue culture plates (Costar, Wilmington, Mass.) that have been previously coated with a double layer of collagen, one layer of which had been ammoniated and a second layer that had been air dried. Ganglia from ten E18 rat embryos were dissociated into 2.5 mls of media and 100 µl of this suspension was added to each well. The cells were allowed to attach for 30 min in a 37° C. incubator with 5% CO2/95% air. The wells were fed with AMO-BDNF100 media overnight.

The next day the cells were washed 3 times for 20 min each time with AMO medium containing no BDNF. The wells were fed with 0.5 ml of this media alone or this media containing either 50 ng/ml NGF, 100 ng/ml BDNF (Amgen, Thousand Oaks, Calif.), 100 ng/ml GDNF (Prepro Tech, Inc., Rocky Hill, N.J.) or 3 ng/ml Neurturin. The cells were incubated at 37° C. in a 5% CO2 /95% air incubator for 3 days, fixed with 10% formalin, stained with crystal violet (1 µl/ml 10% formalin) and counted. Survival was ascertained as noted previously.

The neuronal Death at 72 hours is shown in FIG. 10. Neuronal survival of nodose neurons cultured in BDNF has been previously reported (Thaler et al, *Develop Biol* 161:338-344, 1994 which is incorporated by reference). This was used as the standard for survival for these neurons and given the value of 100% survival. Nodose ganglia that had no trophic support (AMO) showed 20%-30% survival, as did neurons that were cultured in the presence of 50 ng/ml NGF. Neurons cultured in the presence of 3 ng/ml neurturin and absence of BDNF showed survival similar to those neurons cultured in the presence of BDNF (100 ng/ml). GDNF at a concentration of 100 ng/ml promoted greater survival of nodose neurons than did BDNF (100 ng/ml). Similar findings with GDNF were recently reported for sensory neurons from chicken (Ebendal, T. et al, *J Neurosci Res* 40:276-284 1995 which is incorporated by reference).

EXAMPLE 4

This example illustrates the determination of partial amino acid sequences of neurturin isolated from CHO cell conditioned medium.

To obtain N-terminal amino acid sequence from a purified preparation of approximately 1 µg of neurturin, the Mono S fractions 26-29 containing the peak of activity were concentrated to 25 µl by centrifuge ultrafiltration in a microcon-3 concentrators (Amicon, Inc., Beverley, Mass.) and loaded onto a non-reducing 14% SDS polyacrylamide gel. After electrophoretic separation, proteins were electroblotted to a PVDF membrane (Bio-Rad, Hercules, Calif.) and stained with 0.1% Coomassie Blue. The 25 kD band was excised and inserted into the reaction cartridge of an automated sequencer (Model 476, Applied Biosystems (Foster City, Calif.). Phenylthiohydantoin-amino acid (PTH-aa) recovery in the first 2-3 cycles of automated sequencing by Edman degradation indicated a sequencing yield of 4 pmoles, which was approximately 10% of the estimated amount of protein loaded on the SDS gel.

Two N-terminal sequencing runs were performed from two 50 liter purification preparations. In the first run, 1 µg of protein in 3 pooled fractions of 1.5 ml total volume were concentrated to 25 µl and electroblotted at 100V for 2 hrs at 25° C. using an electroblot buffer of 10 mM CAPS pH 11.0 buffer (Sigma, St. Louis, Mo.) containing 5% methanol. The amino acid sequence was obtained from 13 cycles of Edman degradation and the sequencing yield was 4 pmoles as above.

In the second run, 1.5 µg of protein in 4 pooled fractions of 2.0 ml total volume were concentrated to 25 µl and electroblotted at 36V for 12 hours at 4° C. using an electroblot buffer of 25 mM Tris, 192 mM glycine, 0.04% SDS and 17% MeOH. Sequencing yield was 15 pmoles and the sequence after 16 cycles was SGARPXGLRELEVSVS (SEQ ID NO:3). The sequence obtained after 16 cycles corresponded to the shorter sequence obtained in the first run. Definite assignments could not be made at 3 of the amino acid residues in the sequence (residues 1, 6 and 11 from the N-terminal). A search of protein databases did not detect any significantly homologous sequences, suggesting that the purified factor was a novel protein.

This initial N-terminal amino acid sequence data did not enable the isolation of cDNA clones using degenerate oligonucleotides as PCR primers or probes for screening libraries. To facilitate these approaches, additional protein was purified in order to obtain internal amino acid sequence from proteolytic fragments. To obtain internal amino acid sequence from neurturin, an additional 50 liters of CHO cell conditioned medium was purified using only the first 3 chromatographic steps as outlined above, except that the gradient used to elute the Cu++ Chelating Superose column was as follows: 0-60 mM glycine (4 ml), 60 mM glycine (10 ml), 60-300 mM glycine (32 ml). Fractions No. 20-23 containing neurturin were concentrated to 25 µl by ultrafiltration (Amicon microcon 3, Amicon, Beverley, Mass.) and loaded on a non-reducing SDS polyacrylamide gel. After electrophoresis, the gel was stained with Coomassie blue and the 25 kD neurturin band was excised. Neurturin was digested in the gel slice with endoproteinase Lys-C, and the eluted proteolytic fragments were purified by reverse phase HPLC. Only one peak was observed upon HPLC separation of the eluted peptides, which yielded amino acid sequence information for 23 cycles at the 1 pmole signal level using the automated sequencer, (internal fragment P2, SEQ ID NO:5).

Amino acid analysis performed on 10% of the above sample before subjecting it to digestion had indicated that 150 pmoles of protein were present in the gel slice, consisting of 7.6% lysine and 19.5% arginine. The single low level peak from the Lys-C digestion suggested that the digestion and elution of peptides were inefficient. The same gel slice was redigested with trypsin and the eluted peptides separated by HPLC. Two peaks were observed on HPLC, resulting in the elucidation of two additional 10 residue amino acid sequences (4-5 pmole signal level, internal fragment P1, SEQ ID NO:4 and internal fragment P3, SEQ ID NO:6) that were distinct from the N-terminal and previous internal amino acid sequences. The in situ digestion, elution and purification of peptides, and peptide sequencing was performed by the W. M. Keck Foundation Biotechnology Resource Laboratory at Yale University according to standard protocols for this service.

EXAMPLE 5

The following example illustrates the isolation and sequence analysis of mouse and human neurturin CDNA clones.

Degenerate oligonucleotides corresponding to various stretches of confident amino acid sequence data were synthesized and used as primers in the polymerase chain reaction (PCR) to amplify cDNA sequences from reverse transcribed mRNA. A forward primer (M1676; 5'-CCNACNGCN-TAYGARGA, SEQ ID NO:50) corresponding to peptide sequence P2 $Xaa_1$-$Xaa_2$-Val-Glu-Ala-Lys-Pro-Cys-Cys-GlGly-Pro-Thr-Ala-Tyr-Glu-Asp-$Xaa_3$-Val-Ser-Phe-Leu-Ser-Val where $Xaa_1$ and $Xaa_2$ were unknown, $Xaa_3$ was Gln or Glu (SEQ ID NO:5) in combination with a reverse primer (M1677; 5'-ARYTCYTGNARNGTRTGRTA (SEQ ID NO:52) corresponding to peptide sequence P3 (Tyr-His-Thr-Leu-Gln-Glu-Leu-Ser-Ala-Arg) (SEQ ID NO: 6) were used to amplify a 69 nucleotide product from cDNA templates derived from E21 rat and adult mouse brain. The PCR parameters were: 94° C. for 30 sec; 55° C. for 30 sec; 72° C. for 1 min for 35 cycles. The product was subcloned into the Bluescript KS plasmid and sequenced. All nucleotide sequencing was performed using fluorescent dye terminator technology per manufacturer's instructions on an Applied Biosystems automated sequencer Model #373 (Applied Biosystems, Foster City, Calif. ). Plasmid DNA for sequencing was prepared using the. Wizard Miniprep kit (Promega Corp., Madison, Wis.) according to the manufacturer's instructions. The sequence of the amplified product correctly predicted amino acid sequence data internal to the PCR primers.

Primers corresponding to the amplified sequence were used in combination with the degenerate primers in the rapid amplification of cDNA ends (RACE) technique (Frohman, M. A. *Methods in Enzymology* 218:340-356, 1993) using the Marathon RACE kit (CLONTECH, Palo Alto, Calif.) per the manufacturer's instructions, except that first strand CDNA synthesis was carried out at 50° C. using Superscript II reverse transcriptase (Gibco-BRL). Briefly, a double stranded adaptor oligonucleotide was ligated to the ends of double stranded CDNA synthesized from postnatal day 1 rat brain mRNA. Using nested forward neurturin PCR primers (M1676; 5'-CCNACNGCNTAYGARGA, SEQ ID NO:50 and 1678; 5'-GACGAGGGTCCTTCCTGGACGTACACA, SEQ ID N0:53) in combination with primers to the ligated adaptor supplied in the kit (AP1, AP2), the 3' end of the neurturin cDNA was amplified by two successive PCR reactions (1st: M1676 and AP1, using 94° C. for 30 sec, 55° C. for 30 sec and 72° C. for 2 min for 35 cycles; 2nd: M1678 and AP2 using 94° C. for 30 sec and 68° C. for 2 min for 35 cycles). A 5' portion of the rat neurturin cDNA was obtained by two successive PCR reactions using the Tinkered CDNA as template. The 1st reaction utilized primers M1677 (SEQ ID NO:52) and AP1; using 94° C. for 30 sec; 55° C. for 30 sec; and 72° C. for 2 min for 35 cycles. The 2nd reaction used M1679    5'-TAGCGGCTGTGTACGTCCAGGAAGGA-CACCTCGT (SEQ ID NO:54) and AP2 at 94° C. for 30 sec and 68° C. for 2 min for 35 cycles. These reactions resulted in a truncated form of the 5' end of the neurturin cDNA, apparently the result of premature termination of the cDNA during reverse transcription. The 5' and 3' RACE products were subcloned into the plasmid Bluescript KS and sequenced. The sequence of these 3' and 5' RACE products resulted in a partial rat neurturin cDNA sequence of 220 nt. Primers (#467921   5'-CAGCGACGACGCGTGCGCAAAGAGCG, SEQ ID NO:55; and M1679 (SEQ ID NO:54) corresponding to the partial rat CDNA sequence were used (PCR parameters 94° C. for 30 sec and 68° C. for 1 min for 35 cycles) to amplify a 101 nucleotide PCR product from mouse genomid DNA which was homologous to rat neurturin cDNA sequence.

These primers were then used to obtain murine neurturin genomic clones by amplifying gene fragments in a mouse 129/Sv library in a P1 bacteriophage vector (library screening service of Genome Systems, Inc., St. Louis, Mo.). A 1.6 kb Nco I fragment from this P1 clone containing the neurturin gene was identified by hybridization with primer (#465782; 5'-TAYGARGACGAGGTGTCCTTCCTGGACG-TACACAGCCGCTAYCAYAC, SEQ ID NO:56). This Nco I fragment was sequenced and found to contain a stretch of coding sequence corresponding to the N-terminal and internal amino acid sequences obtained from sequencing the active protein isolated from CHO cell conditioned media. Beginning at the N-terminal amino acid sequence of the purified protein, this nucleotide sequence encodes a 100 amino acid protein with a predicted molecular mass of 11.5 kD. A search of protein and nucleic acid databases identified neurturin as a novel protein that is approximately 40% identical to glial derived neurotrophic factor (GDNF). GDNF was purified and cloned as a factor which promotes the survival of midbrain dopaminergic neurons and is a distantly related member of the TGF-β superfamily, which now includes more than 25 different genes that possess a wide variety of proliferative and differentative activities. Although GDNF is less than 20% identical to any other member of the TGF-β family, it contains the 7 cysteine residues which are conserved across the entire family and believed to be the basis of a conserved cysteine knot structure observed in the crystal structure determination of TGF-β. Neurturin also contains these 7 cysteine residues, but like GDNF is less than 20% homologous to any other member of the TGF-β family. Thus, neurturin and GDNF appear to represent a subfamily of growth factors which have significantly diverged from the rest of the TGF-β superfamily.

To determine the sequence of the full length mouse neurturin cDNA, 5' and 3' RACE PCR was performed as above for the rat, using nested primers predicted from the mouse genomic sequence and CDNA from neonatal mouse brain. The 1st reaction for the 3' end used primers: M1777 5'-GCG-GCCATCCGCATCTACGACCGGG (SEQ ID NO:57) and AP1 at 94° C. for 30 sec; 65° C. for 15 sec; and 68° C. for 2 min for 35 cycles. The 2nd reaction used primer #467921 (SEQ ID NO:55) and AP2 at 94° C. for 30 sec; 65° C. for 15 sec; and 68° C. for 2 min for 20 cycles. The 5' end was obtained using for the 1st reaction primer M1759, 5'-CRTAG-GCCGTCGGGCGRCARCACGGGT (SEQ ID NO:58) and AP1 at 94° C. for 30 sec; 65° C. for 15 sec; and 68° C. for 2 min for cycles. The 2nd reaction used primer M1785, 5'-GCGCCGAAGGCCCAGGTCGTAGATGCG (SEQ ID NO:59) and AP2 at 94° C. for 30 sec; 65° C. for 15 sec; and 68° C. for 2 min for 20 cycles. Both sets of PCR reactions included 5% DMSO. The 5' and 3' mouse RACE products were subcloned into the plasmid Bluescript KS and sequenced. Using the sequence of RACE products, a 1.0 kb mouse neurturin CDNA sequence can be assembled. This cDNA sequence contains an open reading frame of 585 nucleotides that encodes a protein with a molecular mass of 24 kD. This full length mouse cDNA sequence is shown in FIG. 7 (SEQ ID NO:12). Consistent with the processing events known to occur for TGF-β family members, the 24 kD neurturin protein contains an amino terminal 19 amino acid signal sequence followed by a pro-domain which contains an RXXR proteolytic processing site immediately before the N-terminal amino acid sequence obtained when sequencing the protein purified from CHO cell conditioned media.

Using these landmarks, the 11.5 kD mature neurturin molecule is predicted to be 11.5 kD and, by analogy to other members of the TGF-β family, is predicted to form a disulfide linked homodimer of 23 kD, consistent with the 25 kD mass of the protein purified from CHO cell conditioned media as estimated by SDS-PAGE analysis.

For isolation of human genomic clones, primers (#467524; 5'-CGCTACTGCGCAGGCGCGTGCGARGCGGC, SEQ ID NO:60 and #10005, 5'-CGCCGACAGCTCTTG-CAGCGTRTGGTA, SEQ ID NO:61) predicted from the sequence of mouse neurturin were used to amplify (PCR parameters: Initial denaturation at 95° C. for 1 min 30 sec followed by 94° C. for 30 sec; 60° C. for 15 sec; and 68° C. for 60 sec for 35 cycles) a 192 nucleotide fragment from human genomic DNA. The sequence of the PCR product demonstrated that it was the human homolog of mouse neurturin. The primers were then used to screen a human genomic library constructed in the P1 vector (library screening service, Genome Systems, Inc.) and two clones containing the human neurturin genomic locus were obtained.

The same strategy was used to determine the human sequence as discussed above for the mouse sequence. An oligo (#30152, GACCTGGGCCTGGGCTACGCGTC-CGACGAG, SEQ ID NO:62) was used as a probe in a Southern blot analysis to identify restriction fragments of the P1 Clones which contained the human neurturin coding sequence. These restriction fragments (Eag I, Pvu II, Hind III, Kpn I) were subcloned into the Bluescript KS plasmid and sequenced.

The results of subcloning and sequencing of human genomic fragments were as follows. The Eag I fragment was found to be approximately 6 kb in size with the 3' Eag I site located 60 bp downstream from the stop codon.

The Pvu II fragment was approximately 3.5 kb in size with the 3' Pvu II site located 250 bp downstream from the stop codon. The Hind III fragment was approximately 4.8 kb in size with the 3' Hind III site located 3 kb downstream from the stop codon. The Kpn I fragment was approximately 4.2 kb in size with the 3' Kpn I site located 3.1 kb downstream from the stop codon.

The second coding exon was sequenced using these subcloned fragments. In addition, sequence was obtained from 250 bp flanking the 3' side of the second exon. The sequence was also obtained from 1000 bp flanking the 5' side of the coding exon. From these flanking sequences, forward primer 30341 (5'-CTGGCGTCCCAMCAAGGGTCTTCG-3', SEQ ID NO:71) and reverse primer 30331 (5'-GCCAGTGGTGC-CGTCGAGGCGGG-3', SEQ ID NO:72) were designed so that the entire coding sequence of the second exon could be amplified by PCR.

The first coding exon was not mapped relative to the restriction sites above but was contained in the Eag I fragment. The sequence of this exon was obtained from the subcloned Eag I fragment using the mouse primer 466215 (5'-GGCCCAGGATGAGGCGCTGGAAGG-3', SEQ ID NO:73), which contains the ATG initiation codon. Further sequence of the first coding exon was obtained with reverse primer 20215 (5'-CCACTCCACTGCCTGAWATTCWAC-CCC-3', SEQ ID NO:74), designed from the sequence obtained with primer 466215. Forward primer 20205 (5'-CCATGTGATTATCGACCATTCGGC-3', SEQ ID NO:75) was designed from sequence obtained with primer 20215. Primers 20205 and 20215 flank the coding sequence of the first coding exon and can be used to amplify this coding sequence using PCR.

The human cDNA and inferred amino acid sequence is shown in FIG. 7 and the mouse cDNA and inferred amino acid sequence is shown in FIG. 8.

EXAMPLE 6

This example illustrates the preparation of expression vectors containing neurturin cDNA.

For expression of recombinant neurturin in mammalian cells the neurturin vector pCMV-NTN-3-1 was constructed. The 585 nucleotide open reading frame of the neurturin cDNA was amplified by PCR using a primer containing the first 27 nucleotides of the neurturin coding sequence (5'-GCGACGCGTACCATGAGGCGCTGGAAG-GCAGCGGCCCTG, SEQ ID NO:63) and a primer containing the last 5 codons and the stop codon (5'-GACGGATCCGCATCACACGCACGCGCACTC) (SEQ ID NO:64) using reverse transcribed postnatal day 1 mouse brain mRNA as template using (PCR parameters: 94° C. for 30 sec; 60° C. for 15 sec; and 68° C. for 2 min for 35 cycles and including 5% DMSO in the reaction). The PCR product was subcloned into the Eco RV site of BSKS and sequenced to verify that it contained no PCR generated mutations. The neurturin coding sequence was then excised from this vector using Mlu I (5' end) and Bam Hi (3' end) and inserted downstream of the CMV IE promoter/enhancer in the mammalian expression vector pCB6 (Brewer, C. B. *Methods in Cell Biology* 43:233-245, 1994) to produce the pCMV-NTN-3-1 vector using these sites.

For expression of recombinant protein in *E. Coli*, the mature coding region of mouse neurturin was amplified by PCR using a primer containing the first 7 codons of the mature coding sequence (5'-GACCATATGCCGGGGGCTCGGC-CTTGTGG) (SEQ ID NO:65) and a primer containing the last 5 codons and the stop codon 5'-GACGGATCCGCATCA-CACGCACGCGCACTC (SEQ ID NO:66) using a fragment containing the murine neurturin gene as template using (PCR parameters: 94° C. for 30 sec; 60° C. for 15 sec and 68° C. for 90 sec for 25 cycles with 5%=DMSO added into the reaction).

The amplified product was subcloned into the Eco RV site of BSKS, the nucleotide sequence was verified, and this fragment was then transferred to the expression vector pET-30a (Novagen, Madison, Wis.) using an Nde 1 site (5' end) and an Eco R1 site (3' end). The pET-neurturin (pET-NTN) vector codes for an initiator methionine in front of the first amino acid of the mature mouse neurturin protein predicted from the N-terminal amino acid sequence of neurturin purified from the CHO cell conditioned media.

EXAMPLE 7

This example illustrates the transient transfection of NIH3T3 cells with the neurturin expression vector pCMV-NTN-3-1 and that the product of the genomic sequence in Example 5 is biologically active.

To demonstrate that the cloned neurturin cDNA was sufficient to direct the synthesis of biologically active neurturin we transiently introduced the pCMV-NTN-3-1 plasmid into NIH3T3 cells using the lipofectamine method of transfection. NIH3T3 cells were plated at a density of 400,000 cells per well (34.6 mm diameter) in 6 well plates (Corning, Corning, N.Y.) 24 hours before transfection. DNA liposome complexes were prepared and added to the cells according to the manufacturer's protocol using 1.5 µg CMV-neurturin plasmid DNA (isolated and purified using a Qiagen (Chatsworth, Calif.) tip-500 column according to manufacturer's protocol) and 10 µl lipofectamine reagent (Gibco BRL, Gaithersburg, Md.) in 1:1 DME/F12 medium containing 5 µg/ml insulin, 5 µg/ml 20 transferrin, and 5 ng/ml sodium selenite (Sigma, St. Louis, Mo.). Five hours after the addition of DNA liposome complexes in 1 ml medium per well, 1 ml DME medium containing 20% calf serum was added to each well. Twenty-four hours after the addition of DNA-liposome complexes, the 2 ml medium above was replaced with 1 ml DME medium containing 10% calf serum, 2 mM glutamine, 100 U/ml penicillin, 100 µ/ml streptomycin, and 25 µg/ml heparin. The cells were incubated for an additional 24 hours before the conditioned medium was harvested, centrifuged to remove cellular debris, and frozen.

As a control, NIH3T3 cells were transfected as above using 1.5 µg CMV-neo expression plasmid (containing no cDNA insert) in place of the 1.5 µg CMV-neurturin plasmid. Conditioned medium from NIH3T3 cells transfected with either control plasmid or CMV-neurturin plasmid was assayed by direct addition to the SCG culture medium at the time of NGF deprivation. Addition of 0.25 ml conditioned medium from CMV-neurturin-transfected cells promoted 70% survival of sympathetic neurons, and >90% survival could be obtained with 0.45 ml of this conditioned medium. No significant survival promoting activity was detected in the conditioned medium of control transfected NIH3T3 cells.

EXAMPLE 8

This example illustrates the preparation of Chinese hamster ovary cells stably transformed with neurturin cDNA.

DG44 cells, a Chinese hamster ovary cell derivative that is deficient in dihydrofolate reductase (DHFR) (Urlaub et al *Cell* 3:405-412, 1983 which is incorporated by reference), were stably co-transfected with expression plasmid (pCMV-NTN-3-1) and a DHFR expression plasmid (HLD) (McArthur, and Stanners *J. Biol. Chem.* 266:6000-6005, 1991 which is incorporated by reference).

On day 1 DG44 cells were plated at $1 \times 10^6$ cells per 10 cm plate in Ham's F12 medium with 10% fetal calf serum (FCS). This density must not be exceeded or cells will overgrow before selection media is added on day 5.

On day 2 cells were transfected with a 9:1 ratio of PCMV-NTN to DHFR expression plasmid using the calcium phosphate method (10 µg DNA/10 cm plate) (Chen and Okayama, *Mol Cell Biol* 7:2745-2752, 1987 which is incorporated by reference).

On day 3 the transfected cells were washed with Ham's F12 medium and fed Ham's F12 with 10% FCS.

On day 5 the cells were washed with MEM alpha medium and fed selection medium, which is MEM alpha with 10% FCS and 400 µg/ml G418. The cells were maintained in selection media, feeding every 4 days. Colonies began to appear approximately 14 days after transfection. Colonies growing in selection media were then transferred to a 24 well plate and trypsinized the next day to disperse the cells. The cells were grown to confluence in either 24 well or 6 well plates in order to screen the cells for expression of recombinant protein. Expression of neurturin was examined in 10 clonal lines and two high expressing lines were detected using the SCG survival assay. These clonal lines were expanded and expression in these selected cell lines was amplified by selection in 50 nM methotrexate (MTX). For selection in MTX, cells were grown to 50% confluence in a 150 cm² flask in selection medium. The medium was changed to MEM alpha containing 50 nM MTX concentration (it was not necessary to use G418 during MTX amplification). After placement in 50 nM MTX, the majority of cells died and colonies of resistant cells reappeared in 1-2 weeks. At this time, the cells were trypsinized to disperse colonies and are split when cells reach confluence. Cells eventually reached the same growth rate as before. The selected cells were screened for expression of recombinant protein. A 2-3 fold increase in expression was observed after selection in 50 nM MTX. Frozen stocks were kept for cell lines obtained from the original selection and the 50 nM MTX selection. Further selection could be continued in increasing MTX until desired levels of expression are obtained.

Using the above method, we isolated cells identified as DG44CHO5-3(G418)(pCMV-NTN-3-1) and DG44CHO5-3 (5OnMMTX)(pCMV-NTN-3-1). Cells from the DG44CHO5-3(5OnMMTX)(pCMV-NTN-3-1) strain expressed levels of approximately 100 µg of biologically active protein per liter of conditioned media determined by direct assay of conditioned medium in SCG assay according to the methods in example 1.

EXAMPLE 9

This example illustrates the expression of neurturin in various tissues.

A survey of neurturin and GDNF expression was performed in rat embryonic tissues (E10, day 10 after conception), neonatal tissues (PI, Postnatal Day 1), and adult tissues (>3 mos) using semi-quantitative RT/PCR (Estus et al., *J Cell Biol* 127:1717-1727, 1994 which is incorporated by reference). The RNA samples were obtained from various tissues and PCR products were detected either by autoradiography after incorporation of $\alpha\text{-}^{32}\text{P-dCTP}$ in the PCR and electrophoresis on a polyacrylamide gel (FIG. 6) or by ethidium bromide staining of DNA after electrophoresis on agarose gels (Tables 3 and 4). The neurturin fragment of 101 base pairs was obtained using the forward primer CAGCGAC-GACGCGTGCGCAAAGAGCG (SEQ ID NO:67) and reverse primer TAGCGGCTGTGTACGTCCAGGAAGGA-CACCTCGT (SEQ ID NO:68) and the GDNF fragment of 194 base pairs was obtained using the forward primer AAAAATCGGGGGTGYGTCTTA (SEQ ID NO:69) and the reverse primer CATGCCTGGCCTACYTTGTCA (SEQ ID NO:70).

No neurturin or GDNF mRNA was detected at the earliest embryonic age (embryonic day 10, El) surveyed.

In neonates (postnatal day 1, P1) both transcripts were expressed in many tissues although neurturin tended to show a greater expression in most tissues than did GDNF. (see table 3).

TABLE 3

|  | NEURTURIN | GDNF |
|---|---|---|
| Liver | +++ | − |
| Blood | +++ | + |
| Thymus | + | − |
| Brain | ++ | + |
| Sciatic nerve | − | + |
| Kidney | ++ | ++ |
| Spleen | ++ | + |
| Cerebellum | ++ | + |
| Heart | ++ | + |
| Bone | + | + |

As shown in Table 3, differences in the tissue distributions of neurturin and GDNF were noted. In particular, no GDNF was detected in liver and thymus where neurturin expression was detected and no neurturin was detected in sciatic nerve where GDNF was detected.

Figure 5:
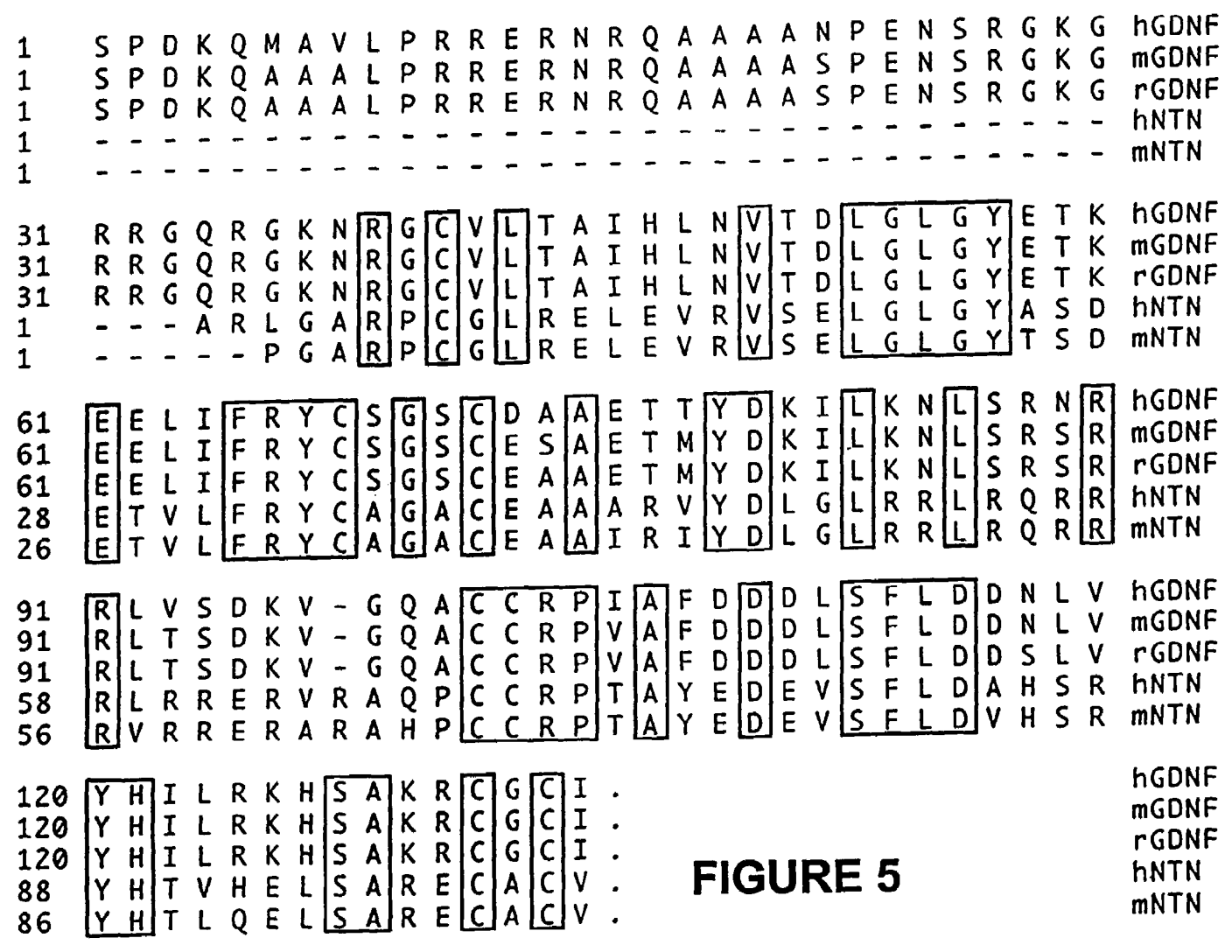

Neurturin and GDNF mRNA were detected in many tissues in the adult animal, but the tissue-specific pattern of expression for these two genes was very different. (table 4, FIG. 5).

TABLE 4

|  | NEURTURIN | GDNF |
|---|---|---|
| Liver | − | − |
| Blood | + | − |
| Thymus | + | ++ |
| Brain | + | − |
| Sciatic nerve | − | − |
| Kidney | ++ | + |
| Spleen | − | + |
| Cerebellum | − | − |
| Uterus | ++ | − |
| Bone marrow | ++ | − |
| Testis | ++ | ++ |
| Ovary | + | + |
| Placenta | + | − |
| Skeletal muscle | + | − |
| Spinal cord | + | − |
| Adrenal gland | ++ | ++ |
| Gut | + | ++ |

As shown in table 4, neurturin was found to be expressed in brain and spinal cord as well as in blood and bone marrow where no GDNF was detected. The level of expression of neurturin in brain and blood was, however, less than that detected in neonatal tissue.

Neurturin was also highly expressed in freshly isolated rat peritoneal mast cells, whereas GDNF showed little or no expression.

EXAMPLE 10

This example illustrates the preparation of antisera to neurturin by immunization of rabbits with a neurturin peptide.

The peptide sequence corresponding to amino acids 73-87 of the mature murine neurturin protein was synthesized and coupled to keyhole limpet hemocyanin (KLH) as described earlier (Harlow and Lane, *Antibodies: a laboratory manual*, 1988. Cold Spring Harbor Laboratory, New York, N.Y. p. 72-81 which is incorporated by reference). The KLH-coupled peptide was submitted to Caltag, Inc. and each of two rabbits were immunized. Immunization was by subcutaneous injection at 7-10 sites. The first injection was with 150 µg KLH-coupled peptide which was resuspended in 0.5 ml saline and emulsified with 0.5 ml complete Freund's adjuvant. Boost injections were begun 4 weeks after the initial injection and were performed once every 7 days as above for a total of 5 injections except that 100 µg of KLH-coupled peptide and incomplete Freund's adjuvant were used. Serum samples were collected 1 week after the fifth boost.

A pooled volume of twenty ml of serum that had been collected from both rabbits one week after the 5th injection was purified. For purification, a peptide affinity column was prepared by coupling the above peptide to cyanogen bromide activated Sepharose 4B according to the manufacturers protocol (Pharmacia Biotech). The serum was diluted 10 fold in 10 mM Tris pH 7.5 buffer and mixed by gentle rocking for 16 hours at 4° C. with 0.5 ml of peptide agarose matrix containing 5 mg of coupled peptide. The matrix was placed into a column, washed with 5 ml of 10 mM Tris pH 7.5, 150 mM NaCl, washed with 5 ml of 10 mM Tris pH 7.5 buffer containing 0.4 M NaCl and eluted with 5.5 ml of 100 mM glycine pH 2.5 buffer. One tenth volume of 1.0 M Tris pH 8.0 buffer was added to the eluate immediately after elution to neutralize the pH. The glycine eluate was dialyzed overnight against 10 mM Tris pH 7.5, 150 mM NaCl.

The affinity-purified antibodies were used in a western blot to demonstrate specific recognition of recombinant neurturin protein. Ten ml of conditioned medium collected from DG44CHO5-3(G418)(pCMV-NTN-3-1) cells was purified over SP Sepharose as described in Example 1 and the proteins electrophoresed on a reducing SDS-PAGE gel in the tricine buffer system (Schagger and von Jagow *Analytical Biochemistry* 166:368-379, 1987). The proteins were electroblotted to a nitrocellulose membrane in 25 mM Tris, 192 mM glycine, 0.04% SDS, 17% methanol at 4° C. for 16 hr. The membrane was incubated with the affinity-purified anti-neurturin peptide antibodies and then with horseradish peroxidase-coupled sheep anti-rabbit IgG (Harlow and Lane, supra, p. 498-510). Bound antibodies were detected with enhanced chemiluminescence (ECL kit, Amersham, Buckinghamshire, England). The anti-neurturin antibodies recognized a single, approximately 11.5 kD protein band in the conditioned medium of the DG44CHO5-3(G418)(pCMV-NTN-3-1) cells. Using these anti-neurturin antibodies, neurturin protein could be detected in 10 ml of conditioned medium from DG44CHO5-3(G418)(pCMV-NTN-3-1) cells but could not be detected in 10 ml of medium conditioned with DG44 cells that had not been transformed with the neurturin expression vector.

EXAMPLE 11

The following example illustrates the identification of additional members of the GDNF/neurturin/persephin gene subfamily.

The TGF-β superfamily currently contains over 25 different gene members (for review see Kingsley, *Genes and Development* 8: 133-146, 1994 which is incorporated by reference). The individual family members display varying degrees of homology with each other and several subgroups within the superfamily can be defined by phylogenetic analysis using the Clustal V program (Higgins et al, *Comput Appl Biosci* 8: 189-191, 1992 which is incorporated by reference) and by bootstrap analysis of phylogenetic trees (Felsenstein, *Evolution* 39:783-791, 1985 which is incorporated by reference). Neurturin or persephin is approximately 40% identical to GDNF but less than 20% identical to any other member of the TGF-β superfamily. Several sequence regions in neurturin can be identified (FIG. 5) that are highly conserved within the GDNF/neurturin/persephin subfamily but not within the TGF-β superfamily. These conserved regions are likely to characterize a subfamily containing previously unisolated genes, which can now be isolated using the conserved sequence regions identified by the discovery and sequencing of the neurturin and persephin genes. Regions of high sequence conservation between neurturin, persephin and GDNF allow the design of degenerate oligonucleotides which can be used either as probes or primers. Conserved-region amino acid sequences have been identified herein to include Val-$Xaa_1$-$Xaa_2$-Leu-Gly-Leu-Gly-Tyr where $Xaa_1$ is Ser, Thr or Ala and $Xaa_2$ is Glu or Asp (SEQ ID NO:108); Glu-$Xaa_1$-$Xaa_2$-$Xaa_3$-Phe-Arg-Tyr-Cys-$Xaa_4$-Gly-$Xaa_5$-Cys in which $Xaa_1$ is Thr, Glu or lys, $Xaa_2$ is Val, Leu or Ile, $Xaa_3$ is Leu or Ile, $Xaa_4$ is Ala or Ser, and $Xaa_5$ is Ala or Ser, (SEQ ID NO:113); and Cys-Cys-$Xaa_1$-Pro-$Xaa_2$-$Xaa_3$-$Xaa_4$-$Xaa_5$-Asp-$Xaa_6$-$Xaa_7$-$Xaa_8$-Phe-Leu-Asp-$Xaa_9$ in which $Xaa_1$ is Arg or Gln, $Xaa_2$ is Thr or Val or Ile, $Xaa_3$ is Ala or Ser, $Xaa_4$ is Tyr or Phe, $Xaa_5$ is Glu, Asp or Ala, $Xaa_6$ is Glu, Asp or no amino acid, $Xaa_7$ is val or leu, $Xaa_8$ is Ser or Thr, and $Xaa_9$ is Asp or Val (SEQ ID NO:114). Nucleotide sequences containing a coding sequence for the above conserved sequences or fragments of the above conserved sequences can be used as probes. Exemplary probe and primer sequences which can be designed from these regions are as follows.

Forward primers,

Primer A (M3119): 5'-GTNDGNGANYTGGGNYTGGGNTA (SEQ ID NO:115) 23 nt which codes for the amino acid sequence, Val-$Xaa_1$-$Xaa_2$-Leu-Gly-Leu-Gly-Tyr where $Xaa_1$ is Thr, Ser or Ala and $Xaa_2$ is Glu or Asp (SEQ ID NO:125);

Primer B (M3123): 5'-GANBTNWCNTTYYTNGANG (SEQ ID NO:116) 19 nt which codes for the amino acid sequence, $Xaa_1$-$Xaa_2$-$Xaa_3$-Phe-Leu-$Xaa_4$-$Xaa_5$ where $Xaa_1$ is Asp or Glu, $Xaa_2$ is Val or Leu, $Xaa_3$ is Thr or Ser, $Xaa_4$ is Asp or Glu, and $Xaa_5$ is Asp or Val (SEQ ID NO:126);

Primer C (M3126): 5'-GANBTNWCNTTYYTNGANGW (SEQ ID NO:117) 20 nt which codes for the amino acid sequence, $Xaa_1$-$Xaa_2$-$Xaa_3$-Phe-Leu-$Xaa_4$-$Xaa_5$ where $Xaa_1$ is Asp or Glu, $Xaa_2$ is Val or Leu, $Xaa_3$ is Thr or Ser, $Xaa_4$ is Asp or Glu, and $Xaa_5$ is Asp or Val (SEQ ID NO:126);

Primer D (M3121): 5'-TTYMGNTAYTGYDSNGGNDSNTG (SEQ ID NO:118) 23 nt which codes for the amino acid sequence, Phe-Arg-Tyr-Cys-$Xaa_1$-Gly-$Xaa_2$-Cys where $Xaa_1$ is Ser or Ala and $Xaa_2$ is Ser or Ala (SEQ ID NO:127);

Primer E (M3122): 5'-GTNDGNGANYTGGGNYTGG (SEQ ID NO:119) 20 nt which codes for the amino acid sequence, Val-$Xaa_1$-$Xaa_2$-Leu-Gly-Leu-Gly where $Xaa_1$ is Thr, Ser or Ala and $Xaa_2$ is Asp or Glu (SEQ ID NO:128); and Primer F (M3176): 5'-GTNDGNGANYTGGGNYTGGGNTT (SEQ ID NO:120) 23 nt which codes for the amino acid sequence, Val-$Xaa_1$-$Xaa_2$-Leu-Gly-Leu-Gly-Phe where $Xaa_1$ is Thr, Ser or Ala and $Xaa_2$ is Glu or Asp (SEQ ID NO:129).

Reverse primers,

Primer G (M3125): 5'-WCNTCNARRAANGWNAVNTC (SEQ ID NO:121) 20 nt whose reverse complementary sequence codes for the amino acid sequence, $Xaa_1$-$Xaa_2$-$Xaa_3$-Phe-Leu-$Xaa_4$-$Xaa_5$ where $Xaa_1$ is Asp or Glu, $Xaa_2$ is Val or Leu, $Xaa_3$ is Thr or Ser, $Xaa_4$ is Asp or Glu, and Xaa5 is Asp or Val (SEQ ID NO:126);

Primer H (M3124): 5'-WCNTCNARRAANGWNAVNT (SEQ ID NO:122) 19 nt whose reverse complementary sequence codes for the amino acid sequence, $Xaa_1$-$Xaa_2$-$Xaa_3$-Phe-Leu-$Xaa_4$-$Xaa_5$ where $Xaa_1$ is Asp or Glu, $Xaa_2$ is Val or Leu, $Xaa_3$ is Thr or Ser, $Xaa_4$ is Asp or Glu, and $Xaa_5$ is Asp or Val (SEQ ID NO:126);

Primer I (M3120): 5'-CANSHNCCNSHRCARTANCK-RAA (SEQ ID NO:123) 23 nt whose reverse complementary sequence codes for the amino acid sequence, Phe-Arg-Tyr-Cys-$Xaa_1$-Gly-$Xaa_2$-Cys where $Xaa_1$ is Ser or Ala and $Xaa_2$ is Ser or Ala (SEQ ID NO:127); and Primer J (M3118): 5'-CANSHNCCNSHRCARTANCK-RAANA (SEQ ID NO:124) 25 nt whose reverse complementary sequence codes for the amino acid sequence, $Xaa_1$-Phe-Arg-Tyr-Cys-$Xaa_2$-Gly-$Xaa_3$-Cys where $Xaa_1$ is Ile or Leu, $Xaa_2$ is Ser or Ala and $Xaa_3$ is Ser or Ala (SEQ ID NO:130).

In addition to the above, the following primers are based upon conserved regions in GDNF and neurturin (SEQ ID NOS:33-35).

Primer 1, GTNWSNGANYTNGGNYTNGGNTA (SEQ ID NO:42) which encodes the amino acid sequence, Val-$Xaa_1$-$Xaa_2$-Leu-Gly-Leu-Gly-Tyr where $Xaa_1$ is Ser or Thr and $Xaa_2$ is Glu or Asp (SEQ ID NO:33);

Primer 2, TTYMGNTAYTGYDSNGGNDSNTGYGA-NKCNGC (SEQ ID NO:43) which encodes amino acid sequence Phe-Arg-Tyr-Cys-$Xaa_1$-Gly-$Xaa_2$-Cys-$Xaa_3$-$Xaa_4$-Ala where $Xaa_1$ is Ala or Ser, $Xaa_2$ is Ala or Ser, $Xaa_3$ is Glu or Asp and $Xaa_4$ is Ser or Ala (SEQ ID NO:36);

Primer 3 reverse GCNGMNTCRCANSHNCCNSHR-TANCKRAA (SEQ ID NO:44) whose reverse complementary sequence encodes amino acid sequence Phe-Arg-Tyr-Cys-$Xaa_1$-Gly-$Xaa_2$-Cys-$Xaa_3$-$Xaa_4$-Ala where $Xaa_1$ is Ala or Ser, $Xaa_2$ is Ala or Ser, $Xaa_3$ is Glu or Asp and $Xaa_4$ is Ser or Ala (SEQ ID NO:37);

Primer 4 reverse TCRTCNTCRWANGCNRYNGGNCK-CARCA (SEQ ID NO:45) whose reverse complementary sequence encodes amino acid sequence Cys-Cys-Arg-Pro-$Xaa_1$-Ala-$Xaa_2$-$Xaa_3$-Asp-$Xaa_4$ where $Xaa_1$ is Ile or Thr or Val, $Xaa_2$ Try or Phe, $Xaa_3$ is Glu or Asp and $Xaa_4$ is Glu or Asp (SEQ ID NO:38);

Primer 5 reverse TCNARRAANSWNAVNTCRTCNT-CRWANGC (SEQ ID NO:46) whose reverse complementary sequence encodes amino acid sequence Ala-$Xaa_1$-$Xaa_2$-Asp-$Xaa_3$-$Xaa_4$-Ser-Phe-Leu-Asp where $Xaa_1$ is Tyr or Phe, $Xaa_2$ Glu or Asp, $Xaa_3$ is Glu or Asp, and $Xaa_4$ is Val or Leu (SEQ ID NO:39);

Primer 6 GARRMNBTNHTNTTYMGNTAYTG (SEQ ID NO:47) which encodes amino acid sequence Glu-$Xaa_1$-$Xaa_2$-$Xaa_3$-Phe-Arg-Tyr-Cys where $Xaa_1$ is Glu or Thr, $Xaa_2$ is Leu or Val and $Xaa_3$ is Ile or Leu (SEQ ID NO:40);

Primer 7 GARRMNBTNHTNTTYMGNTAYTGYD-SNGGNDSNTGHGA (SEQ ID NO:48) which encodes amino acid sequence Glu-$Xaa_1$-$Xaa_2$-$Xaa_3$-Phe-Arg-Tyr-Cys-$Xaa_4$-Gly-$Xaa_5$-Cys-$Xaa_6$ where $Xaa_1$ is Glu or Thr, $Xaa_2$ is Leu or Val, $Xaa_3$ is Ile or Leu, $Xaa_4$ is Ser or Ala, $Xaa_5$ is Ser or Ala and $Xaa_6$ is Glu or Asp (SEQ ID NO:41).

The above sequences can be used as probes for screening libraries of genomic clones or as primers for amplifying gene fragments from genomic DNA or libraries of genomic clones or from reverse transcribed cDNA using RNA templates from a variety of tissues. Genomic DNA or libraries of genomic clones can be used as templates because the neurturin, persephin and GDNF coding sequences for the mature proteins are not interrupted by introns.

A degenerate oligonucleotide can be synthesized as a mixture of oligonucleotides containing all of the possible nucleotide sequences which code for the conserved amino acid sequence. To reduce the number of different oligonucleotides in a degenerate mix, an inosine or universal base (Loakes et al, Nucleic Acids Res 22:4039-43, 1994) can be incorporated in the synthesis at positions where all four nucleotides are possible. The inosine or universal base forms base pairs with each of the four normal DNA bases which are less stabilizing than AT and GC base pairs but which are also less destabilizing than mismatches between the normal bases (i.e. AG, AC, TG, TC).

To isolate family members a primer above can be end labeled with $^{32}$P using T4 polynucleotide kinase and hybridized to libraries of human genomic clones according to standard procedures.

A preferred method for isolating family member genes would be to use various combinations of the degenerate primers above as primers in the polymerase chain reaction using genomic DNA as a template. The various combinations of primers can include sequential PCR reactions utilizing nested primers or the use of a forward primer paired with an oligo dT primer. In addition, one of the degenerate primers can be used with a vector primer, a single primer can be used in an inverted PCR assay or PCR can be performed with one degenerate primer and a random primer. As an example using the above set of primers, primer 2 (SEQ ID NO:43) can be used with primer 4 (SEQ ID NO:45) in PCR with 1 ug of human genomic DNA and cycling parameters of 94° C. for 30 sec, 50° C. for 30 sec, and 72° C. for 60 sec. The above PCR conditions are exemplary only and one skilled in the art will readily appreciate that a range of suitable conditions and primer combinations could be used or optimized such as different temperatures and varying salt concentrations in the buffer medium and the like. It is preferred that DMSO be added to the PCR reaction to a final concentration of 5% inasmuch as this was found to be necessary for amplification of this region of the neurturin gene. The PCR reaction, when run on an agarose gel, should contain products in the size range of 100-150 base pairs since a one amino acid gap is introduced in the neurturin sequence and a five amino acid gap is introduced in the persephin sequence when either sequence is aligned with GDNF, and thus family member genes might also contain a slightly variable spacing between the conserved sequences of primers 2 and 4. The PCR products in the range of 100-150 base pairs should contain multiple amplified gene products including GDNF, neurturin and persephin as well as previously unisolated family members. To identify sequences of these products, they can be gel purified and ligated into the Bluescript plasmid (Stratagene), and then transformed into the XL1-blue E. Coli host strain (Stratagene). Bacterial colonies containing individual subclones can be picked for isolation and plated on nitrocellulose filters in two replicas. Each of the replicate filters can be screened with an oligonucleotide probe for either unique GDNF or unique neurturin or unique persephin sequence in the amplified region. Subclones not hybridizing to either GDNF or neurturin or persephin can be sequenced and if found to encode previously unisolated family members, the sequence can be used to isolate full length cDNA clones and genomic clones as was done for neurturin (Example 5). A similar method was used to isolate new gene members (GDF-3 and GDF-9) of the TGF-β superfamily based on homology between previously identified genes (McPherron J Biol Chem 268: 3444-3449, 1993 which is incorporated by reference).

The inventors herein believe that the most preferred way to isolate family member genes may be to apply the above PCR procedure as a screening method to isolate individual family member genomic clones from a library. This is because there is only one exon for the coding region of both mature neurturin and GDNF. If, for example, the above PCR reaction with primers 2 and 4 generates products of the appropriate size using human genomic DNA as template, the same reaction can be performed using, as template, pools of genomic clones in the P1 vector according to methods well known in the art, for example that used for isolating neurturin human genomic clones (Example 5). Pools containing the neurturin gene in this library have previously been identified and persephin and GDNF-containing pools can be readily identified by screening with GDNF and PSP specific primers. Thus non-neurturin, non-persephin, non-GDNF pools which generate a product of the correct size using the degenerate primers will be readily recognized as previously unisolated family members. The PCR products generated from these pools can be sequenced directly using the automated sequencer and genomic clones can be isolated by further subdivision and screening of the pooled clones as a standard service offered by Genome Systems, Inc.

EXAMPLE 12

The following example illustrates the isolation and identification of persephin utilizing the procedures and primers described in Example 11.

The degenerate PCR strategy devised by the inventors herein has now been successfully utilized to identify a third factor, persephin, that is approximately 35-50% identical to both GDNF and neurturin. The experimental approach was described above and is provided in greater detail as follows. Primers corresponding to the amino acid sequence Val-Xaa1-Xaa2-Leu-Gly-Leu-Gly-Tyr where Xaa1 is Ser or Thr and Xaa2 is Glu or Asp (SEQ ID NO:33) [M1996; 5'-GTNWS-NGANYTNGGNYTNGGNTA (SEQ ID NO:42)] and Phe-Arg-Tyr-Cys-Xaa1-Gly-Xaa2-Cys-Xaa3-Xaa4-Ala where Xaa1 is Ala or Ser, Xaa2 is Ala or Ser, Xaa3 is Glu or Asp and Xaa4 is Ser or Ala (SEQ ID NO:37) [M1999; 5'-GCNGMNT-CRCANSHNCCNSHRCARTANCKRAA (SEQ ID NO:44)] were used to amplify a 77 nt fragment from rat genomic DNA using Klentaq enzyme and buffer under the following conditions: 94° C. for 30 sec; 44° C. for 30 sec; 72° C. for 30 sec for 40 cycles. The resulting product was subcloned into the Bluescript KS plasmid and sequenced. All-nucleotide sequencing was performed using fluorescent dye terminator technology per manufacturer's instructions on an Applied Biosystems automated sequencer Model #373 (Applied Biosystems, Foster City, Calif. ). Plasmid DNA for sequencing was prepared using the Wizard Miniprep kit (Promega Corp., Madison, Wis.) according to the manufacturer's instructions.

The sequence of one of the amplified products predicted amino acid sequence data internal to the PCR primers that was different from that of GDNF or neurturin but had more than 20% identity with GDNF and neurturin, whereas the sequences of others we obtained corresponded to GDNF or neurturin, as would be expected. The novel sequence was thought to identify a new member of this family which we named persephin.

The sequence of this fragment internal to the primers was 5'-TGCCTCAGAGGAGAAGATTATC (SEQ ID NO:90). This encodes the last nucleotide of the Tyr codon, and then encodes the amino acids: Ala-Ser-Glu-Glu-Lys-Ile-Ile (SEQ ID NO:91). This sequence was then aligned with the rat sequences of GDNF and neurturin. This analysis confirmed that persephin was unique.

```
LGLGYETKEELIFRYC   GDNF (rat)   (SEQ ID NO:92)

LGLGYTSDETVLFRYC   NTN (rat)    (SEQ ID NO:93)

LGLGYASEEKIIFRYC   PSP (rat)    (SEQ ID NO:94)
```

To obtain additional persephin sequence, primers containing portions of the unique 22 nt of the amplified fragment above were used in the rapid amplification of cDNA ends (RACE) technique (Frohman, M. A. *Methods in Enzymology* 218:340-356, 1993) using the Marathon RACE kit (CLONTECH, Palo Alto, Calif.) per the manufacturer's instructions, except that first strand cDNA synthesis was carried out at 50° C. using Superscript II reverse transcriptase (Gibco-BRL). Briefly, a double stranded adaptor oligonucleotide was ligated to the ends of double stranded cDNA synthesized from postnatal day 1 rat brain mRNA. Using nested forward persephin PCR primers, (10135; 5'-AGTCGGGGTTGGGG-TATGCCTCA, SEQ ID NO:95 and M2026; 5'-TATGCCT-CAGAGGAGAAGATTATCTT SEQ ID NO:96) in combination with primers to the ligated adaptor supplied in the kit (AP1, AP2), the 3' end of the persephin cDNA was amplified by two successive PCR reactions (1st: 10135 and AP1, using 94° C. for 30 sec, 60° C. for 15 sec and 68° C. for 2 min for 35 cycles; 2nd: M2026 and AP2 using 94° C. for 30 sec, 60 for 15 sec and 68° C. for 2 min for 21 cycles). An approximately 350 nt fragment was obtained from this PCR reaction and this fragment was directly sequenced using primer M2026. The sequence of this 3' RACE product resulted in a partial rat persephin cDNA sequence of approximately 350 nt (SEQ ID NO:97). The predicted amino acid sequence of this CDNA was compared to that of GDNF and neurturin, and found to be approximately 40% homologous to each of these proteins. Importantly, the characteristic spacing of the cyteine residues in members of the TGF-β superfamily was present. Furthermore, in addition to the region of similarity encoded by the degenerate primers used to isolate persephin, another region of high homology shared between GDNF and neurturin, but absent in other members of the TGF-β superfamily, was also present in persephin

```
GDNF  ACCRPVAFDDDLSFLDD  (aa 60-76)  (SEQ ID NO:98)

NTN   PCCRPTAYEDEVSFKDV  (aa 61-77)  (SEQ ID NO:99)

PSP   PCCQPTSYAD-VTFLDD  (aa 57-72)  (SEQ ID NO:100)
```

(Amino acid numbering uses the first Cys residue as amino acid 1).

With the confirmation that persephin was indeed a new member of the GDNF/neurturin subfamily, we isolated murine genomic clones of persephin to obtain additional sequence information. Primers (forward, M2026; 5'-TATGC-CTCAGAGGAGAAGATTATCTT, SEQ ID NO:96 and reverse, M3028; 5'-TCATCAAGGAAGGTCACATCAG-CATA, SEQ ID NO:101) corresponding to rat CDNA sequence were used in a PCR reaction (PCR parameters: 94° C. for 30 sec, 55° C. for 15 sec and 72° C. for 30 sec for 35 cycles) to amplify a 155 nt fragment from mouse genomic DNA which was homologous to rat persephin cDNA sequence. These primers were then used to obtain murine persephin genomic clones from a mouse 129/Sv library in a P1 bacteriophage vector (library screening service of Genome Systems, Inc., St. Louis, Mo.).

Restriction fragments (3.4 kb Nco I and a 3.3 kb Bam H1) from this P1 clone containing the persephin gene were identified by hybridization with a 210 nt fragment obtained by PCR using mouse genomic DNA with primers (forward, M2026; SEQ ID NO:96 and reverse, M3159; 5'-CCACCA-CAGCCACAAGCTGCGGSTGAGAGCTG, SEQ ID NO:102) and PCR parameters: 94° C. for 30 sec, 55° C. for 15 sec and 72° C. for 30 sec for 35 cycles. The Nco I and Bam H1 fragments were sequenced and found to encode a stretch of amino acids corresponding to that present in the rat persephin RACE product, as well as being homologous to the mature regions of both neurturin and GDNF (FIG. 11).

When the amino acid sequences of murine GDNF, neurturin and persephin are aligned using the first cysteine as the starting point (which is done because alterations in the cleavage sites between family members creates variability in the segments upstream of the first cysteine), persephin (91 amino acids) is somewhat smaller than either neurturin (95 amino acids) or GDNF (94 amino acids). The overall identity within this region is about 50% with neurturin and about 40% with GDNF (FIG. 12).

Further nucleotide sequencing of the murine persephin Nco I fragment revealed the nucleotide sequence of the entire murine persephin gene (SEQ ID NO:131; FIG. 17A). An open reading frame extends from the sequence coding for an initiator methionine up to a stop codon at positions 244-246. However, somewhere in this sequence there is an apparent anomaly such that the sequence encoding the RXXR cleavage site (nucleotides at positions 257-268) and the sequence corresponding to the mature persephin protein (positions 269-556) are not co-linear with this open reading frame. Instead, a second reading frame encodes the cleavage site and the mature persephin.

Additional sequencing of the rat persephin has also been performed. Rat genomic fragments were amplified by PCR using Klentaq and rat genomic DNA as a template.

The forward primer #40266 (5'-AATCCCCAGGACAG-GCAGGGAAT; SEQ ID NO:137) corresponding to a region upstream of the mouse persephin gene and a reverse primer M3156 (5'-CGGTACCCAGATCTTCAGCCACCACAGC-CACAAGC, SEQ ID NO:138) corresponding to a region within the mature rat persephin sequence were used with the following parameters (95° C. for 15 sec, 55° C. for 15 sec, 68° C. for 45 sec×30 cycles). The amplified product was kinased with T4 polynucleotide kinase, the ends were blunted with *E. coli* DNA polymerase I (Klenow fragment), and cloned into BSKS plasmid.

Nucleotide sequencing was performed to establish the sequence of the entire rat persephin gene (SEQ ID NO:188; FIG. 18A). An open reading frame was found to extend from the sequence coding for an initiator methionine up to a stop codon at positions 244-246 as was seen with murine persephin. As was also seen with murine persephin, an anomaly was found to occur between the sequence encoding the initiator methionine and that encoding the cleavage site for the mature rat persephin such that two cogent reading frames exist. Irrespective of this anomaly, mammalian cells were found to express persephin from either the murine or rat full length genomic sequence as illustrated below (see Example 14).

To pursue the genesis of this anomaly, we prepared mammalian expression vectors for both murine and rat persephin. To construct the murine plasmid, a P1 clone containing the murine persephin gene was used as a template in a PCR assay. Primers were designed such that the resulting fragment would contain the persephin gene extending from the initiator Methionine to the stop codon. The PCR reaction utilized a forward primer M3175 [5'-TGCTGTCACCATGGCTG-CAGGAAGACTTCGGA] and reverse primer M3156 [5'-CGGTACCCAGATCTTCAGCCACCACAGC-CACAAGC]. To construct the analogous rat plasmid, rat genomic DNA was used as a template in a PCR assay. The PCR reaction utilized a forward primer M3175 [5'-TGCTGT-CACCATGGCTGCAGGAAGACTTCGGA] and reverse primer M3156 [5'-CGGTACCCAGATCTTCAGCCACCA-CAGCCACAAGC]. The amplified products were cloned into BSKS and sequenced to verify that the correct clone had been obtained. The rat and murine persephin fragments were excised using Sma I and Hind III and cloned into a Asp718 (blunted) and Hind III sites of the mammalian expression vector pCB6.

COS monkey cells were transfected with either the rat or murine persephin expression vectors or the non-recombinant vector (pCB6) itself. Forty eight hr later the cells were lysed, the samples were loaded onto a 15% SDS-polyacrylamide gel, and the proteins were separated by electrophoresis. The proteins were then transferred to nitrocellulose by electroblotting. This nitrocellulose membrane was incubated with anti-persephin antibodies (which we raised to mature persephin produced in bacteria from a pET plasmid) to detect the presence of persephin in the lysates. Lysates from cells transfected with either the rat or murine persephin expression vectors, but not the lysate from cells transfected with pCB6, contain high amounts of persephin. The size of the persephin detected was 10-15 kD, consistent with the size predicted for the processed (i.e. mature form of persephin). Conditioned media harvested from these cells also contained mature persephin. These results demonstrate that both the murine and rat persephin genes are capable of directing the synthesis of a properly processed persephin molecule.

To pursue the mechanism by which this occurred, we isolated RNA from cells transfected with either rat or murine persephin expression vector. RT/PCR analysis was performed using primers corresponding to the initiator Met and the stop codon. We detected two fragments: one corresponding to the predicted size of the persephin gene and the other somewhat smaller, suggesting that RNA splicing had occurred. We confirmed this with a number of other primer pairs. Both the large and small persephin fragments were cloned and sequenced. As expected, the larger fragment corresponded to the persephin gene. The small fragment corresponded to a spliced version of persephin. A small 88 nt intron within the pro-domain (situated 154 nt downstream of the start codon) had been spliced out. After this splicing event, the "frameshift" was no longer present (i.e. the initiator Met and the mature region are in-frame) in either rat or mouse persephin (see FIGS. 17B and 18B).

EXAMPLE 13

This example illustrates the preparation of a bacterial expression vector for murine persephin and its introduction into an *E. Coli* for expression of recombinant mature persephin.

The persephin polynucleotide encoding the mature murine persephin protein which begins 5 amino acids upstream of the first framework Cys residue (SEQ ID NO:80) was cloned into the pET expression vector pET-30a at the Nde I and Bgl II sites. This persephin polynucleotide was generated by PCR using the murine persephin P1 genomic clone as a template. A forward primer M3157 (5'-GGACTATCATATGGCCCAC-CACCACCACCACCACCACCACCACGACGAC-GACGACAAGGC CTTGGCTGGTTCATGCCGA, SEQ ID NO:139) encoding an Nde I site, 8 histidine residues, and an enterokinase site, and a reverse primer M3156 (5'-CGGTAC-CCAGATCTTCAGCCACCACAGCCACAAGC, SEQ ID NO:138), which corresponds to the sequence encoding the last 6 amino acid residues of the mature persephin sequence, the stop codon and a Bgl II site, were used. The PCR reaction conditions were 95° C. for 15 sec, 55° C. for 15 sec, 68° C. for 60 sec×25 cycles. This PCR product was subcloned into the EcoRV site of BSKS plasmid and sequenced to verify that it contained no mutations. The persephin sequence was then excised from this vector using Nde I and Bgl II and cloned into the Nde I (5') and Bgl II (3') sites of the bacterial expression vector pET30a (Novagen, Madison, Wis.). This expression vector would, therefore, produce the mature form of the persephin protein possessing an amino terminal tag consisting of 8 histidine residues followed directly by an enterokinase site.

The plasmid was introduced into *E. coli* strain BL21 (DE3). To produce persephin, bacteria harboring this plasmid were grown for 16 hr, harvested, and lysed using 6M guanidine-HCl, 0.1 M $NaH_2PO_{4,\ 0.01}$ M Tris at pH 8.0, and recombinant persephin protein was purified from these lysates via chromatography over a Ni-NTA resin (Qiagen). The protein was eluted using 3 column volumes of Buffer E containing 8 M urea, 0.1 M $NaH_2PO_{4,\ 0.01}$ M Tris, at pH 4.5. The persephin was then renatured by dialysis in renaturation buffer consisting of 0.1 M $NaH_2PO_4$, 0.01 M Tris at pH 8.3, 0.15 M NaCl, 3 mM cysteine, 0.02% Tween-20, 10% glycerol and containing decreasing concentrations of urea beginning with 4 M for 16 hr, followed by 2 M for 16 hr, 1M for 72 hr, and 0.5 M for 16 hr. The persephin concentration was then determined using a Dot Metric assay (Geno Technology, St. Louis, Mo.) and stored at 4° C.

This bacterially produced recombinant persephin was used as an immunogen in rabbits to produce antibodies to mature persephin. All of the immunogen injections and blood drawing were performed at Cal Tag Inc. (Healdsburg, Calif.). The anti-persephin antiserum was demonstrated to specifically recognize persephin, but not neurturin or GDNF, using protein blot analysis. This persephin-specific antiserum was then used to detect persephin in lysates prepared from transfected COS cells.

EXAMPLE 14

This example illustrates the preparation of mammalian expression vectors containing the murine or rat persephin genes and their incorporation into mammalian cell lines for the production of mature persephin. To construct the murine plasmid, a P1 clone containing the murine persephin gene was used as a template in a PCR assay. Primers were designed such that the resulting polynucleotide would contain the persephin gene extending from the initiator Methionine codon to the stop codon 3' to the mature persephin coding sequence (SEQ ID NO:131). The PCR reaction utilized a forward primer M3175 (5'-TGCTGTCACCATGGCTGCAGGAA-GACTTCGGA, SEQ ID NO:140) and reverse primer M3156

(5'-CGGTACCCAGATCTTCAGCCACCACAGCCACA-AGC, SEQ ID NO:138). To construct the analogous rat plasmid, rat genomic DNA was used as a template in a PCR assay. The PCR reaction utilized a forward primer M3175 (5'-TGCTGTCACCATGGCTGCAGGAAGACTTCGGA, SEQ ID NO:140) and reverse primer M3156 (5'-CGGTACCCA-GATCTTCAGCCACCACAGCCACAAGC, SEQ ID NO:138). Both PCR reactions were carried out using Klentaq and the following parameters: 95° C. for 15 sec, 55° C. for 15 sec, 68° C. for 45 sec×25 cycles. The amplified products were kinased with T4 polynucleotide kinase, the ends were blunted with E. coli DNA polymerase I (Klenow fragment), and cloned into BSKS plasmid. Nucleotide sequencing was performed to verify that the correct clone was obtained. The rat and murine persephin polynucleotides were excised using Sma I and Hind III and each cloned into a Asp7l8 (blunted) and Hind III sites of the mammalian expression vector pCB6.

COS monkey cells were transfected with either the rat or murine persephin expression vectors (16 μg per 5 ×10⁵ cells) or the non-recombinant vector (pCB6) itself using the calcium phosphate precipitation method (Chen and Okayama, *Mol Cell Biol* 7:2745-2752, 1987 which is incorporated by reference). Forty eight hr later the cells were lysed in IP buffer containing 50 mM Tris at pH 7.5, 300 mM NaCl, 1% Triton X-100, 1% deoxycholate, 10 mM EDTA, 0.1% SDS, 5 μg/ml leupeptin, 7 μg/ml pepstatin, and 250 μM PMSF. The samples were loaded onto a 15% SDS-polyacrylamide gel and the proteins were separated by electrophoresis. The proteins were then transferred to nitrocellulose by electroblotting. This nitrocellulose membrane was incubated with anti-persephin antibodies to detect the presence of persephin in the lysates.

As is shown in FIG. 19, lysates from cells transfected with either the rat or murine persephin expression vectors, but not the lysate from cells transfected with pCB6, contain high amounts of persephin. The size of the persephin detected was approximately 14 kD which is consistent with the size predicted for the processed, i.e. mature form of persephin. This demonstrates that both the murine and rat persephin genes are capable of directing the synthesis of a properly processed persephin molecule.

EXAMPLE 15

The following example illustrates the isolation and identification of human persephin.

In order to identify the human homologue of persephin or additional members of the GDNF family, degenerate PCR primers were designed based on the human Neurturin and GDNF sequences and used to amplify human genomic DNA. The following primers were used (SEQ ID NOS:225-228):

```
DhNeurturin1 (DN1)    GTSASYGASYTGGGYCTGGGCTAY
REF:B-46Z

DhNeurturin2 (DN2)    TTYMGSTACTGCRSMGGCKCYTGC
REF:B-46X

DhNeurturin3r (DN3)   RWAGGCSRTSGGKCKGCARCAKGS
REF:B-46V

DhNeurturin4r (DN4)   MKCRTCYARRAASGACASSTC
REF:B-46W
```

Human genomic DNA (Clontech 6550-1 0.1 μg/μl) was amplified with all 4 possible primer combinations (DN1-DN3r, DN1-DN4r, DN2-DN3r, DN2-DN4r). Reaction mixtures contained 5 μl of 10x Klentaq buffer, 0.5 μl dNTP (20 mM); 1 μl human genomic DNA, 0.6 μl Klentaq (Clontech) and 1.5 μl of each primers (0.1 OD/μl) in a total volume of 50 μl. The DNA was amplified by touchdown PCR on Perkin Elmer Gene AMP 9600 in the following conditions: initial denaturation at 98° C. for 2', then 5 cycles [98° C. 30 ", 72° C. 1.5 '], 5 cycles (98° C. 30 ", 70° C. 1.5'] and 25 cycles [98° C. 30 ', 68° C. 1.5'] followed by a last extension step at 68° C. for 5'.

PCR products of approximately 130 to 200 bp were identified after electrophoresis on agarose gel, purified and cloned into pCR 2.1 vector using In Vitrogen TA cloning kit (Cat# K2000-01). Clones containing a 130-200 bp insert (after EcoRl digestion) were sequenced and one of them (clone A3) obtained with the primer pair DN1-DN3r had a sequence homologous to mouse persephin and corresponded to human persephin.

The partial sequence of the human persephin genomic DNA in clone A3 is shown below (SEQ ID NO:229):

```
CGGCTTGTGACCGAGCTGGGCCTGGGCTACGCCTCAGAGGAGAAGGTCAT
CTTCCGCTACTGCGCCGGCAGCTGCCCCCGTGGTGCCCGCACCCAGCATG
GCCTGGCGCTGGCCCGGCTGCAGGGCCAGGGCCGAGCCCACGGCGGGCCC
TGCTGCCGCCCCATGGCC
```

In order to identify a source from which to isolate a full length cDNA clone of human persephin, cDNA libraries were screened by PCR using exact match primers designed based on the genomic DNA sequence described above. Two sets of human persephin specific primers were prepared (SEQ ID NOS:230-233),

```
hPSP-5'.1    GAGGAGAAGGTCATCTTCCG         REF:B-95K hPSP-3'.1    GCCGTGGGCTCGGCCCTGGC         REF:B-95L and
hPSP-5'.3    AGAGGAGAAGGTCATCTTCCGCTA    REF:C-62Y hPSP-3'.4    CTCGGCCCTGGCCCTGCAGC         REF:C-62X
``` and used to amplify single stranded DNA from pRK5 cDNA libraries (1 μl of 200 ng/μl) or the Stratagene's Quickscreen panel (3 μl of each library) using the same conditions as described above. PCR products of the expected size (108 bp for hPSP-5 '1 with hPSP-3 '1 and 101 p for hPSP-5 '3 with hPSP-3 '4) were detected in fetal lung, fetal liver, fetal kidney, small intestine, retina, erebellum and hT+13 Lymphoblast.

To isolate cDNA clones encoding human persephin, pRK5 libraries from human tissues were enriched for persephin cDNA clones by extension of single stranded DNA from plasmid libraries grown in a dut⁻/ung⁻-host using either of the following primers (SEQ ID NOS:233-234):

```
hPSP-3'.2    TGCAGCCGGGCCAGCGCCAG         REF:D-68T hPSP-3'.4    CTCGGCCCTGGCCCTGCAGC         REF:C-62X
``` in a reaction containing 10 μl of 10x PCR Buffer (Perkin Elmer), 1 μl dNTP (20 mM), 1 μl library DNA (200 ng), 0.5 μl primer, 86.5 μl H₂O and 1 μl of Amplitaq (Perkin Elmer) added after a hot start. The reaction was denatured for 1 min at 95° C., annealed for 1 min at 50, 60 or 68° C. then extended for 20 min at 72° C. DNA was extracted with phenol/chloroform, ethanol precipitated, then transformed by electroporation into DH10B host bacteria.

Approximately 40,000 colonies from each transformation were lifted on nylon membranes and screened with a DNA probe derived from the sequence of clone A3 (described above). The fragment was labeled by the random oligonucleotide method using [32P]-dCTP. Filters were hybridized overnight at 42° C. in 50% formamide, 5×SSC, 10×Denhardt's, 0.05M sodium phosphate (pH 6.5), 0.1% sodium pyrophosphate, 50 μg/ml of sonicated salmon sperm DNA. Filters were then rinsed in 2×SSC and washed in 0.1×SSC, 0.1% SDS then exposed overnight to Kodak X Ray films. Pure positive clones were obtained after secondary screening and the isolated clones were then sequenced. Human persephin clones were isolated from fetal lung, fetal kidney and fetal liver libraries. All such persephin clones isolated belong to two categories: unspliced (10 clones) or chimeric (6 clones). Unspliced clones were ~900 bp long and contain a region encoding a fragment corresponding to human persephin. However there is no initiation methionine and signal peptide present in that reading frame (Frame+2). A potential upstream initiation codon (ATG) is present in another reading frame (+1) and is followed by a hydrophobic sequence corresponding to a potential signal peptide. This suggests that such cDNAs are incompletely spliced and that an intron remains between the exons encoding the signal peptide and the persephin protein. Consensus splice donor and acceptor sequences can actually be identified at position 340 and 425, respectively. Splicing of an intron located between these positions would lead to a cDNA where the persephin coding sequence is "in frame" with the initiation methionine. Interestingly, aberrant chimeric clones were identified resulting from the joining of a cDNA encoding the predicted exon 2 of persephin exactly at the splice acceptor site present at position 425. The corresponding transcript was probably generated by aberrant splicing but confirms the presence of a splice acceptor site at position 425.

As an alternative approach to isolate a human persephin cDNA clone, 3 million clones of a human cerebellum CDNA library in lambda ZAP (Stratagene cat #935201) were screened with a DNA probe corresponding to clone A3 labeled by the random oligonucleotide method using [32P]-dCTP. The library was screened under high stringency hybridization conditions. The filters were prehybridized for 2 h then hybridized overnight at 42° C. in 50% formamide, 5×SSC, 10×Denhardt's, 0.05 M sodium phosphate (pH 6.5), 0.1% sodium pyrophosphate, 50 μg/ml of sonicated salmon sperm DNA. Filters were then rinsed in 2×SSC and washed once in 0.1×SSC, 0.1% SDS at 60° C. Filters were exposed overnight to Kodak X Ray films. Four positive clones (Cere 1.1, 1.2, 6.1, 6.2) were picked and plaque purified. The plasmid contained within the lambda ZAP phage arms was rescued as described per manufacturer's instructions using Ex Assist helper phage. Sequencing of the four clones indicated that these clones were siblings and contained 2 silent mutations when compared to the human persephin clones isolated from the pRK5 library described above. These silent mutations occur at positions 30 (T→C) and 360 (T→C) of the sequence shown in FIG. 24. Direct sequencing of the human persephin gene revealed that these silent mutations are actual allelic variations in the gene.

In order to determine if the correct protein could be expressed from the unspliced cDNA identified above, constructs were generated where the sequence encoding a Flag tag was inserted just before the stop codon present at position 685 (frame+1) or at position 746 (frame+2) starting from an ATG codon present at position 46 or 193. All four possible constructs were generated by PCR using the following primers (SEQ ID NOS:235-238):

```
hPSP1stMet.F     5' CGC GGA TCC ATG CCT GGA TTC
                    GAG GGT GCA G 3'
REF:B-127R hPSP2ndMet.F     5' CGC GGA TCC ATG GCC GTA GGG
                    AAG TTC CTG C 3'
REF:B-127S hPSP.FLAG.R      5' CTC CCA AGC TTT TAC TTG TCA
                    TCG TCG TCC TTG TAG TCG CCA CCA
                    CAG CCG CAG GCA GCC 3'
REF:A-120C hPSP.sig.FLAG.R  5' CTC CCA AGC TTT TAC TTG TCA
                    TGG TCG TCC TTG TAG TCT CGA GGA
                    AGG CCA CGT CGG TG 3'
REF:A-120B
```

In all four PCR reactions, the Cere 1.2 clone was used as template and amplified with Pfu polymerase on a Stratagene Robocyler gradient cycler 96. PCR conditions were 95° C. for 2', 30 cycles of [95° C. 30 ", 1' at 52, 56, 60 or 63° C., 72° C. for 2 min] followed by a last extension of 5 min at 72° C.

Forward primers have a Bam HI site and the reverse primers have Hind III restriction site. The PCR products digested with Bam HI and Hind III and were subcloned into these sites in pRK5. DNA from each of the construct was transfected overnight into 293 cells using CaP04 method. Serum containing media was conditioned for 24 h then harvested. Cells were also harvested and divided in two; ¼ of each plate for RT-PCR and the remaining ¾ of each plate for immunoprecipitation.

Analysis of expressed proteins was performed by immunoprecipitation. The cell pellet was lysed in 1 ml of lysis buffer (50 mM Tris pH 8.0, 150 mM NaCl, 1 mM EDTA, 1% NP40, Aprotinin, Leupeptin, PMSF, 1 mM NaF and 1 mM Sodium Vanadate) for 20 min at 4° C. The extract was spun for 10 min at 10 K rpm and then the supernatant was transferred to a new tube and precleared with 20 pl Protein A Sepharose for 1 h. From here, 1 ml of the conditioned media was processed in parallel. The protein A sepharose was spun down and 1 μl of anti-Flag antibody (3.6 pg) was added to each tube. After overnight incubation at 4° C., 30 μl of Protein G sepharose were added and the tubes incubated at 4° C. for 1 hour. The protein G beads were then spun down for 1 min, washed 3 times with lysis buffer, resuspended in 20 μl of Laemli buffer in the presence of β-mercapto-ethanol. Samples were denatured for 5 min at 100° C. then loaded on a 16% polyacrylamide gel. Proteins were then transferred to nitrocellulose and analyzed by Western blot using the same anti-Flag antibody overnight at 1 μg/ml in blocking buffer (PBS+0.5% tween+5% nonfat dry milk+3% Goat serum). Following this an anti-mouse HRP.ECL was used for the detection and the membrane was exposed for 90 sec to X-Ray film.

A specific band of 16 kDa was detected in the cell pellet of cells transfected with the construct starting at ATG 193 of frame +1 and with the flag inserted in frame +2 and a specific band of approximately 10 kDa could be detected in the corresponding supernatant. No Flag tagged protein could be detected in any other transfection or in mock transfected cells.

The correctly spliced mRNA was identified by RT-PCR as follows. Total RNA was extracted from the transfected cells (¼ of each pellet) using RNAzol B (Tel-Test Inc.) and treated for 40 min at 37° C. with DNase. RNA was then purified on an RNAasy column (Promega) and collected in a final volume of 50 μl. First strand cDNA was synthesized on 4 pl RNA using superscript RT (GIBCO-BRL) for 1 h at 37° C. then 5' at 95° to inactivate.

Two μl of each RT reaction were then used as template for amplification by PCR in the presence of the following 2 primers (SEQ ID NOS:236 and 239):

```
hPSp2ndMet.F    5'CGCGGATCCATGGCCGTAGGGAAGTTCCTGC 3'
REF:B-127S hPSP.stop.R     TCAGCCACCACAGCCGCAGGCAGCC
REF:D-103N
``` on a Stratagene Robocyler gradient cycler 96. PCR conditions were 98° C. for 1.5', 28 cycles of [98° C. for 30", anneal 1' between 60° C. and 76° C., 72° C. for 1.5'] followed by a last extension of 5 min at 72° C.

Analysis of the PCR product on agarose gel indicates that PCR using the pRK5.hPSP-FLAG.2 plasmid as template gave the expected product of about 570 bp while the RT PCR product, using RNA from cells transfected with this construct as template, was smaller than 500 bp. PCR product from the latter reaction was subcloned into the pCR 2.1 vector using In Vitrogen TA cloning kit (cat #K2000-01) and sequenced. Sequence analysis revealed that the predicted 84 bp intron has been spliced out of the transcript.

In summary, the human persephin cDNA has a 471 bp open reading frame encoding a 156 amino acid long protein (predicted Mr 16.6 kDA). Cleavage of the 23 amino acid long predicted signal peptide will lead to a 133 amino acid pro-persephin molecule (Mr 14.2 kDa); proteolytic cleavage of the pro-persephin at a RXXR consensus sequence should yield a 96 amino acid mature protein with a molecular weight of 10.3 kDa. This predicted size corresponds to the size of the Flag-tagged protein immunoprecipitated from the conditioned media of transfected 293 cells. Furthermore, amino terminal sequencing of Flag-tagged persephin purified from conditioned media of 293 transfected cells confirmed that the first residue of the mature form is Ala 61. Alignment between human persephin and human Neurturin indicates 38% similarity between the two molecules (50% for the mature region) and that human persephin is 30% similar to human GDNF (40% in the mature region).

EXAMPLE 16

This example illustrates the preparation of chimeric or hybrid polypeptide molecules that contain portions derived from persephin (PSP) and portions derived from neurturin (NTN).

As closely related members of the TGFβ family, each of persephin and neurturin is predicted to have a very similar overall structure, yet while neurturin promotes the survival of sympathetic neurons, the closely related persephin does not. Two chimeras were produced by essentially replacing portions of persephin with neurturin, with the crossover point located between the two adjacent, highly conserved third and fourth cysteine residues. The first chimera, named PSP/NTN (SEQ ID NO:141, FIG. 20), contains the first 63 residues of mature murine persephin combined with residues 68 through 100 of mature murine neurturin (using *E. coli* preferred codons). To construct this molecule, two PCR reactions were performed: 1) using the forward primer M2012 (5'-TAATAC-GACTCACTATAGGGGAA, SEQ ID NO:142) and reverse primer M2188 (5'-TCGTCTTCGTAAGCAGTCGGACG-GCAGCAGGGTCGGCCATGGGCTCGAC, SEQ ID NO:143) and the pET30a-murine persephin plasmid as template (see Example 13); and 2) using the forward primer M2190 (5'-TGCTGCCGTCCGACTGCTTACGAAGAC-GA, SEQ ID NO:144) and reverse primer M2186 (5'-GTTAT-GCTAGTTATTGCTCAGCGGT, SEQ ID NO:145) and the pET30a-murine (*E.coli* preferred codons) neurturin plasmid as template (see Example 6). Both PCR reactions were carried out using the following parameters: 94° C. for 30 sec, 55° C. for 30 sec, 72° C. for 30 sec×25 cycles. The products of these two PCR reactions were gel purified, mixed together, and a PCR reaction was performed under the following conditions: 94° C. for 30 sec, 60° C. for 20 min, 68° C. for 5 min. After 8 cycles, an aliquot of this reaction was used as template in a third PCR reaction using the forward primer M2012 and reverse primer M2186 under the following conditions: 94° C. for 30 sec, 55° C. for 30 sec, 72° C. for 30 sec×25 cycles. The resulting product was kinased with T4 polynucleotide kinase, the ends were blunted with *E. coli* DNA polymerase I (Klenow fragment), and cloned into BSKS plasmid. Nucleotide sequencing was performed to verify that the correct clone was obtained. The PSP/NTN fragment was excised using Nde I and Bam H1 and cloned into the corresponding sites of the bacterial expression vector pET30a.

The second chimera, named NTN/PSP (SEQ ID NO:146, FIG. 20), encodes the converse molecule. It contains the first 67 residues of mature murine neurturin (using *E.coli* preferred codons) combined with residues 64 to 96 of mature murine persephin. To construct this molecule, we performed two PCR reactions: 1) using the forward primer M2012 and reverse primer M2183 (5'-CACATCAGCATAGCTG-GTGGGCTGGCAGCACGGGTGAGCACGAGCACGTT, SEQ ID NO:147) and the pET30a-murine (*E.coli* preferred codons) neurturin plasmid as template; and 2) using the forward primer M2187 (5'-TGCTGCCAGCCCACCAGCTAT-GCTG, SEQ ID NO:148) and reverse primer M2186 (5'-GTTATGCTAGTTATTGCTCAGCGGT, SEQ ID NO:145) and the pET30a-murine persephin plasmid as template. Both PCR reactions were carried out using the following parameters: 94° C. for 30 sec, 55° C. for 30 sec, 72° C. for 30 sec×25 cycles. The products of these two PCR reactions were used to construct the final NTN/PSP pET30a plasmid as detailed above for PSP/NTN except that Bgl II was used instead of Bam H1. These chimeric proteins were produced in *E.coli* and purified by Ni-NTA chromatography as described above (Example 13).

The purified proteins were assayed for their ability to promote survival in the SCG sympathetic neuron assay. The NTN/PSP protein did not promote survival, whereas the PSP/NTN protein promoted the survival of sympathetic neurons similar to that observed for neurturin itself. These results indicate that neurturin residues lying downstream of the 2 adjacent, highly conserved cysteine residues are critical for activity in promoting survival in SCG sympathetic neurons. In contrast, the corresponding residues of persephin are not sufficient for promoting survival in sympathetic neurons.

EXAMPLE 17

This example illustrates the neuronal survival promoting activity of persephin in mesencephalic cells.

The profile of survival promoting activity of persephin is different from that of neurturin and GDNF. In contrast to the survival promoting activity produced by neurturin and GDNF in sympathetic and sensory neurons, persephin showed no survival promoting activity in these tissues. We further evaluated the neuronal survival promoting activity of persephin in mesencephalic cells.

Timed-pregnant Sprague-Dawley rats were purchased from Harlan Sprague-Dawley. The mesencephalon was taken from rats measuring 1.2 to 1.4 cm in length and time dated to be embryonic day 14. The cranium was removed and the entire mesencephalon was placed in cold L15. The cooled mesencephalic tissue was resuspended in a serum-free medium consisting of DME/Hams F12 (#11330-032, Life Technologies) 1 mg/ml BSA, Fraction V (A-6793, Sigma Chemical Co.,), 5 µM Insulin (I-5500, Sigma), 10 nM progesterone (P0130, Sigma), 100 µM putrescine, (p7505, Sigma), 30 rM Selenium (S07150, Pflatz & Bauer), 10 ng/ml rat transferrin (012-000-050, Jackson Chrompure), 100 U/ml penicillin, and 100 U/ml of streptomycin. The pooled mesencephalic tissues were triturated approximately 80 times using a bent-tip pipette and the cells were plated in a 24-well dish (CoStar) at a density of 15,000 cells in a 100-µl drop. The dishes were coated with 125 ng/ml poly-d-lysine (p-7280, Sigma) and 25 ng/ml laminin (#40232, Collaborative Biomedical Products). These dissociated cells were allowed to attach for 2 hours at 37° C. in 5% $CO_2$ and then fed with another 500 µl of the above serum-free medium with or without approximately 100 ng/ml of recombinant Persephin. These cells were photographed after 3 days of culture.

Figure 21A:
Figure 21B:
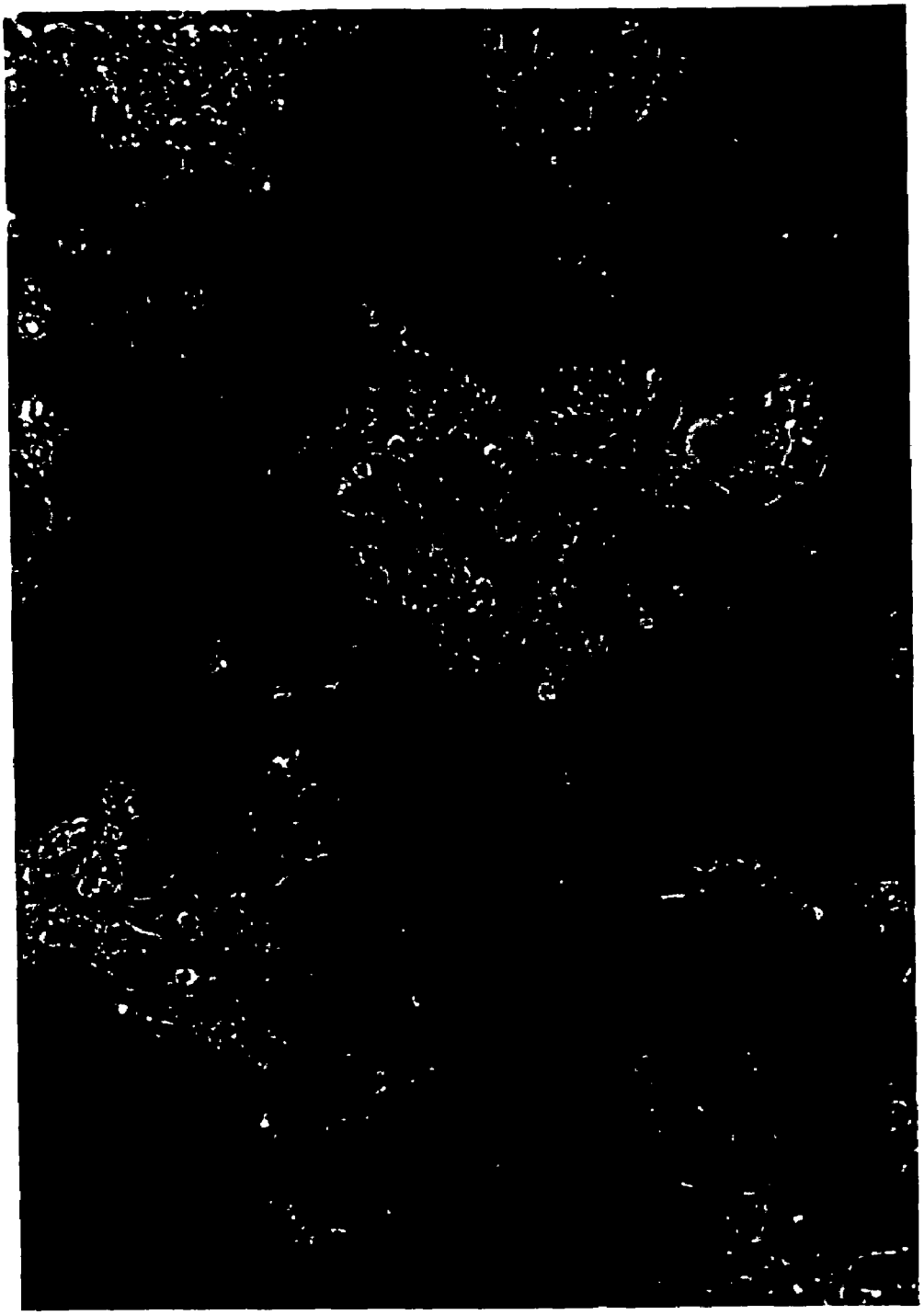

Inspection of the cells over the course of 3 days in culture, showed a gradual decrease in cell number. In the absence of any growth factor, almost all of the cells were dead (FIG. 21A). In the presence of persephin, a large increase in mesencephalic neuronal cell survival was evident (FIG. 21B).

This study was repeated to obtain comparative effects on mesencephalic cell for persephin and the related growth factors, neurturin and GDNF. Mesencephalic tissue was removed from E14 par pps, pooled and dissociated in dispase for 30 min. Cells were then triturated and plated in supplemented N2 media and plated at a density of 20,000 cells per well in an 8-well chamber alike. The cells in a given well were either untreated or treated with a growth factor at 50 ng/ml for four days. Cells were washed once with PBS, fixed with 4% paraformaldehyde for 30 minutes and stained with tyrosine hydroxylase (TOH) antibody (Chemicon, ABC-Vectastain kit) and counted. TOH staining served as a marker for dopaminergice cells inasmuch as TOH is a synthetic enzyme for dopamine. FIG. 22 shows the mean cell counts for untreated and treated cells. Persephin (PSP), neurturin (NTN) and GDNF promoted survival of mesencephalic neuronal cells to a comparable extent.

EXAMPLE 18

This example illustrates the expression of persephin in various tissues.

A survey of persephin expression was performed in adult mouse tissues using semi-quantitative RT/PCR (see Example 9). Poly A RNA was isolated from brain, cerebellum, kidney, lung, heart, ovary, sciatic nerve, dorsal root ganglia, blood and spleen. This was then reverse transcribed to produce cDNA (see Kotzbauer et al. *Nature* 384:467-470, 1996 which is incorporated by reference). The PCR primers used were as follows: forward primer: 5'-CCTCGGAGGAGAAGGT-CATCTTC (SEQ ID NO:149) and reverse primer: 5' TCAT-CAAGGAAGGTCACATCAGCATA (SEQ ID NO:101). PCR was done for 26 cycles with an annealing temperature of 60° C. To control for the presence of genomic DNA, RNA samples which were not reverse transcribed were used for PCR (for example, the tissue control shown in FIG. 22 is labeled "Kidney no RT"). All the samples were found to be without genomic DNA contamination.

As shown in FIG. 23, a band of the correct size (160 bp) was seen in the kidney sample. At higher cycle numbers a persephin band was also seen in brain. Thus, the distribution of expression of persephin in various mouse tissues differs from that of neurturin in rat (Example 8).

Deposit of Strain

The following strain is on deposit under the terms of the Budapest Treaty, with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit, or for the enforceable life of the U.S. patent, whichever is longer. Should a culture become nonviable or be inadvertently destroyed, or, in the case of plasmid-containing strains, lose its plasmid, it will be replaced with a viable culture. The deposited materials mentioned herein are intended for convenience only, and are not required to practice the present invention in view of the description herein, and in addition, these materials are incorporated herein by reference.

| Strain | Deposit Date | ATCC No. |
|---|---|---|
| DG44CHO-pHSP-NGFI-B | Aug. 25, 1995 | CRL 11977 |

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

The invention claimed is:

1. An isolated or purified persephin-specific monoclonal antibody that specifically binds to the persephin polypeptide as set forth in SEQ ID NO: 221 and that does not cross react with a GDNF or Neurturin polypeptide.

2. An isolated or purified persephin-specific monoclonal antibody, wherein said monoclonal antibody specifically binds to amino acid residues 9-14, 38-48, 53-62 or 77-87 of the persephin polypeptide as set forth in SEQ ID NO: 221 and wherein said monoclonal antibody does not cross react with a GDNF or Neurturin polypeptide.

* * * * *

UNITED STATES PATENT AND TRADEMARK OFFICE
CERTIFICATE OF CORRECTION

| | | |
|---|---|---|
| PATENT NO. | : 7,649,082 B2 | Page 1 of 1 |
| APPLICATION NO. | : 11/037782 | |
| DATED | : January 19, 2010 | |
| INVENTOR(S) | : Johnson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this

Twenty-third Day of November, 2010

David J. Kappos
*Director of the United States Patent and Trademark Office*